United States Patent
Medoff

(10) Patent No.: US 9,587,258 B2
(45) Date of Patent: *Mar. 7, 2017

(54) PROCESSING BIOMASS

(71) Applicant: Xyleco, Inc., Wakefield, MA (US)

(72) Inventor: Marshall Medoff, Brookline, MA (US)

(73) Assignee: Xyleco, Inc., Wakefield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/183,564

(22) Filed: Jun. 15, 2016

(65) Prior Publication Data

US 2016/0289709 A1    Oct. 6, 2016

Related U.S. Application Data

(63) Continuation of application No. 14/813,898, filed on Jul. 30, 2015, which is a continuation of application No. 14/750,995, filed on Jun. 25, 2015, which is a continuation of application No. 14/333,675, filed on Jul. 17, 2014, now Pat. No. 9,309,545, which is a continuation of application No. 13/902,246, filed on May 24, 2013, now Pat. No. 8,877,472, which is a continuation of application No. 12/417,900, filed on Apr. 3, 2009, now abandoned.

(60) Provisional application No. 61/139,453, filed on Dec. 19, 2008, provisional application No. 61/073,674, filed on Jun. 18, 2008, provisional application No. 61/049,405, filed on Apr. 30, 2008.

(51) Int. Cl.
| | |
|---|---|
| C12P 7/42 | (2006.01) |
| C12P 7/62 | (2006.01) |
| A61Q 19/00 | (2006.01) |
| A61K 8/97 | (2006.01) |
| B01D 39/18 | (2006.01) |
| C08H 8/00 | (2010.01) |
| C08J 3/28 | (2006.01) |
| C12P 19/44 | (2006.01) |
| C13K 1/02 | (2006.01) |
| C08L 1/02 | (2006.01) |
| C08L 5/14 | (2006.01) |
| C12P 13/04 | (2006.01) |
| D21C 5/00 | (2006.01) |
| D21C 9/00 | (2006.01) |
| A23K 1/00 | (2006.01) |
| A23K 1/14 | (2006.01) |

(52) U.S. Cl.
CPC ............... *C12P 7/62* (2013.01); *A23K 1/002* (2013.01); *A23K 1/146* (2013.01); *A23K 10/12* (2016.05); *A23K 10/30* (2016.05); *A23K 10/37* (2016.05); *A23K 20/163* (2016.05); *A23K 20/189* (2016.05); *A23K 50/10* (2016.05); *A23K 50/80* (2016.05); *A23L 5/00* (2016.08); *A23L 5/30* (2016.08); *A61K 8/97* (2013.01); *A61Q 19/00* (2013.01); *B01D 39/18* (2013.01); *C08H 8/00* (2013.01); *C08J 3/28* (2013.01); *C08L 1/02* (2013.01); *C08L 5/14* (2013.01); *C12P 7/42* (2013.01); *C12P 13/04* (2013.01); *C12P 19/44* (2013.01); *C13K 1/02* (2013.01); *D21C 5/005* (2013.01); *D21C 9/001* (2013.01); *A23K 50/30* (2016.05); *A23K 50/40* (2016.05); *A23K 50/75* (2016.05); *C12P 2201/00* (2013.01); *C12P 2203/00* (2013.01); *Y02E 50/10* (2013.01); *Y02E 50/16* (2013.01); *Y02E 50/17* (2013.01); *Y02E 50/30* (2013.01); *Y02P 60/877* (2015.11)

(58) Field of Classification Search
None
See application file for complete search history.

(56) References Cited

PUBLICATIONS

Byrom, D. "Polymer synthesis by microorganisms: technology and economics" Trends in Biotechnology (1987), 5(9), 246-50. doi: 10.1016/0167-7799(87)90100-4.*

* cited by examiner

*Primary Examiner* — Thane Underdahl
*Assistant Examiner* — Aaron J Kosar
(74) *Attorney, Agent, or Firm* — Wilmer Cutler Pickering Hale and Dorr LLP

(57) ABSTRACT

Biomass (e.g., plant biomass, animal biomass, microbial, and municipal waste biomass) is processed to produce useful products, such as food products and amino acids.

6 Claims, 44 Drawing Sheets

VACUUM SOURCE 252

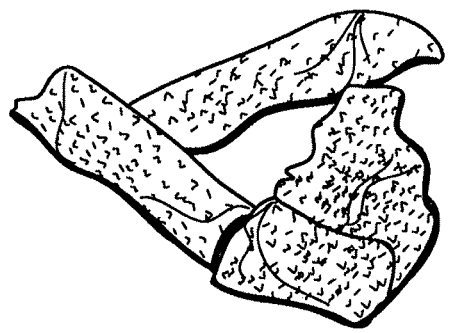
FIG. 7A
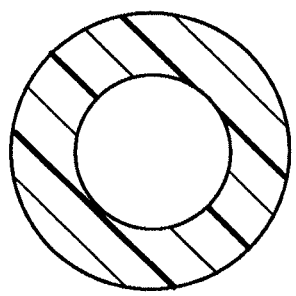 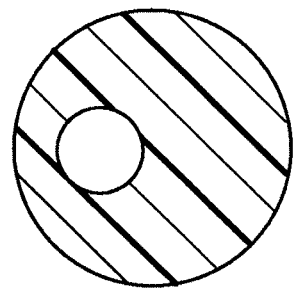
FIG. 7B    FIG. 7C
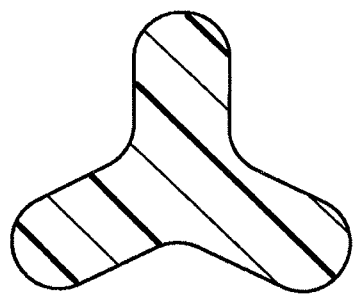
FIG. 7D

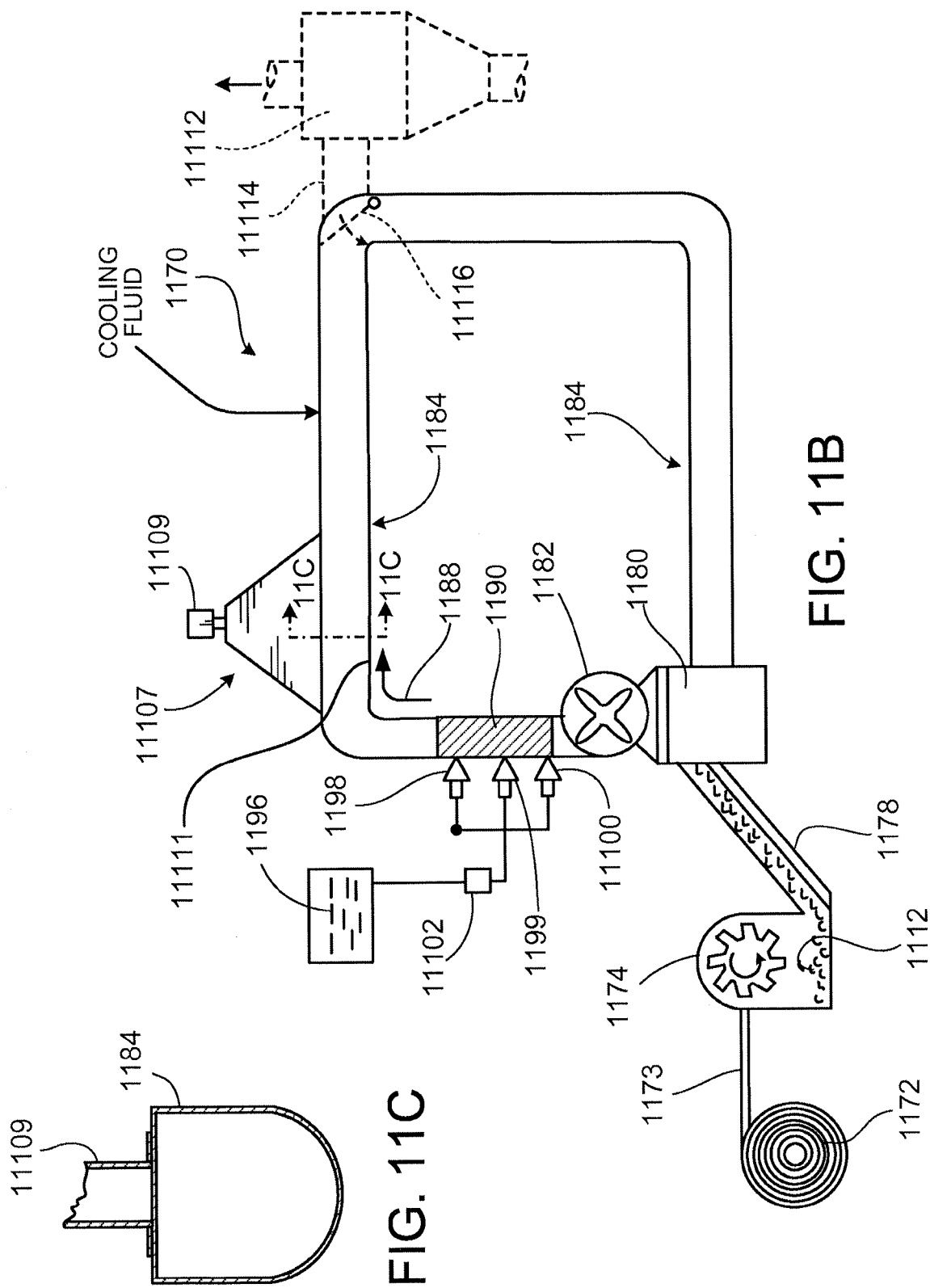

PROCESSING BIOMASS

RELATED APPLICATIONS

This application is a continuation of U.S. Ser. No. 14/813,898 filed Jul. 30, 2015, which is a continuation of U.S. Ser. No. 14/750,995, filed Jun. 25, 2015, which is a continuation of U.S. Ser. No. 14/333,675, filed Jul. 17, 2014, now U.S. Pat. No. 9,309,545 issued Apr. 12, 2016, which is a continuation of U.S. Ser. No. 13/902,246, filed May 24, 2013, now U.S. Pat. No. 8,877,472, issued on Nov. 4, 2014, which is a continuation of U.S. Ser. No. 12/417,900, filed Apr. 3, 2009, now abandoned, which claimed priority to U.S. Provisional Application 61/139,453, filed Dec. 19, 2008, U.S. Provisional Application 61/073,674, filed Jun. 18, 2008 and U.S. Provisional Application 61/049,405, filed Apr. 30, 2008. The entirety of each of these applications is incorporated herein by reference.

TECHNICAL FIELD

This invention relates to processing biomass, to compositions including saccharide units arranged in a molecular chain, to methods of producing amino acids or antibiotics, to methods of producing edible or immunostimulatory material, and to products of such methods.

BACKGROUND

Biomass, particularly biomass waste, is abundantly available. It would be useful to derive products from biomass.

SUMMARY

Exemplary products that can be produced using the methods provided herein include foodstuffs suitable for use in, e.g., ingestion by a human and/or animal, aquaculture, agriculture, hydroponics, pharmaceuticals, nutraceuticals, pharmaceutical delivery vehicles and dosage forms, pharmaceutical excipients, pharmaceutical conjugates, cross-linked matrixes such as hydrogels, absorbent materials, fertilizers, and lignin products. Any product disclosed herein or produced by the methods disclosed herein can be used as-is, or as a precursor or an intermediate in the production of another product.

In many embodiments, products can be produced using Natural Force™ Chemistry. Natural Force™ Chemistry methods use the controlled application and manipulation of physical forces, such as particle beams, gravity, light, etc., to create intended structural and chemical molecular change. In preferred implementations, Natural Force™ Chemistry methods alter molecular structure without chemicals or microorganisms. By applying the processes of Nature, new useful matter can be created without harmful environmental interference.

In one aspect, the present invention includes methods of preparing feed materials for animals (e.g., humans and animals, including but not limited to food animals, pets, zoo animals, etc.), and for plants (e.g., agricultural plants or crops or aquatic plants), and aquatic organisms (e.g., fish, crustaceans, mollusks and the like).

These methods include obtaining a first material including biomass (e.g., plant biomass, animal biomass, microbial, and municipal waste biomass) containing polysaccharides in the form of cellulose, hemicellulose, and/or starch. The molecular structure of the polysaccharides of the first material is then modulated (e.g., increased, decreased, or maintained) to produce a second material with a greater nutrient (e.g., protein, carbohydrate, fat, vitamin, and/or mineral) availability than the first material. The methods can optionally include providing the second material to animals (e.g., humans and/or non-human animals).

In some embodiments, the methods described herein can be used to generate materials suitable for use in maintaining or promoting the growth of microorganisms (e.g., bacteria, yeast, fungi, protists, e.g., an algae, protozoa or a fungus-like protist, e.g., a slime mold), aquatic organisms (e.g., in aquaculture), and/or plants and trees (e.g., in agriculture, hydroponics and silvaculture).

In another aspect, the present invention provides methods of improving the pharmaceutical profile of materials. These methods include obtaining a first material including biomass (e.g., plant biomass, animal biomass, microbial, and municipal waste biomass) containing polysaccharides in the form of cellulose, hemicellulose, and/or starch, and modulating (e.g., increasing, decreasing, or maintaining) the molecular structure of the polysaccharides of the first material to produce a second material, where one of the results of the methods is that the pharmaceutical profile of the second material is better or improved when compared to the pharmaceutical profile of the first material. In some instances, the methods include using first materials with little or no pharmaceutical profile prior to modulating the molecular structure of the first material. The second materials produced using the methods described herein are suitable for administration to an animal.

In a further aspect, the invention provides methods for obtaining a plant-derived pharmaceutical. These methods include processing a material including biomass (e.g., plant biomass, animal biomass, microbial, and municipal waste biomass) containing polysaccharides in the form of cellulose, hemicellulose, and/or starch containing one or more plant made pharmaceuticals, using any one or more of radiation, sonication, pyrolysis, and oxidation to obtain a plant-derived pharmaceutical. In some instances the plant-derived made pharmaceutical can be isolated and/or purified.

In yet another aspect, the present invention provides methods of preparing nutraceuticals for human and/or a non-human animal consumption. These methods include processing a material including biomass (e.g., plant biomass, animal biomass, microbial, and municipal waste biomass) containing polysaccharides in the form of cellulose, hemicellulose, and/or starch so as to change the molecular structure of the polysaccharides of the material (e.g., increase or decrease the molecular weight of the material). These methods can optionally also include administering the resulting materials to humans and non-human animals.

In an alternative aspect, the invention provides methods of preparing biological agents and/or a pharmaceutical agents. These method include processing a material including biomass containing polysaccharides in the form of cellulose, hemicellulose, and/or starch, so as to change the molecular structure of the polysaccharides of the material. The resulting materials can then be combined with one or more biological agents and/or one or more pharmaceutical agents, which can be administered to a subject.

Also provided in the present invention are methods of making hydrogels. These methods include processing a material including biomass containing polysaccharides in the form of cellulose, hemicellulose, and/or starch, and changing the molecular structure of the polysaccharides to produce a material that includes cross-linked polymer chains. The method can further include cross-linking polymer chains in processed material.

In yet another aspect, the present invention provides methods of making an absorbent or adsorbent material. These methods include processing a material including biomass containing polysaccharides in the form of cellulose, hemicellulose, and/or starch, and changing the molecular structure of the polysaccharides to produce an absorbent material. These absorbent materials can be charged, e.g., positively or negatively charged, and can have lipophilic and/or hydrophilic properties. As such, the materials can be used as animal litter or bedding, and/or absorbent material to bind materials in a solution, (e.g., pollutants). In some embodiments, these absorbent materials can be used to bind biological materials in solutions of blood or plasma.

In a further aspect, the present invention provides method's of making fertilizers. These methods include processing a material including biomass containing polysaccharides in the form of cellulose, hemicellulose, and/or starch, and changing the molecular structure of the polysaccharides to produce a material that has a greater solubility than the starting material and which is useful as a fertilizer.

Each of these methods include treating the biomass using one or more of (e.g., one, two, three, or four of) size reduction (e.g., mechanical size reduction of individual pieces of biomass), radiation, sonication, pyrolysis, and oxidation to modulate the materials. In some embodiments, the methods use a radiation dose, e.g., from 0.1 Mrad to 10 Mrad. In some embodiments, the methods use a radiation dose, e.g., from greater than 10 Mrad to 1000 Mrad.

In some aspects, the present invention also provides compositions made using any of the methods described herein. For example, the invention features a composition including saccharide units arranged in a molecular chain, wherein from about 1 out of ever 2 to about 1 out of every 250 saccharide units comprises a carboxylic acid group, or an ester or a salt thereof, and the composition is suitable for consumption as a feed material.

By "suitable for consumption as a feed material," we mean that the composition is not toxic, under conditions of its intended use, to the living being to which it is fed, and provides some nutritional value to the being, e.g., energy and/or nutrients.

In some embodiments, the biomass feedstock is pretreated. In some embodiments, the methods disclosed herein can include a pre-treatment to reduce one or more dimensions of individual pieces of biomass. For example, pretreatment can include reducing one or more dimensions of individual pieces of biomass can include, e.g., shearing, cutting, crushing, smashing, or grinding.

Pressure can be utilized in all of the methods described herein. For example, at least one of the treating methods, e.g., radiation, can be performed on the biomass under a pressure of greater than about 2.5 atmospheres, such as greater than 5 or 10 atmospheres.

Examples of biomass (also referred to as 'biomass feedstock' or 'feedstock') include cellulosic or lignocellulosic materials such as paper, paper products, paper waste, wood, particle board, sawdust, agricultural waste, sewage, silage, grasses, rice hulls, bagasse, cotton, jute, hemp, flax, bamboo, sisal, abaca, straw, corn cobs, corn stover, switchgrass, alfalfa, hay, rice hulls, coconut hair, cotton, cassava, and synthetic celluloses and/or mixtures of these. In some instances, biomass can include unicellular and/or multicellular organisms. Exemplary organisms include, but are not limited to, e.g., protists (e.g., animal (e.g., protozoa such as flagellates, amoeboids, ciliates, and sporozoa) and plant (e.g., algae such alveolates, chlorarachniophytes, cryptomonads, euglenids, glaucophytes, haptophytes, red algae, stramenopiles, and viridaeplantae)), seaweed, giant seaweed, water hyacinth, plankton (e.g., macroplankton, mesoplankton, microplankton, nanoplankton, picoplankton, and femptoplankton), phytoplankton, bacteria (e.g., gram positive bacteria, gram negative bacteria, and extremophiles), yeast and/or mixtures of these. In some instances, biomass can include unicellular or multicellular organisms obtained from the ocean, lakes, and bodies of water including salt water and fresh water. In some instances, biomass can include organic waste materials such as animal waste or excrement or human waste or excrement (e.g., manure and sewage). In some instances, biomass can include any combination of any of these. Other biomass materials are described herein. Still other materials that include cellulose are described in the patents, patent applications and publications that have been incorporated by reference herein. In some instances, biomass can be, e.g., in solution, dry, and frozen.

If biomass is or includes microorganisms, these microorganisms will generally include carbohydrates, e.g., cellulose. These microorganisms can be in a solution, dry, frozen, active, and/or inactive state. In some embodiments, these microorganisms can require additional processing prior to being subjected to the methods described herein. For example, the microorganisms can be in a solution and can be removed from the solution, e.g., by centrifugation and/or filtration. Alternatively or in addition, the microorganisms can be subjected to the methods described herein without these additional steps, e.g., the microorganisms can be used in the solution. In some instances, the biomass can be or can include a natural or a synthetic material.

Irradiation can be, e.g., performed utilizing an ionizing radiation, such as gamma rays, a beam of electrons, or ultraviolet C radiation having a wavelength of from about 100 nm to about 280 nm. The ionizing radiation can include electron beam radiation. For example, the radiation can be applied at a total dose of between about 10 Mrad and about 150 Mrad, such as at a dose rate of about 0.5 to about 10 Mrad/day, or 1 Mrad/s to about 10 Mrad/s. In some embodiments, irradiating includes applying two or more radiation sources, such as gamma rays and a beam of electrons.

In some embodiments, the biomass exhibits a first level of recalcitrance and the carbohydrate material exhibits a second level of recalcitrance that is lower that the first level of recalcitrance. For example, the second level of recalcitrance can be lower than the first level of recalcitrance by at least about 10% (e.g., 20%, 30%, 40%, 50%, 60%, 70%, 80%, 90%, 99%, 100%). In some embodiments, the level of recalcitrance can be reduced by 50%-90%.

The biomass can be prepared by shearing biomass (e.g., a biomass fiber source) to provide a fibrous material. For example, the shearing can be performed with a rotary knife cutter. The fibers of the fibrous material can have, e.g., an average length-to-diameter ratio (L/D) of greater than 5/1. The fibrous material can have, e.g., a BET surface area of greater than 0.25 $m^2/g$ (e.g., 0.3 $m^2/g$, 0.35 $m^2/g$, 0.35 $m^2/g$, 0.4 $m^2/g$, 0.5 $m^2/g$, 1 $m^2/g$, 1.5 $m^2/g$, 2 $m^2/g$, 3 $m^2/g$, 10 $m^2/g$, 25 $m^2/g$, or greater than 25 $m^2/g$).

In some embodiments, the carbohydrate can include one or more β-1,4-linkages and have a number average molecular weight between about 3,000 and 50,000 daltons.

In some examples, the pretreated biomass material can further include a buffer, such as sodium bicarbonate or ammonium chloride, an electrolyte, such as potassium chloride or sodium chloride a growth factor, such as biotin and/or a base pair such as uracil, a surfactant, a mineral, or a chelating agent.

To aid in the reduction of the molecular weight of the cellulose, an enzyme, e.g., a cellulolytic enzyme, and/or a swelling agent, can be utilized with any method described herein.

When a microorganism is utilized, it can be a natural microorganism or an engineered microorganism (e.g., a genetically modified microorganism (GMM)). For example, the microorganism can be a bacterium, e.g., a cellulolytic bacterium, a fungus, e.g., a yeast, a plant or a protist, e.g., an algae, a protozoa or a fungus-like protist, e.g., a slime mold, protists (e.g., animal (e.g., protozoa such as flagellates, amoeboids, ciliates, and sporozoa) and plant (e.g., algae such alveolates, chlorarachniophytes, cryptomonads, euglenids, glaucophytes, haptophytes, red algae, stramenopiles, and viridaeplantae)), seaweed, plankton (e.g., macroplankton, mesoplankton, microplankton, nanoplankton, picoplankton, and femptoplankton), phytoplankton, and/or mixtures of these. In some embodiments, the microorganism is white rot fungus. In some instances, the microorganism can include unicellular and/or multicellular organisms, e.g., the ocean, lakes, and bodies of water including salt water and fresh water. When the organisms are compatible, mixtures can be utilized.

Generally, various microorganisms can produce a number of useful products by operating on, converting, bioconverting, or fermenting the materials. For example, alcohols, organic acids, hydrocarbons, hydrogen, proteins, carbohydrates, fats/oils/lipids, amino acids, vitamins, or mixtures of any of these materials can be produced by fermentation or other processes.

Examples of products that can be produced include mono- and polyfunctional C1-C6 alkyl alcohols, mono- and polyfunctional carboxylic acids, C1-C6 hydrocarbons, and combinations thereof. Specific examples of suitable alcohols include methanol, ethanol, propanol, isopropanol, butanol, ethylene glycol, propylene glycol, 1,4-butane diol, glycerin, and combinations thereof. Specific example of suitable carboxylic acids include formic acid, acetic acid, propionic acid, butyric acid, valeric acid, caproic acid, palmitic acid, stearic acid, oxalic acid, malonic acid, succinic acid, glutaric acid, oleic acid, linoleic acid, glycolic acid, lactic acid, γ-hydroxybutyric acid, and combinations thereof. Examples of suitable hydrocarbons include methane, ethane, propane, pentane, n-hexane, and combinations thereof.

Another aspect of the invention features a method that includes converting a low molecular weight sugar, or a material that includes a low molecular weight sugar, in a mixture with a biomass, a microorganism, and a solvent or a solvent system, e.g., water or a mixture of water and an organic solvent, to any product described herein. Without wishing to be bound by any particular theory, it is believed that having a solid present, such as a high surface area and/or high porosity solid, can increase reaction rates by increasing the effective concentration of solutes and providing a substrate on which reactions can occur. Additional details about such a conversion are described Ser. No. 12/417,840, the entire contents of which is hereby incorporated by reference herein in its entirety.

The term "fibrous material," as used herein, is a material that includes numerous loose, discrete and separable fibers. For example, a fibrous material can be prepared from a bleached Kraft paper fiber source by shearing, e.g., with a rotary knife cutter.

The term "screen," as used herein, means a member capable of sieving material according to size. Examples of screens include a perforated plate, cylinder or the like, or a wire mesh or cloth fabric.

The term "pyrolysis," as used herein, means to break bonds in a material by the application of heat energy. Pyrolysis can occur while the subject material is under vacuum, or immersed in a gaseous material, such as an oxidizing gas, e.g., air or oxygen, or a reducing gas, such as hydrogen.

Oxygen content is measured by elemental analysis by pyrolyzing a sample in a furnace operating at 1300° C. or above.

For the purposes of this disclosure, carbohydrates are materials that are composed entirely of one or more saccharide units or that include one or more saccharide units. The saccharide units can be functionalized about the ring with one or more functional groups, such as carboxylic acid groups, amino groups, nitro groups, nitroso groups or nitrile groups and still be considered carbohydrates. Carbohydrates can be polymeric (e.g., equal to or greater than 10-mer, 100-mer, 1,000-mer, 10,000-mer, or 100,000-mer), oligomeric (e.g., equal to or greater than a 4-mer, 5-mer, 6-mer, 7-mer, 8-mer, 9-mer or 10-mer), trimeric, dimeric, or monomeric. When the carbohydrates are formed of more than a single repeat unit, each repeat unit can be the same or different.

Examples of polymeric carbohydrates include cellulose, xylan, pectin, and starch, while cellobiose and lactose are examples of dimeric carbohydrates. Examples of monomeric carbohydrates include glucose and xylose.

Carbohydrates can be part of a supramolecular structure, e.g., covalently bonded into the structure. Examples of such materials include lignocellulosic materials, such as that found in wood.

A starchy material is one that is or includes significant amounts of starch or a starch derivative, such as greater than about 5 percent by weight starch or starch derivative. For purposes of this disclosure, a starch is a material that is or includes an amylose, an amylopectin, or a physical and/or chemical mixture thereof, e.g., a 20:80 or 30:70 percent by weight mixture of amylose to amylopectin. For example, rice, corn, and mixtures thereof are starchy materials. Starch derivatives include, e.g., maltodextrin, acid-modified starch, base-modified starch, bleached starch, oxidized starch, acetylated starch, acetylated and oxidized starch, phosphate-modified starch, genetically-modified starch and starch that is resistant to digestion.

For purposes of this disclosure, a low molecular weight sugar is a carbohydrate or a derivative thereof that has a formula weight (excluding moisture) that is less than about 2,000, e.g., less than about 1,800, 1,600, less than about 1,000, less than about 500, less than about 350 or less than about 250. For example, the low molecular weight sugar can be a monosaccharide, e.g., glucose or xylose, a disaccharide, e.g., cellobiose or sucrose, or a trisaccharide.

Swelling agents as used herein are materials that cause a discernable swelling, e.g., a 2.5 percent increase in volume over an unswollen state of biomass materials, when applied to such materials as a solution, e.g., a water solution. Examples include alkaline substances, such as sodium hydroxide, potassium hydroxide, lithium hydroxide and ammonium hydroxides, acidifying agents, such as mineral acids (e.g., sulfuric acid, hydrochloric acid and phosphoric acid), salts, such as zinc chloride, calcium carbonate, sodium carbonate, benzyltrimethylammonium sulfate, and basic organic amines, such as ethylene diamine.

In some embodiments of the methods described herein, no chemicals, e.g., no swelling agents, are added to the biomass, e.g., none prior to irradiation. For example, alkaline substances (such as sodium hydroxide, potassium hydroxide, lithium hydroxide and ammonium hydroxides), acidifying agents (such as mineral acids (e.g., sulfuric acid, hydrochloric acid and phosphoric acid)), salts, such as zinc chloride, calcium carbonate, sodium carbonate, benzyltrimethylammonium sulfate, or basic organic amines, such as ethylene diamine, is added prior to irradiation or other processing. In some cases, no additional water is added. For example, the biomass prior to processing can have less than 0.5 percent by weight added chemicals, e.g., less than 0.4, 0.25, 0.15, or 0.1 percent by weight added chemicals. In some instances, the biomass has no more than a trace, e.g., less than 0.05 percent by weight added chemicals, prior to irradiation. In other instances, the biomass prior to irradiation has substantially no added chemicals or swelling agents. Avoiding the use of such chemicals can also be extended throughout, e.g., at all times prior to fermentation, or at all times.

The term "edible," as used herein, means fit to be eaten as food.

A "sheared material," as used herein, is a material that includes discrete fibers in which at least about 50% of the discrete fibers, have a length/diameter (L/D) ratio of at least about 5, and that has an uncompressed bulk density of less than about 0.6 g/cm$^3$.

In some embodiments, changing a molecular structure of biomass, as used herein, means to change the chemical bonding arrangement, such as the type and quantity of functional groups or conformation of the structure. For example, the change in the molecular structure can include changing the recalcitrance level of the material, changing the supramolecular structure of the material, oxidation of the material, changing an average molecular weight, changing an average crystallinity, changing a surface area, changing a degree of polymerization, changing a porosity, changing a degree of branching, grafting on other materials, changing a crystalline domain size, or an changing an overall domain size.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

As used herein, the term "subject" is used throughout the specification to describe an animal, human, or non-human. The term includes, but is not limited to, birds, reptiles, fish, plants, amphibians, and mammals, e.g., humans, other primates, pigs, rodents such as mice and rats, rabbits, guinea pigs, hamsters, cows, horses, cats, dogs, sheep and goats.

The full disclosure of WO2008/073186 is incorporated by reference herein in its entirety. The full disclosures of each of the following U.S. patent applications are hereby incorporated by reference herein: Ser. No. 12/417,707, filed Apr. 3, 2009, now U.S. Pat. No. 7,867,358, issued Jan. 11, 2011; Ser. No. 12/417,720, filed Apr. 3, 2009, now U.S. Pat. No. 7,846,295 issued Dec. 7, 2010; Ser. No. 12/417,699, filed Apr. 3, 2009, now U.S. Pat. No. 7,931,784 issued Apr. 26, 2011; Ser. No. 12/417,840, filed Apr. 3, 2009, now U.S. Pat. No. 8,236,535 issued Aug. 7, 2012; Ser. No. 12/417,731, filed Apr. 3, 2009, now U.S. Pat. No. 8,911,833 issued Dec. 16, 2014; Ser. No. 12/417,880, filed Apr. 3, 2009, now U.S. Pat. No. 8,212,087 issued Jul. 3, 2012; Ser. No. 12/417,723, filed Apr. 3, 2009; Ser. No. 12/417,786, filed Apr. 3, 2009, now U.S. Pat. No. 8,025,098 issued Sep. 27, 2011; Ser. No. 12/417,904, filed Apr. 3, 2009, now U.S. Pat. No. 7,867,359 issued Jan. 11, 2011.

Any carbohydrate material described herein can be utilized in any application or process described in any patent or patent application incorporated by reference herein.

In any of the methods disclosed herein, radiation may be applied from a device that is in a vault.

Other features and advantages of the invention will be apparent from the following detailed description, and from the claims.

DESCRIPTION OF DRAWINGS

FIG. 7A is a densified fibrous material in pellet form.

FIG. 7B is a transverse cross-section of a hollow pellet in which a center of the hollow is in-line with a center of the pellet.

FIG. 7C is a transverse cross-section of a hollow pellet in which a center of the hollow is out of line with the center of the pellet.

FIG. 7D is a transverse cross-section of a tri-lobal pellet.

FIG. 11B is a schematic side view of a system for irradiating a low bulk density material, while FIG. 11C is cross-sectional of the system taken along 11C-11C.

FIG. 30 is a schematic side view of a sonication apparatus, while

DETAILED DESCRIPTION

Figure 1:
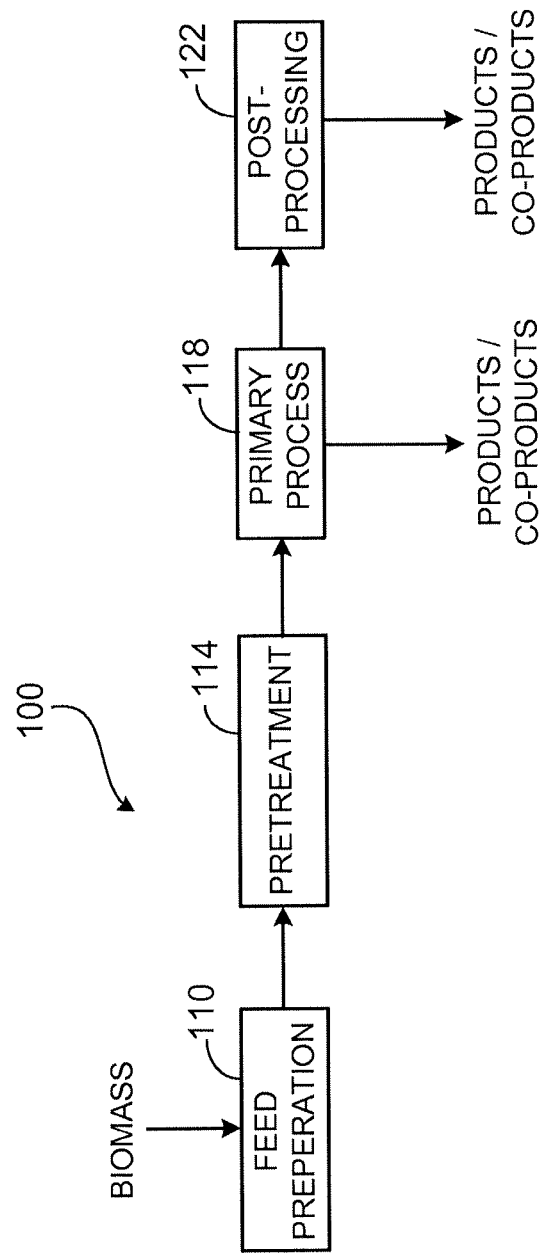
FIG. 1 is a block diagram illustrating conversion of biomass into products and co-products.

Biomass (e.g., plant biomass, animal biomass, microbial biomass, and municipal waste biomass) can be processed using the methods disclosed herein to produce useful products such as food products. In addition, functionalized materials having desired types and amounts of functionality, such as carboxylic acid groups, aldehyde groups, ketone groups, nitrile groups, nitro groups, or nitroso groups, can be prepared using the methods described herein. Such functionalized materials can be, e.g., more soluble, easier to utilize by various microorganisms or can be more stable over the long term, e.g., less prone to oxidation. Systems and processes are described below herein that can use various biomass materials, e.g., cellulosic materials, lignocellulosic materials, starchy materials, or materials that are or that include low molecular weight sugars, as feedstock materials. Biomass materials are often readily available, can be difficult to process, e.g., by fermentation, or can give sub-optimal yields at a slow rate, for example, by fermentation. Biomass materials can be first pretreated, often by size reduction of raw feedstock materials. Pretreated biomass can then be treated using at least one of: radiation (under controlled thermal conditions), sonication, oxidation, pyrolysis, and steam explosion. The various pretreatment systems and methods can be used in combinations of two, three, or even four of these technologies.

Alternatively or in addition, the present invention is based, at least in part, on the observation that the methods described herein can be used to convert biomass into non-energy materials and compositions. Such materials and compositions include, but are not limited to, foodstuffs (e.g., suitable for consumption by humans and/or animals), pharmaceuticals, nutraceuticals, pharmaceutical delivery vehicles and dosage forms, pharmaceutical excipients, pharmaceutical conjugates, cross-linked matrixes such as hydrogels, absorbent materials, fertilizers, and lignin products.

Types of Biomass

Generally, any biomass material that is or includes carbohydrates composed entirely of one or more saccharide units or that include one or more saccharide units can be processed by any of the methods described herein. As used herein, biomass includes, cellulosic, lignocellulosic, hemicellulosic, starch, and lignin-containing materials. For example, the biomass material can be cellulosic or lignocellulosic materials, or starchy materials, such as kernels of corn, grains of rice or other foods, or materials that are or that include one or more low molecular weight sugars, such as sucrose or cellobiose.

For example, such materials can include paper, paper products, wood, wood-related materials, particle board, grasses, rice hulls, bagasse, cotton, jute, hemp, flax, bamboo, sisal, abaca, straw, corn cobs, rice hulls, coconut hair, algae, seaweed (e.g., giant seaweed), water hyacinth, cassava, coffee beans, coffee bean grounds (used coffee bean grounds), cotton, synthetic celluloses, or mixtures of any of these.

Fiber sources include cellulosic fiber sources, including paper and paper products (e.g., polycoated paper and Kraft paper), and lignocellulosic fiber sources, including wood, and wood-related materials, e.g., particle board. Other suitable fiber sources include natural fiber sources, e.g., grasses, rice hulls, bagasse, cotton, jute, hemp, flax, bamboo, sisal, abaca, straw, corn cobs, rice hulls, coconut hair; fiber sources high in α-cellulose content, e.g., cotton; and synthetic fiber sources, e.g., extruded yarn (oriented yarn or un-oriented yarn). Natural or synthetic fiber sources can be obtained from virgin scrap textile materials, e.g., remnants or they can be post consumer waste, e.g., rags. When paper products are used as fiber sources, they can be virgin materials, e.g., scrap virgin materials, or they can be post-consumer waste. Aside from virgin raw materials, post-consumer, industrial (e.g., offal), and processing waste (e.g., effluent from paper processing) can also be used as fiber sources. Also, the fiber source can be obtained or derived from human (e.g., sewage), animal, or plant waste. Additional fiber sources have been described in the art, for example, see U.S. Pat. Nos. 6,448,307, 6,258,876, 6,207,729, 5,973,035 and 5,952,105.

Microbial sources include, but are not limited to, any naturally occurring or genetically modified microorganism or organism that contains or are capable of providing a source of carbohydrates (e.g., cellulose), for example, protists (e.g., animal (e.g., protozoa such as flagellates, amoeboids, ciliates, and sporozoa) and plant (e.g., algae such alveolates, chlorarachniophytes, cryptomonads, euglenids, glaucophytes, haptophytes, red algae, stramenopiles, and viridaeplantae)), seaweed, plankton (e.g., macroplankton, mesoplankton, microplankton, nanoplankton, picoplankton, and femptoplankton), phytoplankton, bacteria (e.g., gram positive bacteria, gram negative bacteria, and extremophiles), yeast and/or mixtures of these. In some instances, microbial biomass can be obtained from natural sources, e.g., the ocean, lakes, bodies of water, e.g., salt water or fresh water, or on land. Alternatively or in addition, microbial biomass can be obtained from culture systems, e.g., large scale dry and wet culture systems.

Examples of biomass include renewable, organic matter, such as plant biomass, microbial biomass, animal biomass (e.g., any animal by-product, animal waste, etc.) and municipal waste biomass including any and all combinations of these biomass materials.

Plant biomass and lignocellulosic biomass include organic matter (woody or non-woody) derived from plants, especially matter available on a sustainable basis. Examples include biomass from agricultural or food crops (e.g., sugarcane, sugar beets or corn kernels) or an extract therefrom (e.g., sugar from sugarcane and corn starch from corn), agricultural crop wastes and residues such as corn stover, wheat straw, rice straw, sugar cane bagasse, and the like. Plant biomass further includes, but is not limited to, trees, woody energy crops, wood wastes and residues such as softwood forest thinnings, barky wastes, sawdust, paper and pulp industry waste streams, wood fiber, and the like. Additionally grass crops, such as switchgrass and the like have potential to be produced on a large-scale as another plant biomass source. For urban areas, the plant biomass feedstock includes yard waste (e.g., grass clippings, leaves, tree clippings, and brush) and vegetable processing waste.

In some embodiments, biomass can include lignocellulosic feedstock can be plant biomass such as, but not limited to, non-woody plant biomass, cultivated crops, such as, but not limited to, grasses, for example, but not limited to, C4 grasses, such as switchgrass, cord grass, rye grass, miscanthus, reed canary grass, or a combination thereof, or sugar processing residues such as bagasse, or beet pulp, agricultural residues, for example, soybean stover, corn stover, rice straw, rice hulls, barley straw, corn cobs, wheat straw, canola straw, rice straw, oat straw, oat hulls, corn fiber, recycled wood pulp fiber, sawdust, hardwood, for example aspen wood and sawdust, softwood, or a combination thereof. Further, the lignocellulosic feedstock can include cellulosic waste material such as, but not limited to, newsprint, cardboard, sawdust, and the like. Lignocellulosic feedstock can include one species of fiber or alternatively, lignocellulosic feedstock can include a mixture of fibers that originate from different lignocellulosic feedstocks. Furthermore, the lignocellulosic feedstock can comprise fresh lignocellulosic feedstock, partially dried lignocellulosic feedstock, fully dried lignocellulosic feedstock, or a combination thereof.

Microbial biomass includes biomass derived from naturally occurring or genetically modified unicellular organisms and/or multicellular organisms, e.g., organisms from the ocean, lakes, bodies of water, e.g., salt water or fresh water, or on land, and that contains a source of carbohydrate (e.g., cellulose). Microbial biomass can include, but is not limited to, for example protists (e.g., animal (e.g., protozoa such as flagellates, amoeboids, ciliates, and sporozoa) and plant (e.g., algae such alveolates, chlorarachniophytes, cryptomonads, euglenids, glaucophytes, haptophytes, red algae, stramenopiles, and viridaeplantae)), seaweed, plankton (e.g., macroplankton, mesoplankton, microplankton, nanoplankton, picoplankton, and femptoplankton), phytoplankton, bacteria (e.g., gram positive bacteria, gram negative bacteria, and extremophiles), yeast and/or mixtures of these. In some instances, microbial biomass can be obtained from natural sources, e.g., the ocean, lakes, bodies of water, e.g., salt water or fresh water, or on land. Alternatively or in addition, microbial biomass can be obtained from culture systems, e.g., large scale dry and wet culture systems.

Animal biomass includes any organic waste material such as animal-derived waste material or excrement or human waste material or excrement (e.g., manure and sewage).

In some embodiments, the carbohydrate is or includes a material having one or more β-1,4-linkages and having a number average molecular weight between about 3,000 and 50,000. Such a carbohydrate is or includes cellulose (I), which is derived from (β-glucose 1) through condensation of β(1→4)-glycosidic bonds. This linkage contrasts itself with that for α(1→4)-glycosidic bonds present in starch and other carbohydrates.

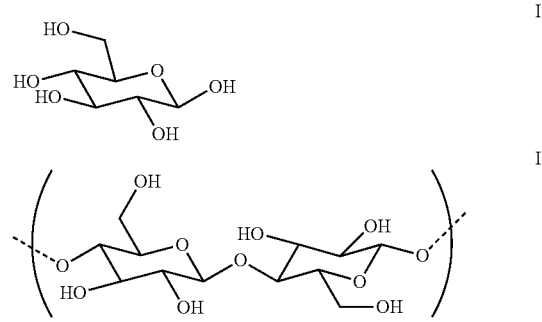

Starchy materials include starch itself, e.g., corn starch, wheat starch, potato starch or rice starch, a derivative of starch, or a material that includes starch, such as an edible food product or a crop. For example, the starchy material can be arracacha, buckwheat, banana, barley, cassava, kudzu, oca, sago, sorghum, regular household potatoes, sweet potato, taro, yams, or one or more beans, such as favas, lentils or peas. Blends of any one or more starchy material is also a starchy material. In particular embodiments, the starchy material is derived from corn. Various corn starches and derivatives are known in the art, see, e.g., "Corn Starch," Corn Refiners Association (11th Edition, 2006).

Biomass materials that include low molecular weight sugars can, e.g., include at least about 0.5 percent by weight of the low molecular sugar, e.g., at least about 2, 3, 4, 5, 6, 7, 8, 9, 10, 12.5, 25, 35, 50, 60, 70, 80, 90 or even at least about 95 percent by weight of the low molecular weight sugar. In some instances, the biomass is composed substantially of the low molecular weight sugar, e.g., greater than 95 percent by weight, such as 96, 97, 98, 99 or substantially 100 percent by weight of the low molecular weight sugar.

Biomass materials that include low molecular weight sugars can be agricultural products or food products, such as sugarcane and sugar beets or an extract therefrom, e.g., juice from sugarcane, or juice from sugar beets. Biomass materials that include low molecular weight sugars can be substantially pure extracts, such as raw or crystallized table sugar (sucrose). Low molecular weight sugars include sugar derivatives. For example, the low molecular weight sugars can be oligomeric (e.g., equal to or greater than a 4-mer, 5-mer, 6-mer, 7-mer, 8-mer, 9-mer or 10-mer), trimeric, dimeric, or monomeric. When the carbohydrates are formed of more than a single repeat unit, each repeat unit can be the same or different.

Specific examples of low molecular weight sugars include cellobiose, lactose, sucrose, glucose and xylose, along with derivatives thereof. In some instances, sugar derivatives are more rapidly dissolved in solution or utilized by microbes to provide a useful material. Several such sugars and sugar derivatives are shown below.

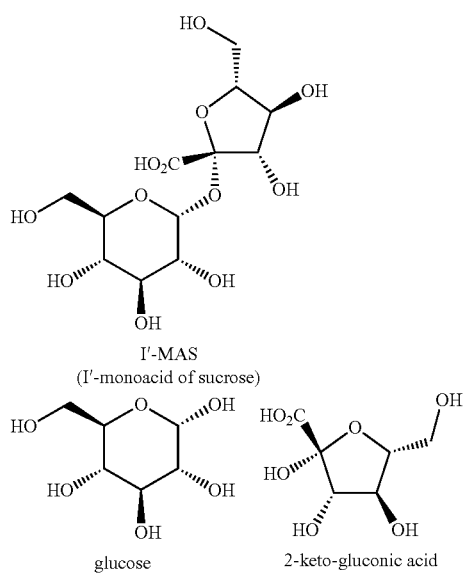

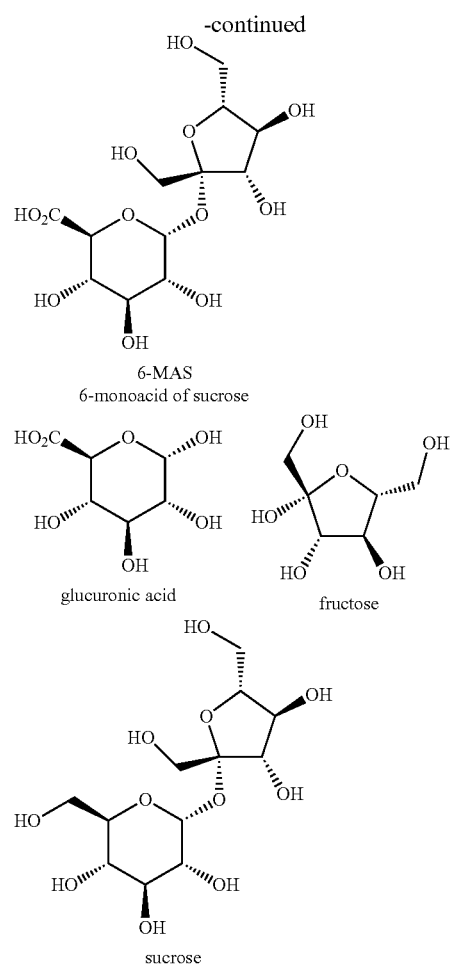

Combinations (e.g., by themselves or in combination of any biomass material, component, product, and/or co-product generated using the methods described herein) of any biomass materials described herein can be utilized for making any of the products described herein. For example, blends of cellulosic materials and starchy materials can be utilized for making any product described herein.

Systems for Treating Biomass

FIG. 1 shows a for converting biomass, particularly biomass with significant cellulosic and lignocellulosic components and/or starchy components, into useful products and co-products. System 100 includes a feed preparation subsystem 110, a pretreatment subsystem 114, a primary process subsystem 118, and a post-processing subsystem 122. Feed preparation subsystem 110 receives biomass in its raw form, physically prepares the biomass for use as feedstock by downstream processes (e.g., reduces the size of and homogenizes the biomass), and stores the biomass both in its raw and feedstock forms.

Biomass feedstock with significant cellulosic and/or lignocellulosic components, or starchy components can have a high average molecular weight and crystallinity that can make processing the feedstock into useful products (e.g., fermenting the feedstock to produce ethanol) difficult. Accordingly it is useful to treat biomass feedstock, e.g., using the treatment methods described herein. As described herein, in some embodiments, the treatment of biomass does not use acids, bases and/or enzymes to process biomass, or only uses such treatments in small or catalytic amounts.

Treatment subsystem 114 receives biomass feedstock from the feed preparation subsystem 110 and prepares the feedstock for use in primary production processes by, for example, reducing the average molecular weight and crystallinity of the feedstock. Primary process subsystem 118 receives treated feedstock from treatment subsystem 114 and produces useful products (e.g., ethanol, other alcohols, pharmaceuticals, and/or food products). In some cases, the output of primary process subsystem 118 is directly useful but, in other cases, requires further processing provided by post-processing subsystem 122. Post-processing subsystem 122 provides further processing to product streams from primary process system 118 which require it (e.g., distillation and denaturation of ethanol) as well as treatment for waste streams from the other subsystems. In some cases, the co-products of subsystems 114, 118, 122 can also be directly or indirectly useful as secondary products and/or in increasing the overall efficiency of system 100. For example, post-processing subsystem 122 can produce treated water to be recycled for use as process water in other subsystems and/or can produce burnable waste which can be used as fuel for boilers producing steam and/or electricity.

The optimum size for biomass conversion plants is affected by factors including economies of scale and the type and availability of biomass used as feedstock. Increasing plant size tends to increase economies of scale associated with plant processes. However, increasing plant size also tends to increase the costs (e.g., transportation costs) per unit of feedstock. Studies analyzing these factors suggest that the appropriate size for biomass conversion plants can range from 100 to 1,000 or more, e.g., 10,000 or more dried tons of feedstock per day depending at least in part on the type of feedstock used. The type of biomass feedstock can also impact plant storage requirements with plants designed primarily for processing feedstock whose availability varies seasonally (e.g., corn stover) requiring more on- or of-site feedstock storage than plants designed to process feedstock whose availability is relatively steady (e.g., waste paper).

Biomass Pretreatment

In some cases, pretreatment methods of processing begin with a physical preparation of the biomass, e.g., size reduction of raw biomass feedstock materials, such as by cutting, grinding, crushing, smashing, shearing or chopping. In some embodiments, methods (e.g., mechanical methods) are used to reduce the size and/or dimensions of individual pieces of biomass. In some cases, loose feedstock (e.g., recycled paper or switchgrass) is pretreated by shearing or shredding. Screens and/or magnets can be used to remove oversized or undesirable objects such as, for example, rocks or nails from the feed stream.

Feed pretreatment systems can be configured to produce feed streams with specific characteristics such as, for example, specific maximum sizes, specific length-to-width, or specific surface areas ratios. As a part of feed pretreatment, the bulk density of feedstocks can be controlled (e.g., increased).

Size Reduction

In some embodiments, the biomass is in the form of a fibrous material that includes fibers provided by shearing the biomass. For example, the shearing can be performed with a rotary knife cutter.

Figure 2:
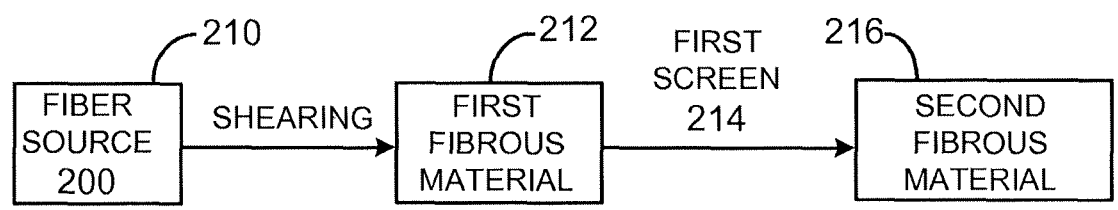
FIG. 2 is block diagram illustrating conversion of a fiber source into a first and second fibrous material.

For example, and by reference to FIG. 2, a biomass fiber source 210 is sheared, e.g., in a rotary knife cutter, to provide a first fibrous material 212. The first fibrous material 212 is passed through a first screen 214 having an average opening size of 1.59 mm or less (1/16 inch, 0.0625 inch) to provide a second fibrous material 216. If desired, fiber source can be cut prior to the shearing, e.g., with a shredder. For example, when a paper is used as the fiber source, the paper can be first cut into strips that are, e.g., ¼- to ½-inch wide, using a shredder, e.g., a counter-rotating screw shredder, such as those manufactured by Munson (Utica, N.Y.). As an alternative to shredding, the paper can be reduced in size by cutting to a desired size using a guillotine cutter. For example, the guillotine cutter can be used to cut the paper into sheets that are, e.g., 10 inches wide by 12 inches long.

In some embodiments, the shearing of fiber source and the passing of the resulting first fibrous material through first screen are performed concurrently. The shearing and the passing can also be performed in a batch-type process.

Figure 3:
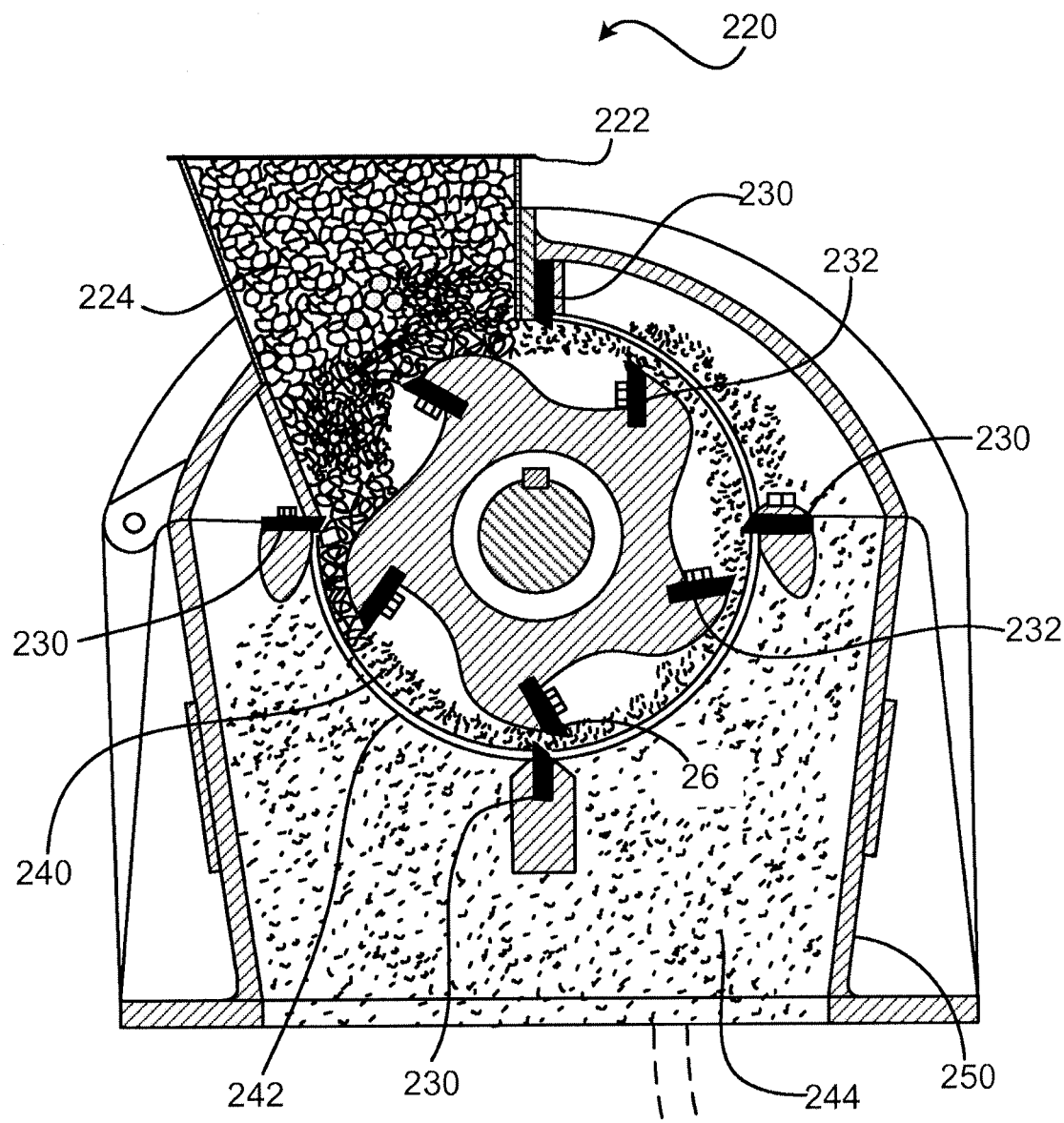
FIG. 3 is a cross-sectional view of a rotary knife cutter.

For example, a rotary knife cutter can be used to concurrently shear the fiber source and screen the first fibrous material. Referring to FIG. 3, a rotary knife cutter 220 includes a hopper 222 that can be loaded with a shredded fiber source 224 prepared by standard methods. Shredded fiber source is sheared between stationary blades 230 and rotating blades 232 to provide a first fibrous material 240. First fibrous material 240 passes through screen 242, and the resulting second fibrous material 244 is captured in bin 250. To aid in the collection of the second fibrous material, the bin can have a pressure below nominal atmospheric pressure, e.g., at least 10 percent below nominal atmospheric pressure, e.g., at least 25 percent below nominal atmospheric pressure, at least 50 percent below nominal atmospheric pressure, or at least 75 percent below nominal atmospheric pressure. In some embodiments, a vacuum source 252 is utilized to maintain the bin below nominal atmospheric pressure.

Shearing can be advantageous for "opening up" and "stressing" the fibrous materials, making the cellulose of the materials more susceptible to chain scission and/or reduction of crystallinity. The open materials can also be more susceptible to oxidation when irradiated.

In some embodiments, shearing can be advantageous for "opening up" and "stressing" the fibrous materials, making the cellulose of the materials more susceptible to ruminant digestion and absorption.

The fiber source can be sheared in a dry state, a hydrated state (e.g., having up to ten percent by weight absorbed water), or in a wet state, e.g., having between about 10 percent and about 75 percent by weight water. The fiber source can even be sheared while partially or fully submerged under a liquid, such as water, ethanol, or isopropanol.

The fiber source can also be sheared in under a gas (such as a stream or atmosphere of gas other than air), e.g., oxygen or nitrogen, or in steam.

Other methods of making the fibrous materials include, e.g., stone grinding, mechanical ripping or tearing, pin grinding, and/or air attrition milling.

If desired, the fibrous materials can be separated, e.g., continuously or in batches, into fractions according to their length, width, density, material type, or some combination of these attributes.

For example, ferrous materials can be separated from any of the fibrous materials by passing a fibrous material that includes a ferrous material past a magnet, e.g., an electromagnet, and then passing the resulting fibrous material through a series of screens, each screen having different sized apertures.

The fibrous materials can also be separated, e.g., by using a high velocity gas, e.g., air. In such an approach, the fibrous materials are separated by drawing off different fractions, which can be characterized photonically, if desired. Such a separation apparatus is discussed in Lindsey et al, U.S. Pat. No. 6,883,667.

The fibrous materials can be pre-treated immediately following their preparation, or they can be dried, e.g., at approximately 105° C. for 4-18 hours, so that the moisture content is, e.g., less than about 0.5% before use.

If desired, lignin can be removed from any of the fibrous materials that include lignin. Also, to aid in the breakdown of the materials that include the cellulose, the material can be treated prior to irradiation with heat, a chemical (e.g., mineral acid, base or a strong oxidizer such as sodium hypochlorite) and/or an enzyme.

In some embodiments, the average opening size of the first screen is less than 0.79 mm (1/32 inch, 0.03125 inch), e.g., less than 0.51 mm (1/50 inch, 0.02000 inch), less than 0.40 mm (1/64 inch, 0.015625 inch), less than 0.23 mm (0.009 inch), less than 0.20 mm (1/128 inch, 0.0078125 inch), less than 0.18 mm (0.007 inch), less than 0.13 mm (0.005 inch), or even less than less than 0.10 mm (1/256 inch, 0.00390625 inch). The screen is prepared by interweaving monofilaments having an appropriate diameter to give the desired opening size. For example, the monofilaments can be made of a metal, e.g., stainless steel. As the opening sizes get smaller, structural demands on the monofilaments can become greater. For example, for opening sizes less than 0.40 mm, it can be advantageous to make the screens from monofilaments made from a material other than stainless steel, e.g., titanium, titanium alloys, amorphous metals, nickel, tungsten, rhodium, rhenium, ceramics, or glass. In some embodiments, the screen is made from a plate, e.g., a metal plate, having apertures, e.g., cut into the plate using a laser. In some embodiments, the open area of the mesh is less than 52%, e.g., less than 41%, less than 36%, less than 31%, less than 30%.

In some embodiments, the second fibrous is sheared and passed through the first screen, or a different sized screen. In some embodiments, the second fibrous material is passed through a second screen having an average opening size equal to or less than that of first screen.

Figure 4:
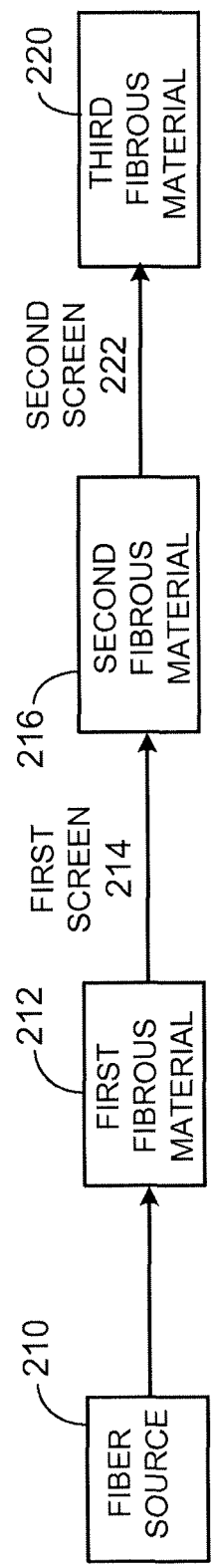
FIG. 4 is block diagram illustrating conversion of a fiber source into a first, second and third fibrous material.

Referring to FIG. 4, a third fibrous material 220 can be prepared from the second fibrous material 216 by shearing the second fibrous material 216 and passing the resulting material through a second screen 222 having an average opening size less than the first screen 214.

Generally, the fibers of the fibrous materials can have a relatively large average length-to-diameter ratio (e.g., greater than 20-to-1), even if they have been sheared more than once. In addition, the fibers of the fibrous materials described herein can have a relatively narrow length and/or length-to-diameter ratio distribution.

As used herein, average fiber widths (e.g., diameters) are those determined optically by randomly selecting approximately 5,000 fibers. Average fiber lengths are corrected length-weighted lengths. BET (Brunauer, Emmet and Teller) surface areas are multi-point surface areas, and porosities are those determined by mercury porosimetry.

The average length-to-diameter ratio of the second fibrous material 14 can be greater than 5/1, e.g., greater than 8/1, e.g., greater than 10/1, greater than 15/1, greater than 20/1, greater than 25/1, or greater than 50/1. An average length of the second fibrous material 14 can be, e.g., between about 0.5 mm and 2.5 mm, e.g., between about 0.75 mm and 1.0 mm, and an average width (e.g., diameter) of the second fibrous material 14 can be, e.g., between about 5 µm and 50 µm, e.g., between about 10 µm and 30 µm.

In some embodiments, a standard deviation of the length of the second fibrous material 14 is less than 60 percent of an average length of the second fibrous material 14, e.g., less than 50 percent of the average length, less than 40 percent of the average length, less than 25 percent of the average length, less than 10 percent of the average length, less than 5 percent of the average length, or even less than 1 percent of the average length.

In some embodiments, a BET surface area of the second fibrous material is greater than 0.1 $m^2/g$, e.g., greater than 0.25 $m^2/g$, greater than 0.5 $m^2/g$, greater than 1.0 $m^2/g$, greater than 1.5 $m^2/g$, greater than 1.75 $m^2/g$, greater than 5.0 $m^2/g$, greater than 10 $m^2/g$, greater than 25 $m^2/g$, greater than 35 $m^2/g$, greater than 50 $m^2/g$, greater than 60 $m^2/g$, greater than 75 $m^2/g$, greater than 100 $m^2/g$, greater than 150 $m^2/g$, greater than 200 $m^2/g$, or even greater than 250 $m^2/g$. A porosity of the second fibrous material 14 can be, e.g., greater than 20 percent, greater than 25 percent, greater than 35 percent, greater than 50 percent, greater than 60 percent, greater than 70 percent, e.g., greater than 80 percent, greater than 85 percent, greater than 90 percent, greater than 92 percent, greater than 94 percent, greater than 95 percent, greater than 97.5 percent, greater than 99 percent, or even greater than 99.5 percent.

In some embodiments, a ratio of the average length-to-diameter ratio of the first fibrous material to the average length-to-diameter ratio of the second fibrous material is, e.g., less than 1.5, e.g., less than 1.4, less than 1.25, less than 1.1, less than 1.075, less than 1.05, less than 1.025, or even substantially equal to 1.

In particular embodiments, the second fibrous material is sheared again and the resulting fibrous material passed through a second screen having an average opening size less than the first screen to provide a third fibrous material. In such instances, a ratio of the average length-to-diameter ratio of the second fibrous material to the average length-to-diameter ratio of the third fibrous material can be, e.g., less than 1.5, e.g., less than 1.4, less than 1.25, or even less than 1.1.

In some embodiments, the third fibrous material is passed through a third screen to produce a fourth fibrous material. The fourth fibrous material can be, e.g., passed through a fourth screen to produce a fifth material. Similar screening processes can be repeated as many times as desired to produce the desired fibrous material having the desired properties.

Densification

As used herein, densification refers to increasing the bulk density of a material. Densified materials can be processed, or any processed materials can be densified, by any of the methods described herein.

A material, e.g., a fibrous material, having a low bulk density can be densified to a product having a higher bulk density. For example, a material composition having a bulk density of 0.05 $g/cm^3$ can be densified by sealing the fibrous material in a relatively gas impermeable structure, e.g., a bag made of polyethylene or a bag made of alternating layers of polyethylene and a nylon, and then evacuating the entrapped gas, e.g., air, from the structure. After evacuation of the air from the structure, the fibrous material can have, e.g., a bulk density of greater than 0.3 $g/cm^3$, e.g., 0.5 $g/cm^3$, 0.6 $g/cm^3$, 0.7 $g/cm^3$ or more, e.g., 0.85 $g/cm^3$. After densification, the product can pre-treated by any of the methods described herein, e.g., irradiated, e.g., with gamma radiation. This can be advantageous when it is desirable to transport the material to another location, e.g., a remote manufacturing plant, where the fibrous material composition can be added to a solution, e.g., to produce ethanol. After piercing the substantially gas impermeable structure, the densified fibrous material can revert to nearly its initial bulk density, e.g., to at least 60 percent of its initial bulk density, e.g., 70 percent, 80 percent, 85 percent or more, e.g., 95 percent of its initial bulk density. To reduce static electricity in the fibrous material, an anti-static agent can be added to the material.

In some embodiments, the structure, e.g., a carrier such as a bag, is formed of a material that dissolves in a liquid, such as water. For example, the structure can be formed from a polyvinyl alcohol so that it dissolves when in contact with a water-based solution. Such embodiments allow densified structures to be added directly to solutions that include a microorganism, without first releasing the contents of the structure, e.g., by cutting.

Figure 5:
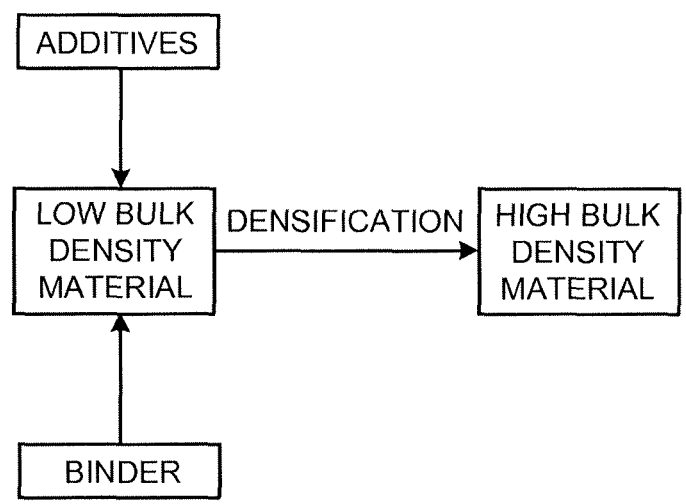
FIG. 5 is block diagram illustrating densification of a material.

Referring to FIG. 5, a biomass material can be combined with any desired additives and a binder, and subsequently densified by application of pressure, e.g., by passing the material through a nip defined between counter-rotating pressure rolls or by passing the material through a pellet mill. During the application of pressure, heat can optionally be applied to aid in the densification of the fibrous material. The densified material can then be irradiated.

In some embodiments, the material prior to densification has a bulk density of less than 0.25 g/cm$^3$, e.g., less than or about 0.20 g/cm$^3$, 0.15 g/cm$^3$, 0.10 g/cm$^3$, 0.05 g/cm$^3$ or less, e.g., 0.025 g/cm$^3$. Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters.

The preferred binders include binders that are soluble in water, swollen by water, or that have a glass transition temperature of less 25° C., as determined by differential scanning calorimetry. Water-soluble binders have a solubility of at least about 0.05 weight percent in water. Water swellable binders are binders that increase in volume by more than 0.5 percent upon exposure to water.

In some embodiments, the binders that are soluble or swollen by water include a functional group that is capable of forming a bond, e.g., a hydrogen bond, with the fibers of the fibrous material, e.g., cellulosic fibrous material. For example, the functional group can be a carboxylic acid group, a carboxylate group, a carbonyl group, e.g., of an aldehyde or a ketone, a sulfonic acid group, a sulfonate group, a phosphoric acid group, a phosphate group, an amide group, an amine group, a hydroxyl group, e.g., of an alcohol, and combinations of these groups, e.g., a carboxylic acid group and a hydroxyl group. Specific monomeric examples include glycerin, glyoxal, ascorbic acid, urea, glycine, pentaerythritol, a monosaccharide or a disaccharide, citric acid, and tartaric acid. Suitable saccharides include glucose, sucrose, lactose, ribose, fructose, mannose, arabinose and erythrose. Polymeric examples include polyglycols, polyethylene oxide, polycarboxylic acids, polyamides, polyamines and polysulfonic acids polysulfonates. Specific polymeric examples include polypropylene glycol (PPG), polyethylene glycol (PEG), polyethylene oxide, e.g., POLYOX®, copolymers of ethylene oxide and propylene oxide, polyacrylic acid (PAA), polyacrylamide, polypeptides, polyethylenimine, polyvinylpyridine, poly(sodium-4-styrenesulfonate) and poly(2-acrylamido-methyl-1-propanesulfonic acid).

In some embodiments, the binder includes a polymer that has a glass transition temperature less 25° C. Examples of such polymers include thermoplastic elastomers (TPEs). Examples of TPEs include polyether block amides, such as those available under the tradename PEBAX®, polyester elastomers, such as those available under the tradename HYTREL®, and styrenic block copolymers, such as those available under the tradename KRATON®. Other suitable polymers having a glass transition temperature less 25° C. include ethylene vinyl acetate copolymer (EVA), polyolefins, e.g., polyethylene, polypropylene, ethylene-propylene copolymers, and copolymers of ethylene and alpha olefins, e.g., 1-octene, such as those available under the tradename ENGAGE®. In some embodiments, e.g., when the material is a fiberized polycoated paper, the material is densified without the addition of a separate low glass transition temperature polymer.

In a particular embodiment, the binder is a lignin, e.g., a natural or synthetically modified lignin.

A suitable amount of binder added to the material, calculated on a dry weight basis, is, e.g., from about 0.01 percent to about 50 percent, e.g., 0.03 percent, 0.05 percent, 0.1 percent, 0.25 percent, 0.5 percent, 1.0 percent, 5 percent, 10 percent or more, e.g., 25 percent, based on a total weight of the densified material. The binder can be added to the material as a neat, pure liquid, as a liquid having the binder dissolved therein, as a dry powder of the binder, or as pellets of the binder.

Figure 6:
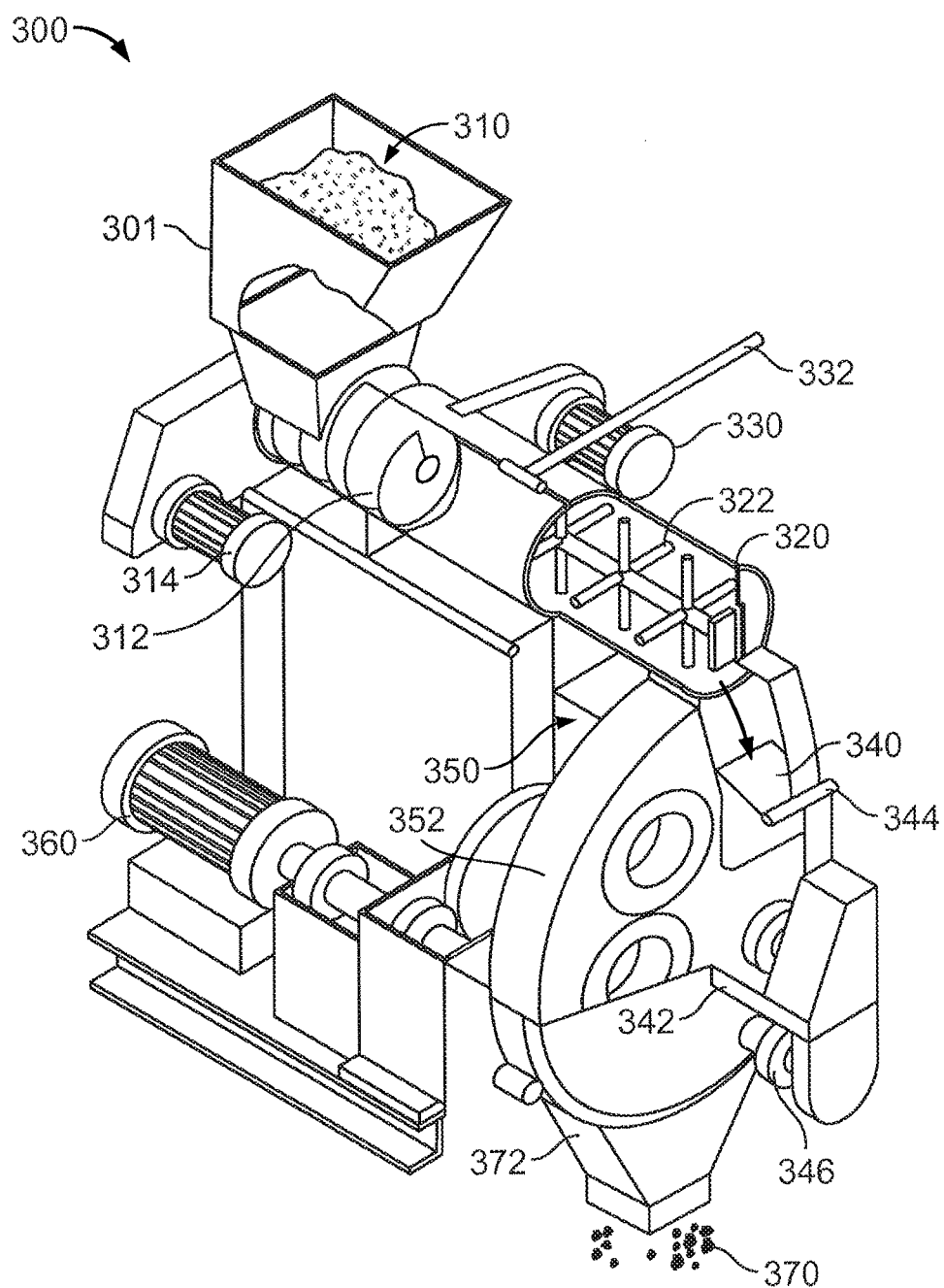
FIG. 6 is a perspective view of a pellet mill.

The densified fibrous material can be made in a pellet mill. Referring to FIG. 6, a pellet mill 300 has a hopper 301 for holding undensified material 310 that includes carbohydrate-containing materials, such as cellulose. The hopper communicates with an auger 312 that is driven by variable speed motor 314 so that undensified material can be transported to a conditioner 320 that stirs the undensified material with paddles 322 that are rotated by conditioner motor 330. Other ingredients, e.g., any of the additives and/or fillers described herein, can be added at inlet 332. If desired, heat can be added while the fibrous material is in conditioner. After conditioned, the material passes from the conditioner through a dump chute 340, and to another auger 342. The dump chute, as controlled by actuator 344, allows for unobstructed passage of the material from conditioner to auger. Auger is rotated by motor 346, and controls the feeding of the fibrous material into die and roller assembly 350. Specifically, the material is introduced into a hollow, cylindrical die 352, which rotates about a horizontal axis and which has radially extending die holes 250. Die 352 is rotated about the axis by motor 360, which includes a horsepower gauge, indicating total power consumed by the motor. Densified material 370, e.g., in the form of pellets, drops from chute 372 and are captured and processed, such as by irradiation.

The material, after densification, can be conveniently in the form of pellets or chips having a variety of shapes. The pellets can then be irradiated. In some embodiments, the pellets or chips are cylindrical in shape, e.g., having a maximum transverse dimension of, e.g., 1 mm or more, e.g., 2 mm, 3 mm, 5 mm, 8 mm, 10 mm, 15 mm or more, e.g., 25 mm. Other convenient shapes include pellets or chips that are plate-like in form, e.g., having a thickness of 1 mm or more, e.g., 2 mm, 3 mm, 5 mm, 8 mm, 10 mm or more, e.g., 25 mm; a width of, e.g., 5 mm or more, e.g., 10 mm, 15 mm, 25 mm, 30 mm or more, e.g., 50 mm; and a length of 5 mm or more, e.g., 10 mm, 15 mm, 25 mm, 30 mm or more, e.g., 50 mm.

Referring now FIG. 7A-7D, pellets can be made so that they have a hollow inside. As shown, the hollow can be generally in-line with the center of the pellet (FIG. 7B), or out of line with the center of the pellet (FIG. 7C). Making the pellet hollow inside can increase the rate of dissolution in a liquid after irradiation.

Referring now to FIG. 7D, the pellet can have, e.g., a transverse shape that is multi-lobal, e.g., tri-lobal as shown, or tetra-lobal, penta-lobal, hexa-lobal or deca-lobal. Making the pellets in such transverse shapes can also increase the rate of dissolution in a solution after irradiation.

Alternatively, the densified material can be in any other desired form, e.g., the densified material can be in the form of a mat, roll or bale.

Examples of Densification

In one example, half-gallon juice cartons made of unprinted white Kraft board having a bulk density of 20 lb/ft$^3$ can be used as a feedstock. Cartons can be folded flat and then fed into a shredder to produce a confetti-like material having a width of between 0.1 inch and 0.5 inch, a length of between 0.25 inch and 1 inch and a thickness equivalent to that of the starting material (about 0.075 inch). The confetti-like material can be fed to a rotary knife cutter, which shears the confetti-like pieces, tearing the pieces apart and releasing fibrous material.

In some cases, multiple shredder-shearer trains can be arranged in series with output. In one embodiment, two shredder-shearer trains can be arranged in series with output from the first shearer fed as input to the second shredder. In another embodiment, three shredder-shearer trains can be arranged in series with output from the first shearer fed as input to the second shredder and output from the second shearer fed as input to the third shredder. Multiple passes through shredder-shearer trains are anticipated to increase decrease particle size and increase overall surface area within the feedstream.

In another example, fibrous material produced from shredding and shearing juice cartons can be treated to increase its bulk density. In some cases, the fibrous material can be sprayed with water or a dilute stock solution of POLYOX™ WSR N10 (polyethylene oxide) prepared in water. The wetted fibrous material can then be processed through a pellet mill operating at room temperature. The pellet mill can increase the bulk density of the feedstream by more than an order of magnitude.

Treatment

Pretreated biomass can be treated for use in primary production processes by, for example, reducing the average molecular weight, crystallinity, and/or increasing the surface area and/or porosity of the biomass. In some embodiments, the biomass can be treated to reduce the recalcitrance of the biomass. Treatment processes can include at least one (e.g., one, two, three, four, or five) of irradiation, sonication, oxidation, pyrolysis, and steam explosion.

Recalcitrance is a term of art that, as used herein, broadly refers to a biomass material's resistance to the accessibility of polysaccharide degrading agents (e.g., microorganisms and/or enzymes (e.g., microbial enzymes)) to polysaccharides contained within biomass (see, e.g., Himmel et al., National Renewable Energy Laboratory (NREL) Technical Report NREL/TP-510-37902, August, 2005 and National Renewable Energy Laboratory (NREL) Technical Report NREL/BR-510-40742, March, 2007). For example, the accessibility of polysaccharides (e.g., cellulose and hemicellulose) in a first biomass material with a first recalcitrance level will be lower than the accessibility of polysaccharides (e.g., cellulose and hemicellulose) in the same lignocellulosic material following treatment to reduce the recalcitrance level of the material. In other words, the level of polysaccharides available to polysaccharide degrading agents will be higher following treatment to reduce recalcitrance.

Assessing Recalcitrance Levels of Lignocellulosic Biomass

The recalcitrance level of a lignocellulosic material can be assessed using a number of art-recognized methods. Examples of such methods include, but are not limited to, surface characterization methods, enzymatic methods, and functional methods.

Exemplary surface characterization methods that can be used to assess the recalcitrance level of lignocellulosic materials are known in the art (for a review see Himmel et al., National Renewable Energy Laboratory (NREL) Technical Report NREL/TP-510-37902, August, 2005 and Ding et al., *Microscopy and Microanalysis,* 14:1494-1495, 2004). For example, the recalcitrance level of lignocellulosic materials can be assessed using microscopic and/or spectroscopic surface analysis methods (e.g., using one or more of the surface analysis methods described below) to identify, assess, and/or quantify changes (e.g., structural changes) in the lignocellulosic materials that indicate a reduction in the recalcitrance of the material. Exemplary changes that can be used as indicia of a reduction in the recalcitrance of lignocellulosic materials include the appearance of pitting or pores, and for surface unwrapping of microfibrils. See, for example, Himmel et al., National Renewable Energy Laboratory (NREL) Technical Report NREL/TP-510-37902, August, 2005 and Ding et al., *Microscopy and Microanalysis,* 14:1494-1495, 2004), which describe the following methods:

(1) Scanning election microscopy (SEM) can be used to visualize the surface morphology of biological and non-biological materials over a wide range of magnifications (as high as 200,000× magnification) and with high depth of field (see, e.g., Gomez et al., *Biotechnology for Biofuels,* 1, Oct. 23, 2008; Sivan et al., *Appl. Microbiol. Biotechnol.,* 72:346-352, 2006). Typically, biological samples, such as lignocellulosic biomass samples, are coated with a thin layer of electron dense material, such as carbon or atomized gold, prior to analysis. For example, samples can be mounted in SEM stubs and coated with gold/palladium. These mounted specimens can then be observed using known methods and devices, e.g., a JEOL JSM 6940LV SEM (Jeol Ltd., Tokyo, Japan) at an accelerating voltage of 5 kV.

(2) More recently, methods have been developed for analyzing samples containing natural moisture, a technique referred to as environmental mode SEM (ESEM), e.g., using the Quanta FEG 400 ESEM (FEI Company). The use of ESEM in the analysis of yeast cells is described by Ren et al., Investigation of the morphology, viability and mechanical properties of yeast cells in environmental SEM, *Scanning,* published online Aug. 5, 2008). Such environmental mode methods can be used to analyze lignocellulosic biomass containing moisture without the use of high electron dense coatings.

(3) Atomic force microscopy (AFM), e.g., using DI-Veeco MultiMode PicoForce system (see, e.g., Stieg et al., *Rev. Sci. Instrum.,* 79:103701, 2008) can also be used. AFM usefully allows analysis of surface topography at very high magnification while also allowing analysis of the attractive and repulsive forces between the scanning probe tip and the sample surface, thus providing height and phase images. AFM is being increasingly applied to the analysis of biological samples due to its high atomic level resolution and its ease of use (samples do not require extensive sample preparation). In addition, AFM can be used to observe dry and hydrated surfaces directly using a tapping-probe.

(4) Transmission electron microscopy (TEM), e.g., using an FEI Tecnai F20, allows the determination of the internal structures of biological and non-biological materials up to at least 350,000× magnification. Typically, the determination of internal structures can be facilitated using shadowing techniques or staining with high contrast compounds. Compositional analysis of materials can also be performed by monitoring secondary X-rays produced by the electron-specimen interaction using energy dispersive X-ray microanalysis. TEM-based methods for analyzing the recalcitrance levels of a lignocellulosic material are described in the art (see, e.g., Rhoads et al., *Can. J. Microbiol.*, 41:592-600, 1995).

(5) Near-field Scanning Optical Microscopy (NFSOM) using, e.g., a DI-Veeco Aurora-3 NSOM (Nikon), permits surfaces to be viewed with a long depth of field light microscope that is adapted to conduct secondary spectrophotometric analysis such as UV/VIS, fluorescence, and laser Raman. In some embodiments, NFSOM can be performed using an Olympus IX71 inverted microscope fitted with a DP70 high resolution CCD camera to perform single molecule microscopy.

(6) Confocal microscopy (CFM) and confocal scanning laser microscopy (CSLM) (see, e.g., National Renewable Energy Laboratory (NREL) Technical Report NREL/BR-510-40742, March, 2007) can be used to generate optical sections that can be used to build a three-dimensional image of a surface and internal structures. Typically, CFM and CSLM are performed in combination with labeling methods, for example fluorescent stains (see, e.g., Sole et al., *Microb. Ecol.*, Published online on Nov. 4, 2008).

In some embodiments, the recalcitrance level of a lignocellulosic material can be assessed using one or more methods known in the art, e.g., methods described herein. The same sample, or a portion thereof, can then be assessed following treatment to observe a change (e.g., a structural change) in the recalcitrance. In some embodiments, the appearance or observance of pitting or pores, and/or surface unwrapping of microfibrils in or on a first lignocellulosic material with a first recalcitrance level will be less than the appearance or observance of pitting or pores, and/or surface unwrapping of microfibrils in the same sample following treatment to reduce the recalcitrance level of the material.

Alternatively or in addition, a change (e.g., decrease) in the recalcitrance level of a lignocellulosic material can be analyzed using enzymatic methods. For example, a lignocellulosic material can be incubated in the presence of one or more cellulases, e.g., before and after treatment using the methods described herein. In some embodiments, an increase in the break down of cellulose by the cellulase indicates a change in the recalcitrant level of the material, e.g., a decrease in the recalcitrance of the material. In some embodiments, the increase in the break down of cellulose by the cellulase causes an increase in the amount of monosaccharide and/or disaccharides in the sample.

In some embodiments, the amount (e.g., concentration) of monosaccharides and/or disaccharides resulting from the activity of an enzyme (e.g., a cellulase) in a sample comprising a first lignocellulosic material with a first recalcitrance level will be lower than the amount (e.g., concentration) of monosaccharide and/or disaccharides resulting from the activity of an enzyme (e.g., a cellulase) in the same sample following treatment to reduce the recalcitrance level of the material.

Alternatively or in addition, a change (e.g., decrease) in the recalcitrance level of a lignocellulosic material can be analyzed using functional methods. For example, a lignocellulosic material can be cultured in the presence of a sugar fermenting microorganism, e.g., using the culture methods disclosed herein, before and after treatment using the methods described herein. In some embodiments, an increase in the level of the one or more products generated by the microorganism indicates a change in the recalcitrant level of the material, e.g., a decrease in the recalcitrance of the material.

In some embodiments, the growth rate of a microorganism and/or product generation by the microorganism in a sample comprising a first lignocellulosic material with a first recalcitrance level will be lower than the growth rate of the microorganism and/or product generation by the microorganism in the same sample following treatment to reduce the recalcitrance level of the material.

In some embodiments, a change in the recalcitrance level of a material can be expressed as; (1) a ratio (e.g., a measure of the recalcitrance level of a material prior to treatment versus a measure of the recalcitrance level or the material post-treatment); (2) a percent change (e.g., decrease) in the recalcitrance level of a material; (3) a percent change (e.g., increase) in the level of polysaccharide available to a polysaccharide degrading agent (e.g., an enzyme) after treatment, as compared to before the treatment, per weight measure of the starting biomass material; or (4) a percent change (e.g., increase) in the solubility of the material in a particular solvent.

In some instances, the second material has cellulose that has a crystallinity ($^T C_2$) that is lower than the crystallinity ($^T C_1$) of the cellulose of the first material. For example, ($^T C_2$) can be lower than ($^T C_1$) by more than about 10 percent, e.g., 15, 20, 25, 30, 35, 40, or even more than about 50 percent.

In some embodiments, the starting crystallinity index (prior to irradiation) is from about 40 to about 87.5 percent, e.g., from about 50 to about 75 percent or from about 60 to about 70 percent, and the crystallinity index after irradiation is from about 10 to about 50 percent, e.g., from about 15 to about 45 percent or from about 20 to about 40 percent. However, in some embodiments, e.g., after extensive irradiation, it is possible to have a crystallinity index of lower than 5 percent. In some embodiments, the material after irradiation is substantially amorphous.

In some embodiments, the starting number average molecular weight (prior to irradiation) is from about 200,000 to about 3,200,000, e.g., from about 250,000 to about 1,000,000 or from about 250,000 to about 700,000, and the number average molecular weight after irradiation is from about 50,000 to about 200,000, e.g., from about 60,000 to about 150,000 or from about 70,000 to about 125,000. However, in some embodiments, e.g., after extensive irradiation, it is possible to have a number average molecular weight of less than about 10,000 or even less than about 5,000.

In some embodiments, the second material can have a level of oxidation ($^T O_2$) that is higher than the level of oxidation ($^T O_1$) of the first material. A higher level of oxidation of the material can aid in its dispersibility, swellability and/or solubility, further enhancing the material's susceptibility to chemical, enzymatic, or biological attack. In some embodiments, to increase the level of the oxidation of the second material relative to the first material, the irradiation is performed under an oxidizing environment, e.g., under a blanket of air or oxygen, producing a second material that is more oxidized than the first material. For example, the second material can have more hydroxyl groups, aldehyde groups, ketone groups, ester groups, or carboxylic acid groups, which can increase its hydrophilicity.

Treatment Combinations

In some embodiments, biomass can be treated by applying at least one (e.g., two, three, four, or five) of the treatment methods described herein, such as two or more of radiation, sonication, oxidation, pyrolysis, and steam explosion either with or without prior, intermediate, or subsequent biomass preparation as described herein. The treatment methods can be applied in any order, in multiples (e.g., two or more applications of a treatment method), or concurrently to the biomass, e.g., a cellulosic and/or lignocellulosic material. In other embodiments, materials that include a carbohydrate are prepared by applying three, four or more of any of the processes described herein (in any order or concurrently). For example, a carbohydrate can be prepared by applying radiation, sonication, oxidation, pyrolysis, and, optionally, steam explosion to a cellulosic and/or lignocellulosic material (in any order or concurrently). The provided carbohydrate-containing material can then be converted by one or more microorganisms, such as bacteria (e.g., gram positive bacteria, gram negative bacteria, and extremophiles), yeast, or mixtures of yeast and bacteria, to a number of desirable products, as described herein. Multiple processes can provide materials that can be more readily utilized by a variety of microorganisms because of their lower molecular weight, lower crystallinity, and/or enhanced solubility. Multiple processes can provide synergies and can reduce overall energy input required in comparison to any single process.

For example, in some embodiments, biomass feedstocks can be provided that include a carbohydrate that is produced by a process that includes irradiating and sonicating (in either order or concurrently) a biomass material, a process that includes irradiating and oxidizing (in either order or concurrently) a biomass material, a process that includes irradiating and pyrolyzing (in either order or concurrently) a biomass material, a treatment process that includes irradiating and pyrolyzing (in either order or concurrently) a biomass material, or a process that includes irradiating and steam-exploding (in either order or concurrently) a biomass material. The provided biomass feedstock can then be contacted with a microorganism having the ability to convert at least a portion, e.g., at least about 1 percent by weight, of the biomass to the product.

In some embodiments, the process does not include hydrolyzing the biomass, such as with an acid, base, and/or enzyme, e.g., a mineral acid, such as hydrochloric or sulfuric acid.

If desired, some or none of the biomass can include a hydrolyzed material. For example, in some embodiments, at least about seventy percent by weight of the biomass is an unhydrolyzed material, e.g., at least at 95 percent by weight of the feedstock is an unhydrolyzed material. In some embodiments, substantially all of the biomass is an unhydrolyzed material. In some embodiments, 100% of the biomass is unhydrolyzed material.

Any feedstock or any reactor or fermentor charged with a feedstock can include a buffer, such as sodium bicarbonate, ammonium chloride or Tris; an electrolyte, such as potassium chloride, sodium chloride, or calcium chloride; a growth factor, such as biotin and/or a base pair such as uracil or an equivalent thereof; a surfactant, such as Tween® or polyethylene glycol; a mineral, such as such as calcium, chromium, copper, iodine, iron, selenium, or zinc; or a chelating agent, such as ethylene diamine, ethylene diamine tetraacetic acid (EDTA) (or its salt form, e.g., sodium or potassium EDTA), or dimercaprol.

When radiation is utilized as or in the treatment, it can be applied to any sample that is dry or wet, or even dispersed in a liquid, such as water. For example, irradiation can be performed on biomass material in which less than about 25 percent by weight of the biomass material has surfaces wetted with a liquid, such as water. In some embodiments, irradiating is performed on biomass material in which substantially none of the biomass material is wetted with a liquid, such as water.

In some embodiments, any processing described herein occurs after the biomass material remains dry as acquired or has been dried, e.g., using heat and/or reduced pressure. For example, in some embodiments, the biomass material has less than about five percent by weight retained water, measured at 25° C. and at fifty percent relative humidity.

If desired, a swelling agent, as defined herein, can be utilized in any process described herein. In some embodiments, when a biomass material is processed using radiation, less than about 25 percent by weight of the biomass material is in a swollen state, the swollen state being characterized as having a volume of more than about 2.5 percent higher than an unswollen state, e.g., more than 5.0, 7.5, 10, or 15 percent higher than the unswollen state. In some embodiments, when radiation is utilized on a biomass material, substantially none of the biomass material is in a swollen state.

In specific embodiments when radiation is utilized, the biomass material includes a swelling agent, and swollen biomass material receives a dose of less than about 10 Mrad.

When radiation is utilized in any process, it can be applied while the biomass is exposed to air, oxygen-enriched air, or even oxygen itself, or blanketed by an inert gas such as nitrogen, argon, or helium. When maximum oxidation is desired, an oxidizing environment is utilized, such as air or oxygen.

When radiation is utilized, it can be applied to biomass under a pressure of greater than about 2.5 atmospheres, such as greater than 5, 10, 15, 20 or even greater than about 50 atmospheres. Irradiation can increase the solubility, swellability, or dispersibility of the biomass in a solvent.

In specific embodiments, the process includes irradiating and sonicating and irradiating precedes sonicating. In other specific embodiments, sonication precedes irradiating, or irradiating and sonicating occur substantially concurrently.

In some embodiments, the process includes irradiating and sonicating (in either order or concurrently) and further includes oxidizing, pyrolyzing or steam exploding.

When the process includes radiation, the irradiating can be performed utilizing an ionizing radiation, such as gamma rays, x-rays, energetic ultraviolet radiation, such as ultraviolet C radiation having a wavelength of from about 100 nm to about 280 nm, a beam of particles, such as a beam of electrons, slow neutrons or alpha particles. In some embodiments, irradiating includes two or more radiation sources, such as gamma rays and a beam of electrons, which can be applied in either order or concurrently.

In specific embodiments, sonicating can performed at a frequency of between about 15 kHz and about 25 kHz, such as between about 18 kHz and 22 kHz utilizing a 1 KW or larger horn, e.g., a 2, 3, 4, 5, or even a 10 KW horn.

In some embodiments, the biomass has a first number average molecular weight and the resulting carbohydrate includes a second cellulose having a second number average molecular weight lower than the first number average molecular weight. For example, the second number average molecular weight is lower than the first number average molecular weight by more than about twenty-five percent, e.g., 2×, 3×, 5×, 7×, 10×, 25×, even 100× reduction.

In some embodiments, the first cellulose has a first crystallinity and the second cellulose has a second crystallinity lower than the first crystallinity, such as lower than about two, three, five, ten, fifteen or twenty-five percent lower.

In some embodiments, the first cellulose has a first level of oxidation and the second cellulose has a second level of oxidation higher than the first level of oxidation, such as two, three, four, five, ten or even twenty-five percent higher.

In some embodiments, the first biomass has a first level of recalcitrance and the resulting biomass has a second level of recalcitrance that is lower than the first level.

Radiation Treatment

One or more irradiation processing sequences can be used to process biomass from a wide variety of different sources to extract useful substances from the feedstock, and to provide partially degraded organic material which functions as input to further processing steps and/or sequences. Irradiation can reduce the recalcitrance, molecular weight and/or crystallinity of feedstock.

In some embodiments, energy deposited in a material that releases an electron from its atomic orbital is used to irradiate the materials. The radiation can be provided by 1) heavy charged particles, such as alpha particles or protons, 2) electrons, produced, for example, in beta decay or electron beam accelerators, or 3) electromagnetic radiation, for example, gamma rays, x rays, or ultraviolet rays. In one approach, radiation produced by radioactive substances can be used to irradiate the feedstock. In some embodiments, any combination in any order or concurrently of (1) through (3) can be utilized. In another approach, electromagnetic radiation (e.g., produced using electron beam emitters) can be used to irradiate the feedstock. The doses applied depend on the desired effect and the particular feedstock. For example, high doses of radiation can break chemical bonds within feedstock components and low doses of radiation can increase chemical bonding (e.g., cross-linking) within feedstock components. In some instances when chain scission is desirable and/or polymer chain functionalization is desirable, particles heavier than electrons, such as protons, helium nuclei, argon ions, silicon ions, neon ions, carbon ions, phosphorus ions, oxygen ions or nitrogen ions can be utilized. When ring-opening chain scission is desired, positively charged particles can be utilized for their Lewis acid properties for enhanced ring-opening chain scission.

Figure 8:
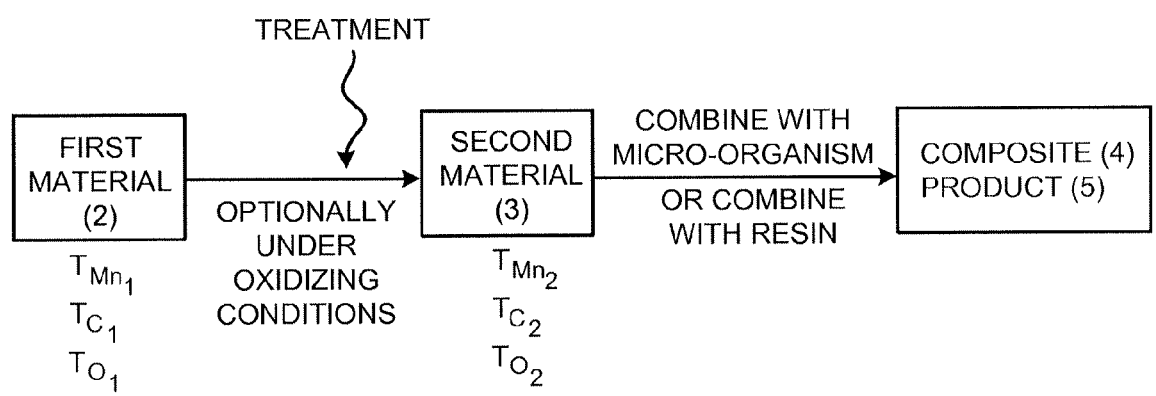
FIG. 8 is a block diagram illustrating a treatment sequence for processing feedstock.

Referring to FIG. 8, in one method, a first material 2 that is or includes cellulose having a first number average molecular weight ($^{T}M_{N1}$) is irradiated, e.g., by treatment with ionizing radiation (e.g., in the form of gamma radiation, X-ray radiation, 100 nm to 280 nm ultraviolet (UV) light, a beam of electrons or other charged particles) to provide a second material 3 that includes cellulose having a second number average molecular weight ($^{T}M_{N2}$) lower than the first number average molecular weight. The second material (or the first and second material) can be combined with a microorganism (e.g., a bacterium or a yeast) that can utilize the second and/or first material to produce a product 5.

Since the second material 3 has cellulose having a reduced recalcitrance, molecular weight relative to the first material, and in some instances, a reduced crystallinity, the second material is generally more dispersible, swellable and/or soluble in a solution containing a microorganism. These properties make the second material 3 more susceptible to chemical, enzymatic and/or biological attack (e.g., by a microorganism) relative to the first material 2, which can greatly improve the production rate and/or production level of a desired product, e.g., ethanol. Radiation can also sterilize the materials.

In some embodiments, the second number average molecular weight ($M_{N2}$) is lower than the first number average molecular weight ($^{T}M_{N1}$) by more than about 10 percent, e.g., 15, 20, 25, 30, 35, 40, 50 percent, 60 percent, or even more than about 75 percent.

Ionizing Radiation

Each form of radiation ionizes the biomass via particular interactions, as determined by the energy of the radiation. Heavy charged particles primarily ionize matter via Coulomb scattering; furthermore, these interactions produce energetic electrons that can further ionize matter. Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, neptunium, curium, californium, americium, and plutonium.

When particles are utilized, they can be neutral (uncharged), positively charged or negatively charged. When charged, the charged particles can bear a single positive or negative charge, or multiple charges, e.g., one, two, three or even four or more charges. In instances in which chain scission is desired, positively charged particles can be desirable, in part, due to their acidic nature. When particles are utilized, the particles can have the mass of a resting electron, or greater, e.g., 500, 1000, 1500, or 2000 or more times the mass of a resting electron. For example, the particles can have a mass of from about 1 atomic units to about 150 atomic units, e.g., from about 1 atomic units to about 50 atomic units, or from about 1 to about 25, e.g., 1, 2, 3, 4, 5, 10, 12 or 15 amu. Accelerators used to accelerate the particles can be electrostatic DC, electrodynamic DC, RF linear, magnetic induction linear or continuous wave. For example, cyclotron type accelerators are available from IBA, Belgium, such as the Rhodotron® system, while DC type accelerators are available from RDI, now IBA Industrial, such as the Dynamitron®. Ions and ion accelerators are discussed in Introductory Nuclear Physics, Kenneth S. Krane, John Wiley & Sons, Inc. (1988), Krsto Prelec, FIZIKA B 6 (1997) 4, 177-206, Chu, William T., "Overview of Light-Ion Beam Therapy", Columbus-Ohio, ICRU-IAEA Meeting, 18-20 Mar. 2006, Iwata, Y. et al., "Alternating-Phase-Focused IH-DTL for Heavy-Ion Medical Accelerators", Proceedings of EPAC 2006, Edinburgh, Scotland, and Leitner, C. M. et al., "Status of the Superconducting ECR Ion Source Venus", Proceedings of EPAC 2000, Vienna, Austria. Typically, generators are housed in a vault, e.g., of lead or concrete.

Electrons interact via Coulomb scattering and bremsstrahlung radiation produced by changes in the velocity of electrons. Electrons can be produced by radioactive nuclei that undergo beta decay, such as isotopes of iodine, cesium, technetium, and iridium. Alternatively, an electron gun can be used as an electron source via thermionic emission.

Electromagnetic radiation interacts via three processes: photoelectric absorption, Compton scattering, and pair production. The dominating interaction is determined by the energy of the incident radiation and the atomic number of the material. The summation of interactions contributing to the absorbed radiation in cellulosic material can be expressed by the mass absorption coefficient (see "Ionization Radiation" in PCT/US2007/022719).

Electromagnetic radiation is subclassified as gamma rays, x rays, ultraviolet rays, infrared rays, microwaves, or radio waves, depending on its wavelength.

Figure 9:
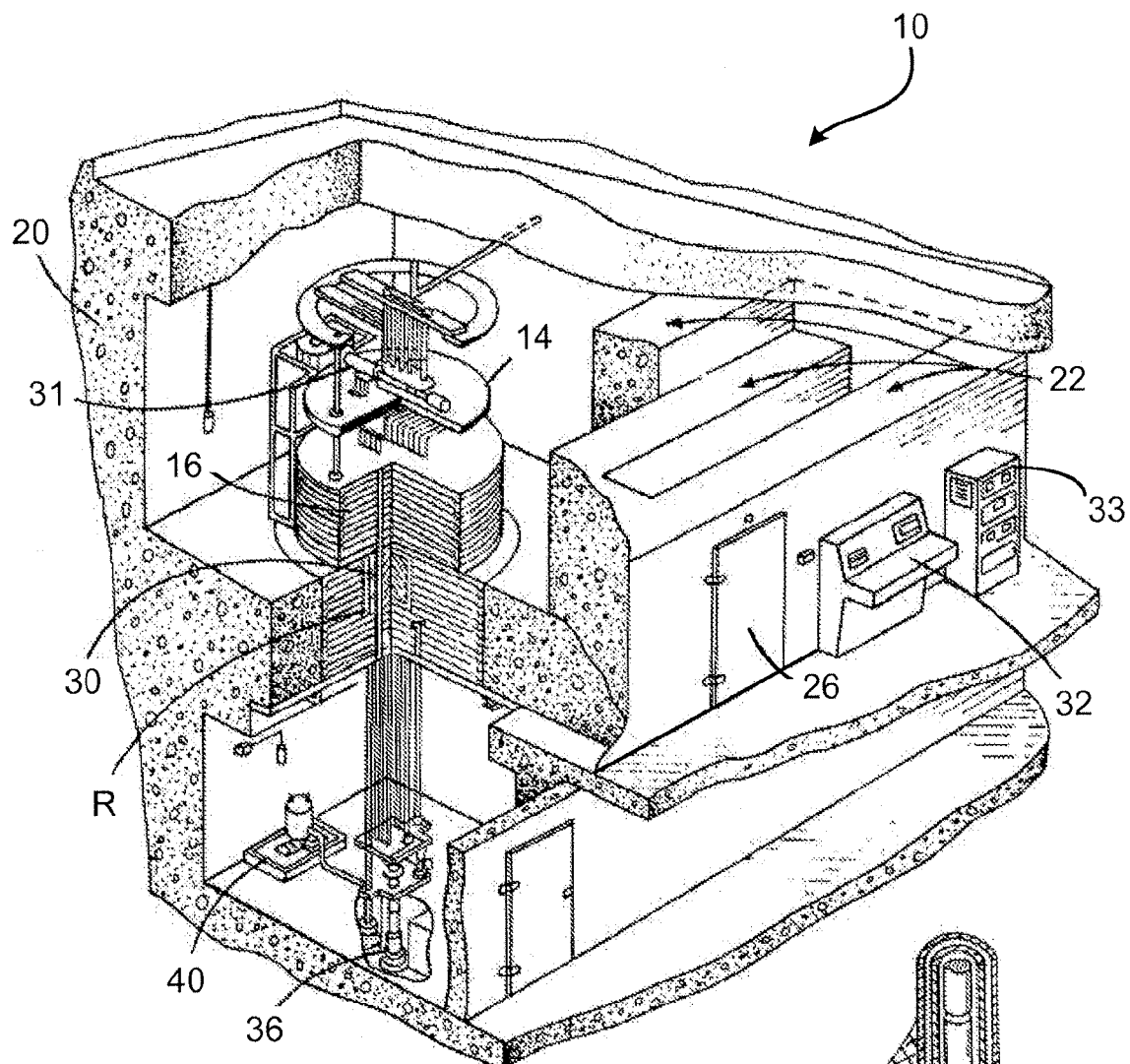
FIG. 9 is a perspective, cut-away view of a gamma irradiator housed in a concrete vault.
Figure 10:
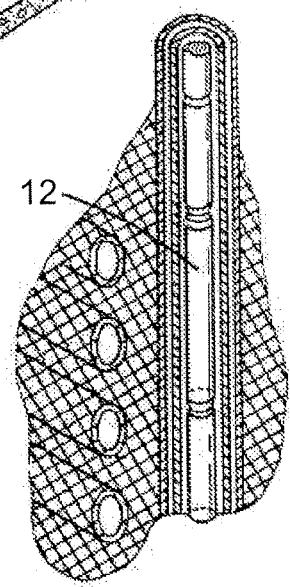
FIG. 10 is an enlarged perspective view of region R of FIG. 9.

For example, gamma radiation can be employed to irradiate the materials. Referring to FIGS. 9 and 10 (an enlarged view of region R), a gamma irradiator 10 includes gamma radiation sources 408, e.g., $^{60}$Co pellets, a working table 14 for holding the materials to be irradiated and storage 16, e.g., made of a plurality iron plates, all of which are housed in a concrete containment chamber (vault) 20 that includes a maze entranceway 22 beyond a lead-lined door 26. Storage 16 includes a plurality of channels 30, e.g., sixteen or more channels, allowing the gamma radiation sources to pass through storage on their way proximate the working table.

In operation, the sample to be irradiated is placed on a working table. The irradiator is configured to deliver the desired dose rate and monitoring equipment is connected to an experimental block 31. The operator then leaves the containment chamber, passing through the maze entranceway and through the lead-lined door. The operator mans a control panel 32, instructing a computer 33 to lift the radiation sources 12 into working position using cylinder 36 attached to a hydraulic pump 40.

Gamma radiation has the advantage of a significant penetration depth into a variety of material in the sample. Sources of gamma rays include radioactive nuclei, such as isotopes of cobalt, calcium, technicium, chromium, gallium, indium, iodine, iron, krypton, samarium, selenium, sodium, thalium, and xenon.

Sources of x rays include electron beam collision with metal targets, such as tungsten or molybdenum or alloys, or compact light sources, such as those produced commercially by Lyncean. Sources for ultraviolet radiation include deuterium or cadmium lamps. Sources for infrared radiation include sapphire, zinc, or selenide window ceramic lamps. Sources for microwaves include klystrons, Slevin type RF sources, or atom beam sources that employ hydrogen, oxygen, or nitrogen gases.

Various other irradiating devices may be used in the methods disclosed herein, including field ionization sources, electrostatic ion separators, field ionization generators, thermionic emission sources, microwave discharge ion sources, recirculating or static accelerators, dynamic linear accelerators, van de Graaff accelerators, and folded tandem accelerators. Such devices are disclosed, for example, in U.S. Provisional Application Ser. No. 61/073,665, the complete disclosure of which is incorporated herein by reference.

Electron Beam

In some embodiments, a beam of electrons is used as the radiation source. A beam of electrons has the advantages of high dose rates (e.g., 1, 5, or even 10 Mrad per second), high throughput, less containment, and less confinement equipment. Electrons can also be more efficient at causing chain scission. In addition, electrons having energies of 4-10 MeV can have a penetration depth of 5 to 30 mm or more, such as 40 mm.

Electron beams can be generated, e.g., by electrostatic generators, cascade generators, transformer generators, low energy accelerators with a scanning system, low energy accelerators with a linear cathode, linear accelerators, and pulsed accelerators. Electrons as an ionizing radiation source can be useful, e.g., for relatively thin piles of materials, e.g., less than 0.5 inch, e.g., less than 0.4 inch, 0.3 inch, 0.2 inch, or less than 0.1 inch. In some embodiments, the energy of each electron of the electron beam is from about 0.3 MeV to about 2.0 MeV (million electron volts), e.g., from about 0.5 MeV to about 1.5 MeV, or from about 0.7 MeV to about 1.25 MeV.

Figure 11:
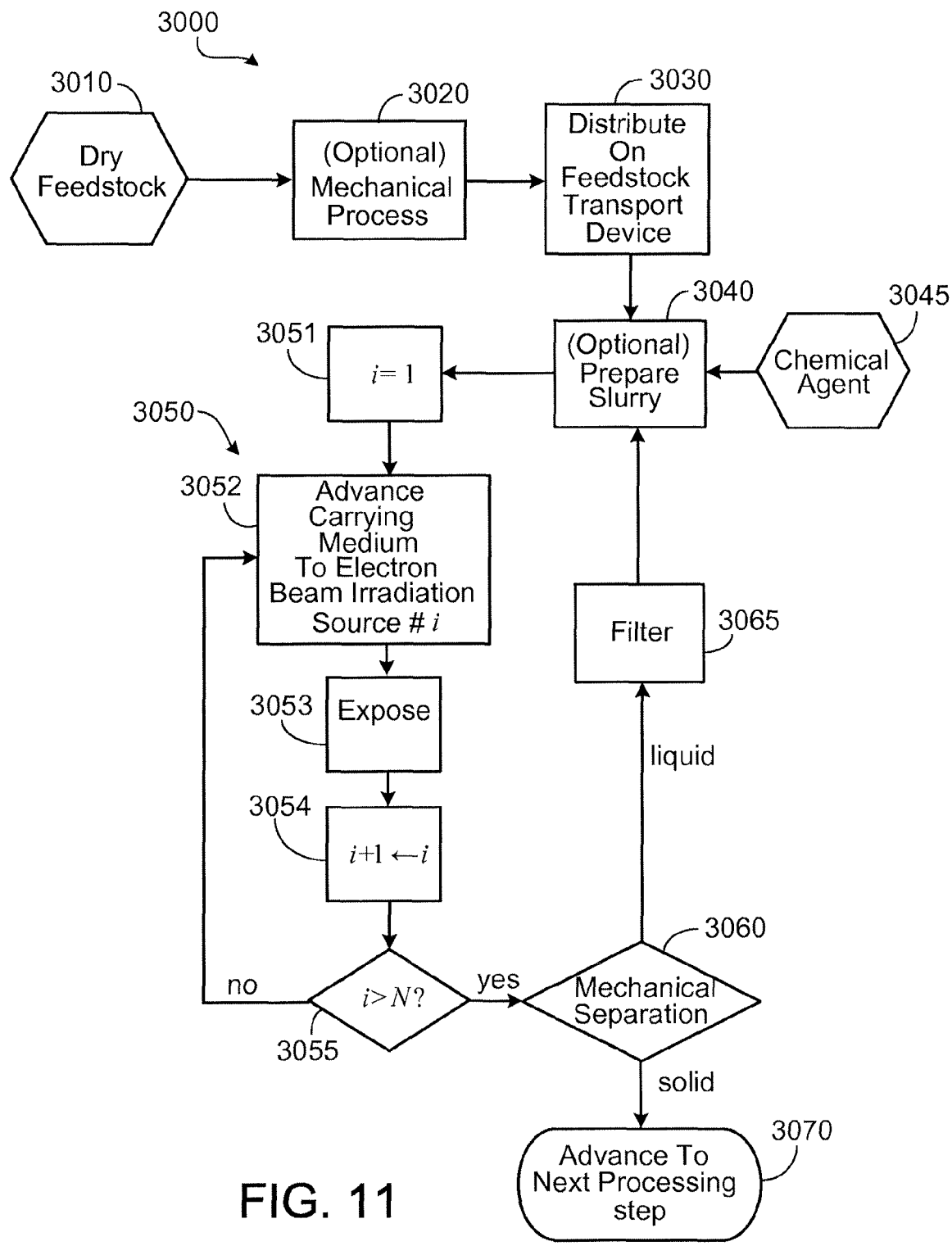
FIG. 11 is a block diagram illustrating an electron beam irradiation feedstock pretreatment sequence.

FIG. 11 shows a process flow diagram 3000 that includes various steps in an electron beam irradiation feedstock pretreatment sequence. In first step 3010, a supply of dry feedstock is received from a feed source. As discussed above, the dry feedstock from the feed source can be pre-processed prior to delivery to the electron beam irradiation devices. For example, if the feedstock is derived from plant sources, certain portions of the plant material can be removed prior to collection of the plant material and/or before the plant material is delivered by the feedstock transport device. Alternatively, or in addition, as expressed in optional step 3020, the biomass feedstock can be subjected to mechanical processing (e.g., to reduce the average length of fibers in the feedstock) prior to delivery to the electron beam irradiation devices.

In step 3030, the dry feedstock is transferred to a feedstock transport device (e.g., a conveyor belt) and is distributed over the cross-sectional width of the feedstock transport device approximately uniformly by volume. This can be accomplished, for example, manually or by inducing a localized vibration motion at some point in the feedstock transport device prior to the electron beam irradiation processing.

In some embodiments, a mixing system introduces a chemical agent 3045 into the feedstock in an optional process 3040 that produces a slurry. Combining water with the processed feedstock in mixing step 3040 creates an aqueous feedstock slurry that can be transported through, for example, piping rather than using, for example, a conveyor belt.

The next step 3050 is a loop that encompasses exposing the feedstock (in dry or slurry form) to electron beam radiation via one or more (say, N) electron beam irradiation devices. The feedstock slurry is moved through each of the N "showers" of electron beams at step 3052. The movement can either be at a continuous speed through and between the showers, or there can be a pause through each shower, followed by a sudden movement to the next shower. A small slice of the feedstock slurry is exposed to each shower for some predetermined exposure time at step 3053.

Electron beam irradiation devices can be procured commercially from Ion Beam Applications, Louvain-la-Neuve, Belgium or the Titan Corporation, San Diego, Calif. Typical electron energies can be 1 MeV, 2 MeV, 4.5 MeV, 7.5 MeV, or 10 MeV. Typical electron beam irradiation device power can be 1 kW, 5 kW, 10 kW, 20 kW, 50 kW, 100 kW, 250 kW, or 500 kW. Effectiveness of depolymerization of the feedstock slurry depends on the electron energy used and the dose applied, while exposure time depends on the power and dose. Typical doses can take values of 1 kGy, 5 kGy, 10 kGy, 20 kGy, 50 kGy, 100 kGy, or 200 kGy.

Tradeoffs in considering electron beam irradiation device power specifications include cost to operate, capital costs, depreciation, and device footprint. Tradeoffs in considering exposure dose levels of electron beam irradiation would be energy costs and environment, safety, and health (ESH) concerns. Tradeoffs in considering electron energies include energy costs; here, a lower electron energy can be advantageous in encouraging depolymerization of certain feedstock slurry (see, for example, Bouchard, et al, Cellulose (2006) 13: 601-610).

It can be advantageous to provide a double-pass of electron beam irradiation in order to provide a more effective depolymerization process. For example, the feedstock transport device could direct the feedstock (in dry or slurry form) underneath and in a reverse direction to its initial transport direction. Double-pass systems can allow thicker feedstock slurries to be processed and can provide a more uniform depolymerization through the thickness of the feedstock slurry.

The electron beam irradiation device can produce either a fixed beam or a scanning beam. A scanning beam can be advantageous with large scan sweep length and high scan speeds, as this would effectively replace a large, fixed beam width. Further, available sweep widths of 0.5 m, 1 m, 2 m or more are available. One suitable device is referenced in Example 22.

Once a portion of feedstock slurry has been transported through the N electron beam irradiation devices, it can be necessary in some embodiments, as in step 3060, to mechanically separate the liquid and solid components of the feedstock slurry. In these embodiments, a liquid portion of the feedstock slurry is filtered for residual solid particles and recycled back to the slurry preparation step 3040. A solid portion of the feedstock slurry is then advanced on to the next processing step 3070 via the feedstock transport device. In other embodiments, the feedstock is maintained in slurry form for further processing.

Heavy Ion Particle Beams

Particles heavier than electrons can be utilized to irradiate carbohydrates or materials that include carbohydrates, e.g., cellulosic materials, lignocellulosic materials, starchy materials, or mixtures of any of these and others described herein. For example, protons, helium nuclei, argon ions, silicon ions, neon ions, carbon ions, phosphorus ions, oxygen ions or nitrogen ions can be utilized. In some embodiments, particles heavier than electrons can induce higher amounts of chain scission. In some instances, positively charged particles can induce higher amounts of chain scission than negatively charged particles due to their acidity.

Heavier particle beams can be generated, e.g., using linear accelerators or cyclotrons. In some embodiments, the energy of each particle of the beam is from about 1.0 MeV/atomic unit to about 6,000 MeV/atomic unit, e.g., from about 3 MeV/atomic unit to about 4,800 MeV/atomic unit, or from about 10 MeV/atomic unit to about 1,000 MeV/atomic unit.

Electromagnetic Radiation

In embodiments in which the irradiating is performed with electromagnetic radiation, the electromagnetic radiation can have, e.g., energy per photon (in electron volts) of greater than $10^2$ eV, e.g., greater than $10^3$, $10^4$, $10^5$, $10^6$, or even greater than $10^7$ eV. In some embodiments, the electromagnetic radiation has energy per photon of between $10^4$ and $10^7$, e.g., between $10^5$ and $10^6$ eV. The electromagnetic radiation can have a frequency of, e.g., greater than $10^{16}$ Hz, greater than $10^{17}$ Hz, $10^{18}$, $10^{19}$, $10^{20}$, or even greater than $10^{21}$ Hz. In some embodiments, the electromagnetic radiation has a frequency of between $10^{18}$ and $10^{22}$ Hz, e.g., between $10^{19}$ to $10^{21}$ Hz.

Doses

In some embodiments, the irradiating (with any radiation source or a combination of sources) is performed until the material receives a dose of at least 0.25 Mrad, e.g., at least 1.0 Mrad, at least 2.5 Mrad, at least 5.0 Mrad, or at least 10.0 Mrad. In some embodiments, the irradiating is performed until the material receives a dose of between 1.0 Mrad and 6.0 Mrad, e.g., between 1.5 Mrad and 4.0 Mrad.

In some embodiments, the irradiating is performed at a dose rate of between 5.0 and 1500.0 kilorads/hour, e.g., between 10.0 and 750.0 kilorads/hour or between 50.0 and 350.0 kilorads/hours.

In some embodiments, two or more radiation sources are used, such as two or more ionizing radiations. For example, samples can be treated, in any order, with a beam of electrons, followed by gamma radiation and UV light having wavelengths from about 100 nm to about 280 nm. In some embodiments, samples are treated with three ionizing radiation sources, such as a beam of electrons, gamma radiation, and energetic UV light.

Alternatively, in another example, a fibrous biomass material that includes a cellulosic and/or lignocellulosic material is irradiated and, optionally, treated with acoustic energy, e.g., ultrasound.

In one example of the use of radiation as a treatment, half-gallon juice cartons made of un-printed polycoated white Kraft board having a bulk density of 20 lb/ft$^3$ are used as a feedstock. Cartons are folded flat and then fed into a sequence of three shredder-shearer trains arranged in series with output from the first shearer fed as input to the second shredder, and output from the second shearer fed as input to the third shredder. The fibrous material produced by the can be sprayed with water and processed through a pellet mill operating at room temperature. The densified pellets can be placed in a glass ampoule which is evacuated under high vacuum and then back-filled with argon gas. The ampoule is sealed under argon. The pellets in the ampoule are irradiated with gamma radiation for about 3 hours at a dose rate of about 1 Mrad per hour to provide an irradiated material in which the cellulose has a lower molecular weight than the starting material.

Quenching and Controlled Functionalization of Biomass

After treatment with one or more ionizing radiations, such as photonic radiation (e.g., X-rays or gamma-rays), e-beam radiation or particles heavier than electrons that are positively or negatively charged (e.g., protons or carbon ions), any of the carbohydrate-containing materials or mixtures described herein become ionized; that is, they include radicals at levels that are detectable with an electron spin resonance spectrometer. The current limit of detection of the radicals is about $10^{14}$ spins at room temperature. After ionization, any biomass material that has been ionized can be quenched to reduce the level of radicals in the ionized biomass, e.g., such that the radicals are no longer detectable with the electron spin resonance spectrometer. For example, the radicals can be quenched by the application of a sufficient pressure to the biomass and/or utilizing a fluid in contact with the ionized biomass, such as a gas or liquid, that reacts with (quenches) the radicals. Using a gas or liquid to at least aid in the quenching of the radicals can be used to functionalize the ionized biomass with a desired amount and kinds of functional groups, such as carboxylic acid groups, enol groups, aldehyde groups, nitro groups, nitrile groups, amino groups, alkyl amino groups, alkyl groups, chloroalkyl groups or chlorofluoroalkyl groups. In some instances, such quenching can improve the stability of some of the ionized biomass materials. For example, quenching can improve the biomass's resistance to oxidation. Functionalization by quenching can also improve the solubility of any biomass described herein, can improve its thermal stability, which can improve material utilization by various microorganisms. For example, the functional groups imparted to the biomass material by the quenching can act as receptor sites for attachment by microorganisms, e.g., to enhance cellulose hydrolysis by various microorganisms.

Figure 11A:
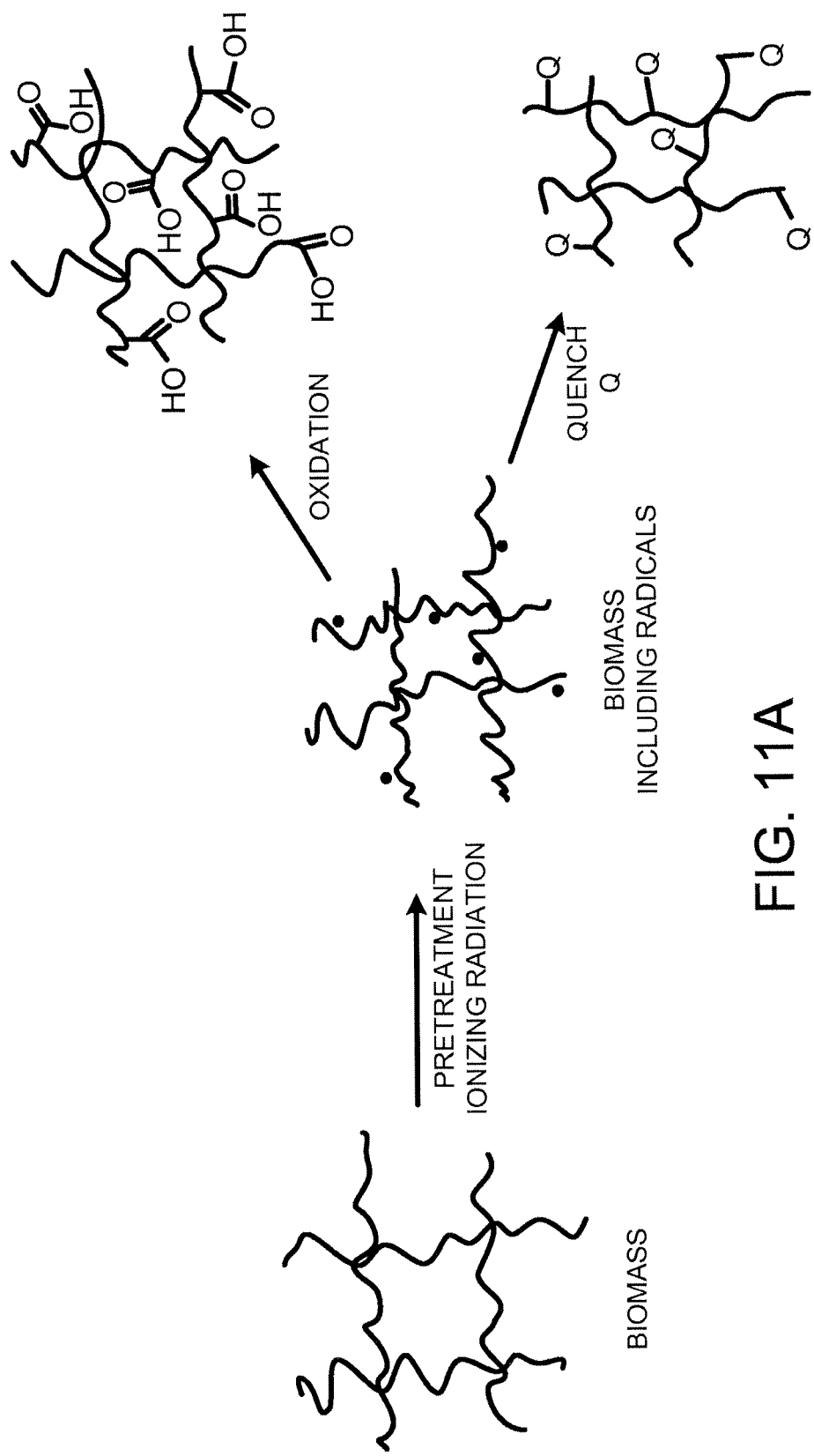
FIG. 11A is a schematic representation of biomass being ionized, and then oxidized or quenched.

FIG. 11A illustrates changing a molecular and/or a supramolecular structure of a biomass feedstock by pretreating the biomass feedstock with ionizing radiation, such as with electrons or ions of sufficient energy to ionize the biomass feedstock, to provide a first level of radicals. As shown in FIG. 11A, if it ionized biomass remains in the atmosphere, it will be oxidized, such as to an extent that carboxylic acid groups are generated by reacting with the atmospheric oxygen. In some instances with some materials, such oxidation is desired because it can aid in the further breakdown in molecular weight of the carbohydrate-containing biomass, and the oxidation groups, e.g., carboxylic acid groups can be helpful for solubility and microorganism utilization in some instances. However, since the radicals can "live" for some time after irradiation, e.g., longer than 1 day, 5 days, 30 days, 3 months, 6 months or even longer than 1 year, materials properties can continue to change over time, which in some instances, can be undesirable. Detecting radicals in irradiated samples by electron spin resonance spectroscopy and radical lifetimes in such samples is discussed in Bartolotta et al., Physics in Medicine and Biology, 46 (2001), 461-471 and in Bartolotta et al., Radiation Protection Dosimetry, Vol. 84, Nos. 1-4, pp. 293-296 (1999). As shown in FIG. 11A, the ionized biomass can be quenched to functionalize and/or to stabilize the ionized biomass. At any point, e.g., when the material is "alive" (still has a substantial quantity of reactive intermediates such as radicals), "partially alive" or fully quenched, the treated biomass can be converted into a product, e.g., a food.

In some embodiments, the quenching includes an application of pressure to the biomass, such as by mechanically deforming the biomass, e.g., directly mechanically compressing the biomass in one, two, or three dimensions, or applying pressure to a fluid in which the biomass is immersed, e.g., isostatic pressing. In such instances, the deformation of the material itself brings radicals, which are often trapped in crystalline domains, in close enough proximity so that the radicals can recombine, or react with another group. In some instances, the pressure is applied together with the application of heat, such as a sufficient quantity of heat to elevate the temperature of the biomass to above a melting point or softening point of a component of the biomass, such as lignin, cellulose or hemicellulose. Heat can improve molecular mobility in the polymeric material, which can aid in the quenching of the radicals. When pressure is utilized to quench, the pressure can be greater than about 1000 psi, such as greater than about 1250 psi, 1450 psi, 3625 psi, 5075 psi, 7250 psi, 10000 psi or even greater than 15000 psi.

In some embodiments, quenching includes contacting the biomass with a fluid, such as a liquid or gas, e.g., a gas capable of reacting with the radicals, such as acetylene or a mixture of acetylene in nitrogen, ethylene, chlorinated ethylenes or chlorofluoroethylenes, propylene or mixtures of these gases. In other particular embodiments, quenching includes contacting the biomass with a liquid, e.g., a liquid soluble in, or at least capable of penetrating into the biomass and reacting with the radicals, such as a diene, such as 1,5-cyclooctadiene. In some specific embodiments, the quenching includes contacting the biomass with an antioxidant, such as Vitamin E. If desired, the biomass feedstock can include an antioxidant dispersed therein, and the quenching can come from contacting the antioxidant dispersed in the biomass feedstock with the radicals. Combinations of these and other quenching materials can be used.

Other methods for quenching are possible. For example, any method for quenching radicals in polymeric materials described in Muratoglu et al., U.S. Patent Application Publication No. 2008/0067724 and Muratoglu et al., U.S. Pat. No. 7,166,650, can be utilized for quenching any ionized biomass material described herein. Furthermore any quenching agent (described as a "sensitizing agent" in the above-noted Muratoglu disclosures) and/or any antioxidant described in either Muratoglu reference can be utilized to quench any ionized biomass material.

Functionalization can be enhanced by utilizing heavy charged ions, such as any of the heavier ions described herein. For example, if it is desired to enhance oxidation, charged oxygen ions can be utilized for the irradiation. If nitrogen functional groups are desired, nitrogen ions or ions that includes nitrogen can be utilized. Likewise, if sulfur or phosphorus groups are desired, sulfur or phosphorus ions can be used in the irradiation.

In some embodiments, after quenching any of the quenched ionized materials described herein can be further treated with one or more of radiation, such as ionizing or non-ionizing radiation, sonication, pyrolysis, and oxidation for additional molecular and/or supramolecular structure change.

Particle Beam Exposure in Fluids

In some cases, the cellulosic or lignocellulosic materials can be exposed to a particle beam in the presence of one or more additional fluids (e.g., gases and/or liquids). Exposure of a material to a particle beam in the presence of one or more additional fluids can increase the efficiency of the treatment.

In some embodiments, the material is exposed to a particle beam in the presence of a fluid such as air. Particles accelerated in any one or more of the types of accelerators disclosed herein (or another type of accelerator) are coupled out of the accelerator via an output port (e.g., a thin membrane such as a metal foil), pass through a volume of space occupied by the fluid, and are then incident on the material. In addition to directly treating the material, some of the particles generate additional chemical species by interacting with fluid particles (e.g., ions and/or radicals generated from various constituents of air, such as ozone and oxides of nitrogen). These generated chemical species can also interact with the material, and can act as initiators for a variety of different chemical bond-breaking reactions in the material. For example, any oxidant produced can oxidize the material, which can result in molecular weight reduction.

In certain embodiments, additional fluids can be selectively introduced into the path of a particle beam before the beam is incident on the material. As discussed above, reactions between the particles of the beam and the particles of the introduced fluids can generate additional chemical species, which react with the material and can assist in functionalizing the material, and/or otherwise selectively altering certain properties of the material. The one or more additional fluids can be directed into the path of the beam from a supply tube, for example. The direction and flow rate of the fluid(s) that is/are introduced can be selected according to a desired exposure rate and/or direction to control the efficiency of the overall treatment, including effects that result from both particle-based treatment and effects that are due to the interaction of dynamically generated species from the introduced fluid with the material. In addition to air, exemplary fluids that can be introduced into the ion beam include oxygen, nitrogen, one or more noble gases, one or more halogens, and hydrogen.

Irradiating Low Bulk Density Biomass Materials and Cooling Irradiated Biomass

During treatment of biomass materials with ionizing radiation, especially at high dose rates, such as at rates greater then 0.15 Mrad per second, e.g., 0.25 Mrad/s, 0.35 Mrad/s, 0.5 Mrad/s, 0.75 Mrad/s or even greater than 1 Mrad/sec, biomass materials can retain significant quantities of heat so that the temperature of the biomass materials become elevated. While higher temperatures can, in some embodiments, be advantageous, e.g., when a faster reaction rate is desired, it is advantageous to control the heating of the biomass to retain control over the chemical reactions initiated by the ionizing radiation, such as cross-linking, chain scission and/or grafting, e.g., to maintain process control. Low bulk density materials, such as those having a bulk density of less than about 0.4 g/cm$^3$, e.g., less than about 0.35, 0.25 or less about 0.15 g/cm$^3$, especially when combined with materials that have thin cross-sections, such as fibers having small transverse dimensions, are generally easier to cool. In addition, photons and particles can generally penetrate further into and through materials having a relatively low bulk density, which can allow for the processing of larger volumes of materials at higher rates, and can allow for the use of photons and particles that having lower energies, e.g., 0.25 Mev, 0.5 MeV, 0.75 MeV or 1.0 MeV, which can reduce safety shielding requirements. Many of the biomass materials described herein can be processed in one or more of the systems shown in FIGS. 11B, 11C, 11D and 11E, which are described below. The systems shown allow one or more types of ionizing radiation, such as relativistic electrons or electrons in combination with X-rays, to be applied to low bulk density biomass materials at highs dose rates, such as at a rate greater than 1.0, 1.5, 2.5 Mrad/s or even greater than about 5.0 Mrad/s, and then to allow for cooling of the biomass prior to applying radiation for a second, third, fourth, fifth, sixth, seventh, eighth, ninth or even a tenth time.

For example, in one method of changing a molecular and/or a supramolecular structure of a biomass feedstock, the biomass is pretreated at a first temperature with ionizing radiation, such as photons, electrons or ions (e.g., singularly or multiply charged cations or anions), for a sufficient time and/or a sufficient dose to elevate the biomass feedstock to a second temperature higher than the first temperature. The pretreated biomass is then cooled below the second temperature. Finally, if desired, the cooled biomass can be treated one or more times with radiation, e.g., with ionizing radiation. If desired, cooling can be applied to the biomass after and/or during each radiation treatment.

In some embodiments, the cooling of the biomass feedstock is to an extent that, after cooling, the biomass is at a third temperature below the first temperature.

For example, and as will be explained in more detail below, treating biomass feedstock with the ionizing radiation can be performed as the biomass feedstock is being pneumatically conveyed in a fluid, such as a in a gas, such as nitrogen or air. To aid in molecular weight breakdown and/or functionalization of the materials, the gas can be saturated with any swelling agent described herein and/or water vapor. For example, acidic water vapor can be utilized. To aid in molecular weight breakdown, the water can be acidified with an organic acid, such as formic, or acetic acid, or a mineral acid, such as sulfuric or hydrochloric acid.

For example, and as will be explained in more detail below, the treating biomass feedstock with the ionizing radiation can be performed as the biomass feedstock falls under the influence of gravity. This procedure can effectively reduce the bulk density of the biomass feedstock as it is being processed and can aid in the cooling of the biomass feedstock. For example, the biomass can be conveyed from a first belt at a first height above the ground and then can be captured by a second belt at a second level above the ground lower than the first level. For example, in some embodiments, the trailing edge of the first belt and the leading edge of the second belt defining a gap. Advantageously, the ionizing radiation, such as a beam of electrons, protons, or other ions, can be applied at the gap to prevent damage to the biomass conveyance system.

In the methods described herein, cooling of the biomass can include contacting the biomass with a fluid, such as a gas, at a temperature below the first or second temperature, such as gaseous nitrogen at or about 77 K. Even water, such as water at a temperature below nominal room temperature (e.g., 25 degrees Celsius) can be utilized.

The biomass feedstock can be treated at a first temperature with ionizing radiation for a sufficient time and/or a sufficient dose, such as from about 1 second to about 10 seconds at a dose rate of about 0.5 Mrad/s to about 5 Mrad/s, to elevate the biomass feedstock to a second temperature higher than the first temperature. After applying the radiation, the biomass can be cooled below the second temperature. The cooled treated biomass is treated with radiation, such as an ionizing radiation, and then the treated biomass is contacted with a microorganism having the ability to convert at least a portion, e.g., at least about 1 percent by weight, of the biomass to the product.

In some embodiments, a method of changing a molecular and/or a supramolecular structure of a biomass feedstock includes optionally, pretreating the biomass feedstock by reducing one or more dimensions of individual pieces of the biomass feedstock and applying ionizing radiation, such as photons, electrons or ions, to the biomass feedstock. In such embodiments, the biomass feedstock to which the ionizing radiation is applied has a bulk density of less than about 0.35 g/cm$^3$, such as less than about 0.3, 0.25, 0.20, or less than about 0.15 g/cm$^3$ during the application of the ionizing radiation. In such embodiments, the biomass feedstock can be cooled, and then ionizing radiation can be applied to the cooled biomass. In some advantageous embodiments, the biomass feedstock is or includes discrete fibers and/or particles having a maximum dimension of not more than about 0.5 mm, such as not more than about 0.25 mm, not more than about 0.1 mm, not more than about 0.05 mm, or not more than about 0.025 mm.

Referring particularly now to FIGS. 11B and 11C, which shows a biomass material generating, treating, conveying, and irradiating device 1170 (shielding not illustrated in the drawings). In operation, paper sheet 1173, e.g., scrap bleached Kraft paper sheet, is supplied from a roll 1172 and delivered to a fiberizing apparatus 1174, such as a rotary shearer. The sheet 1173 is converted into fibrous material 1112 and is delivered to a fiber-loading zone 1180 by conveyer 1178. If desired, the fibers of the fibrous material can be separated, e.g., by screening, into fractions having different L/D ratios. In some embodiments, the fibrous material 1112 of generally a low bulk density and advantageously thin cross-sections, is delivered continuously to zone 1180, and in other embodiments, the fibrous material is delivered in batches. A blower 1182 in loop 1184 is positioned adjacent to the fiber-loading zone 1180 and is capable of moving a fluid medium, e.g., air, at a velocity and volume sufficient to pneumatically circulate the fibrous material 1112 in a direction indicated by arrow 1188 through loop 1184.

In some embodiments, the velocity of air traveling in the loop is sufficient to uniformly disperse and transport the fibrous material around the entire loop 1184. In some embodiments, the velocity of flow is greater than 2,500 feet/minute, e.g., 5,000 feet/minute, 6,000 feet/minute or more, e.g., 7,500 feet/minute or 8,500 feet/minute.

The entrained fibrous material 1112 traversing the loop passes an application zone 1190, which forms part of loop 1184. Here, any desired additives described herein are applied, such as a liquid, such as water, such as acidified or water made basic. In operation, application zone 1190 applies an additive, such as a liquid solution 1196 to the circulating fibrous material via nozzles 98, 99 and 11100. When a liquid is applied, the nozzles produce an atomized spray or mist of, which impacts the fibers as the fibers pass in proximity to the nozzles. Valve 11102 is operated to control the flow of liquid to the respective nozzles 1198, 1199, and 11100. After a desired quantity of additive is applied, the valve 11102 is closed.

In some embodiments, the application zone 1190 is two to one hundred feet long or more, e.g., 125 feet, 150 feet, 250 feet long or more, e.g., 500 feet long. Longer application zones allow for application of over a longer period of time during passage of fibrous material through application zone 1190. In some embodiments, the nozzles are spaced apart from about three to about four feet along the length of loop 1184.

As the fibrous material moves in loop 1184 and through the irradiating portion of the loop 11107 that includes a horn 11109 for delivering ionizing radiation, ionizing radiation is applied to the fibrous material (shielding is not shown).

As the irradiated fibrous material moves around loop 1184, it cools by the action of gases, such as air, circulating at high speeds in the loop and it is bathed in reactive gases, such as ozone and/or oxides of nitrogen, that are produced from the action of the ionizing radiation on the circulating gases, such as air. After passing through the irradiating portion 11107, a cooling fluid, such as a liquid (e.g., water) or a gas, such as liquid nitrogen at 77 K can be injected into loop 1184 to aid in the cooling of the fibrous material. This process can be repeated more than one time if desired, e.g., 2, 3, 4, 5, 6, 7, 8, 9, 10 times or more, e.g., 15 times, to deliver the desired dose to the fibrous material. While, as shown, the long axis of the horn is along the direction of flow, in some implementations, the long axis of the horn is transverse to the direction of the flow. In some implementations, a beam of electrons is utilized as a principal ionizing radiation source and X-rays as a secondary ionizing radiation source. X-rays can be generated by having a metal target, such as a tantalum target 11111, on the inside of loop 1184 such that when electrons strike the target, X-rays are emitted.

After a desired dose is delivered to the fibrous material, the fibrous material can be removed from loop 1184 via a separator 11112, which is selectively connected to loop 1184 by section 11114 and gate valve 11116. When valve 11116 is opened, another valve is also opened to allow air to enter the loop 1184 to compensate for air exiting through separator 11112.

Figure 11E:
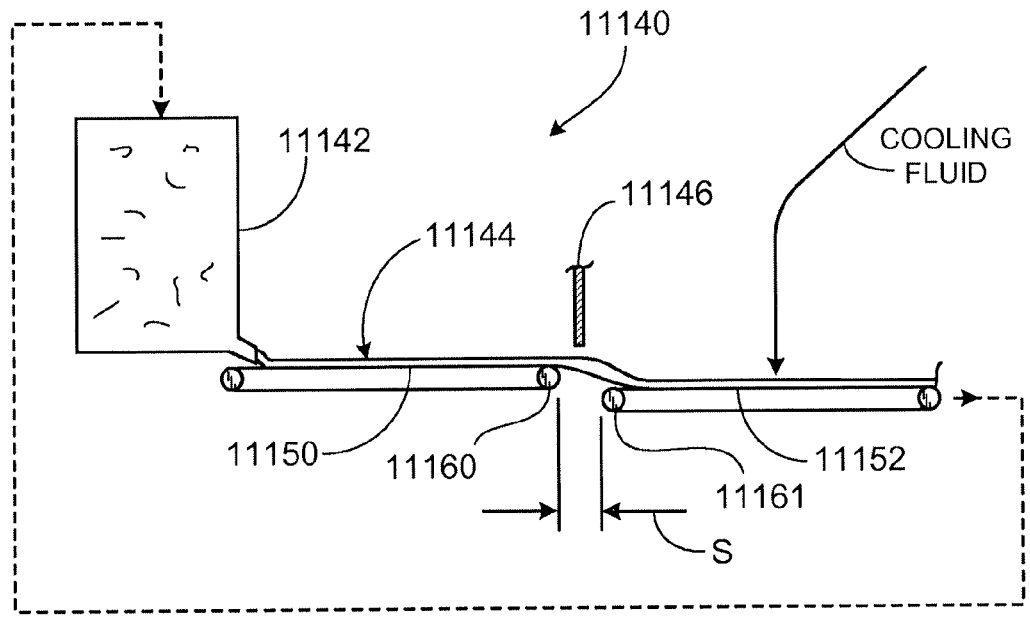
FIG. 11E is a schematic side-view of another system for irradiating a low bulk density material.
Figure 11D:
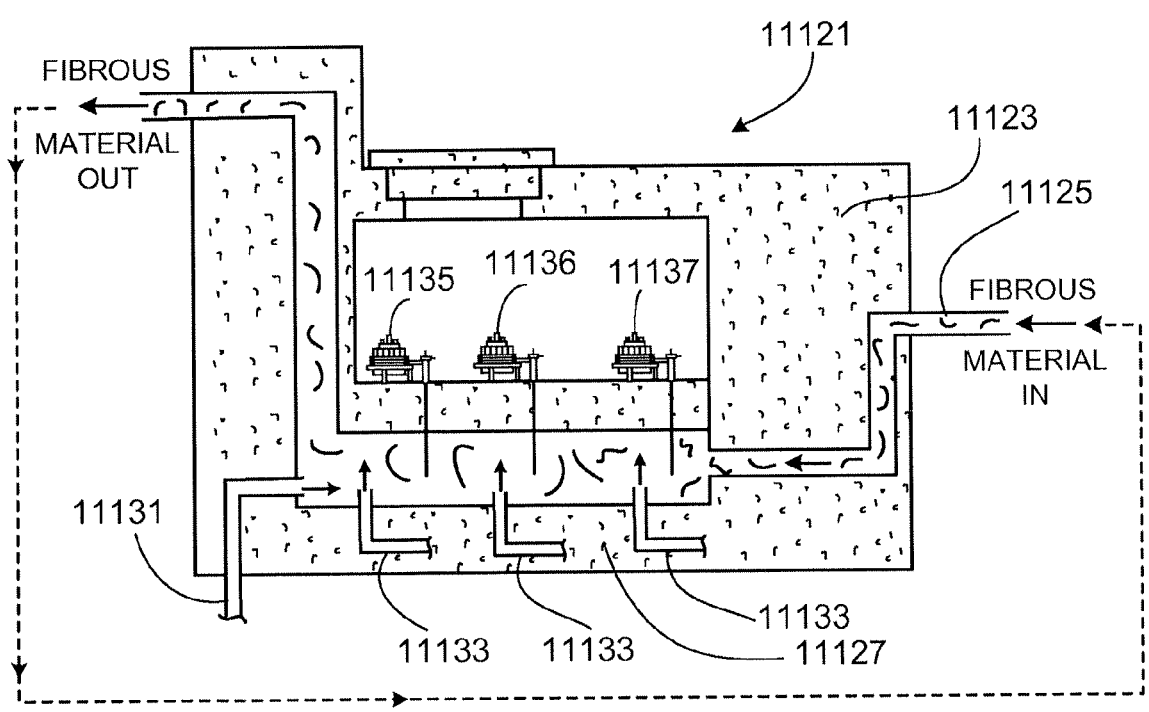
FIG. 11D is a schematic cross-sectional view of a fluidized bed system for irradiating a low bulk density material.

Referring particularly now to FIG. 11D, which shows a fluidized bed fibrous irradiating device 11121 with shielding. Fibrous material in a fluid, such as a gas, such as air under pressure, is delivered to a shielded containment vessel 11123 via piping 11125 and into a shielded fluidized bed portion 11127. Counter-current streams 11131 of fluid, such as a gas, and transverse streams 11133 of fluid, such as a gas, that is the same or different as a fluid delivered counter-currently, combine to cause turbulence in the bed portion. Ionizing radiation is applied to the fluidized bed portion as the fibrous material is conveyed through the bed portion. For example, as shown, three beams of electrons from three Rhodotron® machines 11135, 11136 and 11137 can be utilized. Advantageously, each beam can penetrate into the fluidized bed a different depth and/or each beam can emit electrons of a different energy, such as 1, 3, and 5 MeV. As the irradiated fibrous material moves through the system, it cools by the action of gases, such as air, circulating at high speeds in the system and it is bathed in reactive gases, such as ozone and/or oxides of nitrogen, that are produced from the action of the ionizing radiation on the circulating gases, such as air. If desired, the process can be repeated a desired number of times until the fibrous material has received a desired dose. While the fluidized bed has been illustrated such that its long axis is horizontal with the ground, in other implementations, the long axis of the bed is perpendicular to the ground so that the fibrous material falls under the influence of gravity.

Referring particularly now to FIG. 11E, which shows another fibrous material conveying and irradiating device 11140 without shielding. Fibrous material 11144 is delivered from a bin 11142 to a first conveyer 11150 at a first level above the ground and then the material is transferred to a second conveyer 11152 at a lower height than the first conveyer. The trailing edge 11160 of the first conveyer and the leading edge 11161 of the second conveyer 11152 defines a gap with a spacing S. For example, the spacing S can be between 4 inches and about 24 inches. Material 11144 has enough momentum to free fall under gravity and then to be captured by the second conveyer 11152 without falling into the gap. During the free fall, ionizing radiation is applied to the material. This arrangement can be advantageous in that the ionizing radiation is less likely to damage the conveying system because is not directly contacted by the radiation. After passing through the irradiating portion, a cooling fluid, such as a liquid (e.g., water) or a gas, such as liquid nitrogen at 77 K can be applied to the material to aid in the cooling of the fibrous material. This process can be repeated more than one time if desired, e.g., 2, 3, 4, 5, 6, 7, 8, 9, 10 times or more, e.g., 15 times, to deliver the desired dose to the fibrous material. While, as shown, the long axis of the horn is transverse to the direction of the material flow, other beam arrangements are possible. In some implementations, a beam of electrons is utilized as a principal ionizing radiation source and X-rays as a secondary ionizing radiation source. X-rays can be generated by having a metal target, such as a tantalum target, in the gap on the opposite side of the material, such that as the electrons that pass through the material they strike the target, generating X-rays.

In one example of the use of radiation with oxidation as a pretreatment, half-gallon juice cartons made of un-printed polycoated white Kraft board having a bulk density of 20 lb/ft$^3$ are used as a feedstock. Cartons are folded flat and then fed into a sequence of three shredder-shearer trains arranged in series with output from the first shearer fed as input to the second shredder, and output from the second shearer fed as input to the third shredder. The fibrous material produced by the can be sprayed with water and processed through a pellet mill operating at room temperature. The densified pellets can be placed in a glass ampoule which is sealed under an atmosphere of air. The pellets in the ampoule are irradiated with gamma radiation for about 3 hours at a dose rate of about 1 Mrad per hour to provide an irradiated material in which the cellulose has a lower molecular weight than the fibrous Kraft starting material.

Sonication

One or more sonication processing sequences can be used to treat biomass from a wide variety of different sources to extract useful substances from the feedstock, and to provide partially degraded organic material which functions as input to further processing steps and/or sequences. Sonication can reduce the recalcitrance, molecular weight, and/or crystallinity of feedstock, such as one or more of any of the biomass materials described herein, e.g., one or more carbohydrate sources, such as cellulosic or lignocellulosic materials, or starchy materials.

Referring again to FIG. 8, in one method, a first biomass material 2 that includes cellulose having a first number average molecular weight ($^{T}M_{N1}$) is dispersed in a medium, such as water, and sonicated and/or otherwise cavitated, to provide a second biomass material 3 that includes cellulose having a second number average molecular weight ($^{T}M_{N2}$) lower than the first number average molecular weight. The second material (or the first and second material in certain embodiments) can be combined with a microorganism (e.g., a bacterium or a yeast) that can utilize the second and/or first material to produce a product 5.

Since the second material has cellulose having a reduced molecular weight relative to the first material, and in some instances, a reduced crystallinity as well, the second material is generally more dispersible, swellable, and/or soluble in a solution containing the microorganism, e.g., at a concentration of greater than $10^6$ microorganisms/mL. These properties make the second material 3 more susceptible to chemical, enzymatic, and/or microbial attack relative to the first material 2, which can greatly improve the production rate and/or production level of a desired product, e.g., ethanol. Sonication can also sterilize the materials, but should not be used while the microorganisms are supposed to be alive.

In some embodiments, the second number average molecular weight ($^{T}M_{N2}$) is lower than the first number average molecular weight ($^{T}M_{N1}$) by more than about 10 percent, e.g., 15, 20, 25, 30, 35, 40, 50 percent, 60 percent, or even more than about 75 percent.

In some instances, the second material has cellulose that has a crystallinity ($^{T}C_2$) that is lower than the crystallinity ($^{T}C_1$) of the cellulose of the first material. For example, ($^{T}C_2$) can be lower than ($^{T}C_1$) by more than about 10 percent, e.g., 15, 20, 25, 30, 35, 40, or even more than about 50 percent.

In some embodiments, the starting crystallinity index (prior to sonication) is from about 40 to about 87.5 percent, e.g., from about 50 to about 75 percent or from about 60 to about 70 percent, and the crystallinity index after sonication is from about 10 to about 50 percent, e.g., from about 15 to about 45 percent or from about 20 to about 40 percent. However, in certain embodiments, e.g., after extensive sonication, it is possible to have a crystallinity index of lower than 5 percent. In some embodiments, the material after sonication is substantially amorphous.

In some embodiments, the starting number average molecular weight (prior to sonication) is from about 200,000 to about 3,200,000, e.g., from about 250,000 to about 1,000,000 or from about 250,000 to about 700,000, and the number average molecular weight after sonication is from about 50,000 to about 200,000, e.g., from about 60,000 to about 150,000 or from about 70,000 to about 125,000. However, in some embodiments, e.g., after extensive sonication, it is possible to have a number average molecular weight of less than about 10,000 or even less than about 5,000.

In some embodiments, the second material can have a level of oxidation ($^{T}O_2$) that is higher than the level of oxidation ($^{T}O_1$) of the first material. A higher level of oxidation of the material can aid in its dispersibility, swellability and/or solubility, further enhancing the materials susceptibility to chemical, enzymatic or microbial attack. In some embodiments, to increase the level of the oxidation of the second material relative to the first material, the sonication is performed in an oxidizing medium, producing a second material that is more oxidized than the first material. For example, the second material can have more hydroxyl groups, aldehyde groups, ketone groups, ester groups or carboxylic acid groups, which can increase its hydrophilicity.

In some embodiments, the sonication medium is an aqueous medium. If desired, the medium can include an oxidant, such as a peroxide (e.g., hydrogen peroxide), a dispersing agent and/or a buffer. Examples of dispersing agents include ionic dispersing agents, e.g., sodium lauryl sulfate, and non-ionic dispersing agents, e.g., poly(ethylene glycol).

In other embodiments, the sonication medium is non-aqueous. For example, the sonication can be performed in a hydrocarbon, e.g., toluene or heptane, an ether, e.g., diethyl ether or tetrahydrofuran, or even in a liquefied gas such as argon, xenon, or nitrogen.

Without wishing to be bound by any particular theory, it is believed that sonication breaks bonds in the cellulose by creating bubbles in the medium containing the cellulose, which grow and then violently collapse. During the collapse of the bubble, which can take place in less than a nanosecond, the implosive force raises the local temperature within the bubble to about 5100 K (even higher in some instance; see, e.g., Suslick et al., Nature 434, 52-55) and generates pressures of from a few hundred atmospheres to over 1000 atmospheres or more. It is these high temperatures and pressures that break the bonds. In addition, without wishing to be bound by any particular theory, it is believed that reduced crystallinity arises, at least in part, from the extremely high cooling rates during collapse of the bubbles, which can be greater than about $10^{11}$ K/second. The high cooling rates generally do not allow the cellulose to organize and crystallize, resulting in materials that have reduced crystallinity. Ultrasonic systems and sonochemistry are discussed in, e.g., Olli et al., U.S. Pat. No. 5,766,764; Roberts, U.S. Pat. No. 5,828,156; Mason, Chemistry with Ultrasound, Elsevier, Oxford, (1990); Suslick (editor), Ultrasound: its Chemical, Physical and Biological Effects, VCH, Weinheim, (1988); Price, "Current Trends in Sonochemistry" Royal Society of Chemistry, Cambridge, (1992); Suslick et al., Ann. Rev. Mater. Sci. 29, 295, (1999); Suslick et al., Nature 353, 414 (1991); Hiller et al., Phys. Rev. Lett. 69, 1182 (1992); Barber et al., Nature, 352, 414 (1991); Suslick et al., J. Am. Chem. Soc., 108, 5641 (1986); Tang et al., Chem. Comm., 2119 (2000); Wang et al., Advanced Mater., 12, 1137 (2000); Landau et al., J. of Catalysis, 201, 22 (2001); Perkas et al., Chem. Comm., 988 (2001); Nikitenko et al., Angew. Chem. Inter. Ed. (December 2001); Shafi et al., J. Phys. Chem B 103, 3358 (1999); Avivi et al., J. Amer. Chem. Soc. 121, 4196 (1999); and Avivi et al., J. Amer. Chem. Soc. 122, 4331 (2000).

Sonication Systems

Figure 12:
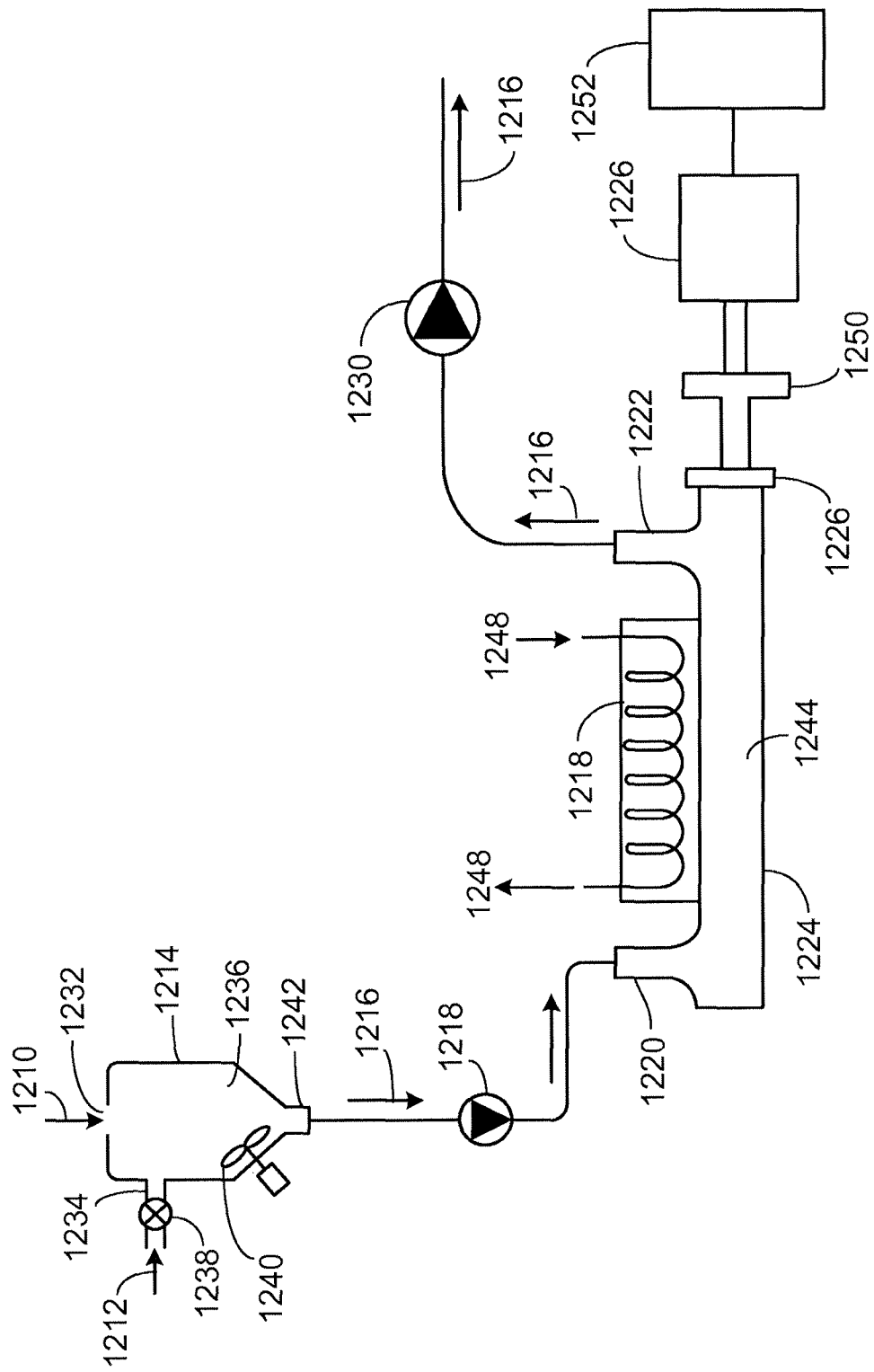
FIG. 12 is a schematic view of a system for sonicating a process stream of cellulosic material in a liquid medium.

FIG. 12 shows a general system in which a biomass material stream 1210 is mixed with a water stream 1212 in a reservoir 1214 to form a process stream 1216. A first pump 1218 draws process stream 1216 from reservoir 1214 and toward a flow cell 1224. Ultrasonic transducer 1226 transmits ultrasonic energy into process stream 1216 as the process stream flows through flow cell 1224. A second pump 1230 draws process stream 1216 from flow cell 1224 and toward subsequent processing.

Reservoir 1214 includes a first intake 1232 and a second intake 1234 in fluid communication with a volume 1236. A conveyor (not shown) delivers biomass material stream 1210 to reservoir 1214 through first intake 1232. Water stream 1212 enters reservoir 1214 through second intake 1234. In some embodiments, water stream 1212 enters volume 1236 along a tangent establishing a swirling flow within volume 1236. In certain embodiments, biomass material stream 1210 and water stream 1212 are introduced into volume 1236 along opposing axes to enhance mixing within the volume.

Valve 1238 controls the flow of water stream 1212 through second intake 1232 to produce a desired ratio of biomass material to water (e.g., approximately 10% cellulosic material, weight by volume). For example, 2000 tons/day of biomass can be combined with 1 million to 1.5 million gallons/day, e.g., 1.25 million gallons/day, of water.

Mixing of material biomass and water in reservoir 1214 is controlled by the size of volume 1236 and the flow rates of biomass and water into the volume. In some embodiments, volume 1236 is sized to create a minimum mixing residence time for the biomass and water. For example, when 2000 tons/day of biomass and 1.25 million gallons/day of water are flowing through reservoir 1214, volume 1236 can be about 32,000 gallons to produce a minimum mixing residence time of about 15 minutes.

Reservoir 1214 includes a mixer 1240 in fluid communication with volume 1236. Mixer 1240 agitates the contents of volume 1236 to disperse biomass throughout the water in the volume. For example, mixer 1240 can be a rotating vane disposed in reservoir 1214. In some embodiments, mixer 1240 disperses the biomass substantially uniformly throughout the water.

Reservoir 1214 further includes an exit 1242 in fluid communication with volume 1236 and process stream 1216. The mixture of biomass and water in volume 1236 flows out of reservoir 1214 via exit 1242. Exit 1242 is arranged near the bottom of reservoir 1214 to allow gravity to pull the mixture of biomass and water out of reservoir 1214 and into process stream 1216.

First pump 1218 (e.g., any of several recessed impeller vortex pumps made by Essco Pumps & Controls, Los Angeles, Calif.) moves the contents of process stream 1216 toward flow cell 1224. In some embodiments, first pump 1218 agitates the contents of process stream 1216 such that the mixture of cellulosic material and water is substantially uniform at inlet 1220 of flow cell 1224. For example, first pump 1218 agitates process stream 1216 to create a turbulent flow that persists along the process stream between the first pump and inlet 1220 of flow cell 1224.

Flow cell 1224 includes a reactor volume 1244 in fluid communication with inlet 1220 and outlet 1222. In some embodiments, reactor volume 1244 is a stainless steel tube capable of withstanding elevated pressures (e.g., 10 bars). In addition or in the alternative, reactor volume 1244 includes a rectangular cross section.

Flow cell 1224 further includes a heat exchanger 1246 in thermal communication with at least a portion of reactor volume 1244. Cooling fluid 1248 (e.g., water) flows into heat exchanger 1246 and absorbs heat generated when process stream 1216 is sonicated in reactor volume 1244. In some embodiments, the flow rate of cooling fluid 1248 into heat exchanger 1246 is controlled to maintain an approximately constant temperature in reactor volume 1244. In addition or in the alternative, the temperature of cooling fluid 1248 flowing into heat exchanger 1246 is controlled to maintain an approximately constant temperature in reactor volume 1244. In some embodiments, the temperature of reactor volume 1244 is maintained at 20 to 50° C., e.g., 25, 30, 35, 40, or 45° C. Additionally or alternatively, heat transferred to cooling fluid 1248 from reactor volume 1244 can be used in other parts of the overall process.

An adapter section 1226 creates fluid communication between reactor volume 1244 and a booster 1250 coupled (e.g., mechanically coupled using a flange) to ultrasonic transducer 1226. For example, adapter section 1226 can include a flange and O-ring assembly arranged, to create a leak tight connection between reactor volume 1244 and booster 1250. In some embodiments, ultrasonic transducer 1226 is a high-powered ultrasonic transducer made by Hielscher Ultrasonics of Teltow, Germany.

In operation, a generator 1252 delivers electricity to ultrasonic transducer 1252. Ultrasonic transducer 1226 includes a piezoelectric element that converts the electrical energy into sound in the ultrasonic range. In some embodiments, the materials are sonicated using sound having a frequency of from about 16 kHz to about 110 kHz, e.g., from about 18 kHz to about 75 kHz or from about 20 kHz to about 40 kHz (e.g., sound having a frequency of 20 kHz to 40 kHz).

The ultrasonic energy is then delivered to the working medium through booster 1248.

The ultrasonic energy traveling through booster 1248 in reactor volume 1244 creates a series of compressions and rarefactions in process stream 1216 with an intensity sufficient to create cavitation in process stream 1216. Cavitation disaggregates the cellulosic material dispersed in process stream 1216. Cavitation also produces free radicals in the water of process stream 1216. These free radicals act to further break down the cellulosic material in process stream 1216.

In general, 5 to 4000 MJ/m$^3$, e.g., 10, 25, 50, 100, 250, 500, 750, 1000, 2000, or 3000 MJ/m$^3$, of ultrasonic energy is applied to process stream 16 flowing at a rate of about 0.2 m$^3$/s (about 3200 gallons/min). After exposure to ultrasonic energy in reactor volume 1244, process stream 1216 exits flow cell 1224 through outlet 1222. Second pump 1230 moves process stream 1216 to subsequent processing (e.g., any of several recessed impeller vortex pumps made by Essco Pumps & Controls, Los Angeles, Calif.).

While certain embodiments have been described, other embodiments are possible.

As an example, while process stream 1216 has been described as a single flow path, other arrangements are possible. In some embodiments for example, process stream 1216 includes multiple parallel flow paths (e.g., flowing at a rate of 10 gallon/min). In addition or in the alternative, the multiple parallel flow paths of process stream 1216 flow into separate flow cells and are sonicated in parallel (e.g., using a plurality of 16 kW ultrasonic transducers).

As another example, while a single ultrasonic transducer 1226 has been described as being coupled to flow cell 1224, other arrangements are possible. In some embodiments, a plurality of ultrasonic transducers 1226 are arranged in flow cell 1224 (e.g., ten ultrasonic transducers can be arranged in a flow cell 1224). In some embodiments, the sound waves generated by each of the plurality of ultrasonic transducers 1226 are timed (e.g., synchronized out of phase with one another) to enhance the cavitation acting upon process stream 1216.

As another example, while a single flow cell 1224 has been described, other arrangements are possible. In some embodiments, second pump 1230 moves process stream to a second flow cell where a second booster and ultrasonic transducer further sonicate process stream 1216.

As still another example, while reactor volume 1244 has been described as a closed volume, reactor volume 1244 is open to ambient conditions in certain embodiments. In such embodiments, sonication pretreatment can be performed substantially simultaneously with other pretreatment techniques. For example, ultrasonic energy can be applied to process stream 1216 in reactor volume 1244 while electron beams are simultaneously introduced into process stream 1216.

As another example, while a flow through process has been described, other arrangements are possible. In some embodiments, sonication can be performed in a batch process. For example, a volume can be filled with a 10% (weight by volume) mixture of biomass in water and exposed to sound with intensity from about 50 W/cm$^2$ to about 600 W/cm$^2$, e.g., from about 75 W/cm$^2$ to about 300 W/cm$^2$ or from about 95 W/cm$^2$ to about 200 W/cm$^2$. Additionally or alternatively, the mixture in the volume can be sonicated from about 1 hour to about 24 hours, e.g., from about 1.5 hours to about 12 hours, or from about 2 hours to about 10 hours. In certain embodiments, the material is sonicated for a pre-determined time, and then allowed to stand for a second pre-determined time before sonicating again.

Figure 13:
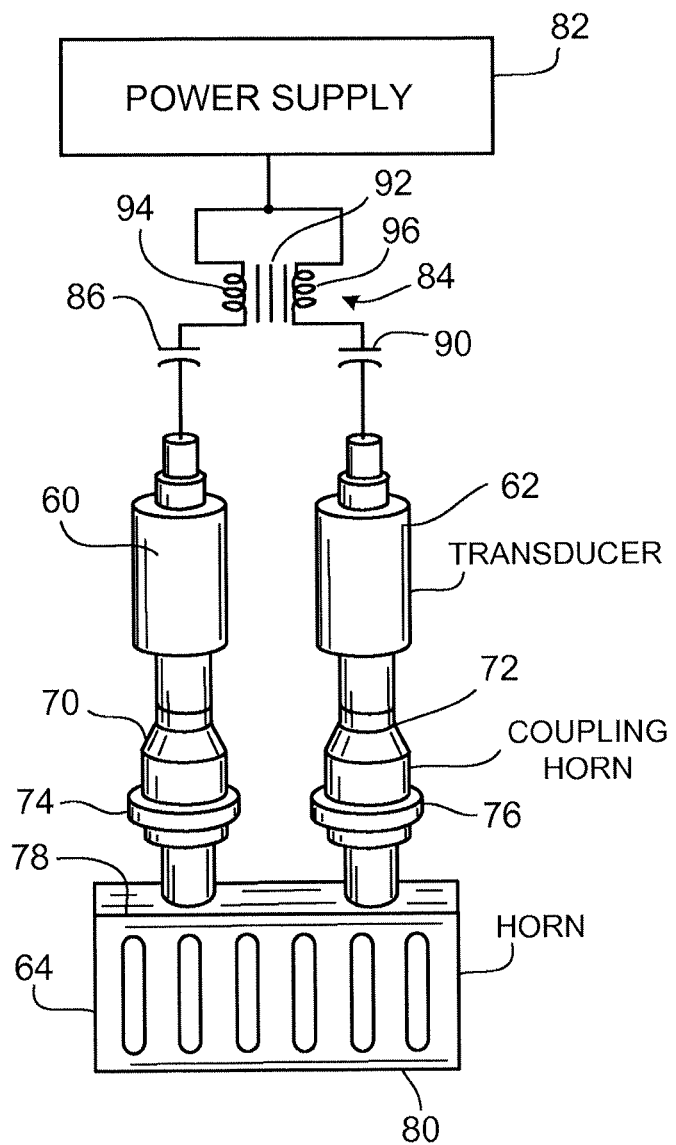
FIG. 13 is a schematic view of a sonicator having two transducers coupled to a single horn.

Referring now to FIG. 13, in some embodiments, two electro-acoustic transducers are mechanically coupled to a single horn. As shown, a pair of piezoelectric transducers 60 and 62 is coupled to a slotted bar horn 64 by respective intermediate coupling horns 70 and 72, the latter also being known as booster horns. The mechanical vibrations provided by the transducers, responsive to high frequency electrical energy applied thereto, are transmitted to the respective coupling horns, which can be constructed to provide a mechanical gain, such as a ratio of 1 to 1.2. The horns are provided with a respective mounting flange 74 and 76 for supporting the transducer and horn assembly in a stationary housing.

The vibrations transmitted from the transducers through the coupling or booster horns are coupled to the input surface 78 of the horn and are transmitted through the horn to the oppositely disposed output surface 80, which, during operation, is in forced engagement with a workpiece (not shown) to which the vibrations are applied.

The high frequency electrical energy provided by the power supply 82 is fed to each of the transducers, electrically connected in parallel, via a balancing transformer 84 and a respective series connected capacitor 86 and 90, one capacitor connected in series with the electrical connection to each of the transducers. The balancing transformer is known also as "balun" standing for "balancing unit." The balancing transformer includes a magnetic core 92 and a pair of identical windings 94 and 96, also termed the primary winding and secondary winding, respectively.

In some embodiments, the transducers include commercially available piezoelectric transducers, such as Branson Ultrasonics Corporation models 105 or 502, each designed for operation at 20 kHz and a maximum power rating of 3 kW. The energizing voltage for providing maximum motional excursion at the output surface of the transducer is 930 volt rms. The current flow through a transducer can vary between zero and 3.5 ampere depending on the load impedance. At 930 volt rms the output motion is approximately 20 microns. The maximum difference in terminal voltage for the same motional amplitude, therefore, can be 186 volt. Such a voltage difference can give rise to large circulating currents flowing between the transducers. The balancing unit 430 assures a balanced condition by providing equal current flow through the transducers, hence eliminating the possibility of circulating currents. The wire size of the windings must be selected for the full load current noted above and the maximum voltage appearing across a winding input is 93 volt.

As an alternative to using ultrasonic energy, high-frequency, rotor-stator devices can be utilized. This type of device produces high-shear, microcavitation forces, which can disintegrate biomass in contact with such forces. Two commercially available high-frequency, rotor-stator dispersion devices are the Supraton™ devices, manufactured by Krupp Industrietechnik GmbH and marketed by Dorr-Oliver Deutschland GmbH of Connecticut, and the Dispax™ devices manufactured and marketed by Ika-Works, Inc. of Cincinnati, Ohio. Operation of such a microcavitation device is discussed in Stuart, U.S. Pat. No. 5,370,999.

While ultrasonic transducer 1226 has been described as including one or more piezoelectric active elements to create ultrasonic energy, other arrangements are possible. In some embodiments, ultrasonic transducer 1226 includes active elements made of other types of magnetostrictive materials (e.g., ferrous metals). Design and operation of such a high-powered ultrasonic transducer is discussed in Hansen et al., U.S. Pat. No. 6,624,539. In some embodiments, ultrasonic energy is transferred to process stream 16 through an electro-hydraulic system.

While ultrasonic transducer 1226 has been described as using the electromagnetic response of magnetorestrictive materials to produce ultrasonic energy, other arrangements are possible. In some embodiments, acoustic energy in the form of an intense shock wave can be applied directly to process stream 16 using an underwater spark. In some embodiments, ultrasonic energy is transferred to process stream 16 through a thermo-hydraulic system. For example, acoustic waves of high energy density can be produced by applying power across an enclosed volume of electrolyte, thereby heating the enclosed volume and producing a pressure rise that is subsequently transmitted through a sound propagation medium (e.g., process stream 1216). Design and operation of such a thermo-hydraulic transducer is discussed in Hartmann et al., U.S. Pat. No. 6,383,152.

Pyrolysis

One or more pyrolysis treatment sequences can be used to process biomass from a wide variety of different sources to extract useful substances from the biomass, and to provide partially degraded organic material which functions as input to further processing steps and/or sequences.

Referring again to the general schematic in FIG. 8, a first biomass material 2 that includes having a first number average molecular weight ($^TM_{N1}$) is pyrolyzed, e.g., by heating the first material in a tube furnace, to provide a second material 3 that includes cellulose having a second number average molecular weight ($^TM_{N2}$) lower than the first number average molecular weight. The second material (or the first and second material in certain embodiments) is/are combined with a microorganism (e.g., a bacterium or a yeast) that can utilize the second and/or first material to produce a product 5 that.

Since the second biomass material has cellulose having a reduced molecular weight relative to the first material, and in some instances, a reduced crystallinity as well, the second material is generally more dispersible, swellable and/or soluble in a solution containing the microorganism, e.g., at a concentration of greater than $10^6$ microorganisms/mL. These properties make the second material 3 more susceptible to chemical, enzymatic and/or microbial attack relative to the first material 2, which can greatly improve the production rate and/or production level of a desired product, e.g., ethanol. Pyrolysis can also sterilize the first and second materials.

In some embodiments, the second number average molecular weight ($^T M_{N2}$) is lower than the first number average molecular weight ($^T M_{N1}$) by more than about 10 percent, e.g., 15, 20, 25, 30, 35, 40, 50 percent, 60 percent, or even more than about 75 percent.

In some instances, the second material has cellulose that has a crystallinity ($^T C_2$) that is lower than the crystallinity ($^T C_1$) of the cellulose of the first material. For example, ($^T C_2$) can be lower than ($^T M_1$) by more than about 10 percent, e.g., 15, 20, 25, 30, 35, 40, or even more than about 50 percent.

In some embodiments, the starting crystallinity (prior to pyrolysis) is from about 40 to about 87.5 percent, e.g., from about 50 to about 75 percent or from about 60 to about 70 percent, and the crystallinity index after pyrolysis is from about 10 to about 50 percent, e.g., from about 15 to about 45 percent or from about 20 to about 40 percent. However, in certain embodiments, e.g., after extensive pyrolysis, it is possible to have a crystallinity index of lower than 5 percent. In some embodiments, the material after pyrolysis is substantially amorphous.

In some embodiments, the starting number average molecular weight (prior to pyrolysis) is from about 200,000 to about 3,200,000, e.g., from about 250,000 to about 1,000,000 or from about 250,000 to about 700,000, and the number average molecular weight after pyrolysis is from about 50,000 to about 200,000, e.g., from about 60,000 to about 150,000 or from about 70,000 to about 125,000. However, in some embodiments, e.g., after extensive pyrolysis, it is possible to have a number average molecular weight of less than about 10,000 or even less than about 5,000.

In some embodiments, the second material can have a level of oxidation ($^T O_2$) that is higher than the level of oxidation ($^T O_1$) of the first material. A higher level of oxidation of the material can aid in its dispersibility, swellability and/or solubility, further enhancing the materials susceptibility to chemical, enzymatic or microbial attack. In some embodiments, to increase the level of the oxidation of the second material relative to the first material, the pyrolysis is performed in an oxidizing environment, producing a second material that is more oxidized than the first material. For example, the second material can have more hydroxyl groups, aldehyde groups, ketone groups, ester groups or carboxylic acid groups, which can increase its hydrophilicity.

In some embodiments, the pyrolysis of the materials is continuous. In other embodiments, the material is pyrolyzed for a pre-determined time, and then allowed to cool for a second pre-determined time before pyrolyzing again.

Pyrolysis Systems

Figure 14:
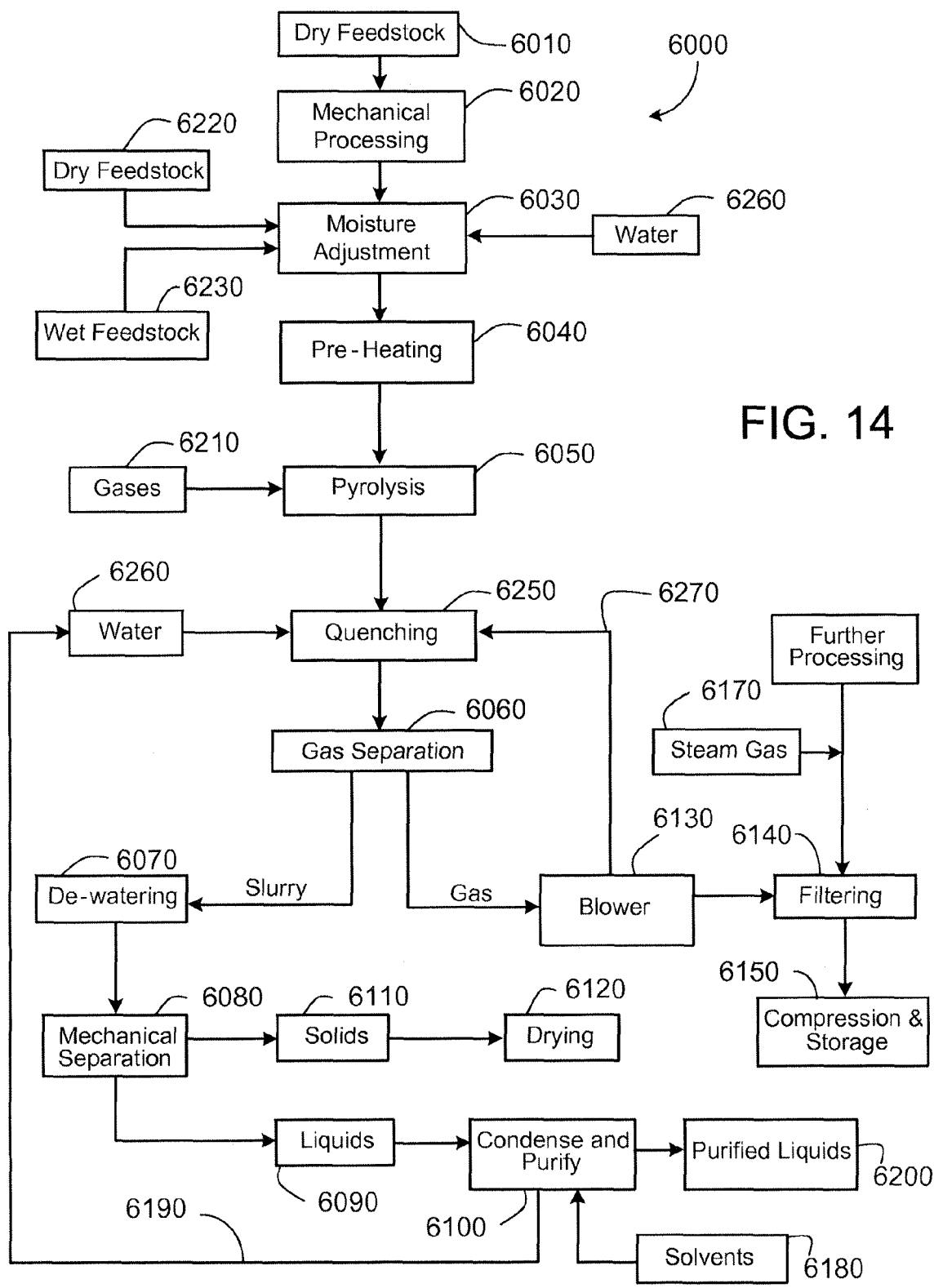
FIG. 14 is a block diagram illustrating a pyrolytic feedstock pretreatment system.

FIG. 14 shows a process flow diagram 6000 that includes various steps in a pyrolytic feedstock pretreatment system. In first step 6010, a supply of dry feedstock is received from a feed source.

As described above, the dry biomass from the feed source can be pre-processed prior to delivery to the pyrolysis chamber. For example, if the biomass is derived from plant sources, certain portions of the plant material can be removed prior to collection of the plant material and/or before the plant material is delivered by the feedstock transport device. Alternatively, or in addition, the biomass feedstock can be subjected to mechanical processing 6020 (e.g., to reduce the average length of fibers in the feedstock) prior to delivery to the pyrolysis chamber.

Following mechanical processing, the biomass undergoes a moisture adjustment step 6030. The nature of the moisture adjustment step depends upon the moisture content of the mechanically processed biomass. Typically, pyrolysis of biomass occurs most efficiently when the moisture content of the feedstock is between about 10% and about 30% (e.g., between 15% and 25%) by weight of the feedstock. If the moisture content of the feedstock is larger than about 40% by weight, the extra thermal load presented by the water content of the biomass increases the energy consumption of subsequent pyrolysis steps.

In some embodiments, if the biomass has a moisture content which is larger than about 30% by weight, drier biomass material 6220, which has a low moisture content, can be blended in, creating a feedstock mixture in step 6030 with an average moisture content that is within the limits discussed above. In certain embodiments, biomass with a high moisture content can simply be dried by dispersing the biomass material on a moving conveyor that cycles the biomass through an in-line heating unit. The heating unit evaporates a portion of the water present in the feedstock.

In some embodiments, if the biomass from step 6020 has a moisture content which is too low (e.g., lower than about 10% by weight), the mechanically processed biomass can be combined with wetter feedstock material 6230 with a higher moisture content, such as sewage sludge. Alternatively, or in addition, water 6240 can be added to the dry biomass from step 6020 to increase its moisture content.

In step 6040, the biomass—now with its moisture content adjusted to fall within suitable limits—can be preheated in an optional preheating step 6040. Treatment step 6040 can be used to increase the temperature of the biomass to between 75° C. and 150° C. in preparation for subsequent pyrolysis of the biomass. Depending upon the nature of the biomass and the particular design of the pyrolysis chamber, preheating the biomass can ensure that heat distribution within the biomass feedstock remains more uniform during pyrolysis, and can reduce the thermal load on the pyrolysis chamber.

The feedstock is then transported to a pyrolysis chamber to undergo pyrolysis in step 6050. In some embodiments, transport of the feedstock is assisted by adding one or more pressurized gases 6210 to the feedstock stream. The gases create a pressure gradient in a feedstock transport conduit, propelling the feedstock into the pyrolysis chamber (and even through the pyrolysis chamber). In certain embodiments, transport of the feedstock occurs mechanically; that is, a transport system that includes a conveyor such as an auger transports the feedstock to the pyrolysis chamber.

Other gases 6210 can also be added to the feedstock prior to the pyrolysis chamber. In some embodiments, for example, one or more catalyst gases can be added to the feedstock to assist decomposition of the feedstock during pyrolysis. In certain embodiments, one or more scavenging agents can be added to the feedstock to trap volatile materials released during pyrolysis. For example, various sulfur-based compounds such as sulfides can be liberated during pyrolysis, and an agent such as hydrogen gas can be added to the feedstock to cause desulfurization of the pyrolysis products. Hydrogen combines with sulfides to form hydrogen sulfide gas, which can be removed from the pyrolyzed feedstock.

Pyrolysis of the feedstock within the chamber can include heating the feedstock to relatively high temperatures to cause partial decomposition of the feedstock. Typically, the feedstock is heated to a temperature in a range from 150° C. to 1100° C. The temperature to which the feedstock is heated depends upon a number of factors, including the composition of the feedstock, the feedstock average particle size, the moisture content, and the desired pyrolysis products. For many types of biomass feedstock, for example, pyrolysis temperatures between 300° C. and 550° C. are used.

The residence time of the feedstock within the pyrolysis chamber generally depends upon a number of factors, including the pyrolysis temperature, the composition of the feedstock, the feedstock average particle size, the moisture content, and the desired pyrolysis products. In some embodiments, feedstock materials are pyrolyzed at a temperature just above the decomposition temperature for the material in an inert atmosphere, e.g., from about 2° C. above to about 10° C. above the decomposition temperature or from about 3° C. above to about 7° C. above the decomposition temperature. In such embodiments, the material is generally kept at this temperature for greater than 0.5 hours, e.g., greater than 1.0 hours or greater than about 2.0 hours. In other embodiments, the materials are pyrolyzed at a temperature well above the decomposition temperature for the material in an inert atmosphere, e.g., from about 75° C. above to about 175° C. above the decomposition temperature or from about 85° C. above to about 150° C. above the decomposition temperature. In such embodiments, the material is generally kept at this temperature for less than 0.5 hour, e.g., less 20 minutes, less than 10 minutes, less than 5 minutes or less than 2 minutes. In still other embodiments, the materials are pyrolyzed at an extreme temperature, e.g., from about 200° C. above to about 500° C. above the decomposition temperature of the material in an inert environment or from about 250° C. above to about 400° C. above the decomposition temperature. In such embodiments, the material us generally kept at this temperature for less than 1 minute, e.g., less than 30 seconds, less than 15 seconds, less than 10 seconds, less than 5 seconds, less than 1 second or less than 500 ms. Such embodiments are typically referred to as flash pyrolysis.

In some embodiments, the feedstock is heated relatively rapidly to the selected pyrolysis temperature within the chamber. For example, the chamber can be designed to heat the feedstock at a rate of between 500° C./s and 11,000° C./s. Typical heating rates for biomass-derived feedstock material are from 500° C./s to 1000° C./s, for example.

A turbulent flow of feedstock material within the pyrolysis chamber is usually advantageous, as it ensures relatively efficient heat transfer to the feedstock material from the heating sub-system. Turbulent flow can be achieved by blowing the feedstock material through the chamber using one or more injected carrier gases 6210, for example. In general, the carrier gases are relatively inert towards the feedstock material, even at the high temperatures in the pyrolysis chamber. Exemplary carrier gases include, for example, nitrogen, argon, methane, carbon monoxide, and carbon dioxide. Alternatively, or in addition, mechanical transport systems such as augers can transport and circulate the feedstock within the pyrolysis chamber to create a turbulent feedstock flow.

In some embodiments, pyrolysis of the feedstock occurs substantially in the absence of oxygen and other reactive gases. Oxygen can be removed from the pyrolysis chamber by periodic purging of the chamber with high pressure nitrogen (e.g., at nitrogen pressures of 2 bar or more). Following purging of the chamber, a gas mixture present in the pyrolysis chamber (e.g., during pyrolysis of the feedstock) can include less than 4 mole % oxygen (e.g., less than 1 mole % oxygen, and even less than 0.5 mole % oxygen). The absence of oxygen ensures that ignition of the feedstock does not occur at the elevated pyrolysis temperatures.

In certain embodiments, relatively small amounts of oxygen can be introduced into the feedstock and are present during pyrolysis. This technique is referred to as oxidative pyrolysis. Typically, oxidative pyrolysis occurs in multiple heating stages. For example, in a first heating stage, the feedstock is heated in the presence of oxygen to cause partial oxidation of the feedstock. This stage consumes the available oxygen in the pyrolysis chamber. Then, in subsequent heating stages, the feedstock temperature is further elevated. With all of the oxygen in the chamber consumed, however, feedstock combustion does not occur, and combustion-free pyrolytic decomposition of the feedstock (e.g., to generate hydrocarbon products) occurs. In general, the process of heating feedstock in the pyrolysis chamber to initiate decomposition is endothermic. However, in oxidative pyrolysis, formation of carbon dioxide by oxidation of the feedstock is an exothermic process. The heat released from carbon dioxide formation can assist further pyrolysis heating stages, thereby lessening the thermal load presented by the feedstock.

In some embodiments, pyrolysis occurs in an inert environment, such as while feedstock materials are bathed in argon or nitrogen gas. In certain embodiments, pyrolysis can occur in an oxidizing environment, such as in air or argon enriched in air. In some embodiments, pyrolysis can take place in a reducing environment, such as while feedstock materials are bathed in hydrogen gas. To aid pyrolysis, various chemical agents, such as oxidants, reductants, acids or bases can be added to the material prior to or during pyrolysis. For example, sulfuric acid can be added, or a peroxide (e.g., benzoyl peroxide) can be added.

As discussed above, a variety of different processing conditions can be used, depending upon factors such as the feedstock composition and the desired pyrolysis products. For example, for cellulose-containing feedstock material, relatively mild pyrolysis conditions can be employed, including flash pyrolysis temperatures between 375° C. and 450° C., and residence times of less than 1 second. As another example, for organic solid waste material such as sewage sludge, flash pyrolysis temperatures between 500° C. and 650° C. are typically used, with residence times of between 0.5 and 3 seconds. In general, many of the pyrolysis process parameters, including residence time, pyrolysis temperature, feedstock turbulence, moisture content, feedstock composition, pyrolysis product composition, and additive gas composition can be regulated automatically by a system of regulators and an automated control system.

Following pyrolysis step 6050, the pyrolysis products undergo a quenching step 6250 to reduce the temperature of the products prior to further processing. Typically, quenching step 6250 includes spraying the pyrolysis products with streams of cooling water 6260. The cooling water also forms a slurry that includes solid, undissolved product material and various dissolved products. Also present in the product stream is a mixture that includes various gases, including product gases, carrier gases, and other types of process gases.

The product stream is transported via in-line piping to a gas separator that performs a gas separation step 6060, in which product gases and other gases are separated from the slurry formed by quenching the pyrolysis products. The separated gas mixture is optionally directed to a blower 6130, which increases the gas pressure by blowing air into the mixture. The gas mixture can be subjected to a filtration step 6140, in which the gas mixture passes through one or more filters (e.g., activated charcoal filters) to remove particulates and other impurities. In a subsequent step 6150, the filtered gas can be compressed and stored for further use. Alternatively, the filtered gas can be subjected to further processing steps 6160. For example, in some embodiments, the filtered gas can be condensed to separate different gaseous compounds within the gas mixture. The different compounds can include, for example, various hydrocarbon products (e.g., alcohols, alkanes, alkenes, alkynes, ethers) produced during pyrolysis. In certain embodiments, the filtered gas containing a mixture of hydrocarbon components can be combined with steam gas 6170 (e.g., a mixture of water vapor and oxygen) and subjected to a cracking process to reduce molecular weights of the hydrocarbon components.

In some embodiments, the pyrolysis chamber includes heat sources that burn hydrocarbon gases such as methane, propane, and/or butane to heat the feedstock. A portion 6270 of the separated gases can be recirculated into the pyrolysis chamber for combustion, to generate process heat to sustain the pyrolysis process.

In certain embodiments, the pyrolysis chamber can receive process heat that can be used to increase the temperature of feedstock materials. For example, irradiating feedstock with radiation (e.g., gamma radiation, electron beam radiation, or other types of radiation) can heat the feedstock materials to relatively high temperatures. The heated feedstock materials can be cooled by a heat exchange system that removes some of the excess heat from the irradiated feedstock. The heat exchange system can be configured to transport some of the heat energy to the pyrolysis chamber to heat (or pre-heat) feedstock material, thereby reducing energy cost for the pyrolysis process.

The slurry containing liquid and solid pyrolysis products can undergo an optional de-watering step 6070, in which excess water can be removed from the slurry via processes such as mechanical pressing and evaporation. The excess water 6280 can be filtered and then recirculated for further use in quenching the pyrolysis decomposition products in step 6250.

The de-watered slurry then undergoes a mechanical separation step 6080, in which solid product material 6110 is separated from liquid product material 6090 by a series of increasingly fine filters. In step 6100, the liquid product material 6090 can then be condensed (e.g., via evaporation) to remove waste water 6190, and purified by processes such as extraction. Extraction can include the addition of one or more organic solvents 6180, for example, to separate products such as oils from products such as alcohols. Suitable organic solvents include, for example, various hydrocarbons and halo-hydrocarbons. The purified liquid products 6200 can then be subjected to further processing steps. Waste water 6190 can be filtered if necessary, and recirculated for further use in quenching the pyrolysis decomposition products in step 6250.

After separation in step 6080, the solid product material 6110 is optionally subjected to a drying step 6120 that can include evaporation of water. Solid material 6110 can then be stored for later use, or subjected to further processing steps, as appropriate.

The pyrolysis process parameters discussed above are exemplary. In general, values of these parameters can vary widely according to the nature of the feedstock and the desired products. Moreover, a wide variety of different pyrolysis techniques, including using heat sources such as hydrocarbon flames and/or furnaces, infrared lasers, microwave heaters, induction heaters, resistive heaters, and other heating devices and configurations can be used.

A wide variety of different pyrolysis chambers can be used to decompose the feedstock. In some embodiments, for example, pyrolyzing feedstock can include heating the material using a resistive heating member, such as a metal filament or metal ribbon. The heating can occur by direct contact between the resistive heating member and the material.

In certain embodiments, pyrolyzing can include heating the material by induction, such as by using a Currie-Point pyrolyzer. In some embodiments, pyrolyzing can include heating the material by the application of radiation, such as infrared radiation. The radiation can be generated by a laser, such as an infrared laser.

In certain embodiments, pyrolyzing can include heating the material with a convective heat. The convective heat can be generated by a flowing stream of heated gas. The heated gas can be maintained at a temperature of less than about 1200° C., such as less than 1000° C., less than 750° C., less than 600° C., less than 400° C. or even less than 300° C. The heated gas can be maintained at a temperature of greater than about 250° C. The convective heat can be generated by a hot body surrounding the first material, such as in a furnace.

In some embodiments, pyrolyzing can include heating the material with steam at a temperature above about 250° C.

Figure 15:
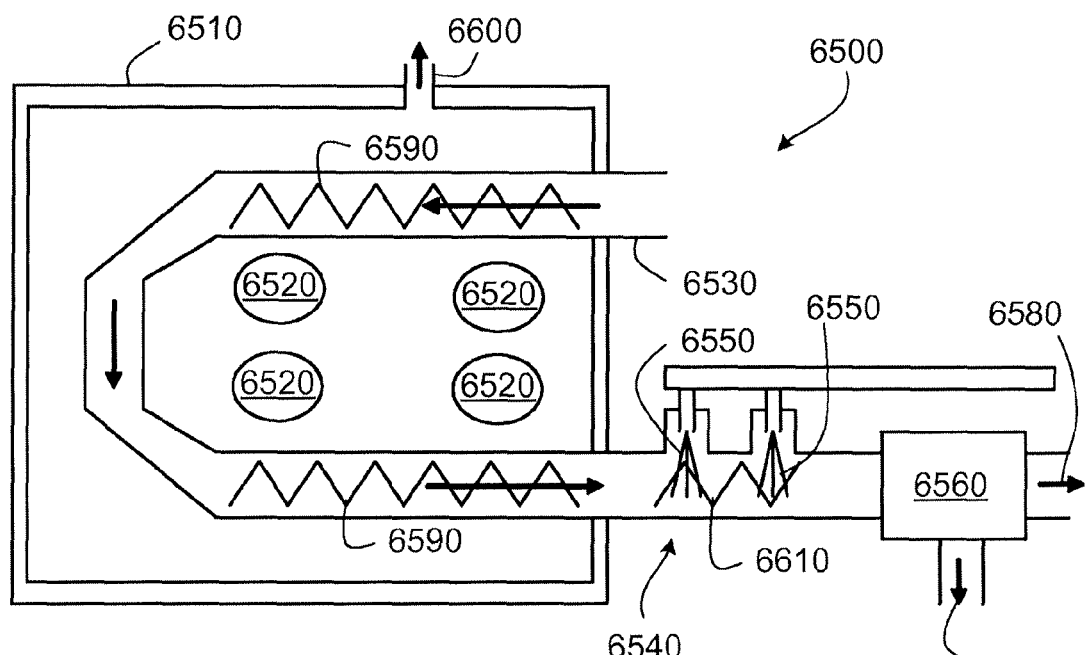
FIG. 15 is a cross-sectional side view of a pyrolysis chamber.

An embodiment of a pyrolysis chamber is shown in FIG. 15. Chamber 6500 includes an insulated chamber wall 6510 with a vent 6600 for exhaust gases, a plurality of burners 6520 that generate heat for the pyrolysis process, a transport duct 6530 for transporting the feedstock through chamber 6500, augers 6590 for moving the feedstock through duct 6530 in a turbulent flow, and a quenching system 6540 that includes an auger 6610 for moving the pyrolysis products, water jets 6550 for spraying the pyrolysis products with cooling water, and a gas separator for separating gaseous products 6580 from a slurry 6570 containing solid and liquid products.

Figure 16:
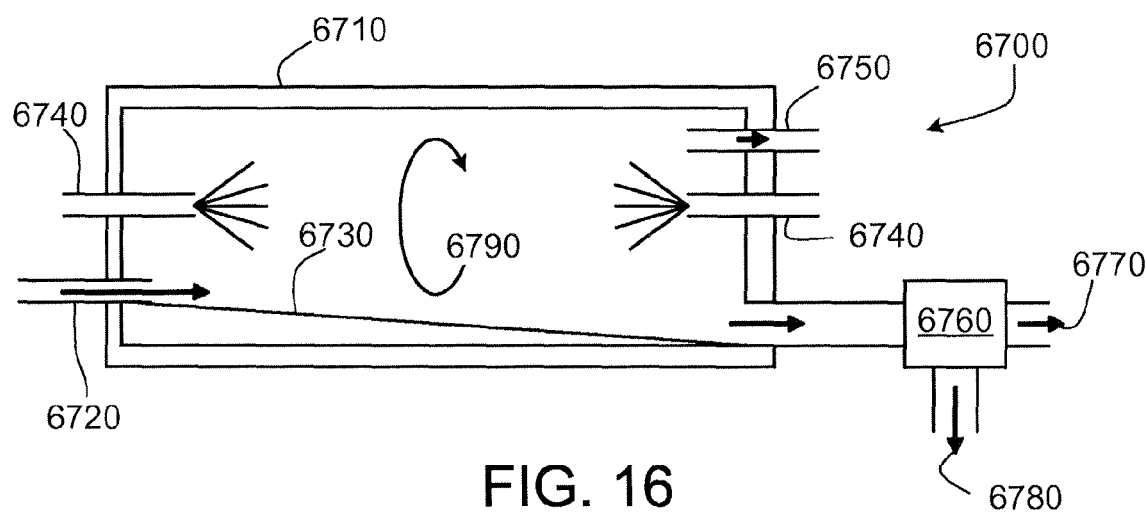
FIG. 16 is a cross-sectional side view of a pyrolysis chamber.

Another embodiment of a pyrolysis chamber is shown in FIG. 16. Chamber 6700 includes an insulated chamber wall 6710, a feedstock supply duct 6720, a sloped inner chamber wall 6730, burners 6740 that generate heat for the pyrolysis process, a vent 6750 for exhaust gases, and a gas separator 6760 for separating gaseous products 6770 from liquid and solid products 6780. Chamber 6700 is configured to rotate in the direction shown by arrow 6790 to ensure adequate mixing and turbulent flow of the feedstock within the chamber.

Figure 17:
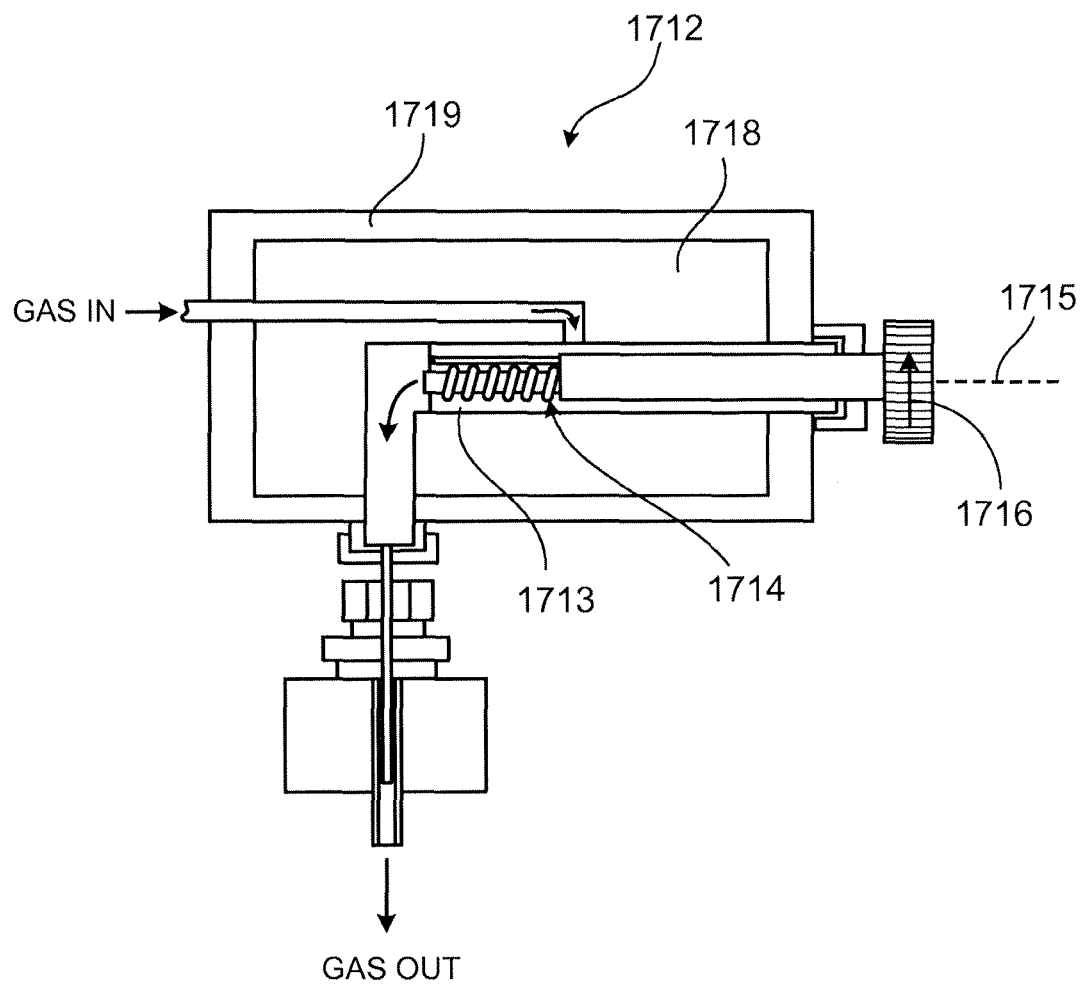
FIG. 17 is a cross-sectional side view of a pyrolyzer that includes a heated filament.

A further embodiment of a pyrolysis chamber is shown in FIG. 17. Filament pyrolyzer 1712 includes a sample holder 1713 with resistive heating element 1714 in the form of a wire winding through the open space defined by the sample holder 1713. Optionally, the heated element can be spun about axis 1715 (as indicated by arrow 1716) to tumble the material that includes the cellulosic material in sample holder 1713. The space 1718 defined by enclosure 1719 is maintained at a temperature above room temperature, e.g., 200 to 250° C. In a typical usage, a carrier gas, e.g., an inert gas, or an oxidizing or reducing gas, traverses through the sample holder 1713 while the resistive heating element is rotated and heated to a desired temperature, e.g., 325° C. After an appropriate time, e.g., 5 to 10 minutes, the pyrolyzed material is emptied from the sample holder. The system shown in FIG. 17 can be scaled and made continuous. For example, rather than a wire as the heating member, the heating member can be an auger screw. Material can continuously fall into the sample holder, striking a heated screw that pyrolizes the material. At the same time, the screw can push the pyrolyzed material out of the sample holder to allow for the entry of fresh, unpyrolyzed material.

Figure 18:
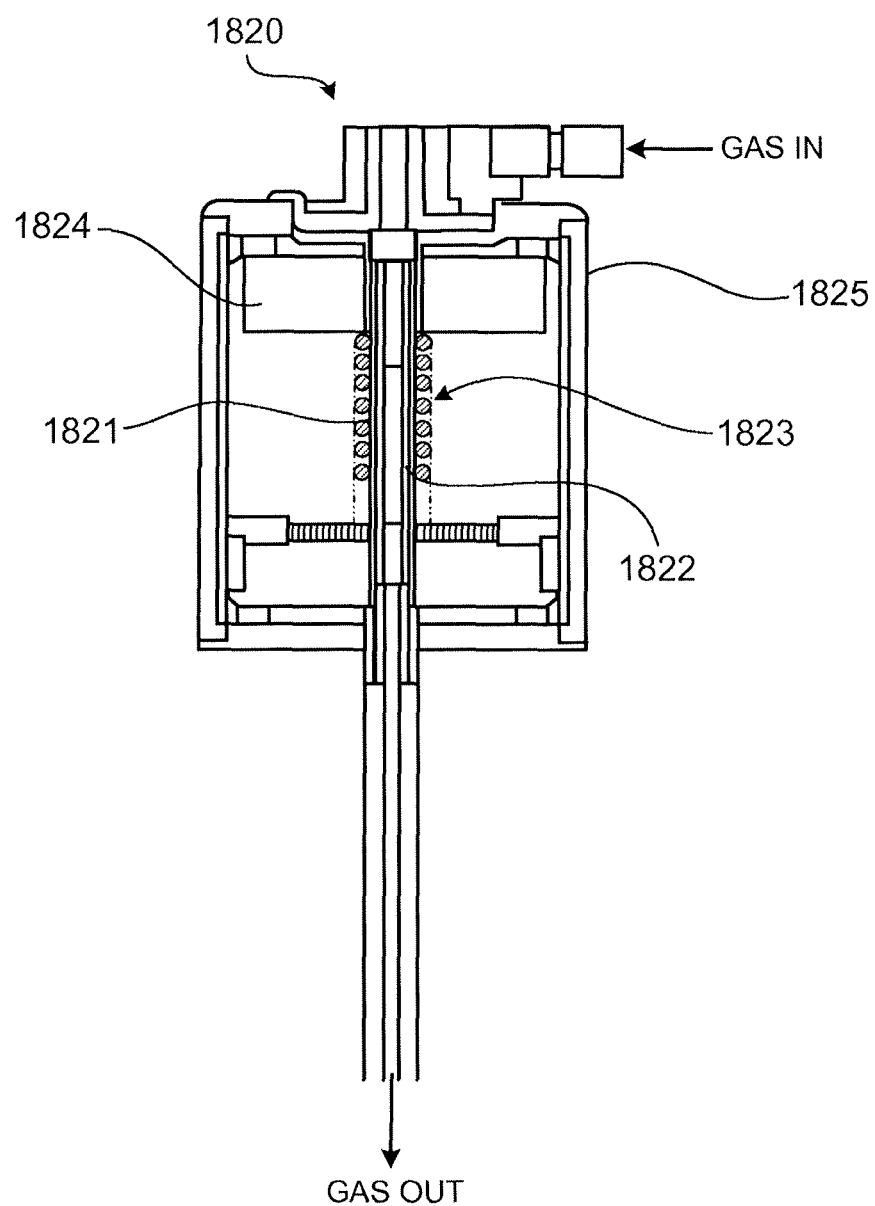
FIG. 18 is a schematic cross-sectional side view of a Curie-Point pyrolyzer.

Another embodiment of a pyrolysis chamber is shown in FIG. 18, which features a Curie-Point pyrolyzer 1820 that includes a sample chamber 1821 housing a ferromagnetic foil 1822. Surrounding the sample chamber 1821 is an RF coil 1823. The space 1824 defined by enclosure 1825 is maintained at a temperature above room temperature, e.g., 200 to 250° C. In a typical usage, a carrier gas traverses through the sample chamber 1821 while the foil 1822 is inductively heated by an applied RF field to pyrolize the material at a desired temperature.

Figure 19:
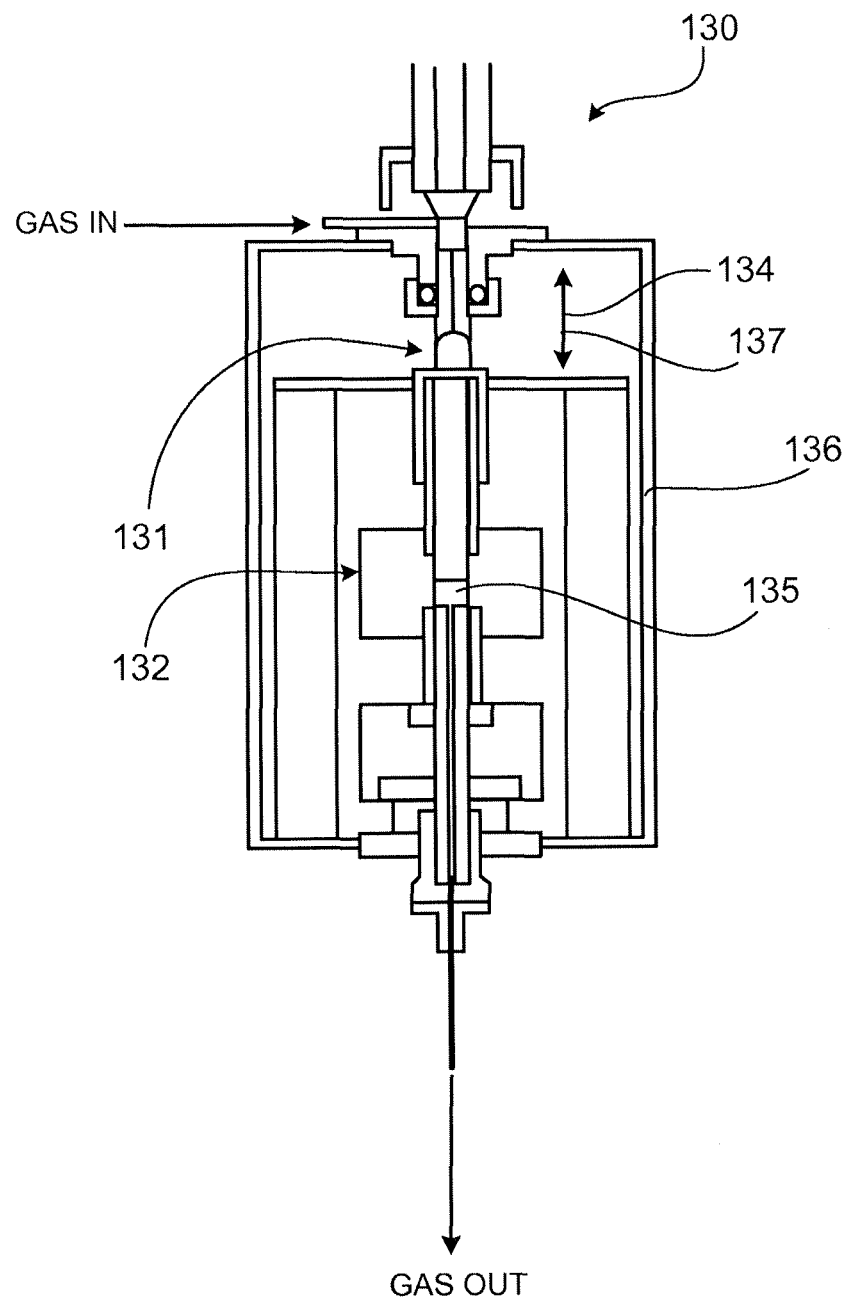
FIG. 19 is a schematic cross-sectional side view of a furnace pyrolyzer.

Yet another embodiment of a pyrolysis chamber is shown in FIG. 19. Furnace pyrolyzer 130 includes a movable sample holder 131 and a furnace 132. In a typical usage, the sample is lowered (as indicated by arrow 137) into a hot zone 135 of furnace 132, while a carrier gas fills the housing 136 and traverses through the sample holder 131. The sample is heated to the desired temperature for a desired time to provide a pyrolyzed product. The pyrolyzed product is removed from the pyrolyzer by raising the sample holder (as indicated by arrow 134).

Figure 20:
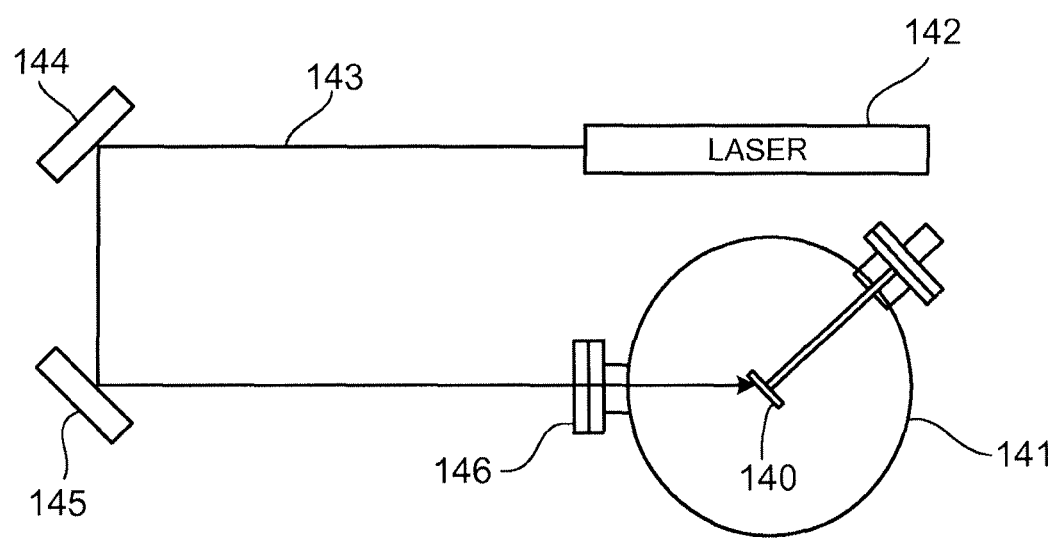
FIG. 20 is a schematic cross-sectional top view of a laser pyrolysis apparatus.

In certain embodiments, as shown in FIG. 20, a cellulosic target 140 can be pyrolyzed by treating the target, which is housed in a vacuum chamber 141, with laser light, e.g., light having a wavelength of from about 225 nm to about 1500 nm. For example, the target can be ablated at 266 nm, using the fourth harmonic of a Nd-YAG laser (Spectra Physics, GCR170, San Jose, Calif.). The optical configuration shown allows the nearly monochromatic light 143 generated by the laser 142 to be directed using mirrors 144 and 145 onto the target after passing though a lens 146 in the vacuum chamber 141. Typically, the pressure in the vacuum chamber is maintained at less than about $10^{-6}$ mm Hg. In some embodiments, infrared radiation is used, e.g., 1.06 micron radiation from a Nd-YAG laser. In such embodiments, a infrared sensitive dye can be combined with the cellulosic material to produce a cellulosic target. The infrared dye can enhance the heating of the cellulosic material. Laser ablation is described by Blanchet-Fincher et al. in U.S. Pat. No. 5,942,649.

Figure 21:
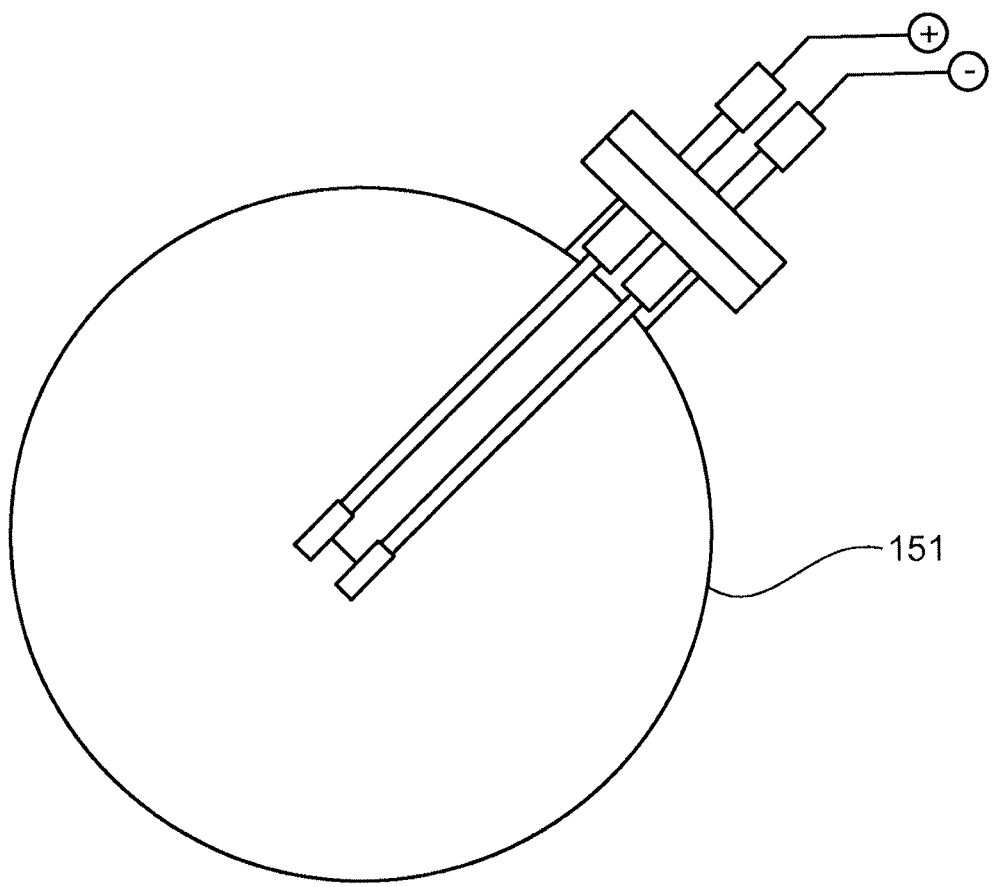
FIG. 21 is a schematic cross-sectional top view of a tungsten filament flash pyrolyzer.

Referring to FIG. 21, in some embodiments, a cellulosic material can be flash pyrolyzed by coating a tungsten filament 150, such as a 5 to 25 mil tungsten filament, with the desired cellulosic material while the material is housed in a vacuum chamber 151. To affect pyrolysis, current is passed through the filament, which causes a rapid heating of the filament for a desired time. Typically, the heating is continued for seconds before allowing the filament to cool. In some embodiments, the heating is performed a number of times to effect the desired amount of pyrolysis.

In certain embodiments, carbohydrate-containing biomass material can be heated in an absence of oxygen in a fluidized bed reactor. If desired, the carbohydrate containing biomass can have relatively thin cross-sections, and can include any of the fibrous materials described herein, for efficient heat transfer. The material can be heated by thermal transfer from a hot metal or ceramic, such as glass beads or sand in the reactor, and the resulting pyrolysis liquid or oil can be transported to a central production plant to manufacture a product.

Oxidation

One or more oxidative processing sequences can be used to process raw biomass feedstock from a wide variety of different sources to extract useful substances from the feedstock, and to provide partially degraded organic material which functions as input to further processing steps and/or sequences.

Referring again to FIG. 8, a first biomass material 2 that includes cellulose having a first number average molecular weight ($^{T}M_{N1}$) and having a first oxygen content ($^{T}O_{1}$) is oxidized, e.g., by heating the first material in a tube furnace in stream of air or oxygen-enriched air, to provide a second material 3 that includes cellulose having a second number average molecular weight ($^{T}M_{N2}$) and having a second oxygen content ($^{T}O_{2}$) higher than the first oxygen content ($^{T}O_{1}$). The second material (or the first and second material in certain embodiments) can be, e.g., combined with a material, such as a microorganism, to provide a composite 4, or another product 5. Providing a higher level of oxidation can improve dispersibility of the oxidized material, e.g., in a solvent.

Such materials can also be combined with a solid and/or a liquid. For example, the liquid can be in the form of a solution and the solid can be particulate in form. The liquid and/or solid can include a microorganism, e.g., a bacterium, and/or an enzyme. For example, the bacterium and/or enzyme can work on the cellulosic or lignocellulosic material to produce a product, such as a protein. Exemplary products are described in FIBROUS MATERIALS AND COMPOSITES," U.S. Ser. No. 11/453,951, filed Jun. 15, 2006.

In some embodiments, the second number average molecular weight is not more 97 percent lower than the first number average molecular weight, e.g., not more than 95 percent, 90, 85, 80, 75, 70, 65, 60, 55, 50, 45, 40, 30, 20, 12.5, 10.0, 7.5, 5.0, 4.0, 3.0, 2.5, 2.0 or not more than 1.0 percent lower than the first number average molecular weight. The amount of reduction of molecular weight will depend upon the application.

For example, in some embodiments the starting number average molecular weight (prior to oxidation) is from about 200,000 to about 3,200,000, e.g., from about 250,000 to about 1,000,000 or from about 250,000 to about 700,000, and the number average molecular weight after oxidation is from about 175,000 to about 3,000,000, e.g., from about 200,000 to about 750,000 or from about 225,000 to about 600,000.

Resins utilized can be thermosets or thermoplastics. Examples of thermoplastic resins include rigid and elastomeric thermoplastics. Rigid thermoplastics include polyolefins (e.g., polyethylene, polypropylene, or polyolefin copolymers), polyesters (e.g., polyethylene terephthalate), polyamides (e.g., nylon 6, 6/12 or 6/10), and polyethyleneimines. Examples of elastomeric thermoplastic resins include elastomeric styrenic copolymers (e.g., styrene-ethylene-butylene-styrene copolymers), polyamide elastomers (e.g., polyether-polyamide copolymers) and ethylene-vinyl acetate copolymer.

In particular embodiments, lignin is utilized, e.g., any lignin that is generated in any process described herein.

In some embodiments, the thermoplastic resin has a melt flow rate of between 10 g/10 minutes to 60 g/10 minutes, e.g., between 20 g/10 minutes to 50 g/10 minutes, or between 30 g/10 minutes to 45 g/10 minutes, as measured using ASTM 1238. In certain embodiments, compatible blends of any of the above thermoplastic resins can be used.

In some embodiments, the thermoplastic resin has a polydispersity index (PDI), e.g., a ratio of the weight average molecular weight to the number average molecular weight, of greater than 1.5, e.g., greater than 2.0, greater than 2.5, greater than 5.0, greater than 7.5, or even greater than 10.0.

In specific embodiments, polyolefins or blends of polyolefins are utilized as the thermoplastic resin.

Examples of thermosetting resins include natural rubber, butadiene-rubber and polyurethanes.

In some embodiments the starting number average molecular weight (prior to oxidation) is from about 200,000 to about 3,200,000, e.g., from about 250,000 to about 1,000,000 or from about 250,000 to about 700,000, and the number average molecular weight after oxidation is from about 50,000 to about 200,000, e.g., from about 60,000 to about 150,000 or from about 70,000 to about 125,000. However, in some embodiments, e.g., after extensive oxidation, it is possible to have a number average molecular weight of less than about 10,000 or even less than about 5,000.

In some embodiments, the second oxygen content is at least about five percent higher than the first oxygen content, e.g., 7.5 percent higher, 10.0 percent higher, 12.5 percent higher, 15.0 percent higher or 17.5 percent higher. In some preferred embodiments, the second oxygen content is at least about 20.0 percent higher than the oxygen content of the first material. Oxygen content is measured by elemental analysis by pyrolyzing a sample in a furnace operating 1300° C. or higher. A suitable elemental analyzer is the LECO CHNS-932 analyzer with a VTF-900 high temperature pyrolysis furnace:

In some embodiments, oxidation of first material 200 does not result in a substantial change in the crystallinity of the cellulose. However, in some instances, e.g., after extreme oxidation, the second material has cellulose that has as crystallinity ($^{T}C_2$) that is lower than the crystallinity ($^{T}C_1$) of the cellulose of the first material. For example, ($^{T}C_2$) can be lower than ($^{T}C_1$) by more than about 5 percent, e.g., 10, 15, 20, or even 25 percent. This can be desirable to enhance solubility of the materials in a liquid, such as a liquid that includes a bacterium and/or an enzyme.

In some embodiments, the starting crystallinity index (prior to oxidation) is from about 40 to about 87.5 percent, e.g., from about 50 to about 75 percent or from about 60 to about 70 percent, and the crystallinity index after oxidation is from about 30 to about 75.0 percent, e.g., from about 35.0 to about 70.0 percent or from about 37.5 to about 65.0 percent. However, in certain embodiments, e.g., after extensive oxidation, it is possible to have a crystallinity index of lower than 5 percent. In some embodiments, the material after oxidation is substantially amorphous.

Without wishing to be bound by any particular theory, it is believed that oxidation increases the number of hydrogen-bonding groups on the cellulose, such as hydroxyl groups, aldehyde groups, ketone groups carboxylic acid groups or anhydride groups, which can increase its dispersibility and/or its solubility (e.g., in a liquid). To further improve dispersibility in a resin, the resin can include a component that includes hydrogen-bonding groups, such as one or more anhydride groups, carboxylic acid groups, hydroxyl groups, amide groups, amine groups or mixtures of any of these groups. In some preferred embodiments, the component includes a polymer copolymerized with and/or grafted with maleic anhydride. Such materials are available from DuPont under the trade name FUSABOND®.

Generally, oxidation of first material 200 occurs in an oxidizing environment. For example, the oxidation can be effected or aided by pyrolysis in an oxidizing environment, such as in air or argon enriched in air. To aid in the oxidation, various chemical agents, such as oxidants, acids or bases can be added to the material prior to or during oxidation. For example, a peroxide (e.g., benzoyl peroxide) can be added prior to oxidation.

Oxidation Systems

Figure 22:
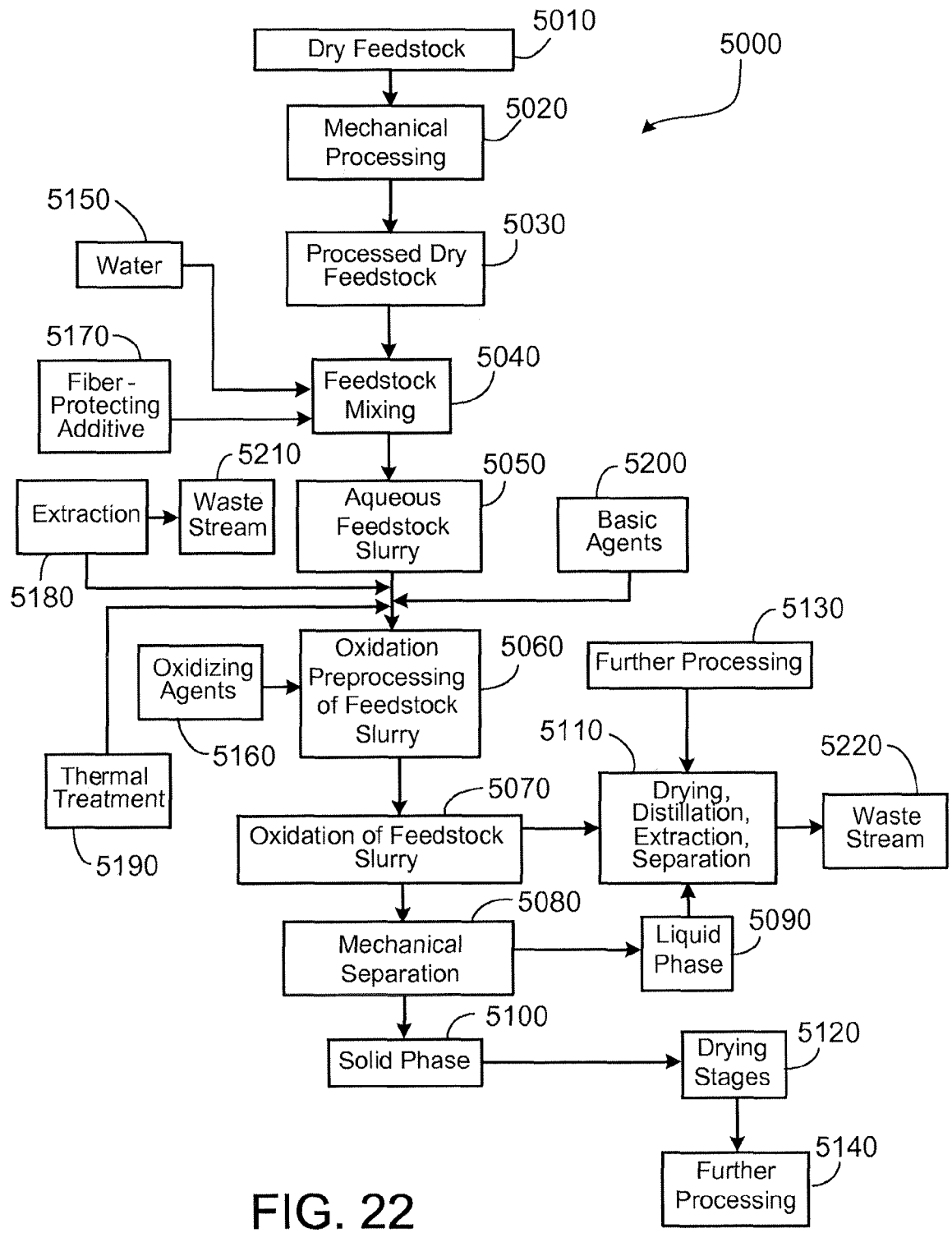
FIG. 22 is a block diagram illustrating an oxidative feedstock pretreatment system.

FIG. 22 shows a process flow diagram 5000 that includes various steps in an oxidative feedstock pretreatment system. In first step 5010, a supply of dry feedstock is received from a feed source. The feed source can include, for example, a storage bed or container that is connected to an in-line oxidation reactor via a conveyor belt or another feedstock transport device.

As described above, the dry feedstock from the feed source can be pretreated prior to delivery to the oxidation reactor. For example, if the feedstock is derived from plant sources, certain portions of the plant material can be removed prior to collection of the plant material and/or before the plant material is delivered by the feedstock transport device. Alternatively, or in addition, the biomass feedstock can be subjected to mechanical processing (e.g., to reduce the average length of fibers in the feedstock) prior to delivery to the oxidation reactor.

Following mechanical processing 5020, feedstock 5030 is transported to a mixing system which introduces water 5150 into the feedstock in a mechanical mixing process. Combining water with the processed feedstock in mixing step 5040 creates an aqueous feedstock slurry 5050, which can then be treated with one or more oxidizing agents.

Typically, one liter of water is added to the mixture for every 0.02 kg to 1.0 kg of dry feedstock. The ratio of feedstock to water in the mixture depends upon the source of the feedstock and the specific oxidizing agents used further downstream in the overall process. For example, in typical industrial processing sequences for lignocellulosic biomass, aqueous feedstock slurry 5050 includes from about 0.5 kg to about 1.0 kg of dry biomass per liter of water.

In some embodiments, one or more fiber-protecting additives 5170 can also be added to the feedstock slurry in feedstock mixing step 5040. Fiber-protecting additives help to reduce degradation of certain types of biomass fibers (e.g., cellulose fibers) during oxidation of the feedstock. Fiber-protecting additives can be used, for example, if a desired product from processing a lignocellulosic feedstock includes cellulose fibers. Exemplary fiber-protecting additives include magnesium compounds such as magnesium hydroxide. Concentrations of fiber-protecting additives in feedstock slurry 5050 can be from 0.1% to 0.4% of the dry weight of the biomass feedstock, for example.

In certain embodiments, aqueous feedstock slurry 5050 can be subjected to an optional extraction 5180 with an organic solvent to remove water-insoluble substances from the slurry. For example, extraction of slurry 5050 with one or more organic solvents yields a purified slurry and an organic waste stream 5210 that includes water-insoluble materials such as fats, oils, and other non-polar, hydrocarbon-based substances. Suitable solvents for performing extraction of slurry 5050 include various alcohols, hydrocarbons, and halo-hydrocarbons, for example.

In some embodiments, aqueous feedstock slurry 5050 can be subjected to an optional thermal treatment 5190 to further prepare the feedstock for oxidation. An example of a thermal treatment includes heating the feedstock slurry in the presence of pressurized steam. In fibrous biomass feedstock, the pressurized steam swells the fibers, exposing a larger fraction of fiber surfaces to the aqueous solvent and to oxidizing agents that are introduced in subsequent processing steps.

In certain embodiments, aqueous feedstock slurry 5050 can be subjected to an optional treatment with basic agents 5200. Treatment with one or more basic agents can help to separate lignin from cellulose in lignocellulosic biomass feedstock, thereby improving subsequent oxidation of the feedstock. Exemplary basic agents include alkali and alkaline earth hydroxides such as sodium hydroxide, potassium hydroxide, and calcium hydroxide. In general, a variety of basic agents can be used, typically in concentrations from about 0.01% to about 0.5% of the dry weight of the feedstock.

Aqueous feedstock slurry 5050 is transported (e.g., by an in-line piping system) to a chamber, which can be an oxidation preprocessing chamber or an oxidation reactor. In oxidation preprocessing step 5060, one or more oxidizing agents 5160 are added to feedstock slurry 5050 to form an oxidizing medium. In some embodiments, for example, oxidizing agents 5160 can include hydrogen peroxide. Hydrogen peroxide can be added to slurry 5050 as an aqueous solution, and in proportions ranging from 3% to between 30% and 35% by weight of slurry 5050. Hydrogen peroxide has a number of advantages as an oxidizing agent. For example, aqueous hydrogen peroxide solution is relatively inexpensive, is relatively chemically stable, is not particularly hazardous relative to other oxidizing agents (and therefore does not require burdensome handling procedures and expensive safety equipment). Moreover, hydrogen peroxide decomposes to form water during oxidation of feedstock, so that waste stream cleanup is relatively straightforward and inexpensive.

In certain embodiments, oxidizing agents 5160 can include oxygen (e.g., oxygen gas) either alone, or in combination with hydrogen peroxide. Oxygen gas can be bubbled into slurry 5050 in proportions ranging from 0.5% to 10% by weight of slurry 5050. Alternatively, or in addition, oxygen gas can also be introduced into a gaseous phase in equilibrium with slurry 5050 (e.g., a vapor head above slurry 5050). The oxygen gas can be introduced into either an oxidation preprocessing chamber or into an oxidation reactor (or into both), depending upon the configuration of the oxidative processing system. Typically, for example, the partial pressure of oxygen in the vapor above slurry 5050 is larger than the ambient pressure of oxygen, and ranges from 0.5 bar to 35 bar, depending upon the nature of the feedstock.

The oxygen gas can be introduced in pure form, or can be mixed with one or more carrier gases. For example, in some embodiments, high-pressure air provides the oxygen in the vapor. In certain embodiments, oxygen gas can be supplied continuously to the vapor phase to ensure that a concentration of oxygen in the vapor remains within certain predetermined limits during processing of the feedstock. In some embodiments, oxygen gas can be introduced initially in sufficient concentration to oxidize the feedstock, and then the feedstock can be transported to a closed, pressurized vessel (e.g., an oxidation reactor) for processing.

In certain embodiments, oxidizing agents 5160 can include nascent oxygen (e.g., oxygen radicals). Typically, nascent oxygen is produced as needed in an oxidation reactor or in a chamber in fluid communication with an oxidation reactor by one or more decomposition reactions. For example, in some embodiments, nascent oxygen can be produced from a reaction between NO and $O_2$ in a gas mixture or in solution. In certain embodiments, nascent oxygen can be produced from decomposition of HOCl in solution. Other methods by which nascent oxygen can be produced include via electrochemical generation in electrolyte solution, for example.

In general, nascent oxygen is an efficient oxidizing agent due to the relatively high reactivity of the oxygen radical. However, nascent oxygen can also be a relatively selective oxidizing agent. For example, when lignocellulosic feedstock is treated with nascent oxygen, selective oxidation of lignin occurs in preference to the other components of the feedstock such as cellulose. As a result, oxidation of feedstock with nascent oxygen provides a method for selective removal of the lignin fraction in certain feedstocks. Typically, nascent oxygen concentrations of between about 0.5% and 5% of the dry weight of the feedstock are used to effect efficient oxidation.

Without wishing to be bound by theory, it is believed that nascent oxygen reacts with lignocellulosic feedstock according to at least two different mechanisms. In a first mechanism, nascent oxygen undergoes an addition reaction with the lignin, resulting in partial oxidation of the lignin, which solubilizes the lignin in aqueous solution. As a result, the solubilized lignin can be removed from the rest of the feedstock via washing. In a second mechanism, nascent oxygen disrupts butane cross-links and/or opens aromatic rings that are connected via the butane cross-links. As a result, solubility of the lignin in aqueous solution increases, and the lignin fraction can be separated from the remainder of the feedstock via washing.

In some embodiments, oxidizing agents 5160 include ozone ($O_3$). The use of ozone can introduce several chemical-handling considerations in the oxidation processing sequence. If heated too vigorously, an aqueous solution of ozone can decompose violently, with potentially adverse consequences for both human system operators and system equipment. Accordingly, ozone is typically generated in a thermally isolated, thick-walled vessel separate from the vessel that contains the feedstock slurry, and transported thereto at the appropriate process stage.

Without wishing to be bound by theory, it is believed that ozone decomposes into oxygen and oxygen radicals, and that the oxygen radicals (e.g., nascent oxygen) are responsible for the oxidizing properties of ozone in the manner discussed above. Ozone typically preferentially oxidizes the lignin fraction in lignocellulosic materials, leaving the cellulose fraction relatively undisturbed.

Conditions for ozone-based oxidation of biomass feedstock generally depend upon the nature of the biomass. For example, for cellulosic and/or lignocellulosic feedstocks, ozone concentrations of from 0.1 $g/m^3$ to 20 $g/m^3$ of dry feedstock provide for efficient feedstock oxidation. Typically, the water content in slurry 5050 is between 10% by weight and 80% by weight (e.g., between 40% by weight and 60% by weight). During ozone-based oxidation, the temperature of slurry 5050 can be maintained between 0° C. and 100° C. to avoid violent decomposition of the ozone.

In some embodiments, feedstock slurry 5050 can be treated with an aqueous, alkaline solution that includes one or more alkali and alkaline earth hydroxides such as sodium hydroxide, potassium hydroxide, and calcium hydroxide, and then treated thereafter with an ozone-containing gas in an oxidation reactor. This process has been observed to significantly increase decomposition of the biomass in slurry 5050. Typically, for example, a concentration of hydroxide ions in the alkaline solution is between 0.001% and 10% by weight of slurry 5050. After the feedstock has been wetted via contact with the alkaline solution, the ozone-containing gas is introduced into the oxidation reactor, where it contacts and oxidizes the feedstock.

Oxidizing agents 5160 can also include other substances. In some embodiments, for example, halogen-based oxidizing agents such as chlorine and oxychlorine agents (e.g., hypochlorite) can be introduced into slurry 5050. In certain embodiments, nitrogen-containing oxidizing substances can be introduced into slurry 5050. Exemplary nitrogen-containing oxidizing substances include NO and $NO_2$, for example. Nitrogen-containing agents can also be combined with oxygen in slurry 5050 to create additional oxidizing agents. For example, NO and $NO_2$ both combine with oxygen in slurry 5050 to form nitrate compounds, which are effective oxidizing agents for biomass feedstock. Halogen- and nitrogen-based oxidizing agents can, in some embodiments, cause bleaching of the biomass feedstock, depending upon the nature of the feedstock. The bleaching can be desirable for certain biomass-derived products that are extracted in subsequent processing steps.

Other oxidizing agents can include, for example, various peroxyacids, peroxyacetic acids, persulfates, percarbonates, permanganates, osmium tetroxide, and chromium oxides.

Following oxidation preprocessing step 5060, feedstock slurry 5050 is oxidized in step 5070. If oxidizing agents 5160 were added to slurry 5050 in an oxidation reactor, then oxidation proceeds in the same reactor. Alternatively, if oxidizing agents 5160 were added to slurry 5050 in a preprocessing chamber, then slurry 5050 is transported to an oxidation reactor via an in-line piping system. Once inside the oxidation reactor, oxidation of the biomass feedstock proceeds under a controlled set of environmental conditions. Typically, for example, the oxidation reactor is a cylindrical vessel that is closed to the external environment and pressurized. Both batch and continuous operation is possible, although environmental conditions are typically easier to control in in-line batch processing operations.

Oxidation of feedstock slurry 5050 typically occurs at elevated temperatures in the oxidation reactor. For example, the temperature of slurry 5050 in the oxidation reactor is typically maintained above 100° C., in a range from 120° C. to 240° C. For many types of biomass feedstock, oxidation is particularly efficient if the temperature of slurry 5050 is maintained between 150° C. and 220° C. Slurry 5050 can be heating using a variety of thermal transfer devices. For example, in some embodiments, the oxidation reactor contacts a heating bath that includes oil or molten salts. In certain embodiments, a series of heat exchange pipes surround and contact the oxidation reactor, and circulation of hot fluid within the pipes heats slurry 5050 in the reactor. Other heating devices that can be used to heat slurry 5050 include resistive heating elements, induction heaters, and microwave sources, for example.

The residence time of feedstock slurry 5050 in the oxidation reactor can be varied as desired to process the feedstock. Typically, slurry 5050 spends from 1 minute to 60 minutes undergoing oxidation in the reactor. For relatively soft biomass material such as lignocellulosic matter, the residence time in the oxidation reactor can be from 5 minutes to 30 minutes, for example, at an oxygen pressure of between 3 and 12 bars in the reactor, and at a slurry temperature of between 160° C. and 210° C. For other types of feedstock, however, residence times in the oxidation reactor can be longer, e.g., as long 48 hours. To determine appropriate residence times for slurry 5050 in the oxidation reactor, aliquots of the slurry can be extracted from the reactor at specific intervals and analyzed to determine concentrations of particular products of interest such as complex saccharides. Information about the increase in concentrations of certain products in slurry 5050 as a function of time can be used to determine residence times for particular classes of feedstock material.

In some embodiments, during oxidation of feedstock slurry 5050, adjustment of the slurry pH can be performed by introducing one or more chemical agents into the oxidation reactor. For example, in certain embodiments, oxidation occurs most efficiently in a pH range of about 9-11. To maintain a pH in this range, agents such as alkali and alkaline earth hydroxides, carbonates, ammonia, and alkaline buffer solutions can be introduced into the oxidation reactor.

Circulation of slurry 5050 during oxidation can be important to ensure sufficient contact between oxidizing agents 5160 and the feedstock. Circulation of the slurry can be achieved using a variety of techniques. For example, in some embodiments, a mechanical stirring apparatus that includes impeller blades or a paddle wheel can be implemented in the oxidation reactor. In certain embodiments, the oxidation reactor can be a loop reactor, in which the aqueous solvent in which the feedstock is suspended is simultaneously drained from the bottom of the reactor and recirculated into the top of the reactor via pumping, thereby ensuring that the slurry is continually re-mixed and does not stagnate within the reactor.

After oxidation of the feedstock is complete, the slurry is transported to a separation apparatus where a mechanical separation step 5080 occurs. Typically, mechanical separation step 5080 includes one or more stages of increasingly fine filtering of the slurry to mechanically separate the solid and liquid constituents.

Liquid phase 5090 is separated from solid phase 5100, and the two phases are processed independently thereafter. Solid phase 5100 can optionally undergo a drying step 5120 in a drying apparatus, for example. Drying step 5120 can include, for example, mechanically dispersing the solid material onto a drying surface, and evaporating water from solid phase 5100 by gentle heating of the solid material. Following drying step 5120 (or, alternatively, without undergoing drying step 5120), solid phase 5100 is transported for further processing steps 5140.

Liquid phase 5090 can optionally undergo a drying step 5110 to reduce the concentration of water in the liquid phase. In some embodiments, for example, drying step 5110 can include evaporation and/or distillation and/or extraction of water from liquid phase 5090 by gentle heating of the liquid. Alternatively, or in addition, one or more chemical drying agents can be used to remove water from liquid phase 5090. Following drying step 5110 (or alternatively, without undergoing drying step 5110), liquid phase 5090 is transported for further processing steps 5130, which can include a variety of chemical and biological treatment steps such as chemical and/or enzymatic hydrolysis.

Drying step 5110 creates waste stream 5220, an aqueous solution that can include dissolved chemical agents such as acids and bases in relatively low concentrations. Treatment of waste stream 5220 can include, for example, pH neutralization with one or more mineral acids or bases. Depending upon the concentration of dissolved salts in waste stream 5220, the solution can be partially de-ionized (e.g., by passing the waste stream through an ion exchange system). Then, the waste stream—which includes primarily water—can be re-circulated into the overall process (e.g., as water 5150), diverted to another process, or discharged.

Typically, for lignocellulosic biomass feedstocks following separation step 5070, liquid phase 5090 includes a variety of soluble poly- and oligosaccharides, which can then be separated and/or reduced to smaller-chain saccharides via further processing steps. Solid phase 5100 typically includes primarily cellulose, for example, with smaller amounts of hemicellulose- and lignin-derived products.

In some embodiments, oxidation can be carried out at elevated temperature in a reactor such as a pyrolysis chamber. For example, referring again to FIG. 17, feedstock materials can be oxidized in filament pyrolyzer 1712. In a typical usage, an oxidizing carrier gas, e.g., air or an air/argon blend, traverses through the sample holder 1713 while the resistive heating element is rotated and heated to a desired temperature, e.g., 325° C. After an appropriate time, e.g., 5 to 10 minutes, the oxidized material is emptied from the sample holder. The system shown in FIG. 2 can be scaled and made continuous. For example, rather than a wire as the heating member, the heating member can be an auger screw. Material can continuously fall into the sample holder, striking a heated screw that pyrolizes the material. At the same time, the screw can push the oxidized material out of the sample holder to allow for the entry of fresh, unoxidized material.

Referring again to FIG. 18, feedstock materials can be oxidized in a Curie-Point pyrolyzer 1820. In a typical usage, an oxidizing carrier gas traverses through the sample chamber 1821 while the foil 1822 is inductively heated by an applied RF field to oxidize the material at a desired temperature.

Referring again to FIG. 19, feedstock materials can be oxidized in a furnace pyrolyzer 130. In a typical usage, the sample is lowered (as indicated by arrow 137) into a hot zone 135 of furnace 132, while an oxidizing carrier gas fills the housing 136 and traverses through the sample holder 131. The sample is heated to the desired temperature for a desired time to provide an oxidized product. The oxidized product is removed from the pyrolyzer by raising the sample holder (as indicated by arrow 134).

Referring again to FIG. 20, feedstock materials can be oxidized by forming a cellulosic target 140, along with an oxidant, such as a peroxide, and treating the target, which is housed in a vacuum chamber 141, with laser light, e.g., light having a wavelength of from about 225 nm to about 1600 nm. The optical configuration shown allows the monochromatic light 143 generated by the laser 142 to be directed using mirrors 144 and 145 onto the target after passing though a lens 146 in the vacuum chamber 141. Typically, the pressure in the vacuum chamber is maintained at less than about $10^{-6}$ mm Hg. In some embodiments, infrared radiation is used, e.g., 1.06 micron radiation from a Nd-YAG laser. In such embodiments, a infrared sensitive dye can be combined with the cellulosic material to produce a cellulosic target. The infrared dye can enhance the heating of the cellulosic material. Laser treatment of polymers is described by Blanchet-Fincher et al. in U.S. Pat. No. 5,942,649.

Referring again to FIG. 21, feedstock materials can be rapidly oxidized by coating a tungsten filament 150, together with an oxidant, such as a peroxide, with the desired cellulosic material while the material is housed in a vacuum chamber 151. To affect oxidation, current is passed through the filament, which causes a rapid heating of the filament for a desired time. Typically, the heating is continued for seconds before allowing the filament to cool. In some embodiments, the heating is performed a number of times to effect the desired amount of oxidation.

Referring again to FIG. 12, in some embodiments, feedstock materials can be oxidized with the aid of sound and/or cavitation. Generally, to effect oxidation, the materials are sonicated in an oxidizing environment, such as water saturated with oxygen or another chemical oxidant, such as hydrogen peroxide.

Referring again to FIGS. 9 and 10, in certain embodiments, ionizing radiation is used to aid in the oxidation of feedstock materials. Generally, to effect oxidation, the materials are irradiated in an oxidizing environment, such as air or oxygen. For example, gamma radiation and/or electron beam radiation can be employed to irradiate the materials.

Other Treatment Processes

Steam explosion can be used alone without any of the processes described herein, or in combination with any of the processes described herein.

Figure 23:
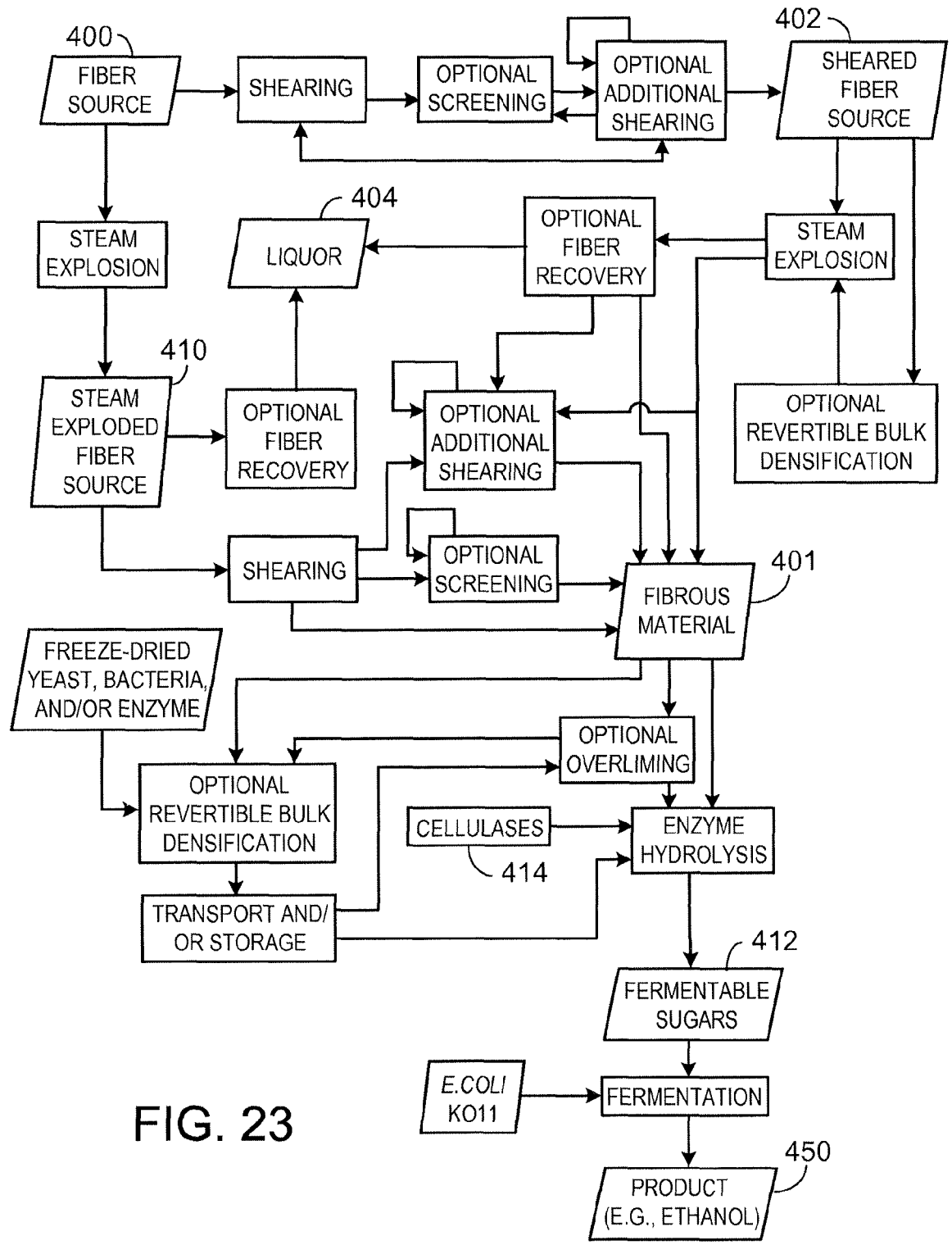
FIG. 23 is block diagram illustrating a general overview of the process of converting a fiber source into a product, e.g., ethanol.

FIG. 23 shows an overview of the entire process of converting a fiber source 400 into a product 450, such as ethanol, by a process that includes shearing and steam explosion to produce a fibrous material 401, which is then hydrolyzed and converted, e.g., fermented, to produce the product. The fiber source can be transformed into the fibrous material 401 through a number of possible methods, including at least one shearing process and at least one steam explosion process.

For example, one option includes shearing the fiber source, followed by optional screening step(s) and optional additional shearing step(s) to produce a sheared fiber source 402, which can then be steam exploded to produce the fibrous material 401. The steam explosion process is optionally followed by a fiber recovery process to remove liquids or the "liquor" 404, resulting from the steam exploding process. The material resulting from steam exploding the sheared fiber source can be further sheared by optional additional shearing step(s) and/or optional screening step(s).

In another method, the fibrous material 401 is first steam exploded to produce a steam exploded fiber source 410. The resulting steam exploded fiber source is then subjected to an optional fiber recovery process to remove liquids, or the liquor. The resulting steam exploded fiber source can then be sheared to produce the fibrous material. The steam exploded fiber source can also be subject to one or more optional screening steps and/or one or more optional additional shearing steps. The process of shearing and steam exploding the fiber source to produce the sheared and steam exploded fibrous material will be further discussed below.

The fiber source can be cut into pieces or strips of confetti material prior to shearing or steam explosion. The shearing processes can take place in a dry (e.g., having less than 0.25 percent by weight absorbed water), hydrated, or even while the material is partially or fully submerged in a liquid, such as water or isopropanol. The process can also optimally include steps of drying the output after steam exploding or shearing to allow for additional steps of dry shearing or steam exploding. The steps of shearing, screening, and steam explosion can take place with or without the presence of various chemical solutions.

In a steam explosion process, the fiber source or the sheared fiber source is contacted with steam under high pressure, and the steam diffuses into the structures of the fiber source (e.g., the lignocellulosic structures). The steam then condenses under high pressure thereby "wetting" the fiber source. The moisture in the fiber source can hydrolyze any acetyl groups in the fiber source (e.g., the acetyl groups in the hemicellulose fractions), forming organic acids such as acetic and uronic acids. The acids, in turn, can catalyze the depolymerization of hemicellulose, releasing xylan and limited amounts of glucan. The "wet" fiber source (or sheared fiber source, etc.) is then "exploded" when the pressure is released. The condensed moisture instantaneously evaporates due to the sudden decrease in pressure and the expansion of the water vapor exerts a shear force upon the fiber source (or sheared fiber source, etc.). A sufficient shear force will cause the mechanical breakdown of the internal structures (e.g., the lignocellulosic structures) of the fiber source.

The sheared and steam exploded fibrous material is then converted into a useful product, such as ethanol. One method of converting the fibrous material is by hydrolysis to produce fermentable sugars, 412, which are then fermented to produce the product. Other known and unknown methods of converting fibrous materials can also be used.

In some embodiments, prior to combining the microorganism, the sheared and steam exploded fibrous material 401 is sterilized to kill any competing microorganisms that can be on the fibrous material. For example, the fibrous material can be sterilized by exposing the fibrous material to radiation, such as infrared radiation, ultraviolet radiation, or an ionizing radiation, such as gamma radiation. The microorganisms can also be killed using chemical sterilants, such as bleach (e.g., sodium hypochlorite), chlorhexidine, or ethylene oxide.

One method to hydrolyze the sheared and steam exploded fibrous material is by the use of cellulases. Cellulases are a group of enzymes that act synergistically to hydrolyze cellulose. Commercially available Accellerase® 1000 enzyme complex, which contains a complex of enzymes that reduces lignocellulosic biomass into fermentable sugars can also be used.

According to current understanding, the components of cellulase include endoglucanases, exoglucanases (cellobiohydrolases), and b-glucosidases (cellobiases). Synergism between the cellulase components exists when hydrolysis by a combination of two or more components exceeds the sum of the activities expressed by the individual components. The generally accepted mechanism of a cellulase system (particularly of $T.$ $longibrachiatum$) on crystalline cellulose is: endoglucanase hydrolyzes internal $\beta$-1,4-glycosidic bonds of the amorphous regions, thereby increasing the number of exposed non-reducing ends. Exoglucanases then cleave off cellobiose units from the nonreducing ends, which in turn are hydrolyzed to individual glucose units by b-glucosidases. There are several configurations of both endo- and exo-glucanases differing in stereospecificities. In general, the synergistic action of the components in various configurations is required for optimum cellulose hydrolysis. Cellulases, however, are more inclined to hydrolyze the amorphous regions of cellulose. A linear relationship between crystallinity and hydrolysis rates exists whereby higher crystallinity indices correspond to slower enzyme hydrolysis rates. Amorphous regions of cellulose hydrolyze at twice the rate of crystalline regions. The hydrolysis of the sheared and steam exploded fibrous material can be performed by any hydrolyzing biomass process.

Steam explosion of biomass sometimes causes the formation of by-products, e.g., toxicants, that are inhibitory to microbial and enzymatic activities. The process of converting the sheared and steam exploded fibrous material into a product can therefore optionally include an overliming step prior to fermentation to precipitate some of the toxicants. For example, the pH of the sheared and steam exploded fibrous material can be raised to exceed the pH of 10 by adding calcium hydroxide ($Ca(OH)_2$) followed by a step of lowering the pH to about 5 by adding $H_2SO_4$. The overlimed fibrous material can then be used as is without the removal of precipitates. As shown in FIG. 23, the optional overliming step occurs just prior to the step of hydrolysis of the sheared and steam exploded fibrous material, but it is also contemplated to perform the overliming step after the hydrolysis step and prior to the fermenting step.

Figure 24:
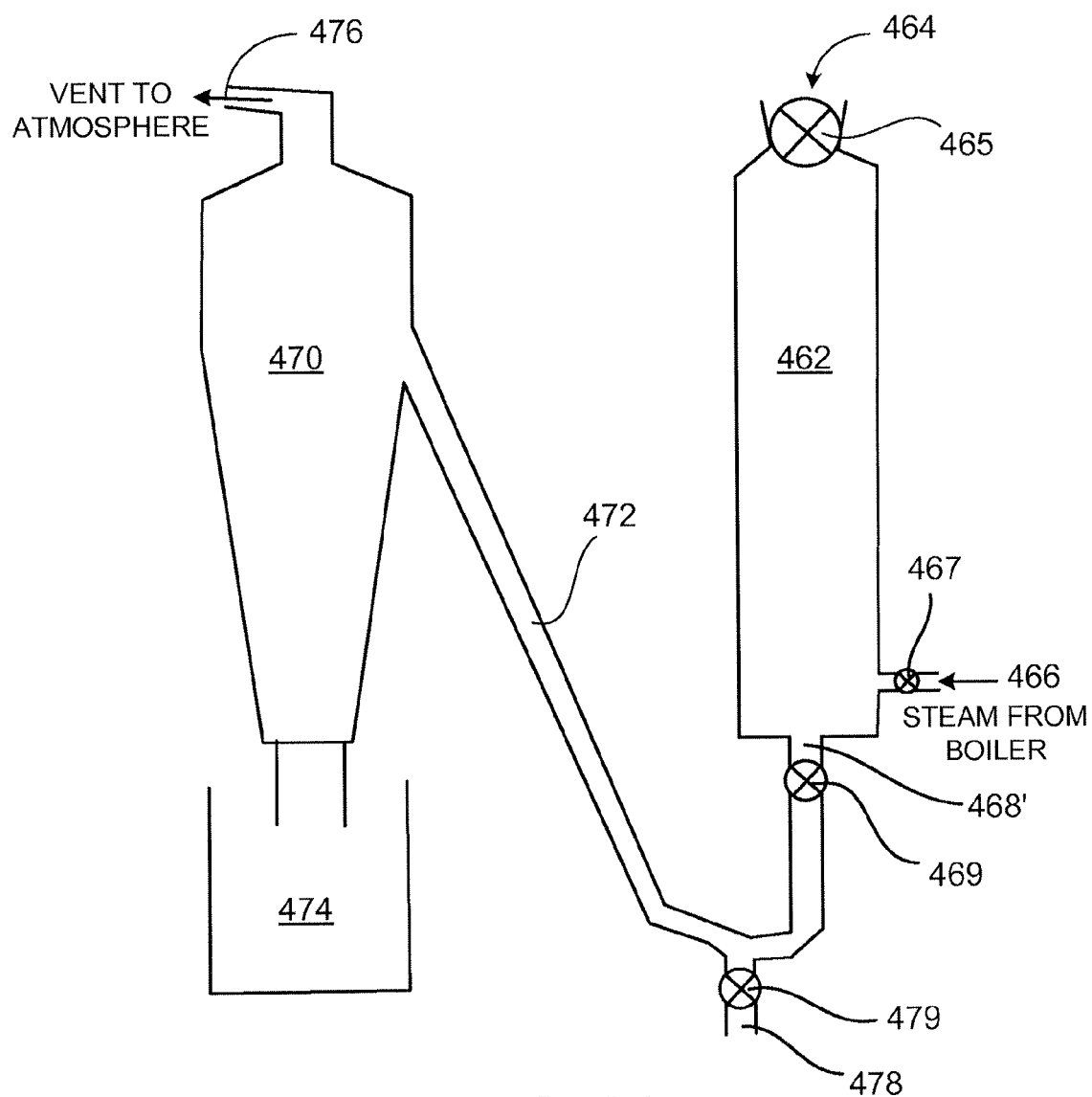
FIG. 24 is a cross-sectional view of a steam explosion apparatus.

FIG. 24 depicts an example of a steam explosion apparatus 460. The steam explosion apparatus 460 includes a reaction chamber 462, in which the fiber source and/or the fibrous material placed through a fiber source inlet 464. The reaction chamber is sealed by closing fiber source inlet valve 465. The reaction chamber further includes a pressurized steam inlet 466 that includes a steam valve 467. The reaction chamber further includes an explosive depressurization outlet 468 that includes an outlet valve 469 in communication with the cyclone 470 through the connecting pipe 472. Once the reaction chamber includes the fiber source and/or sheared fiber source and is sealed by closing valves 465, 467 and 469, steam is delivered into the reaction chamber 462 by opening the steam inlet valve 467 allowing steam to travel through steam inlet 466. Once the reaction chamber reaches target temperature, which can take about 20-60 seconds, the holding time begins. The reaction temperature is held at the target temperature for the desired holding time, which typically lasts from about 10 seconds to 5 minutes. At the end of the holding time period, outlet valve is open to allow for explosive depressurization to occur. The process of explosive depressurization propels the contents of the reaction chamber 462 out of the explosive depressurization outlet 468, through the connecting pipe 472, and into the cyclone 470. The steam exploded fiber source or fibrous material then exits the cyclone in a sludge form into the collection bin 474 as much of the remaining steam exits the cyclone into the atmosphere through vent 476. The steam explosion apparatus further includes wash outlet 478 with wash outlet valve 479 in communication with connecting pipe 472. The wash outlet valve 479 is closed during the use of the steam explosion apparatus 460 for steam explosion, but opened during the washing of the reaction chamber 462. The target temperature of the reaction chamber 462 is preferably between 180 and 240 degrees Celsius or between 200 and 220 degrees Celsius. The holding time is preferably between 10 seconds and 30 minutes, or between 30 seconds and 10 minutes, or between 1 minute and 5 minutes.

Because the steam explosion process results in a sludge of steam exploded fibrous material, the steam exploded fibrous material can optionally include a fiber recovery process where the "liquor" is separated from the steam exploded fibrous material. This fiber recovery step is helpful in that it enables further shearing and/or screening processes and can allow for the conversion of the fibrous material into a product. The fiber recovery process occurs through the use of a mesh cloth to separate the fibers from the liquor. Further drying processes can also be included to prepare the fibrous material or steam exploded fiber source for subsequent processing.

Any processing technique described herein can be used at pressure above or below normal, earth-bound atmospheric pressure. For example, any process that utilizes radiation, sonication, oxidation, pyrolysis, steam explosion, or combinations of any of these processes to provide materials that include a carbohydrate can be performed under high pressure, which, can increase reaction rates. For example, any process or combination of processes can be performed at a pressure greater than about greater than 25 MPa, e.g., greater than 50 MPa, 75 MPa, 100 MPa, 150 MPa, 200 MPa, 250 MPa, 350 MPa, 500 MPa, 750 MPa, 1,000 MPa, or greater than 1,500 MPa.

Combinations of Irradiating, Sonicating, and Oxidizing Devices

In some embodiments, it can be advantageous to combine two or more separate irradiation, sonication, pyrolization, and/or oxidation devices into a single hybrid machine. For such a hybrid machine, multiple processes can be performed in close juxtaposition or even simultaneously, with the benefit of increasing pretreatment throughput and potential cost savings.

For example, consider the electron beam irradiation and sonication processes. Each separate process is effective in lowering the mean molecular weight of cellulosic material by an order of magnitude or more, and by several orders of magnitude when performed serially.

Figure 25:
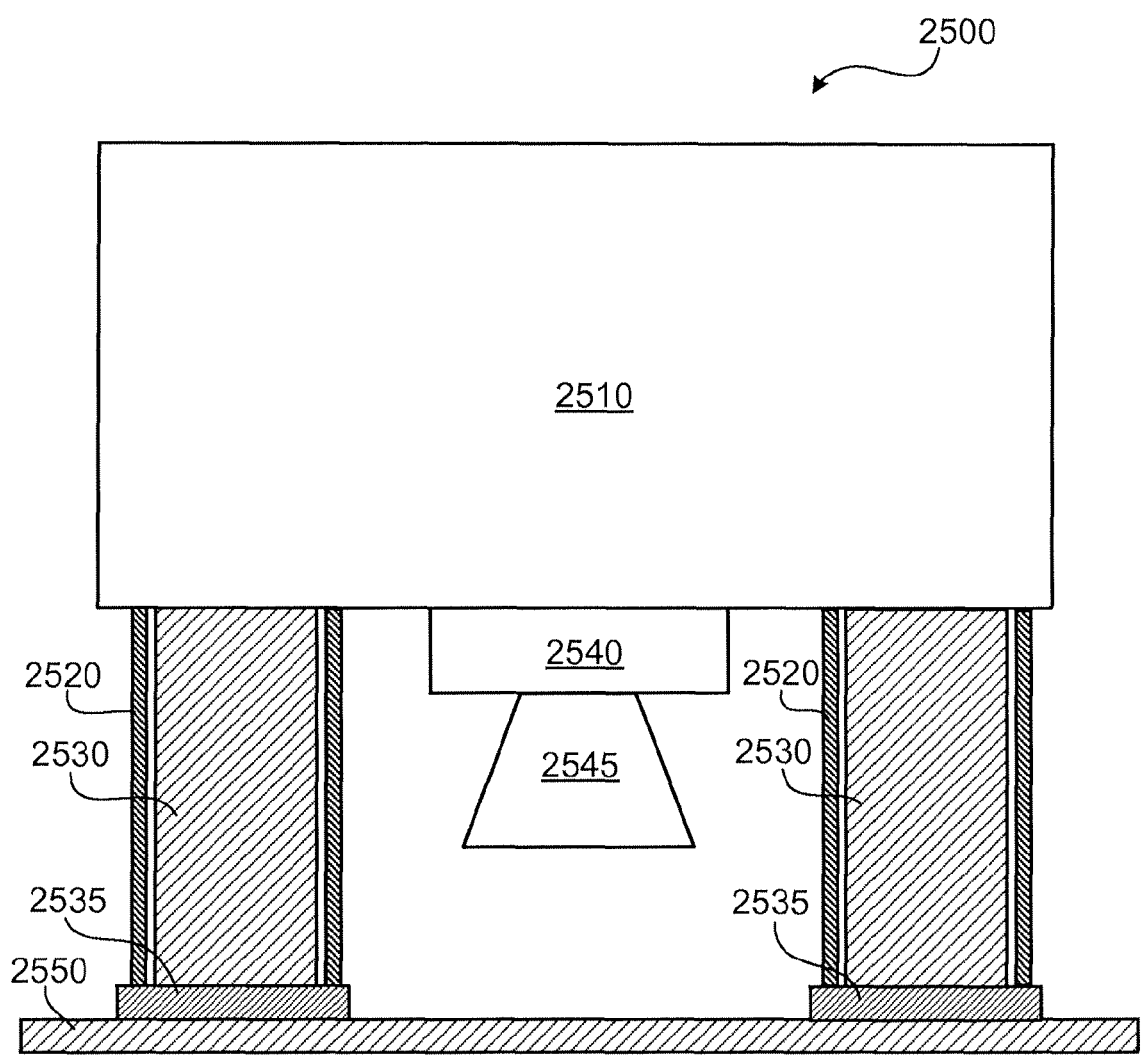
FIG. 25 is a schematic cross-sectional side view of a hybrid electron beam/sonication device.

Both irradiation and sonication processes can be applied using a hybrid electron beam/sonication device as is illustrated in FIG. 25. Hybrid electron beam/sonication device 2500 is pictured above a shallow pool (depth ~3-5 cm) of a slurry of cellulosic material 2550 dispersed in an aqueous, oxidant medium, such as hydrogen peroxide or carbamide peroxide. Hybrid device 2500 has an energy source 2510, which powers both electron beam emitter 2540 and sonication horns 2530.

Electron beam emitter 2540 generates electron beams, which pass though an electron beam aiming device 2545 to impact the slurry 2550 containing cellulosic material. The electron beam aiming device can be a scanner that sweeps a beam over a range of up to about 6 feet in a direction approximately parallel to the surface of the slurry 2550.

On either side of the electron beam emitter 2540 are sonication horns 2530, which deliver ultrasonic wave energy to the slurry 2550. The sonication horns 2530 end in a detachable endpiece 2535 that is in contact with the slurry 2550.

The sonication horns 2530 are at risk of damage from long-term residual exposure to the electron beam radiation. Thus, the horns can be protected with a standard shield 2520, e.g., made of lead or a heavy-metal-containing alloy such as Lipowitz metal, which is impervious to electron beam radiation. Precautions must be taken, however, to ensure that the ultrasonic energy is not affected by the presence of the shield. The detachable endpieces 2535, are constructed of the same material and attached to the horns 2530, are used to be in contact with the cellulosic material 2550 and are expected to be damaged. Accordingly, the detachable endpieces 2535 are constructed to be easily replaceable.

A further benefit of such a simultaneous electron beam and ultrasound process is that the two processes have complementary results. With electron beam irradiation alone, an insufficient dose can result in cross-linking of some of the polymers in the cellulosic material, which lowers the efficiency of the overall depolymerization process. Lower doses of electron beam irradiation and/or ultrasound radiation can also be used to achieve a similar degree of depolymerization as that achieved using electron beam irradiation and sonication separately.

An electron beam device can also be combined with one or more of high-frequency, rotor-stator devices, which can be used as an alternative to ultrasonic energy devices, and performs a similar function.

Further combinations of devices are also possible. For example, an ionizing radiation device that produces gamma radiation emitted from, e.g., $^{60}$Co pellets, can be combined with an electron beam source and/or an ultrasonic wave source.

The radiation devices for pretreating biomass discussed above can also be combined with one or more devices that perform one or more pyrolysis processing sequences. Such a combination can again have the advantage of higher throughput. Nevertheless, caution must be observed, as there can be conflicting requirements between some radiation processes and pyrolysis. For example, ultrasonic radiation devices can require the feedstock be immersed in a liquid oxidizing medium. On the other hand, as discussed previously, it can be advantageous for a sample of feedstock undergoing pyrolysis to be of a particular moisture content. In this case, the new systems automatically measure and monitor for a particular moisture content and regulate the same Further, some or all of the above devices, especially the pyrolysis device, can be combined with an oxidation device as discussed previously.

Primary Processes (Processing Treated Biomass)

Fermentation

Generally, various microorganisms can produce a number of useful products by operating on, e.g., fermenting treated biomass materials. For example, alcohols, organic acids, hydrocarbons, hydrogen, proteins or mixtures of any of these materials can be produced by fermentation or other processes.

The microorganism can be a natural microorganism or an engineered microorganism. For example, the microorganism can be a bacterium, e.g., a cellulolytic bacterium, a fungus, e.g., a yeast, a plant or a protist, e.g., an algae, a protozoa or a fungus-like protist, e.g., a slime mold. When the organisms are compatible, mixtures of organisms can be utilized.

To aid in the breakdown of the treated biomass materials that include cellulose, one or more enzymes, e.g., a cellulolytic enzyme can be utilized. In some embodiments, materials that include cellulose are first treated with the enzyme, e.g., by combining the materials and the enzyme in an aqueous solution. This material can then be combined with the microorganism. In other embodiments, the materials that include the cellulose, the one or more enzymes and the microorganism are combined concurrently, e.g., by combining in an aqueous solution.

Also, to aid in the breakdown of the treated biomass materials, the treated biomass materials can be further treated (e.g., post irradiation) with heat, a chemical (e.g., mineral acid, base or a strong oxidizer such as sodium hypochlorite), and/or an enzyme.

During fermentation, sugars released from cellulolytic hydrolysis or saccharification, are fermented to, e.g., ethanol, by a fermenting microorganism such as yeast. Suitable fermenting microorganisms have the ability to convert carbohydrates, such as glucose, xylose, arabinose, mannose, galactose, oligosaccharides, or polysaccharides into fermentation products. Fermenting microorganisms include strains of the genus *Saccharomyces* spp. e.g., *Saccharomyces cerevisiae* (baker's yeast), *Saccharomyces distaticus*, and *Saccharomyces uvarum*; the genus *Kluyveromyces*, e.g., species *Kluyveromyces marxianus*, and *Kluyveromyces fragilis*; the genus *Candida*, e.g., *Candida pseudotropicalis*, and *Candida brassicae*; the genus *Clavispora*, e.g., species *Clavispora lusitaniae* and *Clavispora opuntiae*; the genus *Pachysolen*, e.g., species *Pachysolen tannophilus*; the genus *Bretannomyces*, e.g., species *Bretannomyces clausenii*; the genus *Pichia*, e.g., species *Pichia stipitis*; and the genus *Saccharophagus*, e.g., species *Saccharophagus degradans* (Philippidis, 1996, "Cellulose Bioconversion Technology", in *Handbook on Bioethanol: Production and Utilization*, Wyman, ed., Taylor & Francis, Washington, D.C., 179-212).

Commercially available yeast include, for example, Red Star®/Lesaffre Ethanol Red (available from Red Star/Lesaffre, USA); FALI® (available from Fleischmann's Yeast, a division of Burns Philip Food Inc., USA); SUPERSTART® (available from Alltech, now Lallemand); GERT STRAND® (available from Gert Strand AB, Sweden); and FERMOL® (available from DSM Specialties).

Bacteria that can ferment biomass to ethanol and other products include, e.g., *Zymomonas mobilis* and *Clostridium thermocellum* (Philippidis, 1996, supra). Leschine et al. (International Journal of Systematic and Evolutionary Microbiology 2002, 52, 1155-1160) describe an anaerobic, mesophilic, cellulolytic bacterium from forest soil, *Clostridium phytofermentans* sp. nov., which converts cellulose to ethanol.

Fermentation of biomass to ethanol and other products can be carried out using certain types of thermophilic or genetically engineered microorganisms, such as *Thermoanaerobacter* species, including *T. mathranii*, and yeast species such as *Pichia* species. An example of a strain of *T. mathranii* is A3M4 described in Sonne-Hansen et al. (Applied Microbiology and Biotechnology 1993, 38, 537-541) or Ahring et al. (Arch. Microbiol. 1997, 168, 114-119).

Yeast and *Zymomonas* bacteria can be used for fermentation or conversion. The optimum pH for yeast is from about pH 4 to 5, while the optimum pH for *Zymomonas* is from about pH 5 to 6. Typical fermentation times are about 24 to 96 hours with temperatures in the range of 26° C. to 40° C., however thermophilic microorganisms prefer higher temperatures.

Enzymes that break down biomass, such as cellulose, to lower molecular weight carbohydrate-containing materials, such as glucose, are referred to as cellulolytic enzymes or cellulase; this process is referred to an "saccharification". These enzymes can be a complex of enzymes that act synergistically to degrade crystalline cellulose. Examples of cellulolytic enzymes include: endoglucanases, cellobiohydrolases, and cellobiases (β-glucosidases). For example, cellulosic substrate is initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble β-1,4-linked dimer of glucose. Finally cellobiase cleaves cellobiose to yield glucose.

A cellulase is capable of degrading biomass and can be of fungal or bacterial origin. Suitable enzymes include cellulases from the genera *Bacillus, Pseudomonas, Humicola, Fusarium, Thielavia, Acremonium, Chrysosporium* and *Trichoderma*, and include species of *Humicola, Coprinus, Thielavia, Fusarium, Myceliophthora, Acremonium, Cephalosporium, Scytalidium, Penicillium* or *Aspergillus* (see, e.g., hsEP 458162), especially those produced by a strain selected from the species *Humicola insolens* (reclassified as *Scytalidium thermophilum*, see, e.g., U.S. Pat. No. 4,435,307), *Coprinus cinereus, Fusarium oxysporum, Myceliophthora thermophila, Meripilus giganteus, Thielavia terrestris, Acremonium* sp., *Acremonium persicinum, Acremonium acremonium, Acremonium brachypenium, Acremonium dichromosporum, Acremonium obclavatum, Acremonium pinkertoniae, Acremonium roseogriseum, Acremonium incoloratum*, and *Acremonium furatum*; preferably from the species *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic enzymes can also be obtained from *Chrysosporium*, preferably a strain of *Chrysosporium lucknowense*. Additionally, *Trichoderma* (particularly *Trichoderma viride, Trichoderma reesei*, and *Trichoderma koningii*), alkalophilic *Bacillus* (see, for example, U.S. Pat. No. 3,844,890 and EP 458162), and *Streptomyces* (see, e.g., EP 458162) can be used.

Cellulolytic enzymes produced using recombinant technology can also be used (see, e.g., WO 2007/071818 and WO 2006/110891).

The cellulolytic enzymes used can be produced by fermentation of the above-noted microbial strains on a nutrient medium containing suitable carbon and nitrogen sources and inorganic salts, using procedures known in the art (see, e.g., Bennettand LaSure (eds.), *More Gene Manipulations in Fungi*, Academic Press, CA 1991). Suitable media are available from commercial suppliers or can be prepared according to published compositions (e.g., in catalogues of the American Type Culture Collection). Temperature ranges and other conditions suitable for growth and cellulase production are known in the art (see, e.g., Bailey and Ollis, *Biochemical Engineering Fundamentals*, McGraw-Hill Book Company, NY, 1986).

Treatment of cellulose with cellulase is usually carried out at temperatures between 30° C. and 65° C. Cellulases are active over a range of pH of about 3 to 7. A saccharification step can last e.g., up to 120 hours. The cellulase enzyme dosage achieves a sufficiently high level of cellulose conversion. For example, an appropriate cellulase dosage is typically between 5.0 and 50 Filter Paper Units (FPU or IU) per gram of cellulose. The FPU is a standard measurement and is defined and measured according to Ghose (1987, Pure and Appl. Chem. 59:257-268).

In particular embodiments, ACCELERASE™ 1000 (GENENCOR) is utilized as the enzyme system at a loading of 0.25 mL per gram of substrate. ACCELLERASE® 1000 enzyme complex is a multiple enzyme cocktail with multiple activities, mainly exoglucanase, endoglucanase, hemicellulase and beta-glucosidase. The cocktail has a minimum endoglucanase activity of 2500 CMC U/g and a minimum beta-glucosidase activity of 400 pNPG U/g. The pH of the cocktail is from about 4.8 to about 5.2. In other particular embodiments, the enzyme system utilized is a blend of CELLUCLAST® 1.5 L and Novozyme 188. For example, 0.5 mL of CELLUCLAST® 1.5 L and 0.1 mL of Novozyme 188 can be used for each gram of substrate. When a higher hemicellulase (xylanase) activity is desired, OPTIMASH™ BG can be utilized.

Gasification

In addition to using pyrolysis for pre-treatment of feedstock, pyrolysis can also be used to process pre-treated feedstock to extract useful materials. In particular, a form of pyrolysis known as gasification can be employed to generate fuel gases along with various other gaseous, liquid, and solid products. To perform gasification, the pre-treated feedstock is introduced into a pyrolysis chamber and heated to a high temperature, typically 700° C. or more. The temperature used depends upon a number of factors, including the nature of the feedstock and the desired products.

Quantities of oxygen (e.g., as pure oxygen gas and/or as air) and steam (e.g., superheated steam) are also added to the pyrolysis chamber to facilitate gasification. These compounds react with carbon-containing feedstock material in a multiple-step reaction to generate a gas mixture called synthesis gas (or "syngas"). Essentially, during gasification, a limited amount of oxygen is introduced into the pyrolysis chamber to allow some feedstock material to combust to form carbon monoxide and generate process heat. The process heat can then be used to promote a second reaction that converts additional feedstock material to hydrogen and carbon monoxide.

In a first step of the overall reaction, heating the feedstock material produces a char that can include a wide variety of different hydrocarbon-based species. Certain volatile materials can be produced (e.g., certain gaseous hydrocarbon materials), resulting in a reduction of the overall weight of the feedstock material. Then, in a second step of the reaction, some of the volatile material that is produced in the first step reacts with oxygen in a combustion reaction to produce both carbon monoxide and carbon dioxide. The combustion reaction releases heat, which promotes the third step of the reaction. In the third step, carbon dioxide and steam (e.g., water) react with the char generated in the first step to form carbon monoxide and hydrogen gas. Carbon monoxide can also react with steam, in a water gas shift reaction, to form carbon dioxide and further hydrogen gas.

Gasification can be used as a primary process to generate products directly from pre-treated feedstock for subsequent transport and/or sale, for example. Alternatively, or in addition, gasification can be used as an auxiliary process for generating fuel for an overall processing system. The hydrogen-rich syngas that is generated via the gasification process can be burned, for example, to generate electricity and/or process heat that can be directed for use at other locations in the processing system. As a result, the overall processing system can be at least partially self-sustaining. A number of other products, including pyrolysis oils and gaseous hydrocarbon-based substances, can also be obtained during and/or following gasification; these can be separated and stored or transported as desired.

A variety of different pyrolysis chambers are suitable for gasification of pre-treated feedstock, including the pyrolysis chambers disclosed herein. In particular, fluidized bed reactor systems, in which the pre-treated feedstock is fluidized in steam and oxygen/air, provide relatively high throughput and straightforward recovery of products. Solid char that remains following gasification in a fluidized bed system (or in other pyrolysis chambers) can be burned to generate additional process heat to promote subsequent gasification reactions.

Processing Treated Biomass
Distillation

After fermentation, the resulting fluids can be distilled using, for example, a "beer column" to separate ethanol and other alcohols from the majority of water and residual solids. The vapor exiting the beer column can be 35% by weight ethanol and fed to a rectification column. A mixture of nearly azeotropic (92.5%) ethanol and water from the rectification column can be purified to pure (99.5%) ethanol using vapor-phase molecular sieves. The beer column bottoms can be sent to the first effect of a three-effect evaporator. The rectification column reflux condenser can provide heat for this first effect. After the first effect, solids can be separated using a centrifuge and dried in a rotary dryer. A portion (25%) of the centrifuge effluent can be recycled to fermentation and the rest sent to the second and third evaporator effects. Most of the evaporator condensate can be returned to the process as fairly clean condensate with a small portion split off to waste water treatment to prevent build-up of low-boiling point compounds.

Waste Water Treatment

Wastewater treatment is used to minimize makeup water requirements of the plant by treating process water for reuse within the plant. Wastewater treatment can also produce fuel (e.g., sludge and biogas) that can be used to improve the overall efficiency of the ethanol production process. For example, as described in further detail below, sludge and biogas can be used to create steam and electricity that can be used in various plant processes.

Wastewater is initially pumped through a screen (e.g., a bar screen) to remove large particles, which are collected in a hopper. In some embodiments, the large particles are sent to a landfill. Additionally or alternatively, the large particles are burned to create steam and/or electricity as described in further detail below. In general, the spacing on the bar screen is between ¼ inch to 1 inch spacing (e.g., ½ inch spacing).

The wastewater then flows to an equalization tank, where the organic concentration of the wastewater is equalized during a retention time. In general, the retention time is between 8 hours and 36 hours (e.g., 24 hours). A mixer is disposed within the tank to stir the contents of the tank. In some embodiments, a plurality of mixers disposed throughout the tank are used to stir the contents of the tank. In certain embodiments, the mixer substantially mixes the contents of the equalization tank such that conditions (e.g., wastewater concentration and temperature) throughout the tank are uniform.

A first pump moves water from the equalization tank through a liquid-to-liquid heat exchanger. The heat exchanger is controlled (e.g., by controlling the flow rate of fluid through the heat exchanger) such that wastewater exiting the heat exchanger is at a desired temperature for anaerobic treatment. For example, the desired temperature for anaerobic treatment can be between 40° C. to 60° C.

After exiting the heat exchanger, the wastewater enters one or more anaerobic reactors. In some embodiments, the concentration of sludge in each anaerobic reactor is the same as the overall concentration of sludge in the wastewater. In other embodiments, the anaerobic reactor has a higher concentration of sludge than the overall concentration of sludge in the wastewater.

A nutrient solution containing nitrogen and phosphorus is metered into each anaerobic reactor containing wastewater. The nutrient solution reacts with the sludge in the anaerobic reactor to produce biogas which can contain 50% methane and have a heating value of approximately 12,000 British thermal units, or Btu, per pound). The biogas exits each anaerobic reactor through a vent and flows into a manifold, where a plurality of biogas streams are combined into a single stream. A compressor moves the stream of biogas to a boiler or a combustion engine as described in further detail below. In some embodiments, the compressor also moves the single stream of biogas through a desulphurization catalyst. Additionally or alternatively, the compressor can move the single stream of biogas through a sediment trap.

A second pump moves anaerobic effluent from the anaerobic reactors to one or more aerobic reactors (e.g., activated sludge reactors). An aerator is disposed within each aerobic reactor to mix the anaerobic effluent, sludge, oxygen (e.g., oxygen contained in air). Within each aerobic reactor, oxidation of cellular material in the anaerobic effluent produces carbon dioxide, water, and ammonia.

Aerobic effluent moves (e.g., via gravity) to a separator, where sludge is separated from treated water. Some of the sludge is returned to the one or more aerobic reactors to create an elevated sludge concentration in the aerobic reactors, thereby facilitating the aerobic breakdown of cellular material in the wastewater. A conveyor removes excess sludge from the separator. As described in further detail below, the excess sludge is used as fuel to create steam and/or electricity.

The treated water is pumped from the separator to a settling tank. Solids dispersed throughout the treated water settle to the bottom of the settling tank and are subsequently removed. After a settling period, treated water is pumped from the settling tank through a fine filter to remove any additional solids remaining in the water. In some embodiments, chlorine is added to the treated water to kill pathogenic bacteria. In some embodiments, one or more physical-chemical separation techniques are used to further purify the treated water. For example, treated water can be pumped through a carbon adsorption reactor. As another example, treated water can pumped through a reverse osmosis reactor.

Waste Combustion

The production of alcohol from biomass can result in the production of various by-product streams useful for generating steam and electricity to be used in other parts of the plant. For example, steam generated from burning by-product streams can be used in the distillation process. As another example, electricity generated from burning by-product streams can be used to power electron beam generators and ultrasonic transducers used in pretreatment.

The by-products used to generate steam and electricity are derived from a number of sources throughout the process. For example, anaerobic digestion of wastewater produces a biogas high in methane and a small amount of waste biomass (sludge). As another example, post-distillate solids (e.g., unconverted lignin, cellulose, and hemicellulose remaining from the pretreatment and primary processes) can be used as a fuel.

The biogas is diverted to a combustion engine connected to an electric generator to produce electricity. For example, the biogas can be used as a fuel source for a spark-ignited natural gas engine. As another example, the biogas can be used as a fuel source for a direct-injection natural gas engine. As another example, the biogas can be used as a fuel source for a combustion turbine. Additionally or alternatively, the combustion engine can be configured in a cogeneration configuration. For example, waste heat from the combustion engines can be used to provide hot water or steam throughout the plant.

The sludge and post-distillate solids can be burned to heat water flowing through a heat exchanger. In some embodiments, the water flowing through the heat exchanger is evaporated and superheated to steam. In certain embodiments, the steam is used in the pretreatment rector and in heat exchange in the distillation and evaporation processes. Additionally or alternatively, the steam expands to power a multi-stage steam turbine connected to an electric generator. Steam exiting the steam turbine is condensed with cooling water and returned to the heat exchanger for reheating to steam. In some embodiments, the flow rate of water through the heat exchanger is controlled to obtain a target electricity output from the steam turbine connected to an electric generator. For example, water can be added to the heat exchanger to ensure that the steam turbine is operating above a threshold condition (e.g., the turbine is spinning fast enough to turn the electric generator).

While certain embodiments have been described, other embodiments are possible.

As an example, while the biogas is described as being diverted to a combustion engine connected to an electric generator, in certain embodiments, the biogas or some portion thereof can also be passed through a fuel reformer to produce hydrogen. The hydrogen is then converted to electricity through a fuel cell.

As another example, while the biogas is described as being burned apart from the sludge and post-distillate solids, in certain embodiments, some or all of the waste by-products can be burned together to produce steam.

Products/Co-Products

In some embodiments, the present invention provides materials generated using the methods described herein. In some cases, such materials can be used in the absence of materials added to the biomass pre or post processing, e.g., materials that are not naturally present in biomass. In such cases, the materials will contain naturally occurring materials, e.g., derived from biomass. Alternatively or in addition, the materials generated using the methods described herein can be combined with other natural and/or synthetic materials, e.g., materials that are not naturally present in biomass.

As described above, in some embodiments, the methods described herein can be used for converting (e.g., fermenting) biomass to an energy product (e.g., an alcohol such as ethanol or a hydrocarbon) and/or other products that result from the conversion process (e.g., organic acids). In such cases, the biomass will be exposed to conditions suitable for such a conversion. Exemplary conditions can include, e.g., at least biomass and one or more microorganisms capable of converting the biomass to energy (e.g., an alcohol) in an environment suitable for those organisms to function. This conversion process can be allowed to proceed to a point where at least a portion of the biomass is converted to energy (e.g., ethanol) and/or other products that result from the conversion process (e.g., as described below) and/or to a point where all (e.g., essentially all) of the materials are converted to energy (e.g., ethanol) and/or other products that result from the conversion process. For example, at least about 10, 20, 30, 40, 50, 60, 70, 80, 90, 95, 98, 99, 99.5, or 100% of the materials exposed to conditions suitable for fermentation is converted to energy (e.g., ethanol) and/or other products that result from the conversion process.

Alternatively or in addition, the methods described herein can be used to modify biomass, e.g., to modify (e.g., increase, decrease, or maintain) the solubility of the native materials, to change the structure of, e.g., to functionalize, the native materials, and/or alter (e.g., lower) the molecular weight and/or crystallinity relative to a native material. Such methods can be performed together or alone. For example, the methods described herein can be used to convert a portion of the biomass to energy. The methods described herein can also be used to modify (e.g., increase, decrease, or maintain) the solubility, to change the structure, e.g., functionalize, and/or alter (e.g., lower) the molecular weight and/or crystallinity of the biomass, or vice versa.

In some embodiments, the methods described herein can be used to obtain (e.g., extract, isolate, and/or increase the availability of, e.g., as compared to unprocessed biomass materials) one or more components contained in an unprocessed biomass material (e.g., a raw material). Exemplary components that can be obtained (e.g., extracted, isolated, and/or increased in availability (e.g., compared to unprocessed biomass materials)) include, but are not limited to sugars (e.g., 1,4-diacids (e.g., succinic acids, fumaric acids, and malic acids), 2,5-furan dicarboxylic acids, 3-hydroxy propionic acid, aspartic acid, glucaric acid, glutamic acid, itaconic acid, 3-hydroxy propionic acid, aspartic acid, glucaric acid, glutamic acid, itaconic acid, levulinic acid, 3-hydroxybutyrolactone, glycerol, sorbitol, and/or xylitol/aribitol), dextrins, cyclodextrins, amylase, amylopectin, germ, proteins, amino acids, peptides, nucleic acids, fats, lipids, fatty acids, gluten, sweeteners (e.g., glucose), sugar alcohols (e.g., arabitol, xylitol, ribitol, mannitol, sorbitol, isomalt, maltitol, and lactitol), oils (e.g., triglyceride vegetable oils (e.g., soybean oil, palm oil, rapeseed oil, sunflower seed oil, peanut oil, cottonseed oil, palm kernel oil, olive oil), corn oil, oat oil, nut oil, and palm oil), minerals, vitamins, toxins, and other chemicals, ash, and flavenoids. Such components can be used in various application described below, e.g., as individual components, in combination with one or more additional components, in combination with processed and/or unprocessed biomass, and/or in combination with one or more additional components not obtained (e.g., extracted, isolated, and/or increased in availability) from biomass. Methods for obtaining one or more of these components are known in the art.

In some embodiments, the methods described herein can be used to increase the availability of one or more components contained in biomass (e.g., unprocessed and/or partially processed biomass). Components with increased availability can be more readily obtained (e.g., extracted and/or isolated), more readily used, and/or can be more readily amenable to an animal (e.g., digested or absorbed by an animal). Components with increased availability can include, for example, components that occur naturally in biomass and/or components that are generated using the methods described herein (e.g., cross-linked species, low molecular weight species). Such components can increase the value of biomass. For example, low molecular weight species are more readily hydrolyzed in the stomach than unprocessed biomass. Thus, biomass containing more readily available low molecular weight species can be used as a more valuable food source, e.g., for animals or insects, or for use in agriculture, aquaculture, e.g., the cultivation of fish, aquatic microorganisms, aquatic plants, seaweed and algae.

In some embodiments, the methods described herein can be used to sterilize biomass to render the materials suitable for consumption by animals and/or humans (e.g., ingestion or implantation), by insects, or for use in agriculture, aquaculture, e.g., the cultivation of fish, aquatic microorganisms, aquatic plants, seaweed and algae. In some embodiments, irradiation treatment of cellulosic material will render the biomass sterile and, therefore, suitable for consumption in animals and/or humans (e.g., ingestion or implantation). The irradiated cellulose can also be used in other products or co-products.

In some embodiments, the methods described herein can be used to process biomass into a material intended for consumption (e.g., ingestion or implantation) in humans and/or non-human animals. Generally, such materials should be essentially free of infectious material (e.g., pathogenic and/or non-pathogenic material), toxins, and/or other materials (e.g., bacterial and fungal spores, insects, and larvae) that can be harmful to the human and/or animal. Methods known in the art and/or described herein can be used to remove, inactivate, and/or neutralize infectious material (e.g., pathogenic and/or non-pathogenic material) and/or toxins that can be harmful to humans and/or animals or that are generally undesirable in a material intended for use in humans and/or animals. For example, the methods can be used to remove, inactivate, and/or neutralize infectious material that can be present in the biomass. Such materials include, e.g., pathogenic and non-pathogenic bacteria, viruses, fungus, parasites, and prions (e.g., infectious proteins). In some instances, the methods described herein can be used to remove, inactivate, and/or neutralize toxins, e.g., bacterial toxins and plant toxins. Alternatively or in addition, the methods described herein can be used to remove, inactivate, and/or neutralize materials that can be present in the biomass that are not necessarily harmful, but are undesirable in a material to be used in humans and/or animals or in agriculture or aquaculture. Exemplary materials include, but are not limited to, bacterial and fungal spores, insects, and larvae.

In some embodiments, the methods described herein can be used to produce the products and co-products and bioconversion products described herein in challenging environments. Such environments can include environments that present space limitations and/or extreme environmental conditions, for example, locations with excessive heat or cold, locations with excessive radiation, locations with excessive pollutants, and/or locations with limited oxygen supply or sunlight. In some embodiments, such environments can include, but are not limited to, for example, on board space craft, on board space stations (e.g., extraterrestrial locations), on board submarines (e.g., nuclear submarines) and other marine vessels or barges or platforms designed to remain at sea for extensive time periods, submarine locations (e.g., civilian and/or military underwater facilities), desert environments, polar environments, subzero environments (e.g., permafrozen locations), elevated environments (e.g., where oxygen supplies can be limited and/or extreme temperatures are present), and remote locations (e.g., self contained locations).

In some embodiments, the products and/or co-products described herein, e.g., resulting from the treatment of biomass using the methods described herein can be, e.g., solids (e.g., particulates (e.g., films), granulates, and/or powders), semi-solids, liquids, gasses, vapors, gels, and combinations thereof.

Alcohols

Alcohols produced using the materials described herein can include, but are not limited to, a monohydroxy alcohol, e.g., ethanol, or a polyhydroxy alcohol, e.g., ethylene glycol or glycerin. Examples of alcohols that can be produced include, but are not limited to, methanol, ethanol, propanol, isopropanol, butanol, e.g., n-, sec- or t-butanol, ethylene glycol, propylene glycol, 1, 4-butane diol, glycerin or mixtures of these alcohols.

In some embodiments, the alcohols produced using the treatment methods disclosed herein can be used in the production of a consumable beverage.

Hydrocarbons

Hydrocarbons include aromatic hydrocarbons or arenes, alkanes, alkenes and alkynes. Exemplary hydrocarbons include methane, ethane, propane, butane, isobutene, hexane, heptane, isobutene, octane, iso-octane, nonane, decane, benzene and tolune.

Organic Acids

The organic acids produced using the methods and materials described herein can include monocarboxylic acids or polycarboxylic acids. Examples of organic acids include formic acid, acetic acid, propionic acid, butyric acid, valeric acid, caproic, palmitic acid, stearic acid, oxalic acid, malonic acid, succinic acid, glutaric acid, oleic acid, linoleic acid, glycolic acid, lactic acid, γ-hydroxybutyric acid, or mixtures of these acids.

Foodstuffs

As described herein, the present invention provides methods useful for modifying biomass, e.g., by modifying (e.g., increasing, decreasing, or maintaining) the solubility of the native materials, changing the structure of (e.g., functionalizing) the native materials, and/or altering (e.g., lowering) the molecular weight and/or crystallinity relative to a native material. The methods can be used to prepare materials with properties that can be favorable for use as or in the production of a foodstuff. For example, the methods can be used to prepare a material with improved (e.g., increased or decreased) solubility, e.g., compared to a native material, which can be used as a more easily absorbed foodstuff. Increased solubility can be assessed, e.g., by dispersing (e.g., dissolving) unprocessed and processed materials in a suitable solvent, removing undissolved material, detecting the materials and/or specific components of the materials (e.g., sugars), and comparing the levels of the detected materials in the processed and unprocessed materials. In some cases, the solvent containing the materials can be modified, e.g., by heating or by adjusting the pH.

Alternatively or in addition, the methods can be used to prepare a material with a higher nutritional value (e.g., higher energy (e.g., more digestively available food energy) and/or nutrient availability) when the material is ingested by an animal, e.g., compared to a native material or unprocessed biomass. Such methods will not necessarily increase the total amount of energy or nutrients present in a set amount (e.g., weight) of a specific type of processed biomass compared to the same amount and type of unprocessed biomass. Rather, the methods described herein can be used to increase the nutritional value (e.g., the availability of energy and/or one or more nutrients) in a set amount (e.g., weight) of a specific type of processed biomass compared to the same amount and type of unprocessed biomass.

Increasing the availability of food energy of a particular type of biomass can be used to increase the metabolizable energy intake (MEI) of that biomass. Methods for measuring food energy are known in the art. MEI is typically calculated by multiplying the number of kilocalories or kilojoules contained in a food item by 85%. In some embodiments, the methods described herein can be used to increase the MEI of biomass.

Methods for comparing the MEI of processed and unprocessed biomass can include, for example, feeding equal amounts of processed or unprocessed biomass to at least two distinct groups of one or more animals, and measuring the growth response of the animals.

Nutrient availability can be assessed by conducting a digestion trial. Protocols for conducting digestion trials are known in the art. For example, total nutrient levels can be determined in processed and/or unprocessed biomass. Equal amounts of processed or unprocessed biomass can be fed to at least two distinct groups of one or more animals. Fecal loss of one or more nutrients is then determined for a defined period of time. Increased nutrient availability is defined as lower amounts of one or more nutrients in the animal feces. Alternatively or in addition, nutrient availability can be assessed by measuring and comparing the levels of one or more nutrients in the blood of animals fed processed and unprocessed biomass.

In some embodiments, the nutritional value of biomass can be increased by increasing the digestibility of one or more, food energy, carbohydrates, sugars, proteins, fats (saturated, monounsaturated, and polyunsaturated), cholesterol, dietary fiber, vitamins (e.g., vitamin A, E, C, B6, B12, carotene, thiamin, riboflavin, and niacin), minerals (e.g., calcium, phosphorus, magnesium, iron, zinc, copper, potassium, selenium, and sodium), and oils when the biomass is ingested by an animal.

In general, the methods described herein can be selected and/or optimized to select a method or combination of methods that result in the most readily soluble, absorbable, and/or digestible material, e.g., with a desired nutrient availability (e.g., a higher nutrient (e.g., protein, amino acid, carbohydrate, mineral, vitamin, fat lipid, and oil) availability than native unprocessed material) that can be used in humans and/or animals as a foodstuff. Because the biomass materials are readily available and cheap, the materials resulting from such methods will provide an economical foodstuff and reduce waste.

In some embodiments, the materials and methods described herein can be used in the production of a foodstuff, e.g., agricultural foodstuffs and foodstuffs suitable for ingestion by mammals, birds, and/or fish. Such animals include, but are not limited to food production animals, domestic animals, zoo animals, laboratory animals, and/or humans.

In some embodiments, materials produced by the methods described herein that are intended for use as foodstuffs (e.g., in humans and/or animals) can be additionally processed, e.g., hydrolyzed. Hydrolization methods are known in the art and include, for example, the use of enzymes, acids, and/or bases to reduce the molecular weight of saccharides. In some embodiments, foodstuffs resulting from the methods described herein can include enzymes (e.g., dried enzymes, active enzymes, and/or enzymes requiring activation).

In some embodiments, materials produced by the methods described herein that are intended for use as foodstuffs (e.g., in humans and/or animals) can be additionally processed to increase sterility of the materials and/or remove, inactivate, and/or neutralize materials that can be present in the biomass, e.g., infectious material (e.g., pathogenic and/or non-pathogenic material), toxins, and/or other materials (e.g., bacterial and fungal spores, insects, and larvae). In general, the methods described herein can be selected and optimized in order to promote optimal removal, inactivation, and/or neutralization of materials that may be undesirable.

Animal Foodstuffs

In excess of 600 million tons of animal foodstuff is produced annually around the world with an annual growth rate of about 2%. Agriculture is one of the largest consumers of animal foodstuffs with farmers in the United States spending in excess of $20 billion dollars per year on agricultural foodstuffs for food producing animals. Other foodstuffs consumers include, for example, pet owners, zoos, and laboratories that keep animals for research studies.

In general, an animal foodstuff should meet or exceed the specific requirements of a target animal, e.g., to maintain or improve the health of a specific type or species of animal, promote the growth of a target animal (e.g., tissue gain), and/or to promote food production. Improved animal foodstuffs (e.g., more soluble, absorbable, and/or digestible foodstuffs) will promote or support these same effects using a smaller amount of foodstuff and/or for a lower cost.

Currently used raw materials in commercially prepared foodstuff include feed grains (e.g., corn, soybean, sorghum, oats, and barley). The feed industry is the largest purchaser of U.S. corn, feed grains, and soybean meal. However, with the escalating price of feed grains such as corn, cheaper alternatives are desired. The most abundantly available foodstuff is biomass, e.g., cellulosic material. In some embodiments, the methods described herein can be used to increase the nutrient availability of any of these materials, e.g., to maintain or improve the health of a specific type or species of animal, promote the growth of a target animal (e.g., tissue gain), and/or to promote food production. The low nutrient availability of commonly used foodstuffs (e.g., hay and grasses) is largely attributed to the high cellulose, hemicellulose, and lignin content of such material. Unlike humans, who cannot digest cellulose, herbivores, e.g., ruminants, are capable of digesting cellulose, at least partially, through a process known as rumination. This process, however, is inefficient and requires multiple rounds of regurgitation. For example, ruminants only digest about 30-50 percent of the cellulose and hemicellulose. In some embodiments, the methods described herein can be used to increase the nutrient availability or nutritional value of any of these materials, e.g., to maintain or improve the health of a specific type or species of animal, promote the growth of a target animal (e.g., tissue gain), and/or to promote food production. The methods described herein use reduced amounts of foodstuffs, at a lower cost, and/or with less waste.

Generally, increasing the nutrient availability of an animal foodstuff will reduce the amount of feed required to be fed to an animal for the animal to receive the same amount of energy. Consequently, the animal will require less foodstuff thus providing a more economical foodstuff.

Various techniques have been attempted to increase the nutrient availability of a foodstuff with limited success. Such techniques include the use of enzymes, such as cellulosic enzymes, to break down cellulosic material into shorter chain oligosaccharides, which can be more readily digested. Although used in Europe and Australia, this practice is expensive and not widely used in developing countries. Other techniques include removing stover to prevent leaf loss, air removal, physically treating the material (e.g., compacting cellulosic material, reducing particle size, and fine grinding), chemical treatment, and overfeeding. Additionally, foodstuffs composed largely from cellulosic material are frequently supplemented with nutrient systems (e.g., premixes). These nutrient systems are typically designed to provide the nutritional requirements of a target animal. Despite ensuring the animals receive the required nutrients, such systems do not make efficient use of the cellulosic material.

The methods described herein provide methods for improving the nutrient availability or nutritional value of biomass (e.g., by modifying (e.g., increasing, decreasing, or maintaining) the solubility of the biomass and/or changing the structure (e.g., functionalizing) of the native materials, and/or altering (e.g., lowering) the molecular weight and/or crystallinity), as described above, thereby producing a more valuable foodstuff. In some embodiments, the methods described herein can be used to increase the nutrient availability of the biomass by breaking down cellulosic material (e.g., cellulose and/or hemicellulose) into shorter chain saccharides and/or monosaccharides. By improving the nutrient availability of the biomass, these methods will result in a more efficient foodstuff that can be used to maintain or improve the health of a specific type or species of animal, promote the growth of a target animal (e.g., tissue gain), and/or to promote food production.

In some embodiments, a useful animal foodstuff can include partially processed biomass, e.g., biomass that has been sheared using the methods described herein. Such partially processed biomass can be more readily hydrolyzed in the stomach of an animal.

In some embodiments, the methods described herein can be used to process biomass to generate the materials described herein. These materials can include, but are not limited to, e.g., polysaccharides with a length of greater than 1000 saccharide units; about 1000 sugar saccharide units; about 800-900 saccharide units; about 700-800 saccharide units; about 600-700 saccharide units; about 500-600 saccharide units; about 400-500 saccharide units; about 300-400 saccharide units; about 200-300 saccharide units; about 100-200 saccharide units; 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, and 1 saccharide units.

In some embodiments, the methods produce disaccharides (e.g., sucrose, lactose, maltose, trehalose, and cellobiose). In some embodiments, the methods produce monosaccharides (e.g., glucose (dextrose), fructose, galactose, xylose, and ribose). These shorter chain molecules will be more easily absorbed by an animal and will thereby increase the nutrient availability of biomass. Consequently, the methods and materials described herein can be used as foodstuffs or in the production of foodstuffs.

In some embodiments, the materials described herein can be used as a foodstuff e.g., agricultural foodstuffs and/or foodstuffs suitable for ingestion by mammals, birds, and/or fish. Alternatively or in addition, the methods described herein can be used to process a raw material suitable for use as or in an animal foodstuff.

Materials that can be usefully processed using the methods described herein include cellulosic and lignocellulosic materials, e.g., arable products, crops, grasses, plants and/or feed grains, for example including, but not limited to, plant material (e.g., forage such as alfalfa meal, hay, Bermuda coastal grass hay, sweet grass, corn plant, and soybean hay), grains (e.g., barley, corn (including organic and genetically modified corn), oats, rice, sorghum, and wheat), plant protein products (e.g., canola meal, cottonseed cakes and meals, safflower meal, and soybean (including organic and genetically modified soybean) feed and meal), processed grain by-products (e.g., distillers products, brewers dried grains, corn gluten, sorghum germ cake and meal, peanut skins, and wheat bran), fruit and fruit by-products (e.g., dried citrus pulp, apple pomace, and pectin pulp), molasses (e.g., beet, citrus, starch, and cane molasses), almond hulls, ground shells, buckwheat hulls, legumes and legume by-products, and other crop by-products. Other raw materials include, but are not limited to, alfalfa, barley, birdsfoot trefoil, brassicas (e.g., chau moellier, kale, rapeseed (canola), rutabaga (swede), and turnip), clover (e.g., alsike clover, red clover, subterranean clover, and white clover), grass (e.g., false oat grass, fescue, Bermuda grass, brome, heath grass, meadow grass, orchard grass, ryegrass, and Timothy grass), maize (corn), millet, oats, sorghum, and soybeans. In some embodiments, the raw material can be animal waste (e.g., ruminant waste) or human waste.

In some embodiments, the foodstuff contains only the materials produced using the methods described herein. Alternatively or in addition, the foodstuff contains additional raw materials (including raw materials not treated using the methods described herein) and additives. Such foodstuffs can be formulated to meet the specific requirements of a target animal, e.g., to maintain or improve the health of a specific type or species of animal, to promote the growth of a target animal, tissue gain, and/or to promote food production. In some cases, a foodstuff can be formulated to meet the nutritional requirements of a target animal for the least cost (the "least cost ration"). Methods for determining the formulation of a foodstuff and the least cost ration are well known to those of skill in the art (see, for example, Pesti and Miller, Animal Feed Formulation: Economic and Computer Applications (Plant and Animal Science), Springer Publishing, Feb. 28, 1993 and world wide web address liveinformatics.com).

Additional raw materials and additives that can be usefully combined with a material produced using the methods described herein include, but are not limited to, animal products (e.g., meat meal, meat meal tankage, meat and bone meal, poultry meal, animal by-product meal, dried animal blood, blood meal, feather meal, egg-shell meal, hydrolyzed whole poultry, hydrolyzed hair, and bone marrow), animal waste, marine products and by-products (e.g., krill, fish parts and meal, fish residue meal, crab parts and meal, shrimp parts and meal, fish oil, fish liver and glandular meal, and other fish by-products), dairy products (e.g., dried cow milk, casein, whey products, and dried cheese), fats and oils (e.g., animal fat, vegetable fat or oil, and hydrolyzed fats), restaurant food waste (e.g., food waste from restaurants, bakeries, and cafeterias), and contaminated/adulterated food treated to destroy pathogens.

Other additives include antibiotics (e.g., tetracyclines, macrolides, fluoroquinolones, and streptogramins), flavoring, brewers oats, by-products of drug manufacture (e.g., spent mycelium and fermentation products), minerals and trace minerals (e.g., bone charcoal, calcium carbonate, chalk rock, iron salts, magnesium salts, oyster shell flour, and sulphate), proteinated minerals (e.g., proteinated selenium and chromium), vitamins (e.g., vitamin A, vitamin D, vitamin $B_{12}$, niacin, and betaine), direct fed organisms/probiotics (e.g., *Aspergillus niger, Baccillus subtillis, Bifidobacterium animalis, B. bifidium, Enterococcus faecium, Aspergillus oryzae, Lactobacillus acidophilus, L. bulgaricus, L. planetarium, Streptococcus lactis*, and *Saccharomyces cerevisiae*), prebiotics (e.g., mannan-oligosaccharides (MOS), fructo-oligosaccharides, and mixed oligo-dextran), flavors (e.g., aloe vera gel concentrate, ginger, capsicum, and fennel), enzymes (e.g., phytase, cellulase, lactase, lipase, pepsin, catalase, xylanase, and pectinase), acetic acid, sulfuric acid, aluminum salts, dextrans, glycerin, beeswax, sorbitol, riboflavin, preservatives (e.g., butylated hydroxyanisole and sodium bisulfite), nutraceuticals (e.g., herbal and botanical products), amino acids, by pass protein, urea, molasses, fatty acids, (e.g., acetic, propionic, and butyric acid) and metabolic modifiers (e.g., somatotropins and adrenergic agonists). In some cases, the materials produced using the methods described herein can be combined or incorporated into a urea molasses mineral block (UMMB).

Foodstuffs prepared using the materials described herein can be in a form suitable for ingestion, e.g., by a target animal. In some cases the foodstuff can be a solid. Alternatively or in addition, the foodstuff can be in a liquid form, e.g., the foodstuff can be in a liquid suspension or solution in a suitable solvent. Exemplary forms include, but are not limited to solids such as powders, tablets, mineral blocks, pellets, biscuit, and mixtures of an unprocessed raw material (e.g., grass) and a material processed using the methods described herein.

In some embodiments, the materials described herein can be incorporated (e.g., mixed) into a foodstuff by a farmer, e.g., for local use and/or small scale distribution. In such cases, the materials described herein can be provided to the farmer in a packaged form, e.g., in a form that is suitable for incorporation into a foodstuff. Alternatively or in addition, the materials described herein can be incorporated (e.g., mixed) into a foodstuff by a foodstuff manufacturer, e.g., for large scale distribution. In such cases, the materials described herein can be provided to the foodstuff manufacturer in a form that is suitable for incorporation into a foodstuff. Alternatively or in addition, the materials described herein can be prepared from a raw material at the site at which the foodstuff is prepared.

In some embodiments, the materials described herein can be distributed alone and ingested by an animal in the absence of any additional raw materials and/or additives.

In some embodiments, the materials will require post-processing prior to use as food. For example, a dryer can be used to remove moisture from the intermediate fermentation products to facilitate storage, handling, and shelf life. Additionally or alternatively, the materials can be ground to a fine particle size in a stainless-steel mill to produce a flour-like substance.

Typically, biomass based foodstuffs are usefully fed only to ruminants that are capable of at least partially digesting cellulose. As the present disclosure provides materials in which the cellulosic material has been broken down into shorter chain sugars, these materials can also be used as a viable foodstuff for animals that are incapable of cellulose or hemicellulose digestion. Therefore, foodstuffs prepared using the materials and methods described herein can be usefully fed to animals including, but not limited to, food production animals, zoo animals, and laboratory animals, and/or domestic animals. The foodstuffs can also be used in agriculture and aquaculture. In addition, because foodstuffs prepared using the materials described herein have a higher nutrient availability, less foodstuff will be required by the animal to receive the same amount of energy, which will reduce the overall cost of the foodstuff. Alternatively, animals will be able to consume more energy, which will result in higher growth rates, tissue gain, milk production, and egg production.

In some embodiments, the materials described herein can be usefully fed to ruminants (e.g., cattle, goats, sheep, horses, elk, bison, deer, camels, alpacas, llamas, giraffes, yaks, water buffalo, wildebeest, and antelope), poultry, pigs, boars, birds, cats, dogs, and fish.

In some embodiments, distillers grains and solubles can be converted into a valuable byproduct of the distillation-dehydration process. After the distillation-dehydration process, distillers grains and solubles can be dried to improve the ability to store and handle the material. The resulting dried distillers grains (DDG) and solubles is low in starch, high in fat, high in protein, high in fiber, and high in phosphorous. Thus, for example, DDG can be valuable as a source of animal feed (e.g., as a feed source for dairy cattle). DDG can be subsequently combined with nutritional additives to meet specific dietary requirements of specific categories of animals (e.g., balancing digestible lysine and phosphorus for swine diets). Alternatively or in addition, biomass processed using the methods described herein can be combined with DDG. The ratio of processed biomass to DDG can be optimized to meet the needs of target animals.

In some embodiments, oils obtained from biomass using the methods described herein can be used in animal feed, e.g., as a pet food additive.

In some embodiments, as obtained from biomass using the methods described herein can be used in animal feed.

Human Foodstuffs

As described above, humans are typically less able to digest cellulose and cellulosic material. Biomass is an abundantly available material, however, that could serve as a novel foodstuff for human consumption. In order for a biomass material (e.g., a material containing cellulose) to be useful as a human foodstuff, however, the nutrient availability of the biomass would have to be increased by (1) increasing the solubility of the biomass; (2) changing the structure (e.g., functionalizing) of the native materials; (3) altering (e.g., lowering) the molecular weight and/or crystallinity relative to a native material; and/or (4) breaking down cellulosic material into smaller saccharides, for example, saccharides with a length of greater than 1000 saccharide units; about 1000 sugar saccharide units; about 800-900 saccharide units; about 700-800 saccharide units; about 600-700 saccharide units; about 500-600 saccharide units; about 400-500 saccharide units; about 300-400 saccharide units; about 200-300 saccharide units; about 100-200 saccharide units; 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, and 1 saccharide units. Such materials will have an increased nutrient availability (as described above), e.g., in humans, and will be useful as a human foodstuff. In general, a useful human foodstuff should, e.g., provide a usable and accessible energy and nutrient source to the human to, e.g., maintain or improve the health of a human, and/or promote the growth of a human (e.g., tissue gain). The methods described herein can be used to produce such a useful human foodstuff, e.g., from a biomass-based material.

In some embodiments, the materials will require processing prior to use as food. For example, a dryer can be used to remove moisture from the intermediate fermentation products to facilitate storage, handling, and shelf life. Additionally or alternatively, the materials can be ground to a fine particle size in a stainless-steel mill to produce a flour-like substance.

Such foodstuffs can include, but are not limited to, for example, energy supplements (e.g., powders and liquids). Alternatively or in addition, the materials described herein can be combined with a first food to increase the nutritional value of the first food. For example, the foodstuffs described herein can be combined with a low energy food to increase the energy of the food.

Alternatively or in addition, the materials described herein can be used to increase the sweetness of the food, e.g., as a sweetening agent, as well as the nutritional value of the food. In such cases, it can be desirable to obtain one or more specific sugars (e.g., a monosaccharide, a disaccharide, a oligosaccharide, and/or a polysaccharide) from the materials, e.g., by isolating the one or more specific sugars from the materials. Methods for isolating sugars are known in the art.

In some embodiments, the materials described herein can be used as a low cost material for food production. For example, the materials can be supplied to bakeries for use in bread and/or confectionary, and to food manufacturers to be used as a filler, e.g., to increase the volume and/or nutritional value of a food.

In some embodiments, the materials can further serve as a source of fiber for human consumption. In such cases, the methods used to break down the cellulolytic material will be configured to provide a less complete reduction in molecular weight, e.g., the methods will result in materials containing some cellulose and/or result in longer chain length polysaccharides that are not easily absorbed by humans. Such materials can be fed to a human in the form of a solid (e.g., a tablet or a granular powder) or a liquid (e.g., a solution, gel, colloid, or suspension).

In some embodiments, the materials described herein can be fed to a human alone or in the combination with a second food that is suitable for human consumption. Such foods include, but are not limited to, breads, dairy products, meats, fish, cereals, fruits, vegetables, beans (e.g., soy), and gums.

In some embodiments, the materials described herein can be combined with protein, fats, carbohydrates, minerals, pharmaceuticals, and vitamins.

Proteins

In some embodiments, the methods described herein can be used to obtain (e.g., extract, isolate, and/or purify proteins (e.g., polypeptides, peptides, and amino acids) from biomass. Such proteins (e.g., polypeptides, peptides, and amino acids) can be used, e.g., alone or in combination with one or more of the materials and biomass components obtained using the methods described herein, in the food industry (e.g., as additives, supplements, and/or fillers), in the cosmetic industry (e.g., in the compounding of cosmetics), and/or in agriculture (e.g., as foodstuffs or to feed or maintain crops) or aquaculture.

In some embodiments, the methods described herein can be used to obtain proteins (e.g., polypeptides, peptides, and amino acids) from e.g., okra seed, *Lipinus mutabilis*, nuts (e.g., macadamia nuts), *Jessenia bataua, Oenocarpus, Stokesia laevis, Veronia galamensis*, and *Apodanthera undulate*.

Fats, Oils, and Lipids

Fats consist of a wide group of compounds that are generally soluble in organic solvents and largely insoluble in water. Fats that are solid at room temperature. Fats that are liquid at room temperature are typically referred to as oils. The term lipids typically refers to solid and liquid fats. As used herein, the terms fats, oils, and lipids include, but are not limited to, edible oils, industrial oils, and those materials having an ester, e.g., triglyceride and/or hydrocarbon.

In some embodiments, the methods described herein can be used to obtain (e.g., extract, isolate, and/or purify) fats (e.g., lipids, and fatty acids) from biomass. Such fats (e.g., lipids, and fatty acids) can be used, e.g., alone or in combination with one or more of the materials and biomass components obtained using the methods described herein, in the food industry (e.g., as additives, supplements, and/or fillers), in the cosmetic industry (e.g., in the compounding of cosmetics), and/or in agriculture (e.g., as foodstuffs).

In some embodiments, the methods described herein can be used to obtain (e.g., extract, isolate, and/or purify) oils from biomass. Such oils can be used, e.g., alone or in combination with one or more of the materials and biomass components obtained using the methods described herein, in the food industry (e.g., as additives, supplements, and/or fillers), in the cosmetic industry (e.g., in the compounding of cosmetics), in agriculture (e.g., as foodstuffs), as biofuels, drying oils (e.g., in paints), and pet food additives.

In some embodiments, the methods described herein can be used to obtain fats, oils, and/or lipids from e.g., sunflower, okra seed, buffalo gourd (*Cucurbita foetidissima*), *Lipinus mutabilis*, nuts (e.g., macadamia nuts), *Jessenia bataua, Oenocarpus, Crambe abyssinica* (*Crambe*), Monoecious jojoba (jojoba), *Cruciferae* sp. (e.g., *Brassica juncea, B. carinata, B. napas* (common rapeseed), and *B. campestris*), *Stokesia laevis, Veronia galamensis*, and *Apodanthera undulate*.

Carbohydrates and Sugars

In some embodiments, the methods described herein can be used to obtain (e.g., extract, isolate, and/or purify) carbohydrates and/or sugars from biomass. Such carbohydrates and sugars can be used, e.g., alone or in combination with one or more of the materials and biomass components obtained using the methods described herein, e.g., in the food industry (e.g., as additives, supplements, syrups, and/or fillers), in the cosmetic industry (e.g., in the compounding of cosmetics), and/or in agriculture (e.g., as foodstuffs).

Vitamins

In some embodiments, the methods described herein can be used to obtain (e.g., extract, isolate, and/or purify) vitamins from biomass. Such vitamins can be used, e.g., alone or in combination with one or more of the materials and biomass components obtained using the methods described herein, e.g., in the food industry (e.g., as additives, and supplements), in the healthcare industry, in the cosmetic industry (e.g., in the compounding of cosmetics), and/or in agriculture.

Minerals

In some embodiments, the methods described herein can be used to obtain (e.g., extract, isolate, and/or purify) minerals from biomass. Such minerals can be used, e.g., alone or in combination with one or more of the materials and biomass components obtained using the methods described herein, e.g., in the food industry (e.g., as additives, and supplements), in the healthcare industry, in the cosmetic industry (e.g., in the compounding of cosmetics), and/or in agriculture.

Ash

In some embodiments, the methods described herein can be used to obtain (e.g., extract, isolate, and/or purify) ash from biomass. Such ash can be used, e.g., alone or in combination with one or more of the materials and biomass components obtained using the methods described herein, e.g., in the food industry (e.g., as an additive, supplement, and/or filler).

Pharmaceuticals

Over 120 currently available pharmaceutical products are plant-derived. As the methods described herein are useful for processing cellulolytic material, these methods can be useful in the isolation, purification, and/or production of plant-based pharmaceuticals.

In some embodiments, the materials described herein can have medicinal properties. For example, the methods described herein can result in the production of a material with novel medicinal properties (e.g., not present in the native material). Alternatively or in addition, the methods described herein can result in the production of a material with increased medicinal properties (e.g., a greater medicinal property than that of the native material).

In some embodiments, the methods described herein can be used to modify (e.g., increase, decrease, or maintain) the solubility of a material, e.g., a material with medicinal properties. Such a material can be more easily administered and/or absorbed, e.g., by a human and/or animal than a native material.

In some embodiments, the methods described herein can be used to functionalize (e.g., alter the structure, expose a reactive side chain, and/or modify the charge) a material with medicinal properties. Such materials can have, e.g., altered reactivity, altered charge, and/or altered solubility.

In some embodiments, the methods described herein can be used to modify the molecular structure of a material, e.g., a material with medicinal properties. Such materials can have altered (e.g., increased or decreased) average molecular weights, average crystallinity, surface area, and/or porosity. Such materials can have, e.g., altered reactivity, altered charge, altered solubility.

In some embodiments, the methods described herein can be used as high efficiency processing methods, e.g., to obtain plant-based pharmaceuticals from a cellulosic raw material such as plants. In some embodiments, the methods described herein can be used to increase the pharmaceutical activity of a plant-based pharmaceutical. For example, in some embodiments, the methods described herein can be applied to plants and/or herbs with medicinal properties. For example, sonication can stimulate bioactivity and/or bioavailability of the medicinal components of plants and/or herbs with medicinal properties. Additionally or alternatively, irradiation can stimulate bioactivity and/or bioavailability of the medicinal components of plants and/or herbs with medicinal properties.

In some embodiments, the methods described herein can be used to increase the solubility of a plant and/or herbal material. Alternatively or in addition, the methods described herein can be used to reduce the toxicity of a plant and/or herbal material without reducing the medicinal properties of the plant and/or herb. In some embodiments, the methods described herein are useful for isolating and/or purifying pharmaceutical compounds from plant material (which without being bound by theory, is possible due to the more efficient break down of cellulosic material) as the methods disrupt, alter, modify, or restructure cellulose, e.g., present in the leaves of plant material. Desired compounds released using the methods described herein can then be isolated from the undesired material, whereas less efficient methods can not allow the release of the desired material from undesired material. Inevitably, therefore, less efficient methods will result in the carry over of undesired material, which can lower the efficacy of the desired (e.g., pharmaceutical compound) and/or be associated with potentially toxic side effects. The methods described herein can, therefore, be used to generate highly purified forms of potentially pharmaceutical compounds, e.g., free of undesirable plant material, that are not obtainable using current practices. These highly purified compounds can be more efficacious then less purified forms of the same compounds. In some embodiments, the increased efficacy attainable using the methods described herein can allow reduced dosing. In turn, this reduction in the amount of material administered to a subject can reduce associated toxicity. Alternatively or in addition, the removal of surplus or undesirable plant material can help reduce or eliminate any toxicity associated with a plant based compound that has not been processed using the methods described herein.

Examples of plants and/or plant material that can be usefully treated using the methods described herein include, for example, sonication and irradiation can be combined in the pretreatment of willow bark to stimulate the isolation, purification, and/or production of salicin. Alternatively or in addition, the methods described herein can be used to process plant material comprising comfrey plants to facilitate the isolation, purification, and/or production of allantoin. Alternatively or in addition, the methods described herein can be used to facilitate the isolation, purification, and/or production benzoin. Alternatively or in addition, the methods described herein can be used to process plant material comprising camphor basil to facilitate the isolation, purification, and/or production of camphor. Alternatively or in addition, the methods described herein can be used to process plant material comprising plants in the genus *Ephedra* to facilitate the isolation, purification, and/or production of ephedrine. Alternatively or in addition, the methods described herein can be used to process plant material comprising *Duboisia myoporoides* R. Br. (Australian cork tree) to facilitate the isolation, purification, and/or production of atropine. In some embodiments, the atropine obtained using the methods described herein will have an increased anticholinergic effect. Alternatively or in addition, the methods described herein can be used to process plant material comprising *Mucuna deeringiana* (velvet bean) to facilitate the isolation, purification, and/or production of L-dopa. In some embodiments, the L-dopa obtained using the methods described herein will have an increased antiparkinsonian effect. Alternatively or in addition, the methods described herein can be used to process plant material comprising *Physostigma venenosum* Balf. (ordeal bean) to facilitate the isolation, purification, and/or production of physostigmine. In some embodiments, the physostigmine obtained using the methods described herein will have an increased anticholinesterase effect. Examples of other plant-based pharmaceuticals in which the methods described herein can be used to process plant material to facilitate the isolation, purification, and/or production of include, but are not limited to, bromelain, chymopapain, cocaine, deserpidine, emetine, hyoscyamine, kawaina, monocrotaline, ouabain, papain, pilocarpine, quinidine, quinine, rescinnami, reserpine, scopolamine, tubocurarine, vinblastine, yohimbine, caprylic-acid, cineole, citric acid, codeine, cresol, guaiacol, lecithin, menthol, phenol pseudephedrine, sorbitol, and tartaric acid.

In some embodiments, the methods described herein can be used to process herbs, e.g., medicinal herbs, including, but not limited to, basil, lemon grass, parsley, peppermint, and celery. Additional medicinal herbs that can be processed using the methods described herein can be found at world wide web address altnature.com.

An emerging technology is the production of pharmaceuticals in plants. Pharmaceutical produced using plants, which are commonly referred to as plant made pharmaceuticals (PMPs), include pharmaceutical compounds and vaccines. Typically, PMPs are expressed in the leaves of the respective plants. Clearly, therefore, the methods described herein can be useful for processing plant material comprising PMPs to facilitate the isolation, purification, and/or production of the PMPs.

Additional exemplary medicinal plants that can be treated using the methods described herein can be found e.g., at world wide web address nps.gov/plants/MEDICINAL/plants.htm.

In some embodiments, material that has been processed using the methods described herein can be combined with a pharmaceutical excipient, e.g., for administration to a subject. Exemplary excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. Dosage forms can be formulated to be suitable for any standard route of administration. For example, administration can be parenteral, intravenous, subcutaneous, or oral or any route of administration approved by the Federal Drug Administration (see world wide web address fda.gov/cder/dsm/DRG/drg00301.htm).

Nutriceuticals and Nutraceuticals

Foods with a medical health benefit, including the prevention and/or treatment of disease, are referred to as nutraceuticals or nutriceuticals. For example, nutraceuticals and nutriceuticals are naturally occurring or artificially generated nutritional supplements capable of promoting a healthy lifestyle, for example, by reducing disease related symptoms, reducing the incidence or severity of disease, and promoting long-term health.

In some embodiments, the methods described herein can be used to generate combinations of monosaccharides, disaccharides, oligosaccharides, and/or polysaccharides that are capable of promoting a healthy lifestyle. In some embodiments, the methods described herein can be used to generate a material that is useful for promoting weight loss in a human. For example, the material can have low nutrient availability with low digestibility, e.g., a fibrous material. Such materials could be used as a dietary supplement, e.g., to suppress hunger and/or to promote satiety. Consuming such materials would allow a subject to avoid consuming high nutrient availability and/or highly digestible foods and thus would facilitate weight loss in the individual.

In some embodiments, the materials described herein can be supplemented with one or more nutritional supplements that are capable of promoting a healthy lifestyle. In such cases, the materials described herein can either enhance the activity of the one or more nutritional supplements and/or enhance the solubility and/or pharmacokinetics of the one or more nutritional supplements. Exemplary nutritional supplements that can be combined with the materials described herein include, but are not limited to, for example, silica, silicon, boron, potassium, iodine, beta-carotene, lycopene, insoluble fiber, monosaturated fatty acids, omega-3 fatty acid, flavonols, sulforaphane, phenols (e.g., caffeic acid and ferulic acid), plant stanols and sterols (including esters thereof), polyols (e.g., sugar alcohols), prebiotics and probiotics (e.g., Lactobacilli and bifidobacteria), phytoestrogens (e.g., isoflavones such as daidzein and genistein), proanthocyanidins, soy protein, sulfides and thiols (e.g., dithiolthiones), vitamins (e.g., vitamin A, vitamin $B_1$, vitamin $B_2$, vitamin $B_3$, vitamin $B_5$, vitamin $B_6$, vitamin $B_7$, vitamin $B_{12}$, vitamin C, vitamin D, vitamin E, vitamin K, including combinations thereof) minerals (e.g., iron, calcium, magnesium, manganese, phosphorus, potassium, zinc, trace minerals, chromium, selenium, including combinations thereof), and folic acid.

Pharmaceutical Dosage Forms and Drug Delivery Compositions

Drug substances are seldom administered alone, but rather as part of a formulation in combination with one or more non-medical agents that serve varied and often specialized pharmaceutical functions. Pharmaceutics is the science of dosage form design, e.g., formulating a drug into a dosage form suitable for administration to a subject. These non-medical agents, referred to as pharmaceutic or pharmaceutical ingredients, can be formulated to solubilize, suspend, thicken, dilute, emulsify, stabilize, preserve, color, flavor, and fashion medicinal agents into efficacious and appealing dosage forms. Such dosage forms can be unique in their physical and pharmaceutical characteristics. The drug and pharmaceutic ingredients will typically be compatible with each other to produce a drug product that is stable, efficacious, attractive, easy to administer, and safe. The product should be manufactured under appropriate measures of quality control and packaged in containers that contribute to promote stability. Methods describing the preparation of specific dosage forms are well known in the art and can be found in, for example, Ansel et al., Pharmaceutical Dosage Forms and Drug Delivery Systems, Seventh Edition, Lippincott, Williams, & Wilkins and, "*Remington's Pharmaceutical Sciences,* 18th Ed., Gennaro, ed., Mack Publishing Co., Easton, Pa., 1990.

In some embodiments, the pretreated materials described herein can be used as pharmaceutic ingredients e.g., inactive ingredients. For example, the materials described herein can be used, e.g., formulated, to solubilize, suspend, thicken, dilute, emulsify, stabilize, preserve, color, flavor, and fashion medicinal agents into efficacious, palatable, and appealing dosage forms. In such cases, the materials described herein can be mixed with a drug and/or conjugated to a drug such that the solubility, concentration, viscosity, emulsion stability, shelf life, color, and flavor of the drug is increased or decreased.

In some embodiments, the methods described herein can be used to modify (e.g., increase, decrease, or maintain) the solubility of a material. Such materials can be used to facilitate the administration of a drug to a subject. For example, certain of the new pretreated materials are exceptionally soluble in liquids, such as water, and can be used, when mixed with active ingredients to form a pharmaceutical composition, to allow the inert ingredients to be easily dissolved in liquids.

Alternatively or in addition, the materials described herein can be used to delay, control, or modify the release of a drug once the drug has been administered to a subject. In such cases, the materials described herein can be used in solid dosage forms and/or controlled-release drug delivery systems; semi-solid and/or transdermal systems; pharmaceutical inserts; liquid dosage forms; sterile dosage forms and delivery systems; and novel and advanced dosage forms, delivery systems and devices. For example, the materials described herein can be formulated, e.g., in the form of a tablet, a capsule (e.g., a hard capsule, a soft capsule, or a microcapsule), a suppository, an injectable solution or suspension (a parenteral), a cream, a ointment, an ophthalmic solution or suspension, an ear drop solution or suspension, an inhalable solution or suspension, a nasal spray, a transdermal patch, an emulsion, a ointment, a cream, a gel, a suspension, a dispersion, a solution (e.g., an intravenous solution), an implant, a coating for an implant, a lotion, a pill, a gel, a powder, and a paste. In some embodiments, the materials described herein can be combined with a radiopharmaceutical.

In some embodiments, the methods described herein can be used to generate a material that can be conjugated to a biological agent and/or a pharmaceutical agent. Such conjugates can be used to facilitate administration of the agent and increase the pharmaceutical properties of the agent.

The formulations and routes of administration can be tailored to the disease or disorder being treated, and for the specific human being treated. When using the materials described herein as pharmaceutic ingredients, it can be necessary to determine the optimal formulation and dosage type. For example, various initial formulations can be developed and examined for desired features (e.g., drug release profile, bioavailabilty, and clinical effectiveness) and for pilot plant studies and production scale up. The formulation that best meets the goals for the product (e.g., drug release profile, bioavailabilty, and clinical effectiveness) can then be selected as the master formula. Each subsequent batch of product can then be prepared to meet the specifications of the master formula. For example, if the product is for systemic use and oral administration is desired, tablets and/or capsules are usually prepared. The age of the intended patient can also be considered when selecting a dosage form. For example, for infants and children younger than five years of age, pharmaceutical liquids rather than solids are preferred for oral administration. In addition, the physical characteristics of the drug or drugs to be formulated with the pharmaceutic ingredients must be understood prior to dosage form development.

Pharmaceutical compositions containing one or more of the compounds described herein will be formulated according to the intended method of administration.

In some cases, the nature of the dosage form is dependent on the mode of administration and can readily be determined by one of ordinary skill in the art. In some embodiments, the dosage form is sterile or sterilizable. In particular, the materials described herein are often sterile when pretreated with radiation as described herein.

In some embodiments, the dosage forms can contain carriers or excipients, many of which are known to skilled artisans. Exemplary excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. Dosage forms can be formulated to be suitable for any standard route of administration. For example, administration can be parenteral, intravenous, subcutaneous, or oral or any route of administration approved by the Federal Drug Administration (see world wideweb address fda.gov/cder/dsm/DRG/drg00301.htm).

In addition to the formulations described previously, the compositions can also be formulated as a depot preparation. Such long-acting formulations can be administered, e.g., by implantation (e.g., subcutaneously). Thus, for example, the compositions can be formulated with suitable polymeric or hydrophobic materials (for example, as an emulsion in an acceptable oil) or ion exchange resins, or as sparingly soluble derivatives, for example, as a sparingly soluble salt.

Pharmaceutical compositions formulated for systemic oral administration can take the form of tablets or capsules prepared by conventional means with pharmaceutically acceptable excipients such as binding agents (for example, pregelatinized maize starch, polyvinylpyrrolidone or hydroxypropyl methylcellulose); fillers (for example, lactose, microcrystalline cellulose or calcium hydrogen phosphate); lubricants (for example, magnesium stearate, talc, or silica); disintegrants (for example, potato starch or sodium starch glycolate); or wetting agents (for example, sodium lauryl sulphate). Many of the functions of these binding agents, fillers, lubricants, and disintegrants can be served by the pretreated materials described herein.

The tablets can be coated by methods well known in the art. Liquid preparations for oral administration can take the form of, for example, solutions, syrups or suspensions, or they can be presented as a dry product for reconstitution with water or other suitable vehicle before use. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound.

In some embodiments, the materials described herein can be used as pharmaceutic ingredients for use in topical iontophoresis, phonophoresis, rapidly dissolving tablets, lyophilized foam, an intravaginal drug delivery system, a vaginal insert, a urethral insert or suppository, an implantable drug delivery pump, an external drug delivery pump, and a liposome.

Hydrogels

In some embodiments, the materials described herein can be used in the formulation of a hydrogel. Hydrogels are three-dimensional networks of hydrophilic polymer chains that are crosslinked through either chemical or physical bonding and are water insoluble and are typically superabsorbent (e.g., can contain over 99% water) and permit gas and nutrient exchange.

In some embodiments, the materials described herein can be used to generate a hydrogel. For example, monosaccharides, oligosaccharides, and polysaccharides contained in the materials described herein can be used to generate a hydrogel. Alternatively or in addition, the materials described herein can be used to generate a hydrogel in combination with other materials such as hyaluronan, gelatin, cellulose, silicone, and one or more components of the extracellular matrix (ECM).

In some embodiments, hydrogels containing the materials described herein can be cross-linked (e.g., chemically cross-linked) and/or oxidized. Alternatively or in addition, hydrogels containing the materials described herein can be cross-linked using low-level irradiation. Doses of low-irradiation that can be used to cross-link the materials described herein include, but are not limited to, for example, 0.1 Mrad to 10 Mrad. Alternatively or in addition, hydrogels containing the materials described herein can be cross-linked using a combination of chemical cross-linking, low-level irradiation, and oxidation.

In some embodiments, the methods described herein can be used to modify (e.g., increase) the average molecular weight of the biomass materials described herein. For example, the methods described herein can be used to increase the average molecular weight of a biomass material by, e.g., 10%, 25%, 50%, 75%, 100%, 150%, 200%, 300%, or as much as 500%.

In some embodiments, the methods described herein can be used to modify (increase or decrease) the Poisson's ratio of a hydrogel.

In some embodiments, hydrogels generated using the materials described herein can include one or more one or more biological cells and/or one or more bioactive agent such as a pharmaceutical agent or a component of the ECM. Candidate pharmaceutical agents, could include but are limited to, a therapeutic antibody, an analgesic, an anesthetic, an antiviral agent, an anti-inflammatory agent, an RNA that mediates RNA interference, a microRNA, an aptamer, a peptide or peptidomimetic, an immunosuppressant, hypoxyapatite, or bioglass.

Hydrogels containing the materials described herein can be used as biodegradable or non-biodegradable implantable (e.g., subdermal implantable) three-dimensional scaffolds, e.g., in wound healing and tissue engineering, implantable disc replacements, drug delivery vehicles (e.g., slow release drug delivery vehicles), on wound dressing, contact lenses, and as superabsorbant materials (e.g., in diapers).

Hydrogels containing the materials described herein can also be combined with medical devices for the treatment of both external and internal wounds. The hydrogels can be applied to bandages for dressing external wounds, such as chronic non-healing wounds, or used as subdermal implants. Alternatively, the present hydrogels can be used in organ transplantation, such as live donor liver transplantation, to encourage tissue regeneration. The hydrogels can be adapted to individual tissue types by equilibrating the water content, biodegradation kinetics, and Poisson's ratio with those of the target tissue to be repaired.

Methods for making hydrogels are well known in the art and can be found, for example, in U.S. 2006/0276608.

Absorbent Materials

In some embodiments, the methods described herein can be used to generate absorbent materials. For example, in some embodiments, biomass can be processed using one or more of the pretreatment methods described herein. Such materials can have, e.g., modified (increased, decreased, maintained) solubility, porosity, surface area, average molecular weight, functionalization (e.g., an increased number of hydrophilic groups). Alternatively or in addition, these materials can be chemically treated to enhance a specific absorption property. For example, the materials can be treated with silanes to render them lipophilic. These material can have the ability to absorb 1, 2, 5, 10, 20, 50, 100, 500, and 1000 times more fluid than native materials and/or 1, 2, 5, 10, 20, 50, 100, 500, and 1000 times the materials own weight. In some embodiments, these materials can be used to adhere (e.g., selectively) to one or more materials (e.g., biological materials in blood or plasma, toxins, pollutants, waste materials, inorganic chemicals, and organic chemicals), e.g., in a solution or in a dry medium.

In some embodiments, the materials described herein can be used as absorbent materials, e.g., for use as animal litter, e.g., for small and large animals, and animal bedding. Methods for making animal litter are well known in the art (see e.g., U.S. Pat. No. 5,352,780).

In some embodiments, the absorbent animal litter will additionally include a scented or fragrant material and/or an odor eliminating material as are known in the art.

In some embodiments, the materials described herein can be used to absorb chemical spills, e.g., by applying the materials to a spill.

In some embodiments, the materials described herein can be used in combination with a filter, e.g., a medical filter or a non-medical filter.

The materials described herein will provide useful absorbent materials due to the high surface area, the high absorbency, the high swelling properties, and the high porosity of the materials described herein.

Pollution Control

In some embodiments, the absorbent materials described herein can be used for pollution control. When used for such applications, the absorbent materials can be used in the form of a solid, liquid, or gas. For example, the materials described herein can be used to absorb oil and/or for clean up of environmental pollution, for example, in water, in the air, and/or on land. The materials described herein can also be used for waste water treatment (e.g., factory waste and sewage treatment), and for water purification.

In some embodiments, the absorbent materials described herein can be used in combination with biologic agents (microorganisms, fungi, green plants or their enzymes) or chemicals to facilitate removal, inactivation, or neutralization of the pollutant from the environment, e.g., using bioremediation.

In some embodiments, the absorbent materials described herein can degrade (e.g., biodegrade). Such a process can be controlled to achieve a desired degradation rate. In some embodiments, the absorbent materials described herein can be resistant to degradation.

In some instances, these absorbent materials can be associated with a structure or carrier such as netting, a membrane, a flotation device, a bag, a shell, a filter, a casing, or a biodegradable substance. Optionally, the structure or carrier itself can be made of the materials described herein.

Air Purification

In some embodiments, biomass processed using the methods described herein can carry a charge (e.g., a positive or negative charge) or can be neutral. In some embodiments, charged (e.g., positively or negatively charged) materials can be used for the removal of contaminants (e.g., microorganisms, spores, mild spores, dust, pollen, allergens, smoke particles, and dust mite feces) from air. In some embodiments, charged (e.g., positively or negatively charged) materials can be used to trap contaminants. Alternatively or in addition, charged (e.g., positively or negatively charged) materials can be used to eliminate contaminants. For example, in some embodiments, the methods described herein can be used to increase the cationic value of a material. In general, cationic compounds have antimicrobial activity. In some cases, charged (e.g., positively or negatively charged) materials can be combined with phenolics, pharmaceuticals, and/or toxins (e.g., listed herein) for the elimination of microorganisms and/or spores.

In some embodiments, charged (e.g., positively or negatively charged) materials can be used in conjunction with a device such as an air purification device. For example, charged (e.g., positively or negatively charged) materials can be mobilized on a surface within an air purification device, e.g., a filter (e.g., a fibrous filter, and/or a fibrous filter n mat form). Alternatively or in addition, charged (e.g., positively or negatively charged) materials can be present in the form of a gas and/or vapor within an air purification device. Alternatively or in addition, charged (e.g., positively or negatively charged) materials can be used in an air handling system (e.g., an air conditioning unit), e.g., within a closed environment such as within a vehicle (e.g., a car, bus, airplane, and train carriage), a room, an office, or a building. For example, charged (e.g., positively or negatively charged) materials can be used can be mobilized on a surface within an air handling system, e.g., a filter. Alternatively or in addition, charged (e.g., positively or negatively charged) materials can be present in the form of a gas and/or vapor within an air handling system. Alternatively or in addition, charged (e.g., positively or negatively charged) materials can be used more locally. In such cases, charged (e.g., positively or negatively charged) materials can be contained and dispensed from a container, e.g., a pressurized canister or a non-pressurized container with a pump. Alternatively or in addition, charged (e.g., positively or negatively charged) materials can be used in a slow release system, e.g., wherein charged (e.g., positively or negatively charged) materials are released into the air over a period of time. Such slow release systems are known in the art and are commercially available. In some embodiments, such slow release systems can use heat (e.g., generated using electricity) to promote release of the charged (e.g., positively or negatively charged) materials.

In some embodiments, charged (e.g., positively or negatively charged) materials can be used in conjunction with an air filter.

In some embodiments, charged (e.g., positively or negatively charged) materials can be used in a device designed to filter the air inhaled and/or exhaled by a human (e.g., masks, a filtration helmets, and/or filtration suits). In some embodiments, such devices can be used to reduce the inhalation of one or more potential pollutants by a human. Alternatively or in addition, such devices can be used to reduce the exhalation of one or more potential pollutants by a human.

In some embodiments, the methods described herein can be used to generate materials useful as aromatics. Such aromatics can be combined with any of the products and co-products described herein. Alternatively or in addition, these aromatics can be used to alter the scent or fragrance of a material (e.g., a solid or liquid) and/or air. In such cases, aromatics can be used in combination with, e.g., candles, perfumes, detergents, soaps, gels, sprays, and air fresheners.

Exemplary aromatics than can be obtained from biomass include, e.g., lignin and bio-aromatics.

Food Preservation

In some embodiments, the methods described herein can be used to generate materials useful for food preservation, or that can be used in food preservation. In such cases, suitable materials can be in the form of a gas, a vapor, a liquid, and/or a solid. In some embodiments, materials (e.g., charged materials) can be used to trap contaminants. Alternatively or in addition, materials (e.g., charged materials) can be used to eliminate contaminants. In some cases, materials (e.g., charged materials) can be combined with phenolics and/or toxins for the elimination of microorganisms and/or spores. For example, materials (e.g., charged materials) can be used for the removal of contaminants (e.g., microorganisms, spores, and mild spores) from an area surrounding food items to prevent, limit, or reduce spoilage of food items. For example, materials (e.g., charged materials) can be present within a container transporting food items. Alternatively or in addition, materials (e.g., charged materials) can be present in a container (e.g., a package or bag) intended for storage of a food item. Such items can be sold with the materials (e.g., charged materials) can already present, or materials (e.g., charged materials) can be added upon adding a food item to the container. Alternatively or in addition, materials (e.g., charged materials) can be present within a cold storage area such as a fridge and/or a freezer.

Herbicides and Pesticides

In some embodiments, the methods described herein can be used to generate toxins (e.g., natural toxins) including, but not limited to, herbicides and pesticides. Such materials include, for example, lectins, glycoalkaloids, patulin, algal toxins, paralytic shellfish poison (PSP), amnesiac shellfish poisons (ASP), diarrhetic shellfish poison (DSP), vitamin A, and mycotoxins.

Fertilizer

In some embodiments, the methods described herein can be used to generate materials that can be used as fertilizer. Biomass is rich in nutrients and is currently used as fertilizer, however, native material has low solubility and is only useful as a fertilizer once partially or fully decomposed, both of which can take substantial amounts of time, require some tending, and require provision of storage space while decomposition takes place. This generally limits the use of biomass as fertilizer.

In some embodiments, the methods described herein can be used to modify biomass into materials with, e.g., modified (e.g., increased) solubility that can be used as fertilizers. Such materials can be distributed over an area in need of fertilization and will be solubilized upon contact with a solution (e.g., water and rain water). This solubilization will render the nutrients in the materials more accessible to the area in need of fertilization.

In some embodiments, the methods described herein can be used to modify biomass into materials for use as fertilizers. Such materials can be combined (e.g., blended) with seeds, nitrates, nitrites, nitrogen, phosphorus, potassium, calcium, lime, vitamins, minerals, pesticides, and any combinations thereof. Alternatively or in addition, such materials can be combined with one or more microorganisms capable of degrading the materials and/or one or more enzymes capable of breaking down the materials. These components can be provided together or separately in liquid or dry forms. In some instances, these materials can be associated with a structure or carrier such as netting, a membrane, a flotation device, a bag, a shell, or a biodegradable substance. Optionally, the structure or carrier itself can be made of the materials described herein. In some embodiments, these materials and combinations of these materials can be mixed in a vessel (e.g., a bag or solid container), e.g., to promote decomposition. Such mixtures can be supplied for use in a vessel (e.g., a bag or solid container).

In some embodiments, the methods described herein can be used to generate materials that can be combined with plant seeds. For example, materials generated using a method described herein can be coated on the surface of seeds, e.g., to protect seeds from rot, to protect seeds from microorganisms, and/or to fertilize seeds.

Chemical and Biological Applications

In some embodiments, the methods described herein can be used to generate materials suitable for use as acids, bases, and/or buffers. Such materials can be used, e.g., to alter and/or buffer the pH of a material (e.g., a solid or liquid) in need of such treatment. Such materials include solids and liquids not suitable for consumption and/or solids and liquids intended for consumption (e.g., food products such as meats, beverages, and dairy products).

In some embodiments, the methods described herein can be used to generate materials suitable for use in maintaining or promoting the growth of microorganisms (e.g., bacteria, yeast, fungi, protists, e.g., an algae, protozoa or a fungus-like protist, e.g., a slime mold), and/or plants and trees.

Lignin

In some embodiments, the methods described herein can also be used to generate lignin, e.g., lignin residue.

Lignin is a phenolic polymer that is typically associated with cellulose in biomass, e.g., plants. In some instances the methods described herein will generate lignin that can be obtained (e.g., isolated or purified) from the biomass feedstock described herein. In some embodiments, the lignin obtained from any of the processes described herein can be, e.g., used as a plasticizer, an antioxidant, in a composite (e.g., a fiber resin composite), as a filler, as a reinforcing material, and in any of the pharmaceutical compositions described herein.

In addition, as described above, lignin-containing residues from primary and pretreatment processes has value as a high/medium energy fuel and can be used to generate power and steam for use in plant processes. However, such lignin residues are a new type of solid fuel and there may be little demand for it outside of the plant boundaries, and the costs of drying it for transportation may subtract from its potential value. In some cases, gasification of the lignin residues can be used to convert it to a higher-value product with lower cost.

In some embodiments, lignin can be combined with one or more of the products and co-products described herein. For example, lignin can be combined with one or more herbicides and/or pesticides, e.g., to generate a slow release system, e.g., where one or more herbicides and/or pesticides are released over a period of time. Such slow release systems can be combined with the fertilizers described herein. Alternatively or in addition, lignin can be combined with charged (e.g., positively or negatively charged) materials to generate a slow release air purification system. In some embodiments, lignin can be used, e.g., alone or in combination with one or more of the products and co-products described herein, as a composite, e.g., for use as a plastic additive and/or a resin.

An example of the structure of a lignin is shown below.

facilities. Interstitial cell matter could be valuable, but might require significant purification. Markets for furfural and acetic acid are in place.

Bioconversion Products

As described above, the methods described herein can be used to process biomass to obtain/produce, for example, foodstuffs (e.g., animal (including aquatic), human, and/or microbial foodstuffs), proteins, fats and oils, carbohydrates and sugars, vitamins, minerals, ash, pharmaceuticals, nutriceuticals and nutraceuticals, pharmaceutical dosage forms,

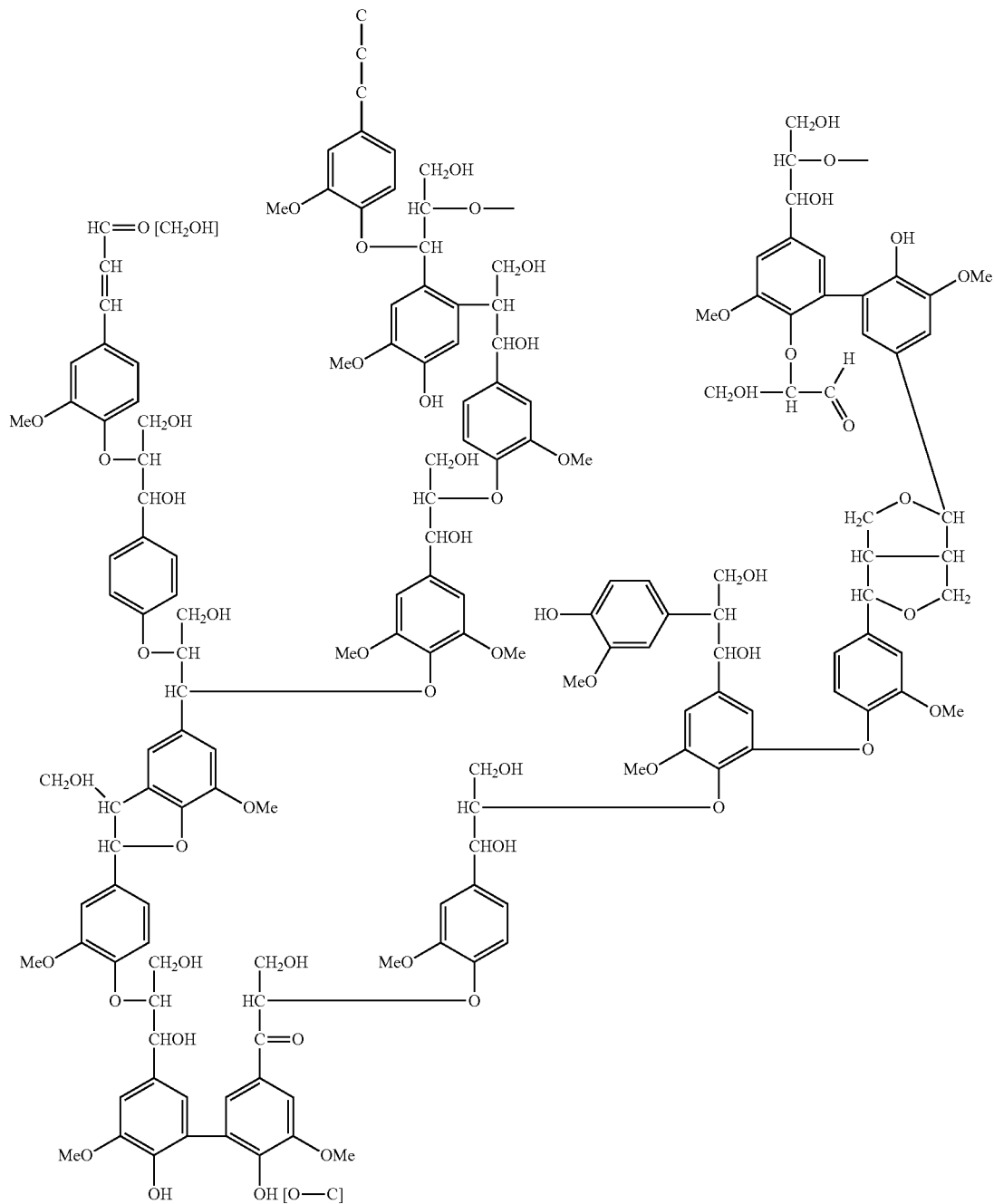

Other Products

Figure 43A:
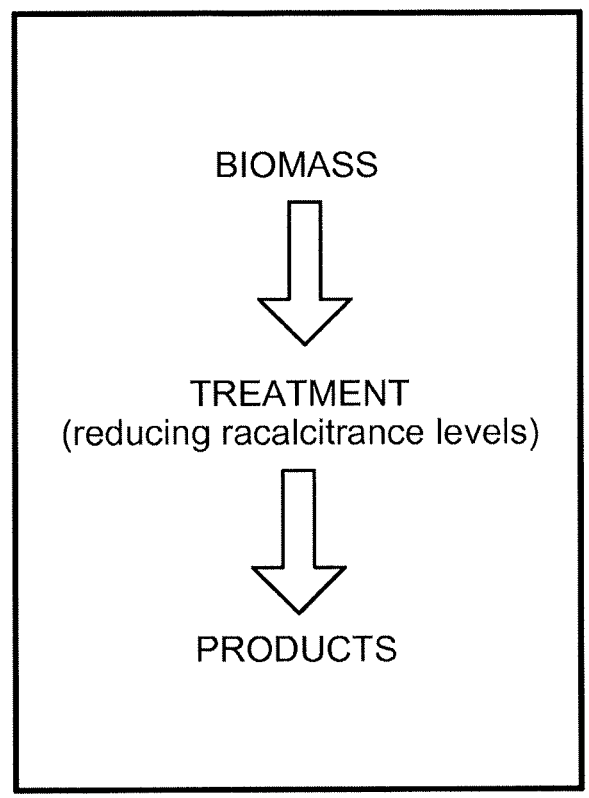
FIGS. 43A and 43B are schematic diagrams showing the processing steps for generating products and co-products from biomass (A) and for generating products using a bioconversion step.

Cell matter, furfural, and acetic acid have been identified as potential co-products of biomass-to-fuel processing hydrogels, absorbent materials, air purification materials, food preservatives, herbicides and pesticides, fertilizers, acids, bases and buffers, and lignin. As shown in FIG. 43A, in general, these methods involve processing biomass, e.g., changing (e.g., lowering) the recalcitrance level of the biomass, to obtain products, e.g., derived directly from the biomass and/or to produce products comprising these materials.

Figure 43B:
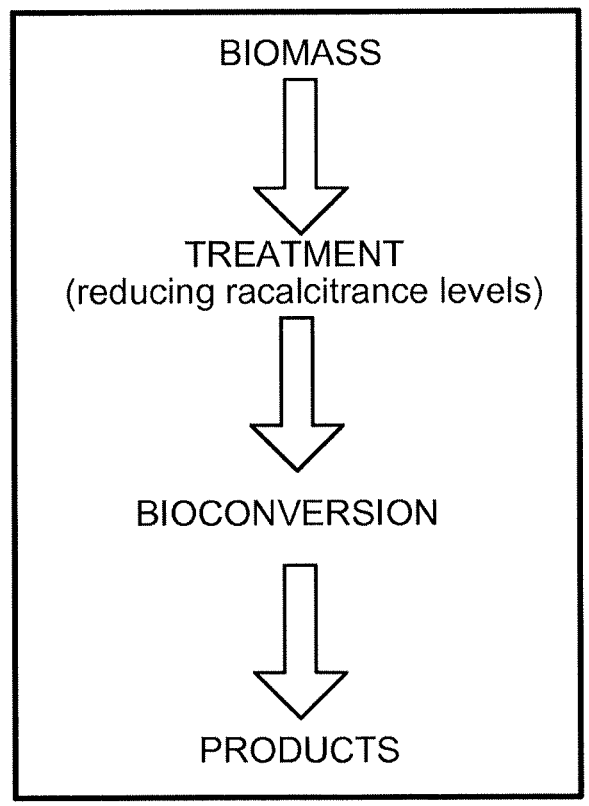

Alternatively or in addition, the methods described herein can be used to process a first material (e.g., biomass), e.g., to change (e.g., lower) the recalcitrance level of the biomass, to produce a second material that can be used as a substrate for additional processes, e.g., to generate materials and products present (e.g., substantially present) or abundant in the first material. In some embodiments, the additional processes can include a bioconversion step as shown in FIG. 43B. In some embodiments, the bioconversion step can include the use of microorganisms. Examples of methods including a bioconversion step are described above, for example, in the use of the methods described herein to produce energy products (e.g., ethanol), alcohols, and/or organic acids, all of which are not necessarily present (e.g., not substantially present) or abundant in natural unprocessed biomass. Further examples of such methods are described below.

Edible Products

In some embodiments, the methods described herein can be performed in combination with a bioconversion step (e.g., see FIG. 43B) to produce an edible product (e.g., an ingestible product such as a food product, e.g., an edible starch and/or protein) for use with animals or humans. One advantage of such methods over conventional agricultural food production methods is that the methods described herein do not require large areas of land and can be performed in environments that do not favor conventional food production methods.

Malnutrition, particularly protein calorie malnutrition, is a increasing problem around the world, especially in the developing world. Insufficient calories and protein contribute to increased infectious disease, stunt physical growth, and retard brain and mental development. These malnutrition problems are caused by increasing global populations coupled with inadequate food supplies in developing countries and aging food production methods. Without change in population growth, supplies, and food production methods, malnutrition will also become a serious problem within developed countries. One solution to these problems is to increase food supply. This will be difficult under conventional agricultural practice, however, due to limited availability of land for agriculture and the well-documented changing global climate. In addition, conventional agricultural practices are not favorable in certain environments, for example, environments that present excessive heat or cold, limited oxygen, and/or limited sunlight. An alternative solution is to modify the usage of currently available materials (e.g., biomass) to create alternative food supplies, for example, to increase the nutritional value or usability of already available materials.

The use of microbial proteins as a food for consumption by animals and humans is known in the art and is monitored by The Food and Agriculture Organization of the United Nations (FAO). The FAO in collaboration with the World Health Organization (WHO) has published several publicly available reports outlining guidelines and the standards required for foods derived from biotechnology (see, e.g., Joint FAO/WHO Expert Consultation on Foods Derived from Biotechnology, 1996; Steve Taylor, Joint FAO/WHO Expert Consultation on Foods Derived from Biotechnology, 2001 (Biotech 01/03); David Ow, Joint FAO/WHO Expert Consultation on Foods Derived from Biotechnology, 2000 (Biotech 00/14)). These guidelines outline the safety issues to be considered when using microorganisms to produce foods, types of organisms that are suitable for such application, and the requirements of the proteins produced (see, e.g., Commission of Genetic Resources for Food and Agriculture, $11^{th}$ Session, Rome Jun. 11-15, 2007, publication reference CGRFA-11/07/Circ.3).

The use of microbes and microbial proteins as a food source is supported by their known long-term use as foods. For example, the Indonesian plant Tempeh is combined with the fungus (e.g., mold) *Rhizopus oligosporus* and consumed. Algae are used as a source of food by shore side populations of Lake Chad and Lake Texcoco in Mexico, and several thousand tons of spirulina are now produced as a protein rich food source in Mexico. In the mid 1960s, a quarter of a million tons of food yeast were being produced and the Soviet Union planned an annual production of 900,000 tons of food yeast by 1970 to compensate for agricultural protein deficits (Bunker, "New Food," 2nd Int. Congr. Food Sci. and Technol., Warsaw. p. 48 (1966)). Due to marked improvements in crop production, increased communication between countries with food surpluses and deficits, and the increasing cost of oil, microbial protein production did not develop as forecast. Nevertheless, protein derived from the fungus *Fusarium venenatum* is currently approved for consumption in Europe and is sold in the U.S. under the trademark Quorn® (for a review see Wiebe, *Mycologist*, 18:17-20, 2004).

The use of microbial proteins as a food source for animals and humans is further supported by the observation that the chemical composition and levels of microbial protein from bacteria, fungi (e.g., yeast and mold), and algae is comparable to that of soybean oilmeal. Furthermore, the amino acid composition and digestibility (including total energy (kcal/kg) based on data collected in pigs) of microbial proteins from yeast, bacteria, fungi, and algae is also reported to be comparable to soybean oilmeal (see, for example, Young et al., U.S. Pat. No. 4,938,972).

In some embodiments, the food products described below can be produced using a fed-batch fermentation process in which nutrients are added in a controlled manner in accordance with the requirements of the culture solution.

Proteins

Methods for obtaining microbial proteins using cellulosic materials are described in the art (see, e.g., Ramasamy et al., J. Appl. Biotechnol., 46:117-124, 1979, Young et al., Biotechnol Lett., 14:863-868, 1992, Anupama and Ravindra, *Brazilian Archives or Biology and Biotechnol.*, 44:79-88, 2001, U.S. Pat. Nos. 3,627,095, 4,379,844, 4,447,530, 4,401,680, 4,526,721, 5,047,332, and 4,938,972).

In some embodiments, the methods described herein can be performed in combination with a bioconversion step (e.g., see FIG. 43B) to produce proteins. In some embodiments, the second material is used as a substrate for microorganisms, which convert the organic matter present in the second material into proteins, e.g., microbial proteins (e.g., when combined with a nitrogen source). In some embodiments, the proteins can be used as or in ingestible products (e.g., foods) for consumption by animals and/or humans.

The term microbial proteins includes single cell proteins (SCP), a term coined in the 1960s to embrace microbial biomass produced by fermentation in which the microbial cells are generally isolated from the substrate, and microbial biomass products (MBP), a material in which the substrate is not purified from the SCP.

Exemplary microbial proteins can be obtained from cells of bacteria, fungi (e.g., yeasts and moulds), and or algae.

When cultured correctly, these cells can contain in excess of 40% protein on a dry weight basis. One advantage of using microbial proteins as a potential food source is that microbial protein is a readily renewable and easily obtainable resource. For example, 1000 kg of yeast can produce 12000 kg of new cells containing 6000 kg of protein in 24 hours.

In some embodiments, microbial proteins can be produced using the methods described herein to process a first material (e.g., biomass) into a second material (e.g., a substrate) that is supplied to one or more of a bacteria, fungus (e.g., yeasts and mould), and/or algae, e.g., in the presence of nitrogen or a nitrogen source, in the presence or absence of oxygen and at a temperature and pH, as required by the organism or mixture of organisms to synthesize protein (e.g., at a level above the normal level of protein synthesis in the cell). In general, these methods include the use of any microorganism that synthesizes protein in the presence of the materials generated using the methods described herein. Such organisms will typically be suitable or capable of being made suitable for consumption by animals and/or humans. In some embodiments, the microorganism can be non-pathogenic and/or an organism that is generally regarded as safe (GRAS). Additional selection criteria to be considered when choosing a microorganism can include, for example, consideration of whether the organism is capable of or can be modified to produce large quantities of proteins (e.g., edible proteins or proteins that can be rendered edible); whether isolated cultures of the organism are commercially available and/or whether the organism can be efficiently isolated; whether the microorganism can be readily maintained in culture; whether the microorganism is genetically stable; and whether the organism can efficiently utilize the substrates generated using the methods described herein (e.g., whether the microorganism can be cultured on the supplied substrate).

In some embodiments, the microorganisms can be modified (e.g., engineered) to express one or more recombinant proteins, for example, proteins that are not normally encoded by the microorganisms. For example, these proteins can be proteins known to be of a high nutritional value for humans and/or animals (e.g., as determined by assessing the biological value (BV) of a protein (e.g., the proportion of the absorbed nitrogen retained) and/or net protein utilization (NPU) of a protein (e.g., the proportion of ingested protein retained). In experimental animals NPU can be directly estimated by carcass analysis and values are therefore likely to be more accurate than when BV and NPU are derived from N balance data, as it is done in human studies. The inaccuracies inherent in N balance studies are known, no matter how carefully conducted. NPU and BV thus measure the same parameter (N retained, except that BV is calculated from N absorbed and NPU from N ingested (for a review see, e.g., Bender, Relation Between Protein Efficiency and Net Protein Utiliization, Measurement of Protein Utilization, 10: 135-143, 1956). In some embodiments, proteins of high nutritional value can have a high BV at an intake level (mg/kg) required to obtain the recommended daily protein requirement of the animal and/or human and can contain suitable levels of all essential amino acids (EAA) required for protein generation in the animal or human (EAAs include e.g., phenylalanine (FAO recommended daily intake is 2.2 g); methionine (FAO recommended daily intake is 2.2 g); leucine (FAO recommended daily intake is 2.2 g); valine (FAO recommended daily intake is 1.6 g); lysine (FAO recommended daily intake is 1.6 g); isoleucine (FAO recommended daily intake is 1.4 g); threonine (FAO recommended daily intake is 1.0 g); and tryptophan (FAO recommended daily intake is 0.5 g)). In some embodiments, the proteins of high nutritional value can be synthetic proteins, e.g., designed to have high BV at intake levels required to obtain the recommended daily protein requirement of the animal and/or human and can contain suitable levels of all EAAs required for protein generation in the animal or human. In some embodiments, proteins of high nutritional value can be labeled (e.g., tagged), e.g., to facilitate identification and/or purification of the protein. Such proteins are also referred to herein as microbial proteins.

Exemplary fungi that can be used in the methods described herein include, but are not limited to, *Aspergillus niger*, *A. funigatus*, *A. terreus*, *Cochliobolus specifer*, *Myrothecium verrucaria*, *Rhizoctonia solani*, *Spicaria fusispora*, *Penicillium* sp., *Gliocladium* sp., *Fusarium* sp., *Trichosporon cutaneum*, *Neurospora sitophila*, *Chaetomiium cellulolyticum*, *Fusarium venenatum* (formally *F. graminearum*) strain A 3/5 (e.g., ATCC 20334. Suitable culture conditions for this organism are disclosed in U.S. Plant Patent No. 4347 and European Patent No. 123, 434). *F. solani*, *F. oxysporium*, and *Paecilomyces variotii*, mycelium, *Rhizopus oligosporus*, *Candida utilis*, and *Saccharomyces cerevisiae*. Exemplary algae that can be used in the methods described herein include, but are not limited to, *Spirulina* sp., *Scenedesmus acutus*, *Spirulina maxima*, and *Cosmarium turpinii*. Exemplary bacteria that can be used in the methods described herein include, but are not limited to, *Rhodospirillum* sp., and *Rhodopseudomonas* sp., *Corynebacterium glutamicum*, *Escherichia coli*, *Alcaligenes faecalis*, *Thermomonospora fusca* (Actinomycetaceae) and *Pseudomonas* JM 127.

In some embodiments, microbial proteins can be fed to animals and/or humans as SCP, e.g., without isolation from the microorganism or mixture of microorganisms. In such cases, SCP containing cells can be concentrated using, for example, filtration, precipitation, coagulation, centrifugation, and the use of semi-permeable membranes. SCP containing cells can also be dried, e.g., to about 10% moisture and/or condensed and acidified to limit spoilage. In some embodiments, SCP can be fed to animals and/or humans shortly (e.g., within 12 hours, 24 hours, 48 hours) after production without further treatment of the SCP. In some embodiments, SCP can be consumed in the absence of further food sources (see the FAO publication for the recommended daily intake of SCP by animals and humans). Alternatively or in addition, SCP can be combined, e.g., mixed with other food sources prior to or at the same time as consumption by an animal and/or human. SCP can be combined with dry and/or wet food sources to create SCP mixtures. In some embodiments, SCP-containing mixtures can be processed, e.g., as described by Tannenbaum (U.S. Pat. No. 3,925,562). For example, SCP microorganisms can be combined with a protein complement (e.g., vegetable protein) and texturized into a paste suitable for use as a food additive. Such processes can be used to add desirable texture properties to SCP.

In some embodiments, the protein utilization and nitrogen digestibility of SCP proteinaceous material can be increased by homogenizing the cells (see, for example, Yang et al., J. Food Sci., 42:1247-1250, 2006). Thus, in some embodiments, microbial proteins can be extracted or isolated from the microorganism or mixture of microorganisms prior to consumption by animals and/or humans. For example, microbial proteins can be extracted by chemically, enzymatically, and/or mechanically disrupting the microbial cell wall and/or membranes, e.g., to release the intracellular contents of the cells. Microbial proteins can then be isolated or purified from contaminating materials using protein isolation techniques known in the art. In some embodiments, microbial proteins can be isolated or purified by way of a detectable tag fused to the protein.

In some embodiments, microbial proteins can be modified, e.g., glycosylated and/or folded prior to use, e.g., to make them more or less antigenic.

In some embodiments, microbial proteins can be isolated and hydrolyzed to single amino acids, peptides, and/or polypeptide, e.g., prior to consumption by animals and/or humans. Methods for protein hydrolysis are known in the art.

In some embodiments, microbial proteins can be purified (to at least 50%, e.g., to 60%, 70%, 80%, 90%, 95%, 99% or 100% weight/weight, weight/volume, or volume/volume) and optionally concentrated. The structure of the proteins can then be modified to resemble the fibrous structure of animal muscle protein before the product is flavored using meat flavors and fats. In some embodiments, microbial proteins can be used as the primary protein source in a meat analogue. Alternatively, microbial proteins can be used to supplement currently commercially available meat analogues, for example, those sold under the tradename Quorn® and soy protein based products.

Fats, Oils, Lipids and Hydrocarbons

In some embodiments, the methods described herein can be performed in combination with a bioconversion step (e.g., see FIG. 43B) to generate fats and/or oils.

The market place for fats and oils is large and extremely diversified, ranging from bulk commodities used for food and technical purposes to more specialized oils. The use of microbial fats and oils is known in the art (for a review on this topic see, e.g., Pryde, New Sources of Fats and Oils, Amer Oil Chemists Society, (American Oil Chemist Society (AOCS), 1981).

In some embodiments, the fats and/or oils generated using the methods described herein can be used, for example, as substitutes for animal and plant based fats and oils, in the production of energy products, flammables (solid and/or liquid), in food preparation and cooking, as flavor enhancers (e.g., for food products), as or in animal feed, as or in food supplements, as or in pharmaceuticals, as or in nutriceuticals, as or in cosmetics, and as or in post operative nutritive therapy.

In some embodiments, microbial fats and/or oils can be produced using the methods described herein to process a first material (e.g., biomass) into a second material (e.g., a substrate) that is supplied to one or more of a bacteria, fungi (e.g., yeasts and moulds), and/or algae, in the presence or absence of oxygen and at a temperature and pH, as required by the organism or mixture of organisms to synthesize fats and/or oils (e.g., at a level above the normal level of fat and/or oil synthesis in the cell). In general, these methods include the use of any microorganism that synthesizes fats and/or oils in the presence of the materials generated using the methods described herein. In some embodiments, the microorganism can be non-pathogenic and/or an organism that is generally regarded as safe (GRAS). Additional selection criteria to be considered when choosing a microorganism include, for example, consideration of whether the organism is capable of producing or can be modified to produce large quantities of fats and oils; whether isolated cultures of the organism are commercially available and/or whether the organism can be efficiently isolated; whether the microorganism can be readily maintained in culture; whether the microorganism is genetically stable; and whether the organism can efficiently utilize the substrates generated using the methods described herein (e.g., whether the microorganism can be cultured on the supplied substrate).

In some embodiments, microorganisms that can be used in the methods described herein, e.g., to generate or produce microbial fats and/or oils include, for example, bacteria (e.g., mycobacteria, corynebacteria, and norcardia), algae (e.g., Chlorophyta (Cladophora rupestris, Blidingia minima, Enteromorpha intestinalis), Phaeophyta (Agarum cribrosum, Ascophyllum nodosum, and Laminaria digitata), and Rhodophyta (Polysiphonia lanosa, palmaria palmate, Halosaccion ramentaceum, and Porphyra leucosticte)), seaweeds and seagrasses, yeast (e.g., Candida 107, Crytococcus terricolus, Hansenula saturnus, Lipomyces lipofera, L. starkeyi, Rhodotorula gracilis, R. toruloides, and Candida curvata), and molds (e.g., Aspergillus nidulans, A. terreus, Fusarium monoiliforme, Mucor circinelloides, Penicillium spinulosum, Rhizopus sp.), In some embodiments, microbial fats and/or oils generated using the methods disclosed herein can be separated, e.g., isolated from the microbial cells prior to use. Alternatively or in addition, the microbial fats and oils generated using the methods disclosed herein can be used without being separated from the microbial cells.

Some microorganisms can be used to produce hydrocarbons. For example, as discussed in the Background section of U.S. 2008/0293060, the disclosure of which is incorporated herein by reference, numerous organisms, such as bacteria, algae and plants, can synthesize hydrocarbons, e.g. n-alkanes of various carbon chain lengths, as previously described (Dennis, M. W. & Kolattukudy, P. E. (1991) Archives of biochemistry and biophysics 287, 268-275; Kunst, L. & Samuels, A. L. (2003) Progress in lipid research 42, 51-80; Tillman, J. A., Seybold, S. J., Jurenka, R. A., & Blomquist, G. J. (1999) Insect biochemistry and molecular biology 29, 481-514; Tornabene, T. G. (1982) Experientia 38.1-4, each of which is incorporated by reference).

Exemplary species that synthesize hydrocarbons are listed in Table A and Table B below.

TABLE A

Hydrocarbon producing prokaryotes

| Strain | ATCC # or Reference |
|---|---|
| Micrococcus luteus | ATCC 272 |
| Micrococcus luteus | ATCC 381 |
| Micrococcus luteus | ATCC 398 |
| Micrococcus sp. | ATCC 401 |
| Micrococcus roseus | ATCC 412 |
| Micrococcus roseus | ATCC 416 |
| Micrococcus roseus | ATCC 516 |
| Micrococcus sp. | ATCC 533 |
| Micrococcus luteus | ATCC 540 |
| Micrococcus luteus | ATCC 4698 |
| Micrococcus luteus | ATCC 7468 |
| Micrococcus luteus | ATCC 27141 |
| Jeotgalicoccus sp. | ATCC 8456 |
| Stenotrophomonas maltophilia | ATCC 17674 |
| Stenotrophomonas maltophilia | ATCC 17679 |
| Stenotrophomonas maltophilia | ATCC 17445 |
| Stenotrophomonas maltophilia | ATCC 17666 |
| Desulfovibrio desulfuricans | ATCC 29577 |
| Vibrio furnissii M1 | Park, 2005, J. Bact., vol. 187, 1426-1429 |
| Clostridium pasteurianum | Bagaeva and Zinurova, 2004, Biochem (Moscow), vol. 69, 427-428 |
| Anacystis (Synechococcus) nidulans | Winters et al., 1969, Science, vol. 163, 467-468 |
| Nostoc muscorum | Winters et al., 1969, Science, vol. 163, 467-468 |

TABLE A-continued

Hydrocarbon producing prokaryotes

| Strain | ATCC # or Reference |
|---|---|
| Cocochloris elabens | Winters et al., 1969, Science, vol. 163, 467-468 |
| Chromatium sp. | Jones and Young, 1970, Arch. Microbiol., vol. 70, 82-88 |

TABLE B

Hydrocarbon producing eukaryotes

| Organism | ATCC # or Reference |
|---|---|
| Cladosporium resinae | ATCC 22711 |
| Saccharomycodes ludwigii | ATCC 11311 |
| Saccharomyces cerevisiae | Baraud et al., 1967, Compt. Rend. Acad. Aci. Paris, vol. 265, 83-85 |
| Botyrococcus braunii | Dennis and Kolattukudy, 1992, PNAS, vol. 89, 5306-5310 |
| Musca domestica | Reed et al., 1994, PNAS, vol. 91, 10000-10004 |
| Arabidopsis thaliana | Aarts et al., 1995, Plant Cell, vol. 7, 2115-2127 |
| Pisum sativum | Schneider and Kolattukudy, 2000, Arch. Biochem. Biophys., vol. 377, 341-349 |
| Podiceps nigricollis | Cheesborough and Kolattukudy, 1988, J. Biol. Chem., vol 263, 2738-2743 |

Carbohydrates, Sugars, Biopolymers, and Polymer Precursors

A large variety of biopolymers, for example, such as polysaccharides, polyesters, and polyamides, are naturally produced by microorganisms (for a review see Microbial Production of Biopolymers and Polymer Precursors, Rehm, ed, (Caister Academic Press, 2009)). These biopolymers range from viscous solutions to plastics and their physical properties are dependent on the composition and molecular weight of the polymer.

In some embodiments, the methods described herein can be performed in combination with a bioconversion step (e.g., see FIG. 43B) to generate carbohydrates, sugars, biopolymers, and polymer precursors. In some embodiments, the methods described herein can be used to process a first material (e.g., biomass) to generate a second material that can be used as a substrate for microorganisms (e.g., bacteria, fungi (e.g., yeasts and moulds), and/or algae) capable of generating, for example, xanthan, alginate, cellulose, cyanophycin, poly(gamma-glutamic acid), levan, hyaluronic acid, organic acids, oligosaccharides and polysaccharides, and polyhydroxyalkanoates. Uses of these carbohydrates, sugars, biopolymers, and polymer precursors include, for example, as food additives, in cosmetics, in plastic manufacturing, in fabric manufacturing, and in pharmaceutical and nutraceuticals.

In general, these methods include the use of any microorganism that synthesizes one or more of carbohydrates, sugars, biopolymers, and/or polymer precursors in the presence of the materials generated using the methods described herein. In some embodiments, these methods include the use of any microorganism that synthesizes one or more of xanthan, alginate, cellulose, cyanophycin, poly(gamma-glutamic acid), levan, hyaluronic acid, organic acids, oligosaccharides and polysaccharides, and polyhydroxyalkanoates in the presence of the materials generated using the methods described herein. In some embodiments, suitable organisms will be suitable or capable of being made suitable for consumption by animals and/or humans or will be generally regarded as safe (GRAS).

Additional selection criteria to be considered when choosing a microorganism include, for example, consideration of whether the organism is capable or can be modified to produce large quantities of one or more of carbohydrates, sugars, biopolymers, and/or polymer precursors (e.g., xanthan, alginate, cellulose, cyanophycin, poly(gamma-glutamic acid), levan, hyaluronic acid, organic acids, oligosaccharides and polysaccharides, and polyhydroxyalkanoates); whether isolated cultures of the organism are commercially available and/or whether the organism can be efficiently isolated; whether the microorganism can be readily maintained in culture; whether the microorganism is genetically stable; and whether the organism can efficiently utilize the substrates generated using the methods described herein (e.g., whether the microorganism can be cultured on the supplied substrate).

Vitamins

In some embodiments, the methods described herein can be performed in combination with a bioconversion step (e.g., see FIG. 43B) to generate vitamins, for example, including, but not limited to, vitamin Riboflavin (vitamin B2), vitamin B12, and vitamin C.

In some embodiments, the substrate is used by the microorganism *Ashbya gossii* and the vitamin generated is Riboflavin (vitamin B2).

In some embodiments, the substrate is used by the microorganisms *Bacillus megatherium, Pseudomonas denitrificans*, and/or species of the genus *Propionibacterium* and the vitamin generated is vitamin B12.

In some embodiments, the substrate is used by the microorganism *Saccharomyces* sp. and the vitamin generated is vitamin C.

In some embodiments, vitamin products can be produced using a fed-batch fermentation process in which nutrients are added in a controlled manner in accordance with the requirements of the culture solution.

Mushrooms

In some embodiments, the methods described herein can be used to process a first material (e.g., biomass), e.g., to change (e.g., lower) the recalcitrance level of the biomass, to produce a second material that can be used as a substrate for the cultivation or growth mushrooms. These mushrooms can be used as a higher quality food source than the first material (e.g., biomass) and the second material that can be ingested by animals and/or humans as a food.

Mushrooms are fungi that grow above ground on a suitable food source. As used herein, the term mushroom refers to edible mushrooms including, but not limited to, fungi with a stem (stipe), a cap (pileus), and gills (lamellae) on the underside of the cap and fungi without stems, the fleshy fruiting bodies of some *Ascomycota*, the woody or leathery fruiting bodies of some *Basidiomycota*, and spores of edible mushrooms. In some embodiments, the term mushroom includes fungi edible to animals.

In some embodiments, mushrooms useful in the present disclosure include, but are not limited to, for example, mushrooms, mushroom mycelia, and mushroom spores of the mushrooms *Pleurotus sajor-caju, Basidiomycota, Agaricomycetes, Vilvariella volvacea* (the padi mushroom), *Pleurotus ostreatus* (the oyster mushroom), *Agaricus bisporus, Flammulina velutipes, Pleurotus eryngii*, Ganoderma mushrooms and Cordyceps.

Methods for cultivating mushrooms are known in the art (see, e.g., U.S. Pat. No. 6,737,065). Following cultivation, mushrooms can be harvested and stored for later use or can be used immediately. Mushrooms have relatively low protein content (e.g., 2-5%) on a fresh weight basis, however, the protein content of mushrooms can be increased by drying the mushrooms (e.g., 30-50% on dry weight basis). In some embodiments, therefore, mushrooms generated using the methods described herein can be dried (e.g., freeze dried) or dehydrated prior to use, e.g., ingestion. In some embodiments, mushrooms can be mixed with a protein complement and binding agent and can be textured.

Hydroponics

In some embodiments, the methods described herein can be used to process a first material (e.g., biomass), e.g., to change (e.g., lower) the recalcitrance level of the biomass, to produce a second material that can be used in hydroponics. Hydroponics is a method of growing plants using mineral nutrient solutions, without soil. Plants may be grown with their roots in the mineral nutrient solution only (solution culture) or in an inert medium (medium culture), such as perlite, gravel, or mineral wool. The three main types of solution culture are static solution culture, continuous flow solution culture and aeroponics. Materials formed using the processes disclosed herein can be used alone or combined with macronutrients, e.g., potassium nitrate, calcium nitrate, potassium phosphate, and magnesium sulfate, to form a hydroponic solution. Various micronutrients may also be included to supply essential elements, e.g., Fe (iron), Mn (manganese), Cu (copper), Zn (zinc), B (boron), Cl (chlorine), and Ni (nickel). Chelating agents may be added to enhance the solubility of iron. Different hydroponic solutions may be utilized throughout the plant life cycle to enhance growing conditions.

Aquaculture

In some embodiments, the methods described herein can be used to process a first material (e.g., biomass), e.g., to change (e.g., lower) the recalcitrance level of the biomass, to produce a second material that can be used in aquaculture. For example, the second material can be used to feed or otherwise maintain aquatic species. Aquaculture is the farming of freshwater and saltwater organisms including mollusks, crustaceans and aquatic plants. Unlike fishing, aquaculture, also known as aquafarming, implies the cultivation of aquatic populations under controlled conditions. Mariculture refers to aquaculture practiced in marine environments. Particular kinds of aquaculture include algaculture (the production of kelp/seaweed and other algae), fish farming, shrimp farming, oyster farming, and the growing of cultured pearls. Aquaponics integrates fish farming and plant farming using the symbiotic cultivation of plants and aquatic animals in a recirculating environment.

Production of Edible *Fusarium venenatum*

In some embodiments, the methods described herein can be used to process a first material (e.g., biomass), e.g., to change (e.g., lower) the recalcitrance level of the biomass, to produce a second material that can be used as a substrate that can be used as a substrate for the generation of edible *Fusarium venenatum* (e.g., which is marketed under the trade name Quorn®). Methods for producing Quorn® are described, for example, in U.S. Pat. Nos. 5,935,841, 6,270, 816, 5,980,958, and 3,809,614, and are reviewed in Weibe (Weibe, *Mycologist*, 18:17-20, 2004). Current Quorn® production methods use glucose as the primary carbon source. Substituting glucose with the substrate described herein would reduce the cost associated with Quorn® production as the substrates provided herein provide a cheaper carbon source than glucose.

Alcoholic Beverages

In some embodiments, the methods described herein can be used to process a first material (e.g., biomass), e.g., to change (e.g., lower) the recalcitrance level of the biomass, to produce a second material that can be used as a substrate for the generation of alcohol that is suitable for consumption by humans. Such alcohols can be used as or in the production of alcoholic beverages. For example, alcohols produced using the methods described herein can be used as or in the production of beers, wines, spirits, and/or alcopops.

Health Product

In some embodiments, the methods described herein can be used to process a first material (e.g., biomass), e.g., to change (e.g., lower) the recalcitrance level of the biomass, to produce a second material that can be used as a substrate as or in the generation of health products for animal or human use. Such health products can include, for example, pharmaceuticals, nutriceuticals, cosmetics, cosmeceuticals, and beauty products (e.g., creams and lotions (e.g., for use on skin and/or hair)). In some embodiments, these health products can include, for example, functional foods that do not necessarily provide any nutritional value, but that increase motility of the gastrointestinal tract, or that can be used to reduce cholesterol levels (e.g., high fiber products including soluble and/or insoluble fiber and soluble and/or insoluble fiber containing products).

Amino Acids and Amino Acid Derivatives

Biotechnological processes have been used in the industrial production of amino acids for 50 years (for a recent review see Leuchtenberger et al., *Appl. Microbiol. Biotechnol.*, 69:1-8, 2005). Major products include flavor enhancers and animal feed products such as $_L$-lysine, $_L$-threonine, and $_L$-tryptophan, which are commonly, produced using high-performance strains of *Corynebacterium glutamicum* (see Kinoshita et al., Gen. Appl. Microbiol., 3:193-205, 1957, and Kalinowshki et al., J. Biotechnol., 104:5-25, 2003) and *Escherichia coli* and substrates such as molasses, sucrose, or glucose (Leuchtenberer, supra).

In some embodiments, the methods described herein can be used to process a first material (e.g., biomass), e.g., to change (e.g., lower) the recalcitrant level of the biomass, to produce a second material that can be used as a substrate for microorganisms (e.g., bacteria, fungi (e.g., yeasts and moulds), and/or algae) capable of generating amino acids and/or amino acid derivatives (e.g., when combined with a nitrogen source). These amino acids and derivatives can be used, for example, as flavor enhancers (e.g., for food products), in animal feed, as food supplements, and in the production of pharmaceuticals, nutriceuticals, cosmetics, and in post-operative nutritive therapy.

In some embodiments, amino acids and amino acid derivatives that can be expressed using the methods described herein include, but are not limited to, for example, $_L$-amino acids and $_D$-amino acids such as $_L$-glutamic acid (monosodium glutamate (MSG)), $_L$-apartic acid, $_L$-phenylalanine, $_L$-lysine, $_L$-threonine, $_L$-tryptophan, $_L$-valine, $_L$-leucine, $_L$-isoleucine, $_L$-methionine, $_L$-histidine, and $_L$-phenylalanine, $_L$-lysine, $_{DL}$-methionine, and $_L$-tryptophan.

For example, the aromatic amino acids tryptophan, phenylalanine, and tyrosine are biosynthesized from glucose through the shikimic acid pathway (shown below).

Biosynthesis Pathway of Aromatic Amino Acids
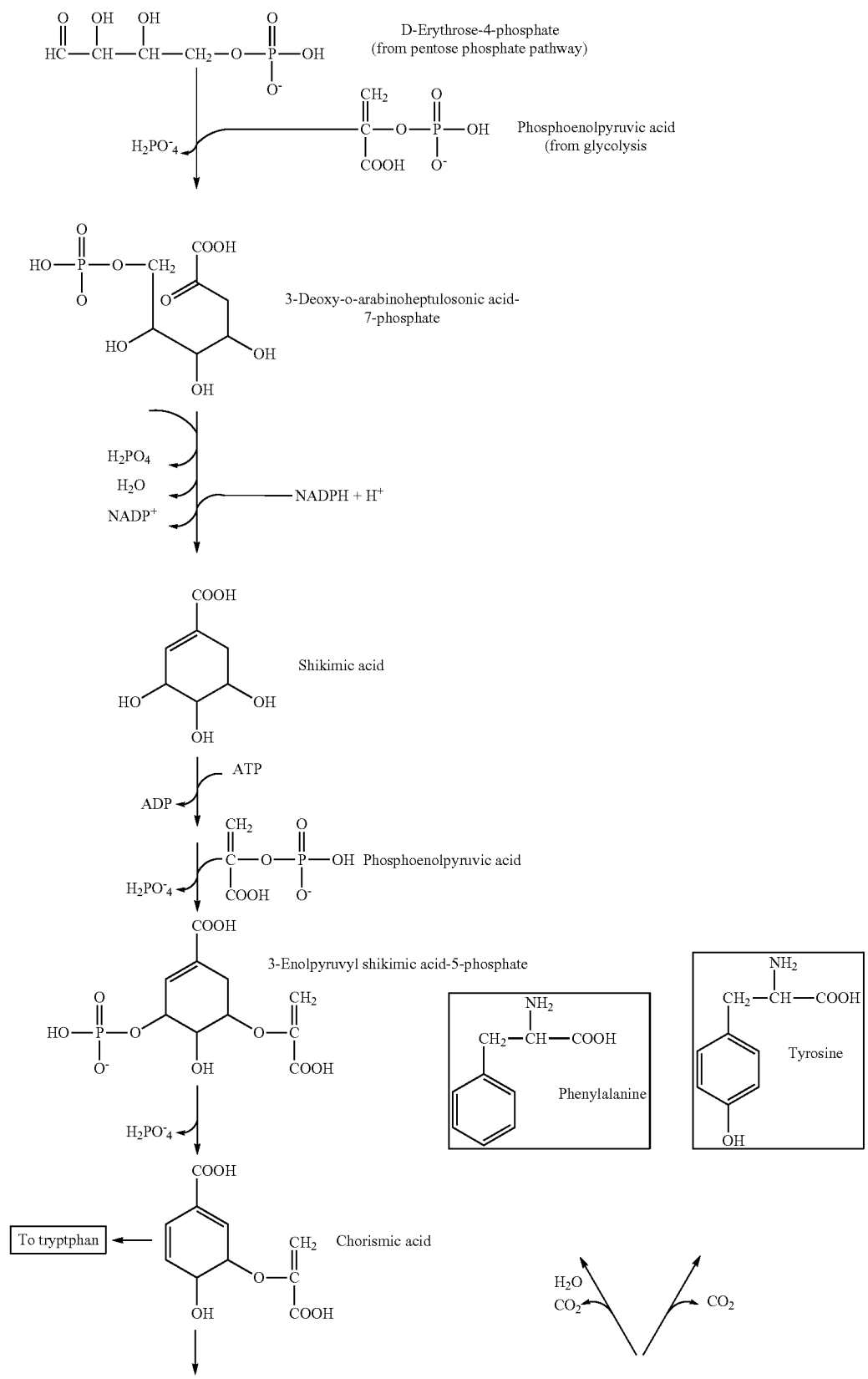

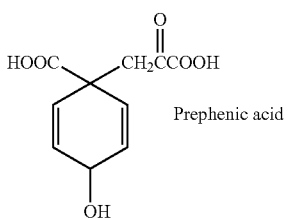
Prephenic acid

→ Transamination

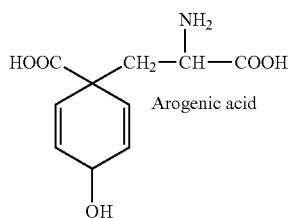
Arogenic acid

The shikimic acid pathway converts simple carbohydrate precursors derived from glycolysis and the pentose phosphate pathway to the aromatic amino acids. One of the pathway intermediates is shikimic acid, which lends its name to this entire sequence of reactions. The shikimic acid pathway is present in plants, fungi, and bacteria but is not found in animals. Animals have no way to synthesize the three aromatic amino acids—phenylalanine, tyrosine, and tryptophan-, which are therefore essential nutrients in animal diets.

In some embodiments, these amino acids can be modified to produce amino acid derivatives. Amino acid derivatives include, but certainly are not limited to the following groups.

Amino Alcohols

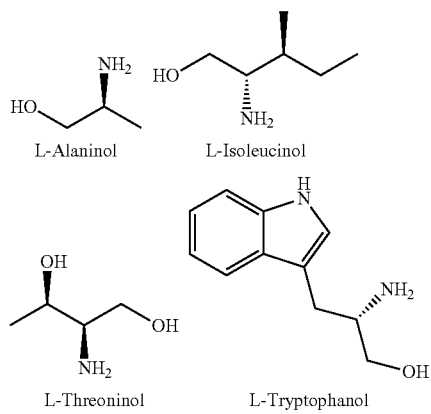

L-Alaninol   L-Isoleucinol

L-Threoninol   L-Tryptophanol

Amino Aldehydes

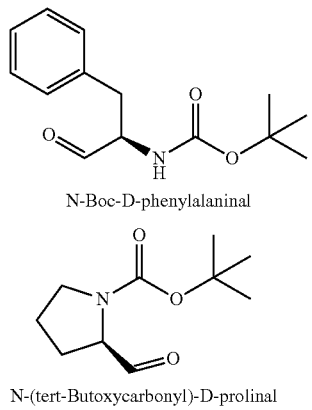

N-Boc-D-phenylalaninal

N-(tert-Butoxycarbonyl)-D-prolinal

Amino Lactones

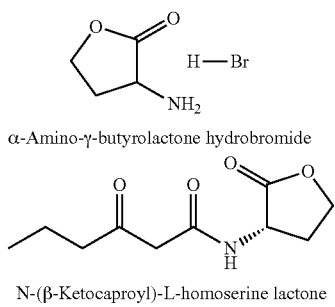

α-Amino-γ-butyrolactone hydrobromide

N-(β-Ketocaproyl)-L-homoserine lactone

N-Methyl Amino Acids

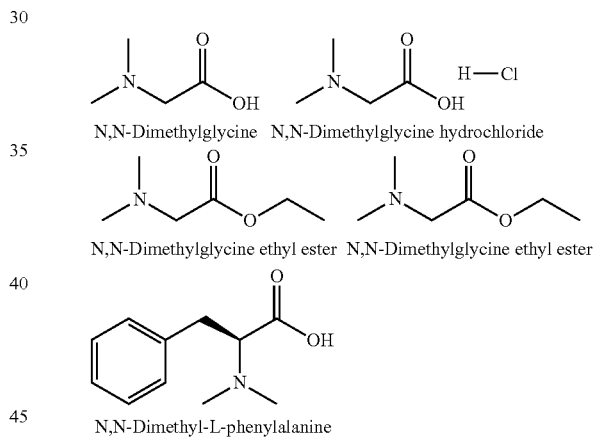

N,N-Dimethylglycine   N,N-Dimethylglycine hydrochloride

N,N-Dimethylglycine ethyl ester   N,N-Dimethylglycine ethyl ester

N,N-Dimethyl-L-phenylalanine

In some embodiments, microorganisms (e.g., bacteria, fungi (e.g., yeasts and molds), and/or algae) suitable for use in the generation of amino acids can be, but are not limited to, non-pathogenic organisms and/or organisms that are GRAS. Additional selection criteria to be considered when choosing a microorganism include, for example, consideration of whether the organism is capable of producing or can be modified to produce large quantities of a single product; whether isolated cultures of the organism are commercially available and/or whether the organism can be efficiently isolated; whether the microorganism can be readily maintained in culture; whether the microorganism is genetically stable; and whether the microorganism can be cultured on the supplied substrate. Alternatively or in addition, the microorganism can be a wild type (e.g., unmodified) or genetically modified microorganism (e.g., a mutant), for example, a microorganism that has or can be modified to over-express one or more selected amino acids and/or amino acid derivatives. Exemplary microorganisms include, but are not limited to, lactic acid bacteria (LAB), *E. coli*, Bacillus subtilis, and *Corynebacterium glutamicum* (e.g., ATCC 13032).

In some embodiments, amino acids and amino acid derivatives can be expressed using a fed-batch fermentation process in which nutrients are added in a controlled manner in accordance with the requirements of the culture solution. In some embodiments, the methods and/or materials described herein can be incorporated into the processes currently used by Ajinomoto (Japan), ADM (U.S.A.), Cheil-Jedang (South Korea), Global BioChem (China), and BASF and Degussa (Germany) in the generation of amino acids and amino acid derivatives.

Antibiotics

In some embodiments, the methods described herein can be used to process a first material (e.g., biomass), e.g., to change (e.g., lower) the recalcitrance level of the biomass, to produce a second material that can be used as a substrate by microorganisms (e.g., bacteria, fungi (e.g., yeasts and moulds), and/or algae) capable of generating antibiotics, for example, including, but not limited to, tetracycline, streptomycin, cyclohexamide, Neomycin, cycloserine, erythromycin, kanamycin, lincomycin, nystatin, polymyxin B, bacitracin, daptomycin, vancomycin, and the ansamycins or the natural products presented below.

12-Membered macrolides

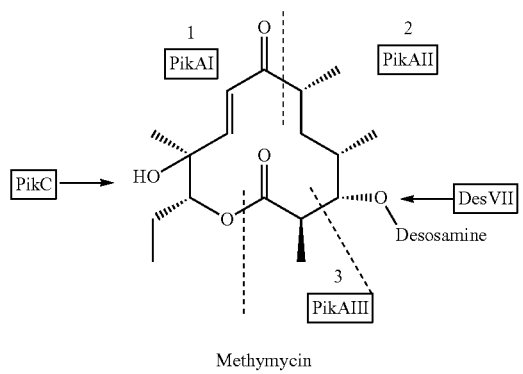

Methymycin

14-Membered macrolides

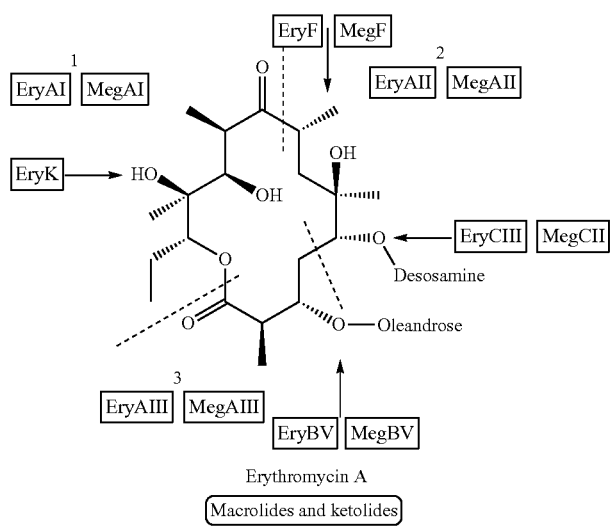

Erythromycin A

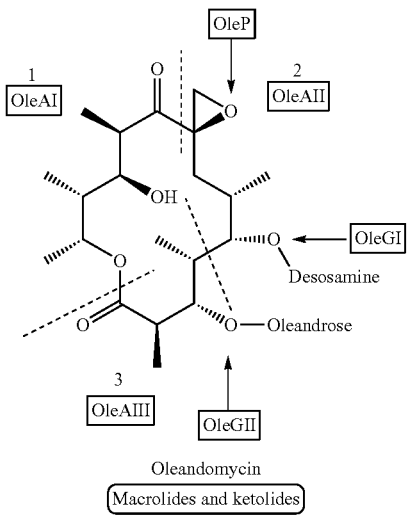

Oleandomycin

Macrolides and ketolides

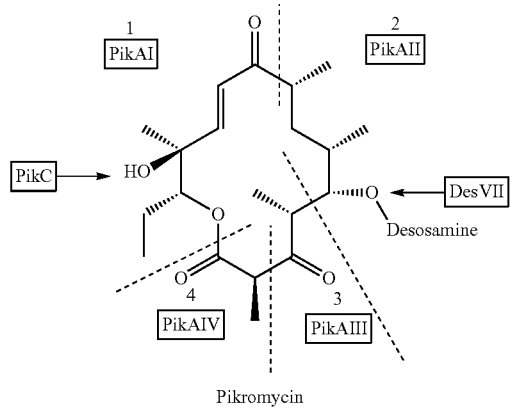

Pikromycin

16-Membered Macrolides
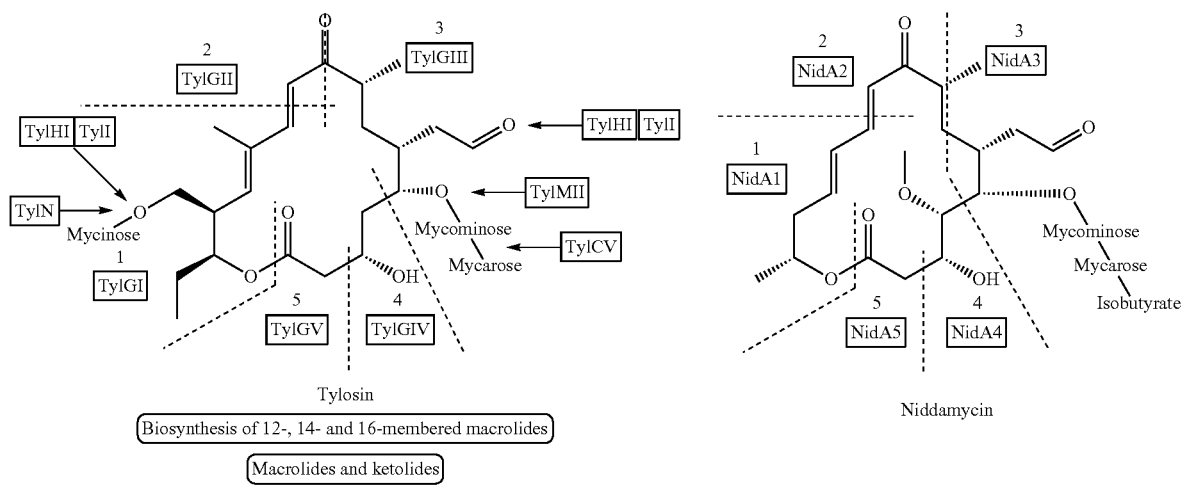
Tylosin
Biosynthesis of 12-, 14- and 16-membered macrolides
Macrolides and ketolides
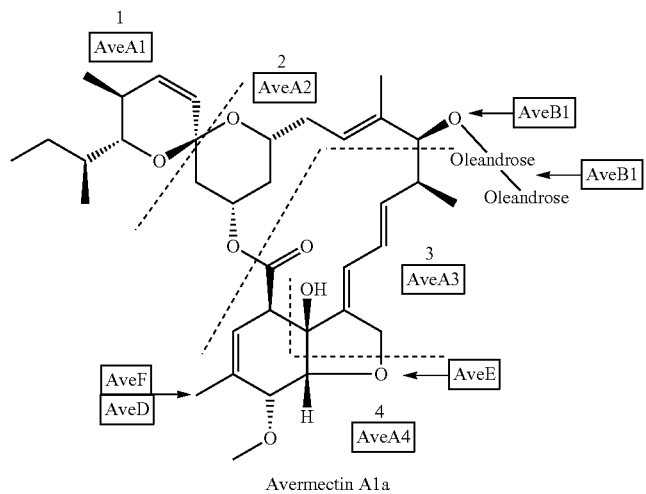
Avermectin A1a
Rapamycin and related compounds
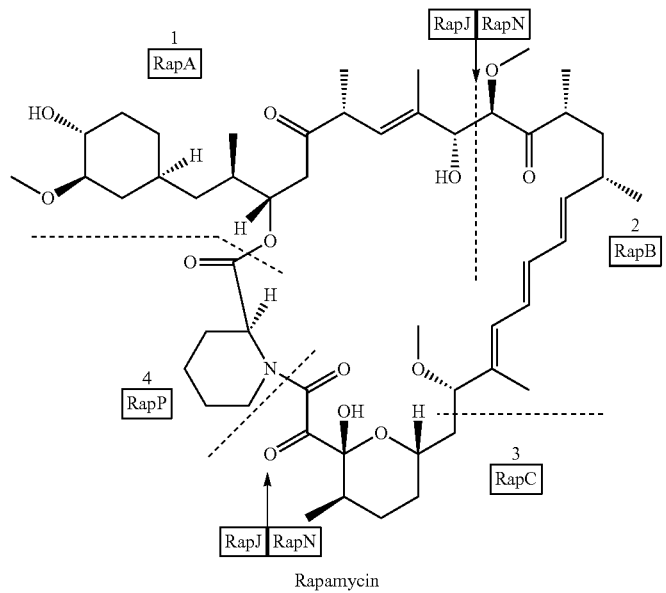
Rapamycin -continued
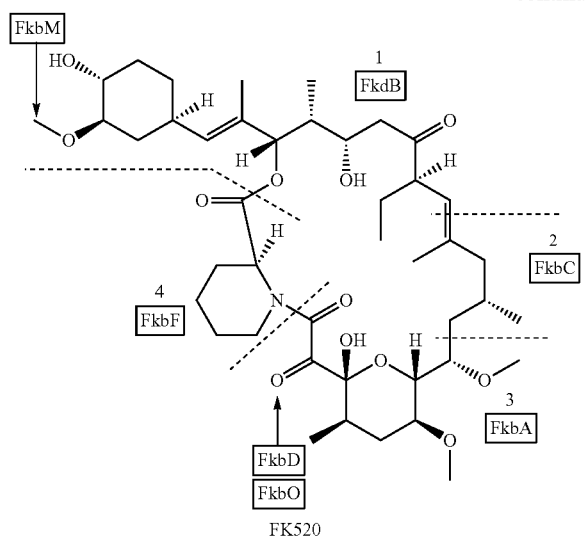
FK520
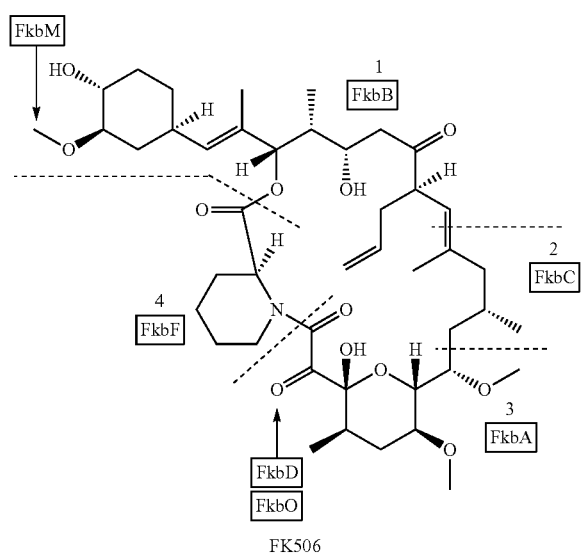
FK506
Ansamycin antibiotics
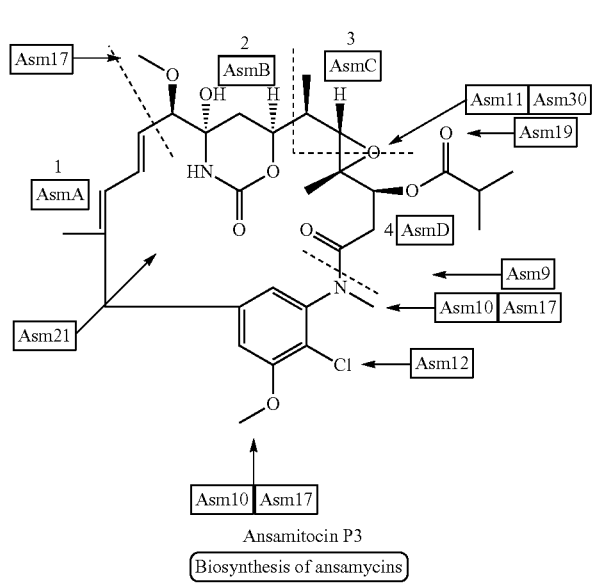
Ansamitocin P3
Biosynthesis of ansamycins
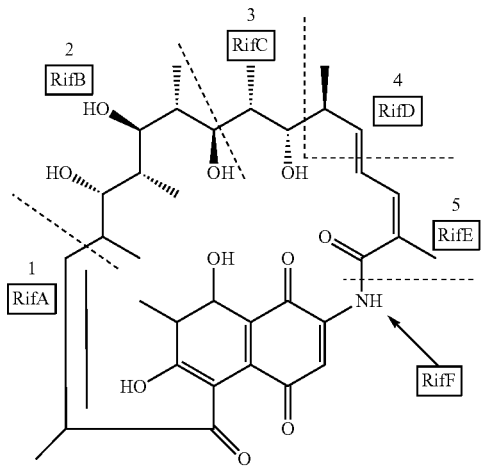
Proansamycin X -continued
Polyene macrolides
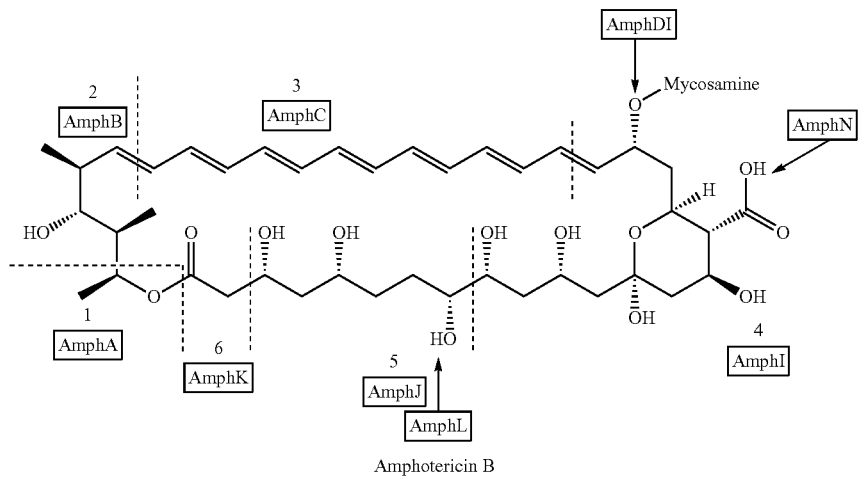
Amphotericin B
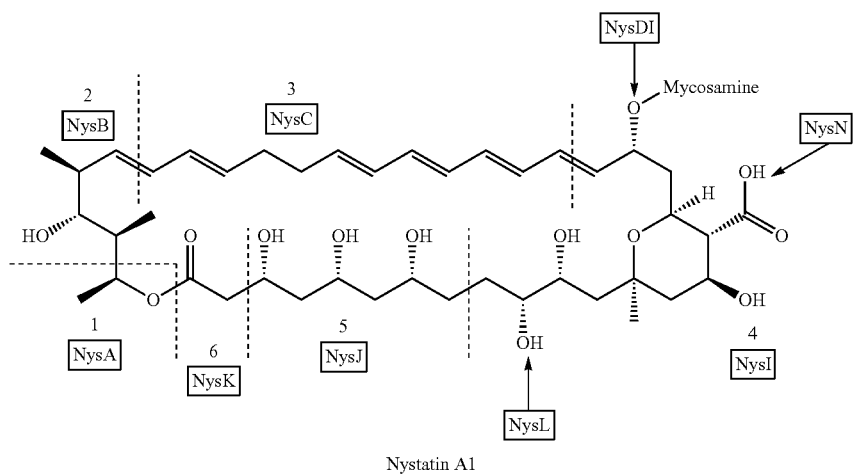
Nystatin A1
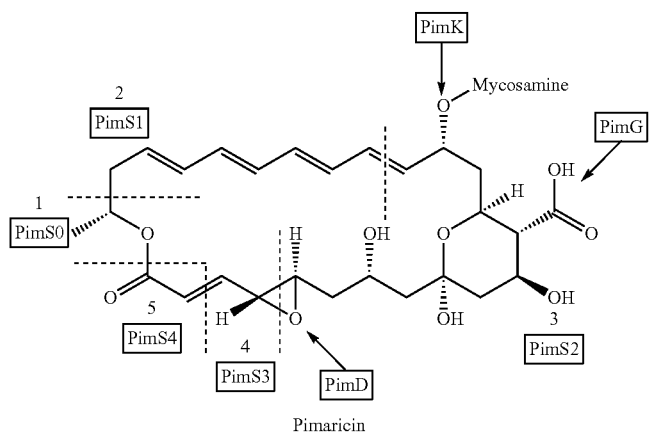
Pimaricin -continued
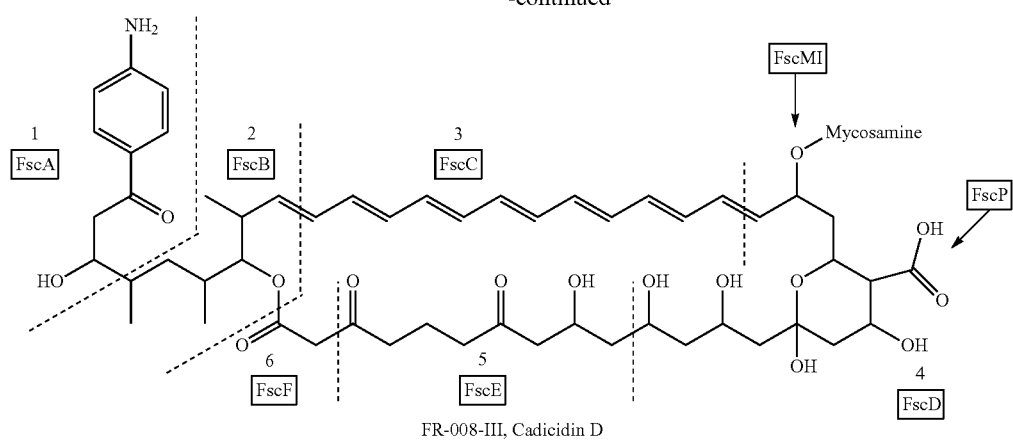
FR-008-III, Cadicidin D
Myxobacterial products
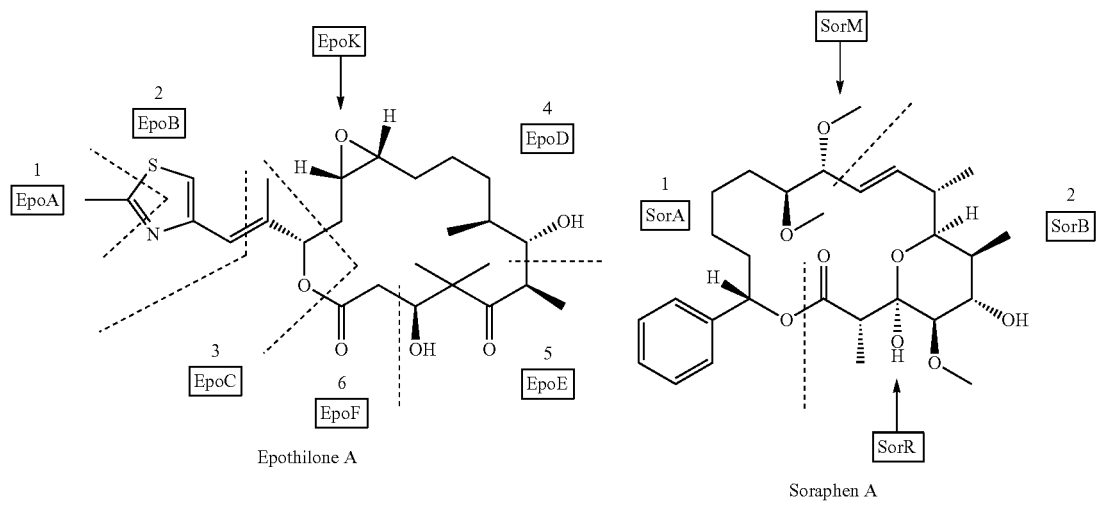
Epothilone A
Soraphen A
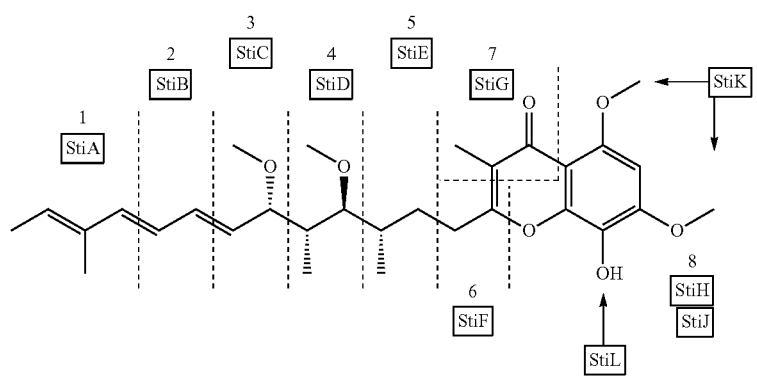
Stigmatellin A -continued

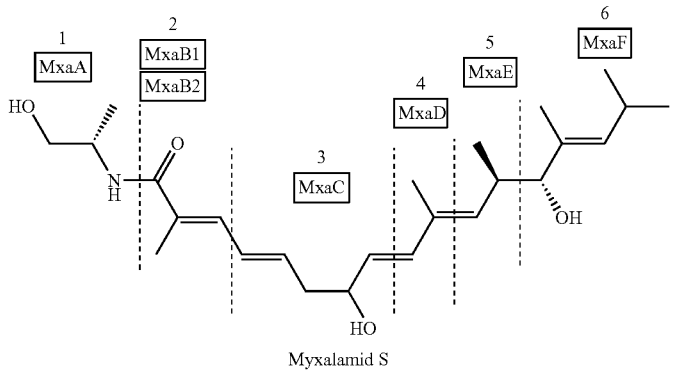

Myxalamid S

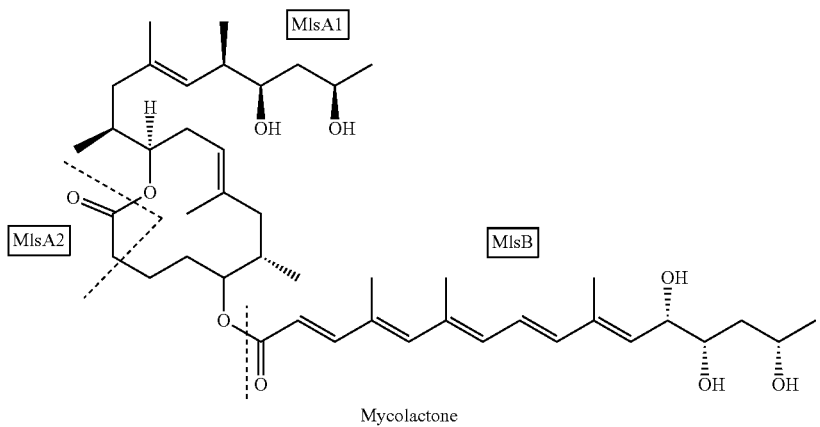

Mycolactone

In some embodiments, the substrate is used by the microorganism *Streptomyces remosus* and the antibiotic generated is tetracycline.

In some embodiments, the substrate is used by the microorganism *Streptomyces griseus* and the antibiotic generated is streptomycin and or cyclohexamide. The biosynthesis of streptomycin is illustrated below in starting from D-glucose.

Biosynthesis of Streptomycin

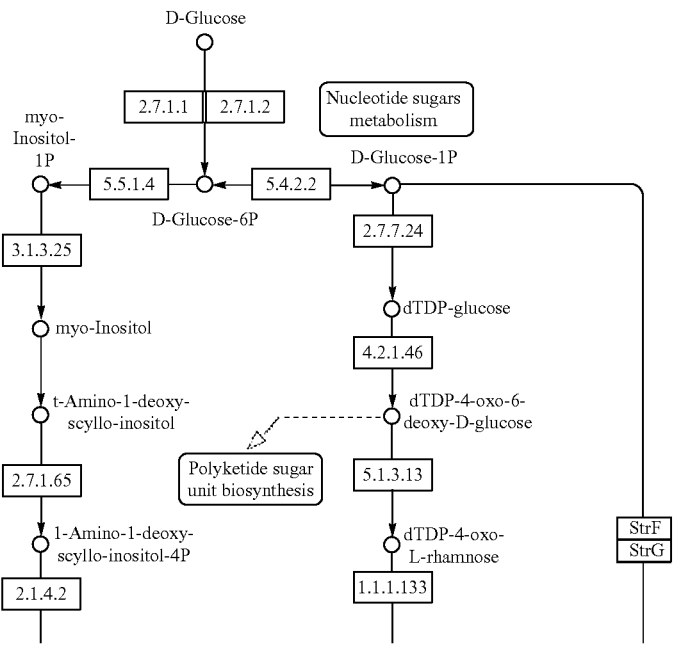

-continued

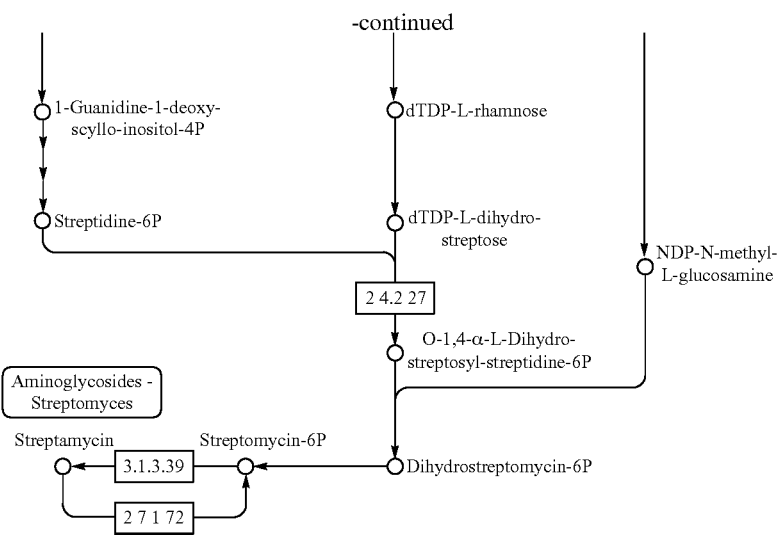

In some embodiments, the substrate is used by the microorganism *Streptomyces frodiae* and the antibiotic generated is neomycin.

In some embodiments, the substrate is used by the microorganism *Streptomyces orchidaceus* and the antibiotic generated is cycloserine.

In some embodiments, the substrate is used by the microorganism *Streptomyces erythreus* and the antibiotic generated is erythromycin.

In some embodiments, the substrate is used by the microorganism *Streptomyces kanamyceticus* and the antibiotic generated is kanamycin.

In some embodiments, the substrate is used by the microorganism *Streptomyces lincolnensis* and the antibiotic generated is lincomycin.

In some embodiments, the substrate is used by the microorganism *Streptomyces noursei* and the antibiotic generated is nystatin.

In some embodiments, the substrate is used by the microorganism *Bacillus polymyxa* and the antibiotic generated is polymyxin B.

In some embodiments, the substrate is used by the microorganism *Bacillus licheniformis* and the antibiotic generated is bacitracin.

In some embodiments, the substrate is used by the microorganism *Streptomyces roseosporus* and the antibiotic generated is daptomycin.

In some embodiments, the substrate is used by the microorganism *Amycolatopsis orientalis* and the antibiotic generated is vancomycin. The biosynthesis of vancomycin is described below starting from a glucose derivative.

Biosynthesis of Vancomycin

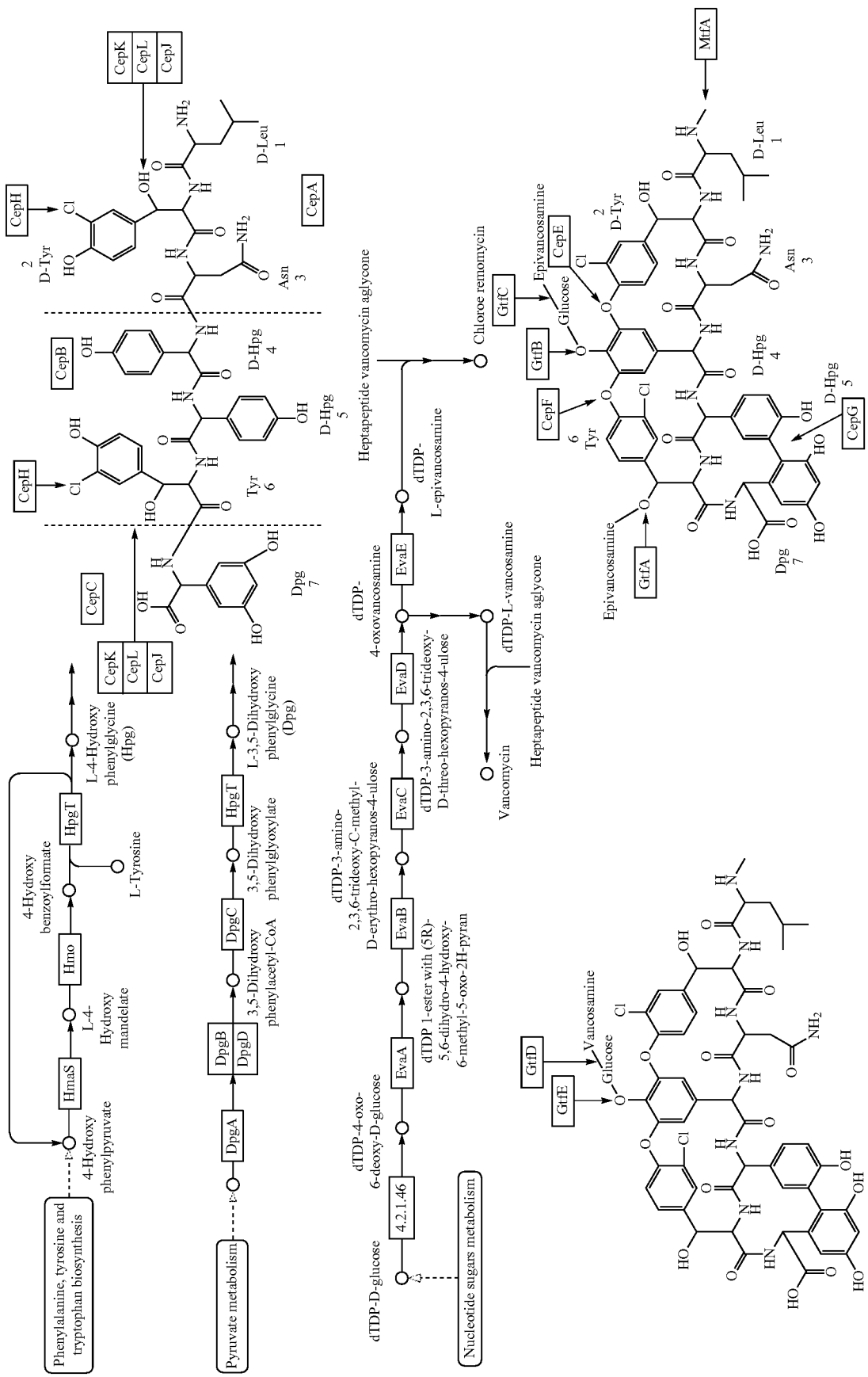

In some embodiments, the substrate is used by the two *Streptomyces hygroscopicus* strains and the antibiotics generated belong to the ansamycin family. The biosynthesis of the ansamycins is described below, starting from a glucose derivative.

Ansamycin Biosynthesis

Carotenoids

In some embodiments, the methods described herein can be used to process a first material (e.g., biomass) to generate a second material that can be used as a substrate by microorganisms (e.g., bacteria, yeast, fungi, mould, and or algae) capable of generating carotenoids, including, for example,

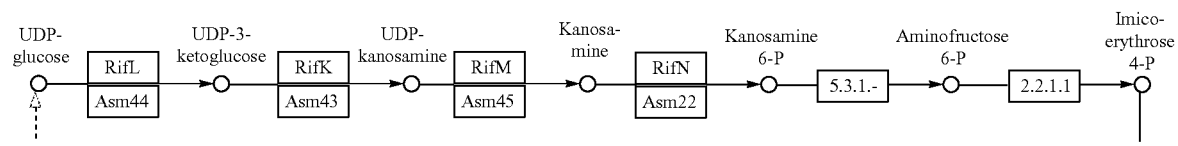

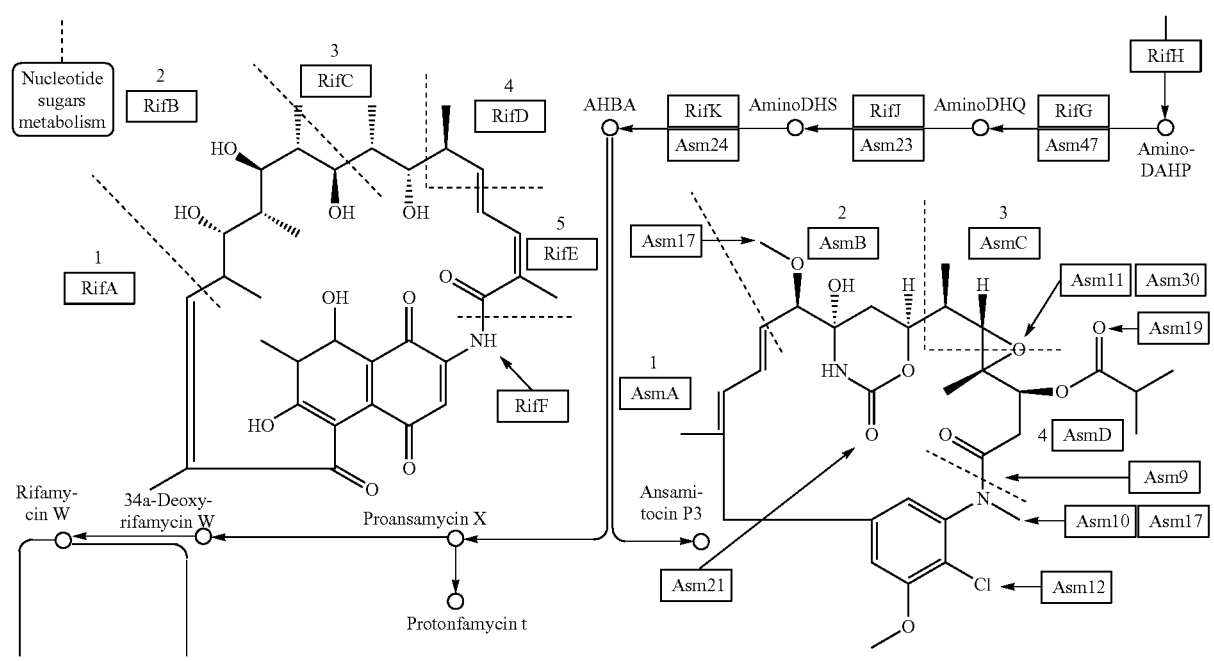

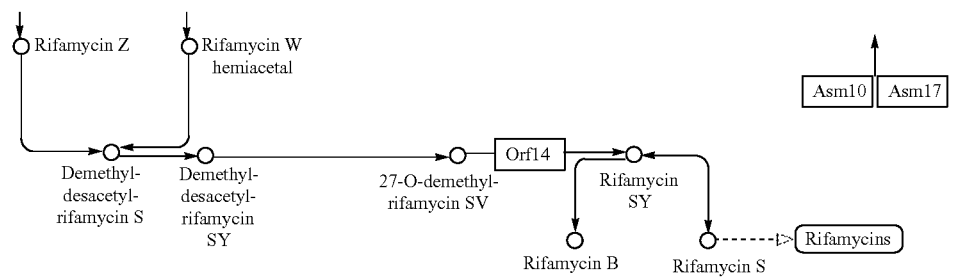

β-carotene, lycopene, and astaxanthin. Carotenoids are water-soluble natural pigments of 30-50 carbon atoms. The industrial use of carotenoids involves their application in nutrient supplementation, for pharmaceutical purposes, as food colorants, and in animal feeds.

Representative Carotenoids in Industry

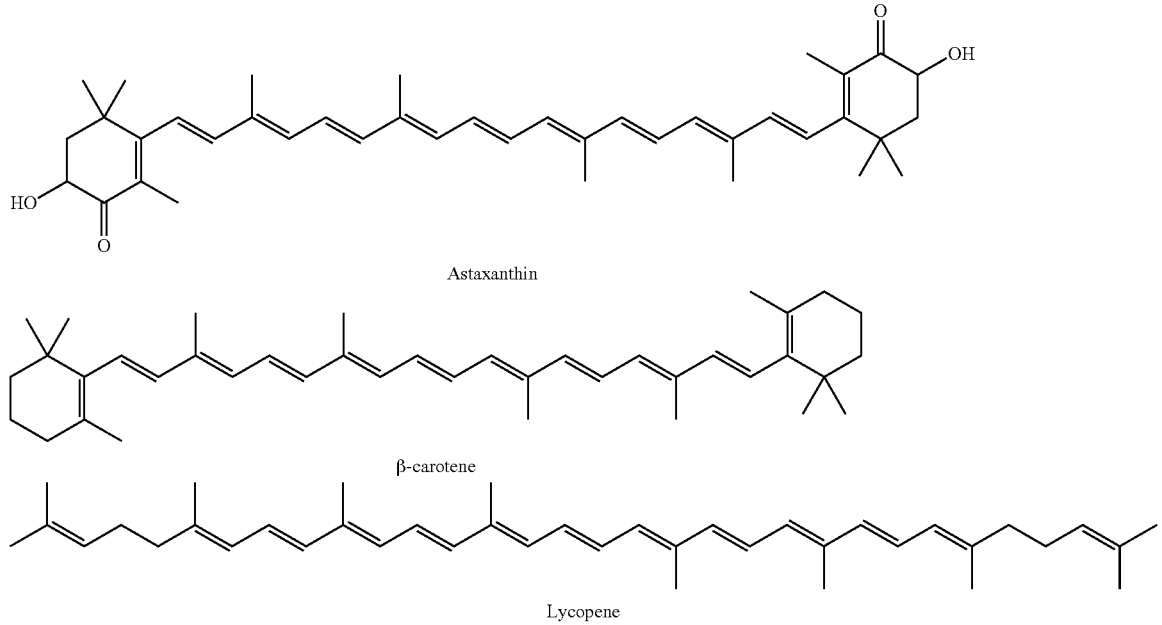

Astaxanthin

β-carotene

Lycopene

In some embodiments, antibiotic products can be produced using a fed-batch fermentation process in which nutrients are added in a controlled manner in accordance with the requirements of the culture solution.

Vaccines

In some embodiments, vaccines are immunostimulatory molecules (e.g., small molecules, peptides, and/or antigenic molecules). In some embodiments, the methods described herein can be used to process a first material (e.g., biomass), e.g., to change (e.g., lower) the recalcitrant level of the biomass, to produce a second material that can be used as a substrate by microorganisms (e.g., bacteria, fungi (e.g., yeasts and moulds), and/or algae) capable of generating vaccines, including, for example, flu vaccine (e.g., a universal flu vaccine, for example, the VaxInnate M2e universal influenza vaccine).

In some embodiments, vaccine products can be produced using a fed-batch fermentation process in which nutrients are added in a controlled manner in accordance with the requirements of the culture solution.

Specialty Chemicals

In some embodiments, the methods described herein can be used to process a first material (e.g., biomass), e.g., to change (e.g., lower) the recalcitrant level of the biomass, to produce a second material that can be used as a substrate by microorganisms (e.g., bacteria, fungi (e.g., yeasts and moulds), and/or algae) capable of generating specialty chemicals, for example, thickeners, xanthan (E 415), acidity regulators, citric acid (E 330), natamycin (E 235), nisin (E 234), and lysozyme (E 1105). In some embodiments, the methods described herein can be used to produce fine chemicals, e.g., flavorings and aromatics.

In some embodiments, chemical products can be produced using a fed-batch fermentation process in which nutrients are added in a controlled manner in accordance with the requirements of the culture solution.

Alcohols

In some embodiments, the methods described herein can be used to process a first material (e.g., biomass), e.g., to change (e.g., lower) the recalcitrant level of the biomass, to produce a second material that can be used as a substrate by microorganisms (e.g., bacteria, fungi (e.g., yeasts and moulds), and/or algae) capable of generating alcohols in addition to the energy products (e.g., ethanol) disclosed above, for example, including but not limited to acetone and butanol. In some embodiments, the substrate is used by the microorganism Clostridium acetobutylicum and the alcohol generated is acetone. In some embodiments, the substrate is used by the microorganism Clostridium acetobutylicum mutant IFP 904 (ATCC 39058) and the alcohols produced are acetone and butanol.

In some embodiments, alcohol products described herein can be produced using a fed-batch fermentation process in which nutrients are added in a controlled manner in accordance with the requirements of the culture solution.

Acids and Bases

In some embodiments, the methods described herein can be used to process a first material (e.g., biomass), e.g., to change (e.g., lower) the recalcitrant level of the biomass, to produce a second material that can be used as a substrate by microorganisms (e.g., bacteria, fungi (e.g., yeasts and moulds), and/or algae) capable of generating acids and bases. In some embodiments, the substrate is used by the microorganisms Acetobacter and/or Gluconobacter and the acid generated is acetic acid (e.g., for use in the production of vinegar).

In some embodiments, acid and base products can be produced using a fed-batch fermentation process in which nutrients are added in a controlled manner in accordance with the requirements of the culture solution.

Enzymes

In some embodiments, the methods described herein can be used to process a first material (e.g., biomass), e.g., to change (e.g., lower) the recalcitrant level of the biomass, to produce a second material that can be used as a substrate by microorganisms (e.g., bacteria, fungi (e.g., yeasts and moulds), and/or algae) capable of generating enzymes.

Exemplary enzymes that can be produced using the methods described herein include, but are not limited to, e.g., rennet, glucoamylase, polygalacturonase, cellulase, alpha-amylase, protease, betaglucanase, pullulanase, amyloglucosidase, phospholipase, xylanase, mono glucose oxidase, novo lipase, ultra lipase, lipase, maltogenic amylase, alpha-acetodecarboxylase, tender protease, pectinesterase, carbohydrase, cellobiose oxidase, lipase, pectin lyase, mono xylanase, transferase, wheat xylanase, phytase, subtillisin, It-I alpha-amylase, pectate, mannanase, trypsin, and laccase. The uses of such enzymes (e.g., alone or in combinations of one or more of the enzymes) in, for example, the juice industry, the brewing industry, the starch industry, the baking industry, the oils and fats industry, the meat industry, the dairy industry, the alcohol industry, the animal feed industry, the detergent industry, the textile industry, and the personal care industry are known in the art.

In some embodiments, enzyme products can be produced using a fed-batch fermentation process in which nutrients are added in a controlled manner in accordance with the requirements of the culture solution.

Growth Factors

In some embodiments, the methods described herein can be used to process a first material (e.g., biomass), e.g., to change (e.g., lower) the recalcitrant level of the biomass, to produce a second material that can be used as a substrate by microorganisms (e.g., bacteria, fungi (e.g., yeasts and moulds), and/or algae) capable of generating growth factors.

Exemplary growth factors that can be produced using the methods described herein include, but are not limited to, insulin-like-growth factor, keratinocyte growth factor (KGF)-1 and -2, epidermal growth factor, fibroblast growth factor, granulocyte-macrophage colony-stimulating factor, human growth hormone, interleukin-1, platelet-derived growth factor, and transforming growth factor-β.

In some embodiments, growth factor products can be produced using a fed-batch fermentation process in which nutrients are added in a controlled manner in accordance with the requirements of the culture solution.

Plastics

In some embodiments, the methods described herein can be used to process a first material (e.g., biomass), e.g., to change (e.g., lower) the recalcitrant level of the biomass, to produce a second material that can be used as a substrate by microorganisms (e.g., bacteria, fungi (e.g., yeasts and moulds), and/or algae) capable of generating plastics or plastic precursors. In some embodiments, the substrate is used by the microorganism *Alcagenes eutrophus* and the molecules generated are Poly-B-hydroxybutyrate and Poly-B-hydroxyvalerate.

In some embodiments, plastic products can be produced using a fed-batch fermentation process in which nutrients are added in a controlled manner in accordance with the requirements of the culture solution.

Fertilizers

In some embodiments, the methods described herein can be used to process a first material (e.g., biomass), e.g., to change (e.g., lower) the recalcitrant level of the biomass, to produce a second material that can be used as a substrate by microorganisms (e.g., bacteria, fungi (e.g., yeasts and moulds), and/or algae) capable of generating materials that can be used as or in fertilizers (e.g., proteins, fats and oils, carbohydrates, and/or minerals). In some embodiments, fertilizers generated using the methods described herein can be protein-based or protein-rich fertilizers (see Paungfoolonhienne et al., *PNAS*, 104:4524-4529, 2008, for a review of protein-based fertilizers).

Culture Methods

As detailed above, the methods described herein can be used to process a first material (e.g., biomass), e.g., to change (e.g., lower) the recalcitrant level of the biomass, to produce a second material that can be used as a substrate by microorganisms (e.g., bacteria, fungi (e.g., yeasts and moulds), and/or algae) to generate materials and products not necessarily present (e.g., not substantially present) or abundant in the first material. The choice of microorganisms will depend on the product to be produced.

Microorganism Selection

Several additional factors can also be considered when selecting suitable microorganisms for use in the methods described herein. For example, if the microorganisms are to be used to generate a health product for use with animals or humans, or if the microorganisms are to be used as or in the production of a food, the microorganisms selected will typically be non-pathogenic and/or generally regarded as safe (GRAS). In addition, the microorganisms selected should be capable of producing large quantities of the desired product or should be able to be modified to produce large quantities of the desired product. In some embodiments, the microorganisms can also be commercially available and/or efficiently isolated, readily maintainable in culture, genetically stable and/or well characterized. Selected microorganisms can be wild type (e.g., unmodified) or genetically modified microorganisms (e.g., mutated organisms). In some embodiments, a genetically modified microorganism can be adapted to increase its production of the desired product and/or to increase the microorganisms tolerance to one or more environmental and/or experimental factors, for example, the microorganism can be modified (e.g., engineered) to tolerate temperature, pH, acids, bases, nitrogen, and oxygen levels beyond a range normally tolerated by the microorganism. Alternatively or in addition, the microorganisms can be modified (e.g., engineered) to tolerate the presence of additional microorganisms. In some embodiments, the microorganisms can be modified (e.g., engineered) to grow at a desired rate under desired conditions.

Culture Solutions

As detailed above, the methods described herein can be used to process a first material (e.g., biomass), e.g., to change (e.g., lower) the recalcitrant level of the biomass, to produce a second material that can be used as a substrate by microorganisms (e.g., bacteria, fungi (e.g., yeasts and moulds), and/or algae), e.g., in or as a culture solution. Typically, culture solutions can be formulated based on their ability to support the growth of the selected microorganisms. In addition to the biomass-based substrates generated herein, culture solutions can also optionally include an additional carbon source (e.g., glucose), water, salts, amino acids or an amino acid source. In some embodiments, culture solutions can include a supplemental nitrogen source. The pH of these culture solutions can be adapted to the requirement of the selected microorganism. Culture solutions can also optionally include one or more antibiotics to prevent contamination.

Certain culture solutions are commercially available, for example, commercially available growth medias include, Luria Bertani (LB) medium, terrific broth (TB) medium, yeast and mould (YM) broth (yeast extract 3 g/L, malt extract 3 g/L, peptone 5 g/L, and dextrose 10 g/L and pH 6.0-pH 8.0), YPG media (yeast extract, 3 g; mycological peptone, 5 g; D-glucose, 10 g per liter of water) and bacto peptone. Growth medias can be purchased from commercial sources (e.g., Sigma Aldrich or Difco). Culture solutions useful in the present methods are provided in the art, for example, in Ramasamy et al., *J. Appl. Biotechnol.*, 46:117-124, 1979, Young et al., *Biotechnol Lett.*, 14:863-868, 1992, Anupama and Ravindra, *Brazilian Archives or Biology and Biotechnol.*, 44:79-88, 2001, U.S. Pat. Nos. 3,627,095, 4,379,844, 4,447,530, 4,401,680, 4,526,721, 5,047,332, and 4,938,972. In some embodiments, any one of these commercially available or published culture solutions can be supplemented with the biomass substrates generated herein.

In some embodiments, however, the use of commercially available medias will not be the most economically viable option. In such cases, culture solutions can be prepared manually. In some embodiments, culture solutions can contain, in addition to the biomass substrates generated herein, per liter of water at pH 4-7.5: 1.88-2.357 g $(NH_4)_2SO_4$, 0.75-1.5 g $KH_2PO_4$, 0.25-5 g $MgSO_4.7H_2O$, 0.25-0.5 g $FeS)_4.7H_2O$, 0.25-0.5 $ZnSO_4.7H_2O$, 0.1-1 ml trace element solution. In some embodiments, the culture solution can further include 114 mg boric acid, 480 mg ammonium molybdate, 780 mg cupric sulphate, and 144 mg manganese chloride. In some embodiments, the culture solution can further comprise 0.5 g yeast extract and can be used for the culture of yeast. In some embodiments, the culture solution can further comprise 1.0 g yeast extract and can be used for the culture of *Zymomonas mobilis*. In some embodiments, the culture solution can be adapted for the fermentation of ethanol and can contain, in addition to the biomass substrates generated herein, per liter of water, sugars equivalent to 80-160 g glucose, 1 g $KH_2PO_4$, 1.5 g $NH_4Cl$, 0.16 g $MgSO_4.7H_2O$, 0.08 g $CaCl_2$, and 1.0 g yeast extract.

In some embodiments, the selected microorganism can be a yeast and the growth media can contain, in addition to the biomass substrates generated herein, 1.7 g/L yeast nitrogen base, 2.27 g/L urea, 6.56 g/L peptone at pH 5.0.

In some embodiments, the selected microorganisms can be cultured in the presence of a nitrogen source and/or an additional nitrogen source (e.g., when the desired products are proteins or amino acids). In such cases, the nitrogen source can include any nitrogen source, for example, animal waste (e.g., poultry manure), human waste, inorganic nitrogen sources, nitrite, nitrate, anhydrous ammonia, ammonium nitrate, diammonium phosphate, monoammonium phosphate, beef, or yeast extract. In some embodiments, animal waste and human waste can be sterilized (e.g., filtered or autoclaved) prior to use.

The selected microorganisms can be cultured on a small scale (e.g., using standard laboratory equipment and methods known in the art) or on a large scale (e.g., using fermentation or industrial fermentation methods). The choice of culture solution will depend on the desired culture scale.

Culture Conditions

Cell culture conditions (e.g., temperature, pH and oxygen requirements) for most organisms are known in the art, and, if required, can be easily optimized as required. For example, culture conditions can be conducted batchwise or continuously. The temperature used for cell culture can be selected according to the selected microorganisms so a to produce acceptable yields and substrate, particularly carbon, conversion ratios. Exemplary temperatures are within the range of 25-40° C. Similarly, the pH used for cell culture can be kept within a range at which maximum growth is exhibited for the selected microorganisms. Exemplary pH ranges are pH 5.0-8.0, e.g., pH 6.0-7.0. In addition, oxygenation levels can be adjusted to be maintained at a level that ensures optimal growth of the selected microorganism. For example, aerobic organisms can be cultured in an oxygenated environment. Alternatively, anaerobic organisms can be cultured in an anaerobic environment.

Culture Methods

In some embodiments, the selected microorganisms can be cultured using without the use of fermentation equipment. For example a first lignocellulosic biomass material with a first recalcitrant level can be processed to produce a second material with an altered (e.g., lowered) recalcitrant level. This second material can then be used in a bioconversion step to produce a product not present in the first lignocellulosic biomass material. In some embodiments, this second material can be combined (e.g., in a liquid medium or culture) in a cell culture flask with one or more microorganisms under conditions suitable for growth of the microorganisms and generation of the product. The culture can then be incubated for a period of time sufficient to generate the product.

In some embodiments, all cell culture equipment is sterilized or is sterile prior to use.

Small Scale Methods

In some embodiments, the selected microorganisms can be cultured using bench-top fermentation equipment. For example a first lignocellulosic biomass material with a first recalcitrant level can be processed to produce a second material with an altered (e.g., lowered) recalcitrant level. This second material can then be used in a bioconversion step to produce a product not present in the first lignocellulosic biomass material. In some embodiments, the second material can be combined with selected microorganisms and cultured in a bench top fermentor, e.g., a Braun (B. Braun Biotech, Aylesbury, Bucks) Biostat ER3 fermentor with a working volume of 2.8 liters, in a growth media and under culture conditions suitable for growth of the microorganisms and generation of the product. The process can then be maintained for a period of time sufficient to generate the product. Exemplary set points can include: temperature 20-45° C.; pH 3-9 (which can be maintained by autotitration); with defined agitation and air flow rates (e.g., about 1000 rpm and 2 L/minute, respectively). In addition, foaming can optionally be suppressed by the timed addition of an anti-foaming agent, e.g., a polypropylene glycol antifoam oil.

Large Scale Methods

In some embodiments, the selected microorganisms can be cultured using large scale fermentation equipment (e.g., stirred tank bioreactors and/or airlift bioreactors). For example a first lignocellulosic biomass material with a first recalcitrant level can be processed to produce a second material with an altered (e.g., lowered) recalcitrant level. This second material can then be used in a bioconversion step to produce a product not present in the first lignocellulosic biomass material. In some embodiments, the second material can be combined with selected microorganisms and cultured, e.g., in a stirred tank bioreactor (e.g., a 300 L stirred tank bioreactor). Alternatively or in addition, the second material can be combined with selected microorganisms and cultured in a airlift (pressure cycle) bioreactor (e.g., a 40,000 L airlift bioreactor as manufactured by RHM and ICI for the production of Quorn®). In both cases, the second material can be combined with selected microorganisms in a culture solution and under culture conditions suitable for growth of the microorganisms and generation of the product. The process can then be maintained for a period of time sufficient to generate the product.

Figure 44:
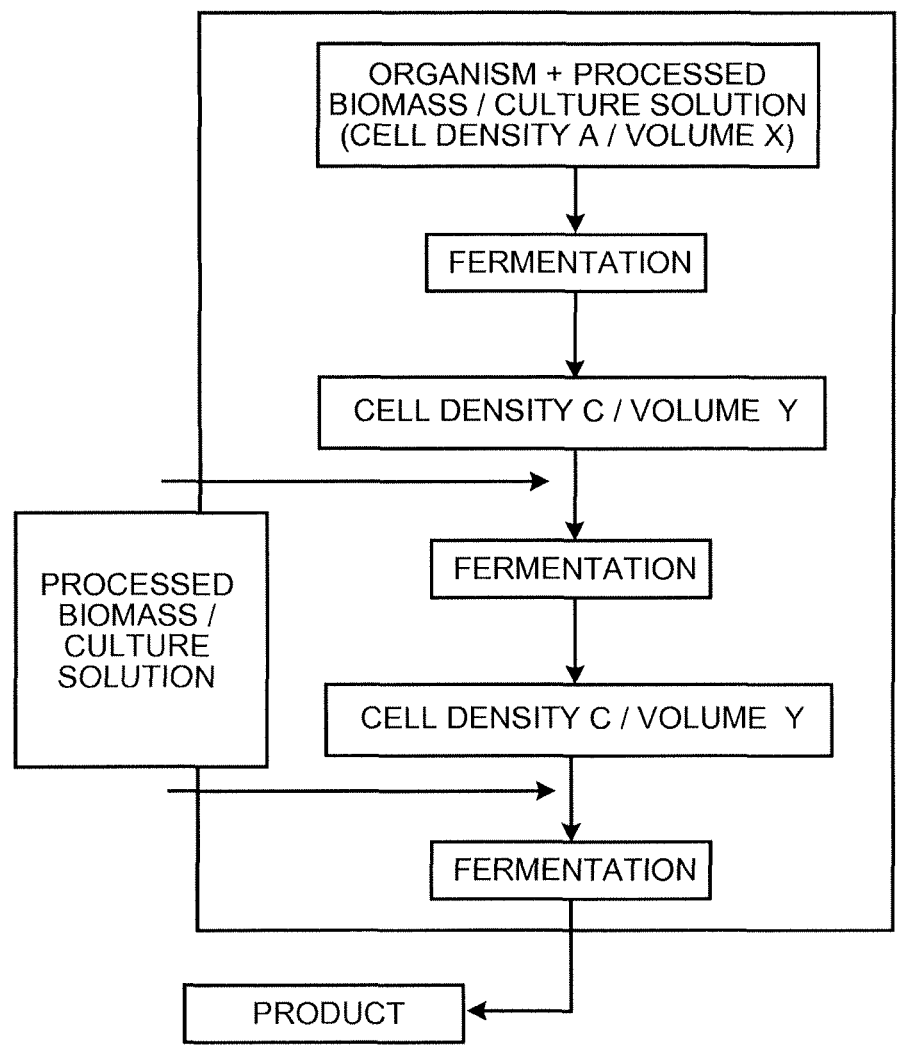
FIG. 44 is a schematic diagram showing a variable volume fed-batch fermentation process.
Figure 45:
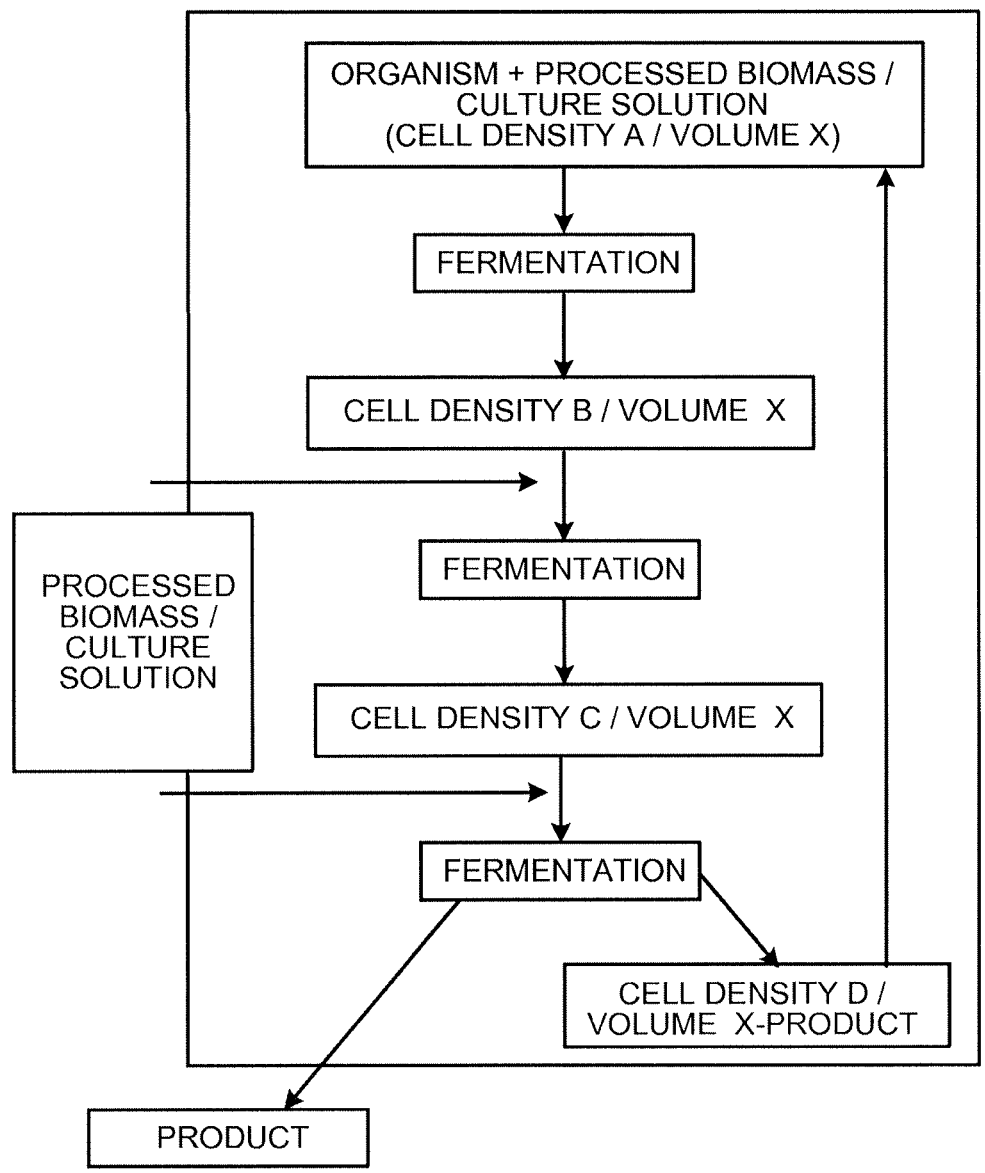
FIG. 45 is a schematic diagram showing a fixed volume fed-batch fermentation process.
Figure 46:
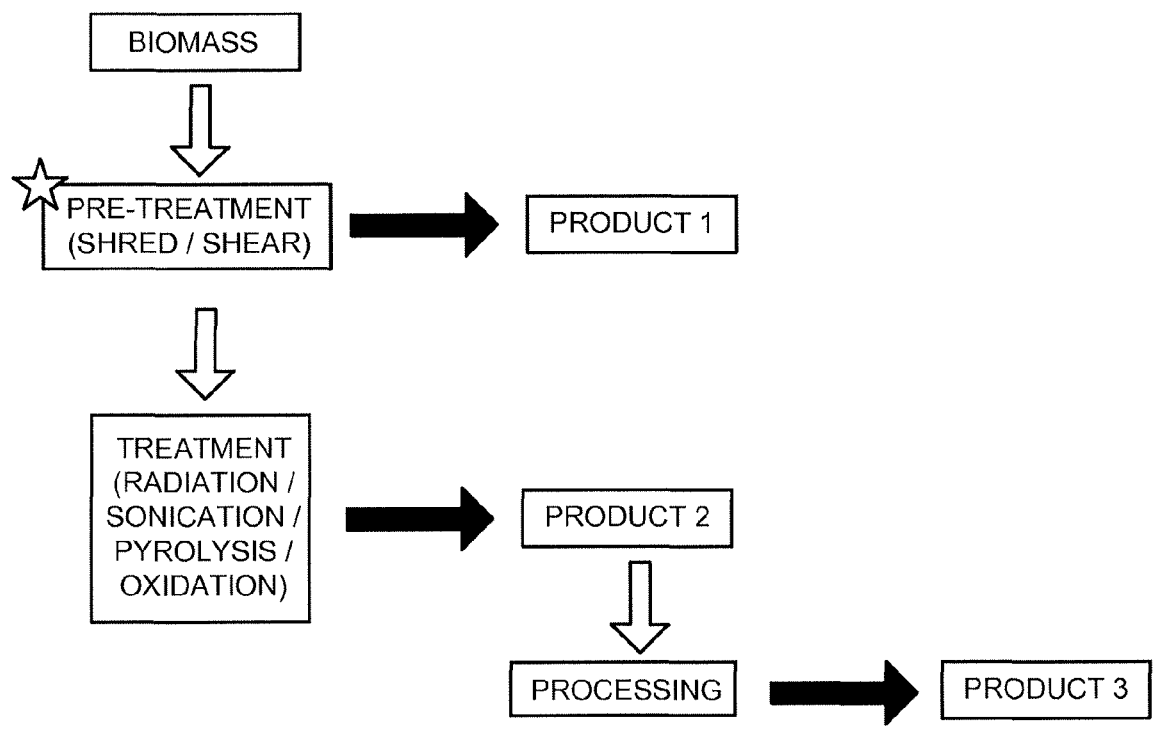
FIG. 46 is a schematic diagram showing the processing steps required for the production of products 1, 2, and 3. Star indicates a step is optional. Black arrow indicates that an optional densification step can be performed.

In some embodiments, the selected microorganisms can be cultured using fed-batch fermentation (e.g., fixed volume fed-batch or variable volume fed-batch) in which nutrients are added in a controlled manner in accordance with the requirements of the culture solution (see FIG. 44 and FIG. 45). In a fixed volume fed-batch fermentation process growth limiting substrates are added to the culture solution in a highly concentrated form or a gas form that does not alter the volume of the culture solution. Once fermentation reaches a certain stage, a volume of the culture solution can optionally be removed and replaced with fresh culture solution. In such a step, the volume of culture solution not removed from the fermentor serves as the starter culture for the next cycle and the removed volume contains the desired product. Such a process is referred to in the art as cyclic fed-batch culture for fixed volume culture. One advantage of using cyclic fed-batch culture for fixed volume culture is that desired products can be obtained prior to the end of the fermentation process. In addition, a cyclic fed-batch culture for fixed volume culture process can be continuous. In a variable volume fed-batch fermentation process, growth-limiting substrates are added as required to promote further growth of the culture in a concentration equal to the concentration of the starting culture. Consequently, the total volume of the culture increases. This process can be repeated until the volume of the culture reaches the capacity of the fermentor. Larger fermentation tanks are advantageous in this method as such tanks accommodate larger volumes of culture solution. The desired products can then be obtained from the culture solution, e.g., at the end of the fermentation process. Both these fed-batch processes allow optimal yields and productivities. In some embodiments, the process can include providing continuously oxygenated water, e.g., using an air-lift fermentation system.

Fed-batch processes are also described in European Patent Application No. 533039.

Following fermentation, the selected microorganism and/or product can be harvested and optionally isolated and/or purified. Methods for harvesting microorganisms from culture solutions include, for example, centrifugation and/or filtration.

Further Processing for Food Products

Cultures for use, e.g., as ingestible foods for animals and/or humans can be further processed, e.g., using the methods discloses in U.S. Pat. Nos. 5,935,841; 6,270,816; 5,980,958; and 3,809,614. Alternatively or in addition, a harvested organism can be treated to reduce its nucleic acid content, e.g., using the process of UK Patent No. 1,440,642; separated, if desired, e.g., using the process of UK Patent No. 1,473,654, or by filtration or centrifugation; and its palatability can be modified, e.g., using the procedures of UK Patent Nos. 1,508,635; 1,502,455; 1,496,113; and/or 1,587,828.

Humans do not possess the enzyme uricase to catalyze the conversion of uric acid to the more soluble allantoin. Consumption of microbial cells, which contain high levels of nucleic acid, can, therefore, lead to elevated levels of uric acid and complications associated therewith in humans. In some embodiments, therefore, nucleic acids can be removed or reduced from samples containing microbial cells or food products derived from microbial cells (e.g., proteins, fats and oils, and carbohydrates) prior to consumption by humans, for example, using methods as described by Lawford and Lewis (U.S. Pat. No. 4,330,464). In some embodiments, nucleic acids can be removed or reduced from samples containing microbial cells or food products derived from microbial cells (e.g., proteins, fats and oils, and carbohydrates) prior to consumption by humans, e.g., using the methods described in U.S. Pat. No. 6,270,816. For example, microbial cells can be killed and the nucleic acid simultaneously reduced by rapidly heating the culture solution to at least 60° C. This process can be used to promote loss of cell viability and reduction of a portion of cellular nucleic acid (e.g., DNA and RNA) into the supernatant. Following heating, the culture solution can be centrifuged and rinsed to remove the nucleic acids.

In some embodiments, the protein:RNA ratio for protein in a sample for human consumption should be at least 12:1. In some embodiments, the total nucleic acid content of a sample for human consumption can be reduced to about 2% (e.g., 2%, less than 2%, 0.1-2.0%, 0.1-1.5%, 0.1-1%, 0.1-0.5%, 0.1-0.3%, 0.1%) of the dry weight of the sample.

In some embodiments, nutritional and/or toxicological evaluations of samples containing microbial cells or food products derived from microbial cells (e.g., proteins, fats and oils, and carbohydrates) can be performed prior to ingestion by animals (e.g., for each target species).

In some embodiments, microbial proteins can be dried, lyophilized, or in solution, and can be present in an isolated form or in the presence of one or more additional food sources.

In some embodiments, samples containing microbial cells or food products derived from microbial cells (e.g., proteins, fats and oils, and carbohydrates) can be formulated as edible gels. Gel quality can be assessed using Strain and stress tests, e.g., using the torsion technique of Wu et al., *J. Tex. Studies,* 16: 53-74 (1985), or with a Rheo Tex model gelometer AP-83 (Sun Sciences Co. Seattle, Wash., USA). In general, values of strain (elastic component) greater than 1.9 to 2.0 and stress values of 30-35 kPa are a reliable indication of gel strength.

In some embodiments, samples containing microbial cells or food products derived from microbial cells (e.g., proteins, fats and oils, and carbohydrates) can be flavored and/or colored, e.g., to increase palatability for the target species.

In some embodiments, samples containing microbial cells or food products derived from microbial cells (e.g., proteins, fats and oils, and carbohydrates) can be used as or in the generation of meat analogues. "Meat analogue" is an industrial term for meat substitutes or synthetic meats made primarily from non-animal source, e.g., plant proteins.

In some embodiments, the health and nutritional values of the food products derived from microbial cells (e.g., proteins, fats and oils, and carbohydrates) described herein are considered prior to consumption by animals and/or humans.

Food Formulations

In some embodiments, the food products described herein can be used as or in the production of food products (e.g., solid or liquid food products). In some embodiments, the food products can be used alone or can be combined. In some embodiments, the food products can be combined with texturizing materials (e.g., wheat protein). In some embodiments, the food products disclosed herein can be formulated as meat alternatives (see, e.g., Quorn®, manufactured by Marlow Foods, UK). In some embodiments, the food products disclosed herein can be combined with other proteins, protein sources, or foods., e.g., mycoprotein, textured vegetable protein, tofu, tempeh, miso, soya products, and/or wheat protein.

In some embodiments, any of the products and co-products described herein can be combined with a flavorings and/or colorings, for example, fine chemical flavors and aromas.

Process Water

In the processes disclosed herein, whenever water is used in any process, it may be grey water, e.g., municipal grey water, or black water. In some embodiments, the grey or black water is sterilized prior to use. Sterilization may be accomplished by any desired technique, for example by irradiation, steam, or chemical sterilization.

EXAMPLES

The following Examples are intended to illustrate, and do not limit the teachings of this disclosure.

Example 1

Preparation of Fibrous Material from Polycoated Paper

A 1500 pound skid of virgin, half-gallon juice cartons made of un-printed polycoated white Kraft board having a bulk density of 20 lb/ft$^3$ was obtained from International Paper. Each carton was folded flat, and then fed into a 3 hp Flinch Baugh shredder at a rate of approximately 15 to 20 pounds per hour. The shredder was equipped with two 12 inch rotary blades, two fixed blades and a 0.30 inch discharge screen. The gap between the rotary, and fixed blades was adjusted to 0.10 inch. The output from the shredder resembled confetti having a width of between 0.1 inch and 0.5 inch, a length of between 0.25 inch and 1 inch and a thickness equivalent to that of the starting material (about 0.075 inch).

Figure 26:
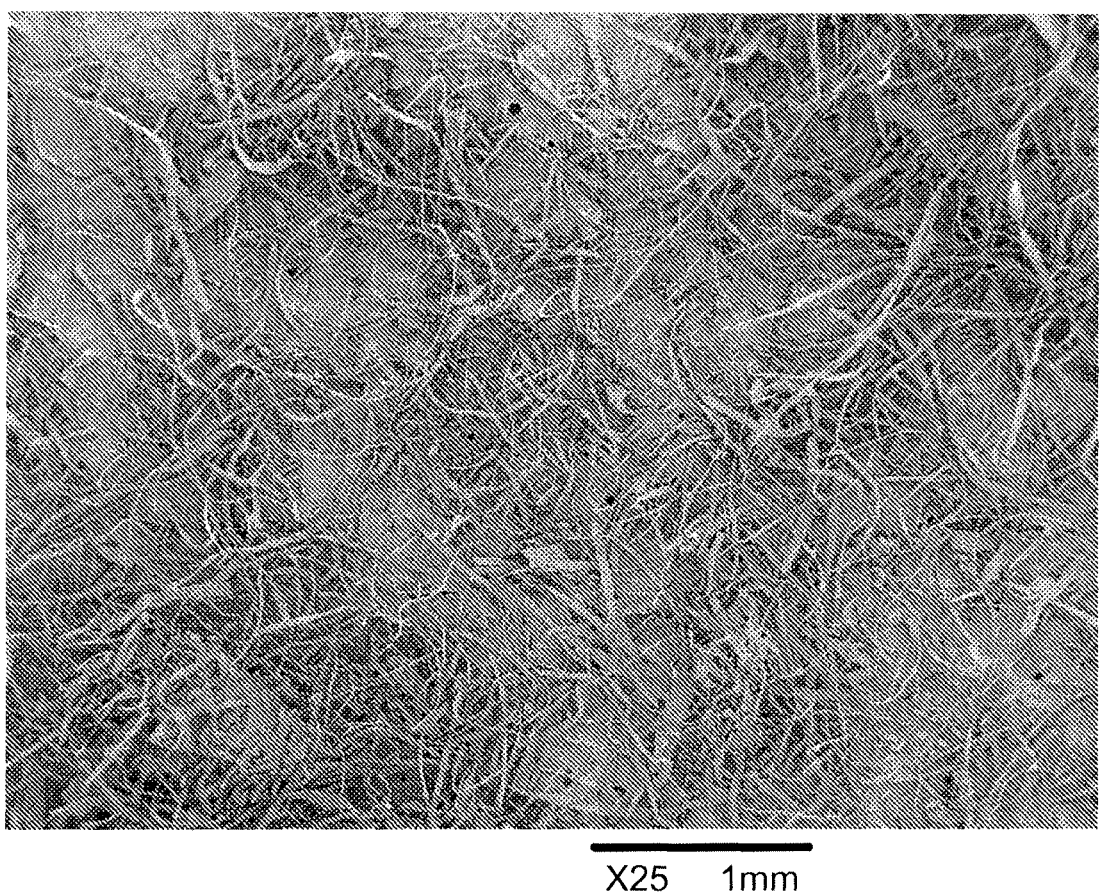
FIG. 26 is a scanning electron micrograph of a fibrous material produced from polycoated paper at 25× magnification. The fibrous material was produced on a rotary knife cutter utilizing a screen with ⅛ inch openings.

The confetti-like material was fed to a Munson rotary knife cutter, Model SC30. Model SC30 is equipped with four rotary blades, four fixed blades, and a discharge screen having ⅛ inch openings. The gap between the rotary and fixed blades was set to approximately 0.020 inch. The rotary knife cutter sheared the confetti-like pieces across the knife-edges, tearing the pieces apart and releasing a fibrous material at a rate of about one pound per hour. The fibrous material had a BET surface area of 0.9748 m$^2$/g+/−0.0167 m$^2$/g, a porosity of 89.0437 percent and a bulk density (@0.53 psia) of 0.1260 g/mL. An average length of the fibers was 1.141 mm and an average width of the fibers was 0.027 mm, giving an average L/D of 42:1. A scanning electron micrograph of the fibrous material is shown in FIG. 26 at 25× magnification.

Example 2

Preparation of Fibrous Material from Bleached Kraft Board

Figure 27:
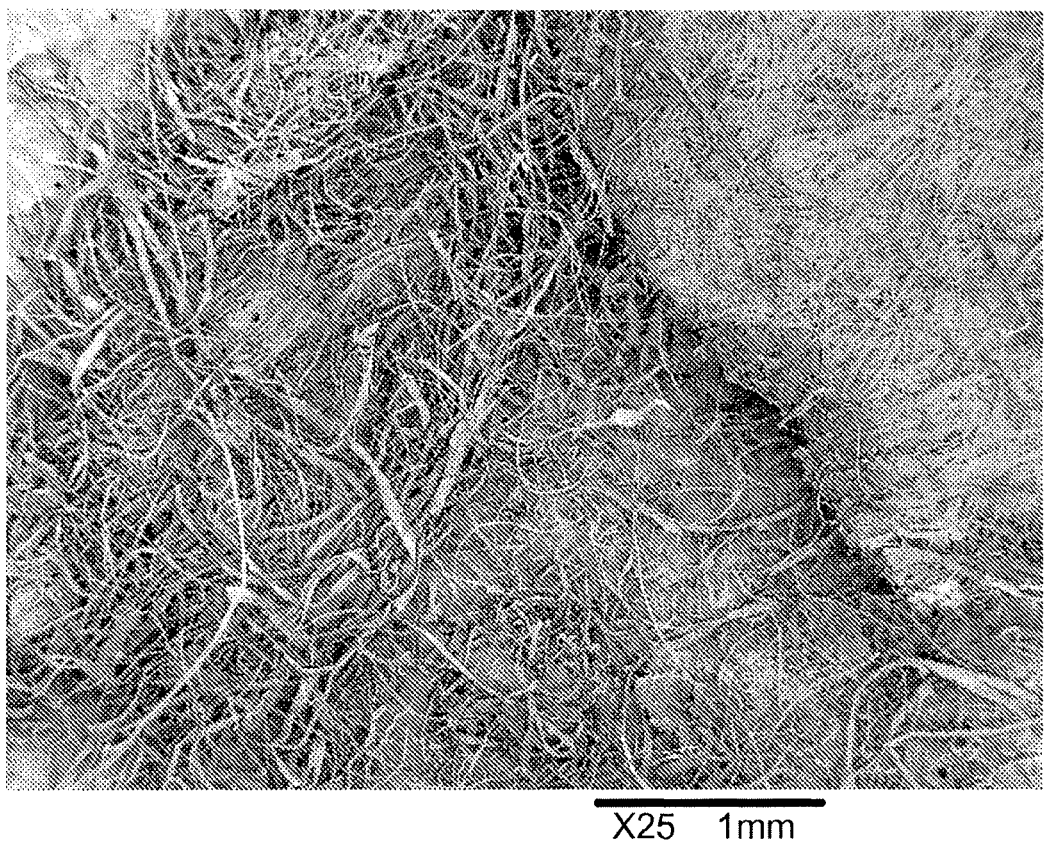
FIG. 27 is a scanning electron micrograph of a fibrous material produced from bleached Kraft board paper at 25× magnification. The fibrous material was produced on a rotary knife cutter utilizing a screen with ⅛ inch openings.

A 1500 pound skid of virgin bleached white Kraft board having a bulk density of 30 lb/ft$^3$ was obtained from International Paper. The material was folded flat, and then fed into a 3 hp Flinch Baugh shredder at a rate of approximately 15 to 20 pounds per hour. The shredder was equipped with two 12 inch rotary blades, two fixed blades and a 0.30 inch discharge screen. The gap between the rotary and fixed blades was adjusted to 0.10 inch. The output from the shredder resembled confetti having a width of between 0.1 inch and 0.5 inch, a length of between 0.25 inch and 1 inch and a thickness equivalent to that of the starting material (about 0.075 inch). The confetti-like material was fed to a Munson rotary knife cutter, Model SC30. The discharge screen had ⅛ inch openings. The gap between the rotary and fixed blades was set to approximately 0.020 inch. The rotary knife cutter sheared the confetti-like pieces, releasing a fibrous material at a rate of about one pound per hour. The fibrous material had a BET surface area of 1.1316 m$^2$/g+/−0.0103 m$^2$/g, a porosity of 88.3285 percent and a bulk density (@0.53 psia) of 0.1497 g/mL. An average length of the fibers was 1.063 mm and an average width of the fibers was 0.0245 mm, giving an average L/D of 43:1. A scanning electron micrograph of the fibrous material is shown in FIG. 27 at 25× magnification.

Example 3

Preparation of Twice Sheared Fibrous Material from Bleached Kraft Board

Figure 28:
FIG. 28 is a scanning electron micrograph of a fibrous material produced from bleached Kraft board paper at 25× magnification. The fibrous material was twice sheared on a rotary knife cutter utilizing a screen with 1/16 inch openings during each shearing.

A 1500 pound skid of virgin bleached white Kraft board having a bulk density of 30 lb/ft$^3$ was obtained from International Paper. The material was folded flat, and then fed into a 3 hp Flinch Baugh shredder at a rate of approximately 15 to 20 pounds per hour. The shredder was equipped with two 12 inch rotary blades, two fixed blades and a 0.30 inch discharge screen. The gap between the rotary and fixed blades was adjusted to 0.10 inch. The output from the shredder resembled confetti (as above). The confetti-like material was fed to a Munson rotary knife cutter, Model SC30. The discharge screen had 1/16 inch openings. The gap between the rotary and fixed blades was set to approximately 0.020 inch. The rotary knife cutter the confetti-like pieces, releasing a fibrous material at a rate of about one pound per hour. The material resulting from the first shearing was fed back into the same setup described above and sheared again. The resulting fibrous material had a BET surface area of 1.4408 m$^2$/g+/−0.0156 m$^2$/g, a porosity of 90.8998 percent and a bulk density (@0.53 psia) of 0.1298 g/mL. An average length of the fibers was 0.891 mm and an average width of the fibers was 0.026 mm, giving an average L/D of 34:1. A scanning electron micrograph of the fibrous material is shown in FIG. 28 at 25× magnification.

Example 4

Preparation of Thrice Sheared Fibrous Material from Bleached Kraft Board

A 1500 pound skid of virgin bleached white Kraft board having a bulk density of 30 lb/ft$^3$ was obtained from International Paper. The material was folded flat, and then fed into a 3 hp Flinch Baugh shredder at a rate of approximately 15 to 20 pounds per hour. The shredder was equipped with two 12 inch rotary blades, two fixed blades and a 0.30 inch discharge screen. The gap between the rotary and fixed blades was adjusted to 0.10 inch. The output from the shredder resembled confetti (as above). The confetti-like material was fed to a Munson rotary knife cutter, Model SC30. The discharge screen had ⅛ inch openings. The gap between the rotary and fixed blades was set to approximately 0.020 inch. The rotary knife cutter sheared the confetti-like pieces across the knife-edges. The material resulting from the first shearing was fed back into the same setup and the screen was replaced with a 1/16 inch screen. This material was sheared. The material resulting from the second shearing was fed back into the same setup and the screen was replaced with a 1/32 inch screen. This material was sheared.

Figure 29:
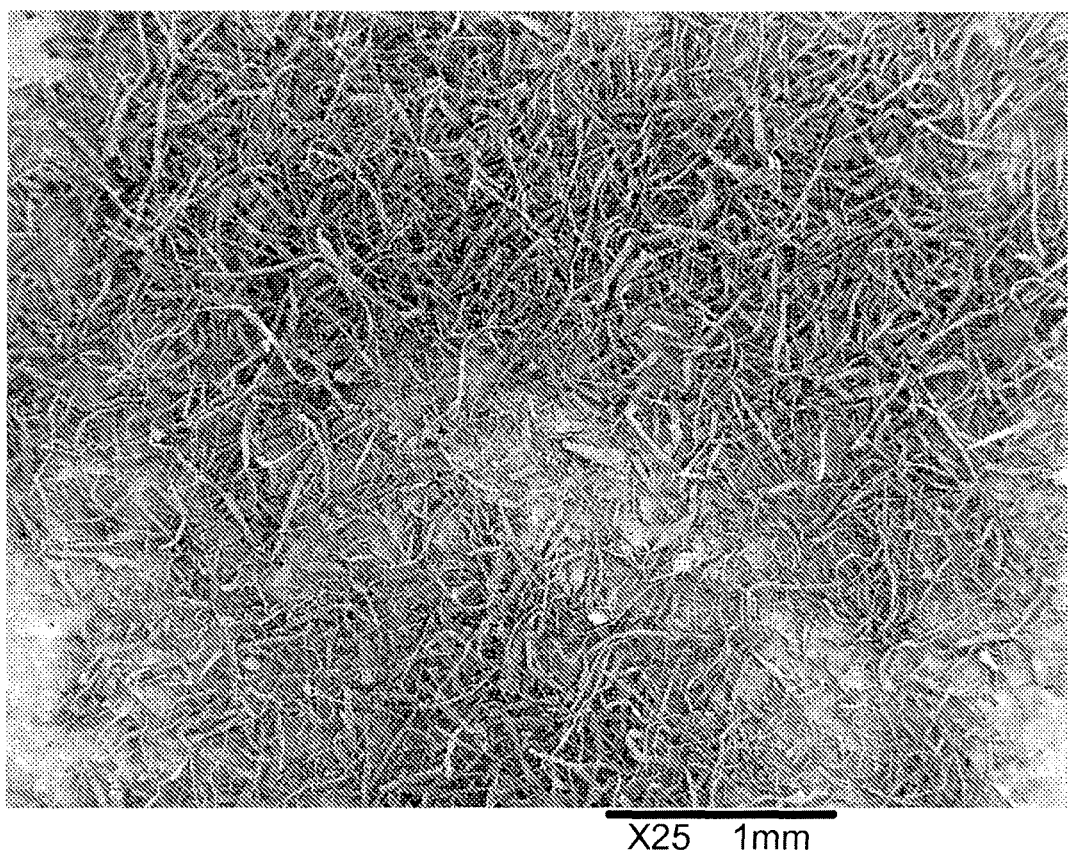
FIG. 29 is a scanning electron micrograph of a fibrous material produced from bleached Kraft board paper at 25× magnification. The fibrous material was thrice sheared on a rotary knife cutter. During the first shearing, a ⅛ inch screen was used; during the second shearing, a 1/16 inch screen was used, and during the third shearing a 1/32 inch screen was used.

The resulting fibrous material had a BET surface area of 1.6897 m²/g+/−0.0155 m²/g, a porosity of 87.7163 percent and a bulk density (@0.53 psia) of 0.1448 g/mL. An average length of the fibers was 0.824 mm and an average width of the fibers was 0.0262 mm, giving an average L/D of 32:1. A scanning electron micrograph of the fibrous material is shown in FIG. 29 at 25× magnification.

Example 5

Preparation of Densified Fibrous Material from Bleached Kraft Board without Added Binder Fibrous material was prepared according to Example 2. Approximately 1 lb of water was sprayed onto each 10 lb of fibrous material. The fibrous material was densified using a California Pellet Mill 1100 operating at 75° C. Pellets were obtained having a bulk density ranging from about 7 lb/ft³ to about 15 lb/ft³.

Example 6

Preparation of Densified Fibrous Material from Bleached Kraft Board with Binder Fibrous material was prepared according to Example 2.
A 2 weight percent stock solution of POLYOX™ WSR N10 (polyethylene oxide) was prepared in water.
Approximately 1 lb of the stock solution was sprayed onto each 10 lb of fibrous material. The fibrous material was densified using a California Pellet Mill 1100 operating at 75° C. Pellets were obtained having a bulk density ranging from about 15 lb/ft³ to about 40 lb/ft³.

Example 7

Reducing the Molecular Weight of Cellulose in Fibrous Kraft Paper by Gamma Radiation with Minimum Oxidation Fibrous material is prepared according to Example 4, and then densified according to Example 5.
The densified pellets are placed in a glass ampoule having a maximum capacity of 250 mL. The glass ampoule is evacuated under high vacuum ($10^{-5}$ torr) for 30 minutes, and then back-filled with argon gas. The ampoule is sealed under argon. The pellets in the ampoule are irradiated with gamma radiation for about 3 hours at a dose rate of about 1 Mrad per hour to provide an irradiated material in which the cellulose has a lower molecular weight than the fibrous Kraft starting material.

Example 8

Reducing the Molecular Weight of Cellulose in Fibrous Kraft Paper by Gamma Radiation with Maximum Oxidation Fibrous material is prepared according to Example 4, and then densified according to Example 5.
The densified pellets are placed in a glass ampoule having a maximum capacity of 250 mL. The glass ampoule is sealed under an atmosphere of air. The pellets in the ampoule are irradiated with gamma radiation for about 3 hours at a dose rate of about 1 Mrad per hour to provide an irradiated material in which the cellulose has a lower molecular weight than the fibrous Kraft starting material.

Example 9

Methods of Determining Molecular Weight of Cellulosic and Lignocellulosic Materials by Gel Permeation Chromatography Cellulosic and lignocellulosic materials for analysis were treated according to Example 4. Sample materials presented in the following tables include Kraft paper (P), wheat straw (WS), alfalfa (A), and switchgrass (SG). The number "132" of the Sample ID refers to the particle size of the material after shearing through a 1/32 inch screen. The number after the dash refers to the dosage of radiation (MRad) and "US" refers to ultrasonic treatment. For example, a sample ID "P132-10" refers to Kraft paper that has been sheared to a particle size of 132 mesh and has been irradiated with 10 MRad.

TABLE 1

Peak Average Molecular Weight of Irradiated Kraft Paper

| Sample Source | Sample ID | Dosage[1] (MRad) | Ultrasound[2] | Average MW ± Std Dev. |
|---|---|---|---|---|
| Kraft Paper | P132 | 0 | No | 32853 ± 10006 |
|  | P132-10 | 10 | " | 61398 ± 2468** |
|  | P132-100 | 100 | " | 8444 ± 580 |
|  | P132-181 | 181 | " | 6668 ± 77 |
|  | P132-US | 0 | Yes | 3095 ± 1013 |

**Low doses of radiation appear to increase the molecular weight of some materials
[1]Dosage Rate = 1 MRad/hour
[2]Treatment for 30 minutes with 20 kHz ultrasound using a 1000 W horn under re-circulating conditions with the material dispersed in water.

TABLE 2

Peak Average Molecular Weight of Irradiated Materials

| Sample ID | Peak # | Dosage[1] (MRad) | Ultrasound[2] | Average MW ± Std Dev. |
|---|---|---|---|---|
| WS132 | 1 | 0 | No | 1407411 ± 175191 |
|  | 2 | " | " | 39145 ± 3425 |
|  | 3 | " | " | 2886 ± 177 |
| WS132-10* | 1 | 10 | " | 26040 ± 3240 |
| WS132-100* | 1 | 100 | " | 23620 ± 453 |
| A132 | 1 | 0 | " | 1604886 ± 151701 |
|  | 2 | " | " | 37525 ± 3751 |
|  | 3 | " | " | 2853 ± 490 |
| A132-10* | 1 | 10 | " | 50853 ± 1665 |
|  | 2 | " | " | 2461 ± 17 |
| A132-100* | 1 | 100 | " | 38291 ± 2235 |
|  | 2 | " | " | 2487 ± 15 |
| SG132 | 1 | 0 | " | 1557360 ± 83693 |
|  | 2 | " | " | 42594 ± 4414 |
|  | 3 | " | " | 3268 ± 249 |
| SG132-10* | 1 | 10 | " | 60888 ± 9131 |
| SG132-100* | 1 | 100 | " | 22345 ± 3797 |
| SG132-10-US | 1 | 10 | Yes | 86086 ± 43518 |
|  | 2 | " | " | 2247 ± 468 |
| SG132-100-US | 1 | 100 | " | 4696 ± 1465 |

*Peaks coalesce after treatment
**Low doses of radiation appear to increase the molecular weight of some materials
[1]Dosage Rate = 1 MRad/hour
[2]Treatment for 30 minutes with 20 kHz ultrasound using a 1000 W horn under re-circulating conditions with the material dispersed in water.

Gel Permeation Chromatography (GPC) is used to determine the molecular weight distribution of polymers. During GPC analysis, a solution of the polymer sample is passed through a column packed with a porous gel trapping small molecules. The sample is separated based on molecular size with larger molecules eluting sooner than smaller molecules. The retention time of each component is most often detected by refractive index (RI), evaporative light scattering (ELS), or ultraviolet (UV) and compared to a calibration curve. The resulting data is then used to calculate the molecular weight distribution for the sample.

A distribution of molecular weights rather than a unique molecular weight is used to characterize synthetic polymers. To characterize this distribution, statistical averages are utilized. The most common of these averages are the "number average molecular weight" ($M_n$) and the "weight average molecular weight" ($M_w$). Methods of calculating these values are described in Example 9 of PCT/US/2007/022719.

The polydispersity index or PI is defined as the ratio of $M_w/M_s$. The larger the PI, the broader or more disperse the distribution. The lowest value that a PI can be is 1. This represents a monodisperse sample; that is, a polymer with all of the molecules in the distribution being the same molecular weight.

The peak molecular weight value ($M_P$) is another descriptor defined as the mode of the molecular weight distribution. It signifies the molecular weight that is most abundant in the distribution. This value also gives insight to the molecular weight distribution.

Most GPC measurements are made relative to a different polymer standard. The accuracy of the results depends on how closely the characteristics of the polymer being analyzed match those of the standard used. The expected error in reproducibility between different series of determinations, calibrated separately, is ca. 5-10% and is characteristic of the limited precision of GPC determinations. Therefore, GPC results are most useful when a comparison between the molecular weight distributions of different samples is made during the same series of determinations.

The lignocellulosic samples required sample preparation prior to GPC analysis. First, a saturated solution (8.4% by weight) of lithium chloride (LiCl) was prepared in dimethyl acetamide (DMAc). Approximately 100 mg of each sample was added to approximately 10 g of a freshly prepared saturated LiCl/DMAc solution, and the mixtures were heated to approximately 150° C.-170° C. with stirring for 1 hour. The resulting solutions were generally light- to dark-yellow in color. The temperature of the solutions was decreased to approximately 100° C. and heated for an additional 2 hours. The temperature of the solutions was then decreased to approximately 50° C. and the sample solutions were heated for approximately 48 to 60 hours. Of note, samples irradiated at 100 MRad were more easily solubilized as compared to their untreated counterpart. Additionally, the sheared samples (denoted by the number 132) had slightly lower average molecular weights as compared with uncut samples.

The resulting sample solutions were diluted 1:1 using DMAc as solvent and were filtered through a 0.45 μm PTFE filter. The filtered sample solutions were then analyzed by GPC. The peak average molecular weight (Mp) of the samples, as determined by Gel Permeation Chromatography (GPC), are summarized in Tables 1 and 2, as above, under analysis conditions set forth in Table 3. Each sample was prepared in duplicate and each preparation of the sample was analyzed in duplicate (two injections) for a total of four injections per sample. The EasiCal polystyrene standards PS1A and PS1B were used to generate a calibration curve for the molecular weight scale from about 580 to 7,500,00 Daltons.

TABLE 3

| GPC Analysis Conditions | |
|---|---|
| Instrument: | Waters Alliance GPC 2000 |
| Columns (3): | Plgel 10μ Mixed-B<br>S/N's: 10M-MB-148-83; 10M-MB-148-84; 10M-MB-174-129 |
| Mobile Phase (solvent): | 0.5% LiCl in DMAc (1.0 mL/min.) |
| Column/Detector Temperature: | 70° C. |
| Injector Temperature: | 70° C. |
| Sample Loop Size: | 323.5 μL |

Example 10

Determining Crystallinity of Irradiated Material by X-Ray Diffraction

X-ray diffraction (XRD) is a method by which a crystalline sample is irradiated with monoenergetic x-rays. The interaction of the lattice structure of the sample with these x-rays is recorded and provides information about the crystalline structure being irradiated. The resulting characteristic "fingerprint" allows for the identification of the crystalline compounds present in the sample. Using a whole-pattern fitting analysis (the Rietvelt Refinement), it is possible to perform quantitative analyses on samples containing more than one crystalline compound.

Each sample was placed on a zero background holder and placed in a Phillips PW 1800 diffractometer using Cu radiation. Scans were then run over the range of 5° to 50° with a step size of 0.05° and a counting time of 2 hours each.

Once the diffraction patterns were obtained, the phases were identified with the aid of the Powder Diffraction File published by the International Centre for Diffraction Data. In all samples the crystalline phase identified was cellulose—Ia, which has a triclinic structure.

The distinguishing feature among the 20 samples is the peak breadth, which is related to the crystallite domain size. The experimental peak breadth was used to compute the domain size and percent crystallinity, which are reported in Table 4.

TABLE 4

XRD Data Including Domain Size and % Crystallinity

| Sample ID | Domain Size (Å) | % Crystallinity |
|---|---|---|
| P132 | 55 | 55 |
| P132-10 | 46 | 58 |
| P132-100 | 50 | 55 |
| P132-181 | 48 | 52 |
| P132-US | 26 | 40 |
| A132 | 28 | 42 |
| A132-10 | 26 | 40 |
| A132-100 | 28 | 35 |
| WS132 | 30 | 36 |
| WS132-10 | 27 | 37 |
| WS132-100 | 30 | 41 |
| SG132 | 29 | 40 |
| SG132-10 | 28 | 38 |
| SG132-100 | 28 | 37 |
| SG132-10-US | 25 | 42 |

TABLE 4-continued

XRD Data Including Domain Size and % Crystallinity

| Sample ID | Domain Size (Å) | % Crystallinity |
|---|---|---|
| SG132-100-US | 21 | 34 |

Percent crystallinity ($X_c\%$) is measured as a ratio of the crystalline area to the total area under the x-ray diffraction peaks, and equals $100\% \times (A_c/(A_a+A_c))$, where
$A_c$=Area of crystalline phase
$A_a$=Area of amorphous phase
$X_c$=Percent of crystallinity To determine the percent crystallinity for each sample it was necessary to first extract the amount of the amorphous phase. This is done by estimating the area of each diffraction pattern that can be attributed to the crystalline phase (represented by the sharper peaks) and the non-crystalline phase (represented by the broad humps beneath the pattern and centered at 22° and 38°).

A systematic process was used to minimize error in these calculations due to broad crystalline peaks as well as high background intensity, First, a linear background was applied and then removed. Second, two Gaussian peaks centered at 22° and 38° with widths of 10-12° each were fitted to the humps beneath the crystalline peaks. Third, the area beneath the two broad Gaussian peaks and the rest of the pattern were determined. Finally, percent crystallinity was calculated by dividing the area beneath the crystalline peak by the total intensity (after background subtraction). Domain size and % crystallinity of the samples as determined by X-ray diffraction (XRD) are presented in Table 4, above.

Example 11

Porosimetry Analysis

Mercury pore size and pore volume analysis (Table 5) is based on forcing mercury (a non-wetting liquid) into a porous structure under tightly controlled pressures. Since mercury does not wet most substances and will not spontaneously penetrate pores by capillary action, it must be forced into the voids of the sample by applying external pressure. The pressure required to fill the voids is inversely proportional to the size of the pores. Only a small amount of force or pressure is required to fill large voids, whereas much greater pressure is required to fill voids of very small pores.

TABLE 5

Pore Size and Volume Distribution by Mercury Porosimetry

| Sample ID | Total Intrusion Volume (mL/g) | Total Pore Area (m²/g) | Median Pore Diameter (Volume) (μm) | Median Pore Diameter (Area) (μm) | Average Pore Diameter (4V/A) (μm) | Bulk Density @ 0.50 psia (g/mL) | Apparent (skeletal) Density (g/mL) | Porosity (%) |
|---|---|---|---|---|---|---|---|---|
| P132 | 6.0594 | 1.228 | 36.2250 | 13.7278 | 19.7415 | 0.1448 | 1.1785 | 87.7163 |
| P132-10 | 5.5436 | 1.211 | 46.3463 | 4.5646 | 18.3106 | 0.1614 | 1.5355 | 89.4875 |
| P132-100 | 5.3985 | 0.998 | 34.5235 | 18.2005 | 21.6422 | 0.1612 | 1.2413 | 87.0151 |
| P132-181 | 3.2866 | 0.868 | 25.3448 | 12.2410 | 15.1509 | 0.2497 | 1.3916 | 82.0577 |
| P132-US | 6.0005 | 14.787 | 98.3459 | 0.0055 | 1.6231 | 0.1404 | 0.8894 | 84.2199 |
| A132 | 2.0037 | 11.759 | 64.6308 | 0.0113 | 0.6816 | 0.3683 | 1.4058 | 73.7990 |
| A132-10 | 1.9514 | 10.326 | 53.2706 | 0.0105 | 0.7560 | 0.3768 | 1.4231 | 73.5241 |
| A132-100 | 1.9394 | 10.205 | 43.8966 | 0.0118 | 0.7602 | 0.3760 | 1.3889 | 72.9264 |
| SG132 | 2.5267 | 8.265 | 57.6958 | 0.0141 | 1.2229 | 0.3119 | 1.4708 | 78.7961 |
| SG132-10 | 2.1414 | 8.643 | 26.4666 | 0.0103 | 0.9910 | 0.3457 | 1.3315 | 74.0340 |
| SG132-100 | 2.5142 | 10.766 | 32.7118 | 0.0098 | 0.9342 | 0.3077 | 1.3590 | 77.3593 |
| SG132-10-US | 4.4043 | 1.722 | 71.5734 | 1.1016 | 10.2319 | 0.1930 | 1.2883 | 85.0169 |
| SG132-100-US | 4.9665 | 7.358 | 24.8462 | 0.0089 | 2.6998 | 0.1695 | 1.0731 | 84.2010 |
| WS132 | 2.9920 | 5.447 | 76.3675 | 0.0516 | 2.1971 | 0.2773 | 1.6279 | 82.9664 |
| WS132-10 | 3.1138 | 2.901 | 57.4727 | 0.3630 | 4.2940 | 0.2763 | 1.9808 | 86.0484 |
| WS132-100 | 3.2077 | 3.114 | 52.3284 | 0.2876 | 4.1199 | 0.2599 | 1.5611 | 83.3538 |

The AutoPore® 9520, a device for determining pore density, can attain a maximum pressure of 414 MPa or 60,000 psia. There are four low pressure stations for sample preparation and collection of macropore data from 0.2 psia to 50 psia. There are two high pressure chambers that collect data from 25 psia to 60,000 psia. The sample is placed in a bowl-like apparatus called a penetrometer, which is bonded to a glass capillary stem with a metal coating. As mercury invades the voids in and around the sample, it moves down the capillary stem. The loss of mercury from the capillary stem results in a change in the electrical capacitance. The change in capacitance during the experiment is converted to volume of mercury based on the stem volume of the penetrometer in use. A variety of penetrometers with different bowl (sample) sizes and capillaries are available to accommodate most sample sizes and configurations. Table 6 below defines some of the key parameters calculated for each sample.

TABLE 6

Definition of Parameters

| Parameter | Description |
|---|---|
| Total Intrusion Volume: | The total volume of mercury intruded during an experiment. This can include interstitial filling between small particles, porosity of sample, and compression volume of sample. |
| Total Pore Area: | The total intrusion volume converted to an area assuming cylindrical shaped pores. |
| Median Pore Diameter (volume): | The size at the 50$^{th}$ percentile on the cumulative volume graph. |
| Median Pore Diameter (area): | The size at the 50$^{th}$ percentile on the cumulative area graph. |
| Average Pore Diameter: | The total pore volume divided by the total pore area (4V/A). |
| Bulk Density: | The mass of the sample divided by the bulk volume. Bulk volume is determined at the filling pressure, typically 0.5 psia. |
| Apparent Density: | The mass of sample divided by the volume of sample measured at highest pressure, typically 60,000 psia. |
| Porosity: | (Bulk Density/Apparent Density) × 100% | rity. The amount of sample needed varies depending on the size of the particles. In general, samples with fine particles require less material than samples with coarse particles.

Example 12

Particle Size Analysis

The technique of particle sizing by static light scattering is based on Mie theory (which also encompasses Fraunhofer theory). Mie theory predicts the intensity vs. angle relationship as a function of the size for spherical scattering particles provided that other system variables are known and held constant. These variables are the wavelength of incident light and the relative refractive index of the sample material. Application of Mie theory provides the detailed particle size information. Table 7 summarizes particle size using median diameter, mean diameter, and modal diameter as parameters.

TABLE 7

Particle Size by Laser Light Scattering (Dry Sample Dispersion)

| Sample ID | Median Diameter (μm) | Mean Diameter (μm) | Modal Diameter (μm) |
|---|---|---|---|
| A132 | 380.695 | 418.778 | 442.258 |
| A132-10 | 321.742 | 366.231 | 410.156 |
| A132-100 | 301.786 | 348.633 | 444.169 |
| SG132 | 369.400 | 411.790 | 455.508 |
| SG132-10 | 278.793 | 325.497 | 426.717 |
| SG132-100 | 242.757 | 298.686 | 390.097 |
| WS132 | 407.335 | 445.618 | 467.978 |
| WS132-10 | 194.237 | 226.604 | 297.941 |
| WS132-100 | 201.975 | 236.037 | 307.304 |

Particle size was determined by laser light scattering (dry sample dispersion) using a Malvern Mastersizer 2000 using the following conditions:

Feed Rate: 35%

Disperser Pressure: 4 Bar

Optical Model: (2.610, 1.000i), 1.000

An appropriate amount of sample was introduced onto a vibratory tray. The feed rate and air pressure were adjusted to ensure that the particles were properly dispersed. The key component is selecting an air pressure that will break up agglomerations, but does not compromise the sample integ- Example 13

Surface Area Analysis

Surface area of each sample was analyzed using a Micromeritics ASAP 2420 Accelerated Surface Area and Porosimetry System. The samples were prepared by first degassing for 16 hours at 40° C. Next, free space (both warm and cold) with helium is calculated and then the sample tube is evacuated again to remove the helium. Data collection begins after this second evacuation and consists of defining target pressures which controls how much gas is dosed onto the sample. At each target pressure, the quantity of gas adsorbed and the actual pressure are determined and recorded. The pressure inside the sample tube is measured with a pressure transducer. Additional doses of gas will continue until the target pressure is achieved and allowed to equilibrate. The quantity of gas adsorbed is determined by summing multiple doses onto the sample. The pressure and quantity define a gas adsorption isotherm and are used to calculate a number of parameters, including BET surface area (Table 8).

TABLE 8

Summary of Surface Area by Gas Adsorption

| Sample ID | Single point surface area @ P/Po = | (m2/g) | BET Surface Area (m$^2$/g) |
|---|---|---|---|
| P132 | 0.250387771 | 1.5253 | 1.6897 |
| P132-10 | @ P/Po = 0.239496722 | 1.0212 | 1.2782 |
| P132-100 | @ P/Po = 0.240538100 | 1.0338 | 1.2622 |
| P132-181 | @ P/Po = 0.239166091 | 0.5102 | 0.6448 |
| P132-US | @ P/Po = 0.217359072 | 1.0983 | 1.6793 |
| A132 | @ P/Po = 0.240040610 | 0.5400 | 0.7614 |
| A132-10 | @ P/Po = 0.211218936 | 0.5383 | 0.7212 |
| A132-100 | @ P/Po = 0.238791097 | 0.4258 | 0.5538 |

TABLE 8-continued

Summary of Surface Area by Gas Adsorption

| Sample ID | Single point surface area @ P/Po = | (m2/g) | BET Surface Area (m²/g) |
|---|---|---|---|
| SG132 | @ P/Po = 0.237989353 | 0.6359 | 0.8350 |
| SG132-10 | @ P/Po = 0.238576905 | 0.6794 | 0.8689 |
| SG132-100 | @ P/Po = 0.241960361 | 0.5518 | 0.7034 |
| SG132-10-US | @ P/Po = 0.225692889 | 0.5693 | 0.7510 |
| SG132-100-US | @ P/Po = 0.225935246 | 1.0983 | 1.4963 |
| WS132 | @ P/Po = 0.237823664 | 0.6582 | 0.8663 |
| WS132-10 | @ P/Po = 0.238612476 | 0.6191 | 0.7912 |
| WS132-100 | @ P/Po = 0.238398832 | 0.6255 | 0.8143 |

The BET model for isotherms is a widely used theory for calculating the specific surface area. The analysis involves determining the monolayer capacity of the sample surface by calculating the amount required to cover the entire surface with a single densely packed layer of krypton. The monolayer capacity is multiplied by the cross sectional area of a molecule of probe gas to determine the total surface area. Specific surface area is the surface area of the sample aliquot divided by the mass of the sample.

Example 14

Fiber Length Determination

Fiber length distribution testing was performed in triplicate on the samples submitted using the Techpap MorFi LB01 system. The average length and width are reported in Table 9.

TABLE 9

Summary of Lignocellulosic Fiber Length and Width Data

| Sample ID | Arithmetic Average (mm) | Average Length Weighted in Length (mm) | Statistically Corrected Average Length Weighted in Length (mm) | Width (μm) |
|---|---|---|---|---|
| P132-10 | 0.484 | 0.615 | 0.773 | 24.7 |
| P132-100 | 0.369 | 0.423 | 0.496 | 23.8 |
| P132-181 | 0.312 | 0.342 | 0.392 | 24.4 |
| A132-10 | 0.382 | 0.423 | 0.650 | 43.2 |
| A132-100 | 0.362 | 0.435 | 0.592 | 29.9 |
| SG132-10 | 0.328 | 0.363 | 0.521 | 44.0 |
| SG132-100 | 0.325 | 0.351 | 0.466 | 43.8 |
| WS132-10 | 0.353 | 0.381 | 0.565 | 44.7 |
| WS132-100 | 0.354 | 0.371 | 0.536 | 45.4 |

Example 15

Ultrasonic Treatment of Irradiated and Un-Irradiated Switchgrass

Switchgrass was sheared according to Example 4. The switchgrass was treated by ultrasound alone or irradiation with 10 Mrad or 100 Mrad of gamma rays, and then sonicated. The resulting materials correspond to G132-BR (un-irradiated), G132-10-BR (10 Mrad and sonication) and G132-100-BR (100 Mrad and sonication), as presented in Table 1. Sonication was performed on each sample for 30 minutes using 20 kHz ultrasound from a 1000 W horn under re-circulating conditions. Each sample was dispersed in water at a concentration of about 0.10 g/mL.

Figure 30:
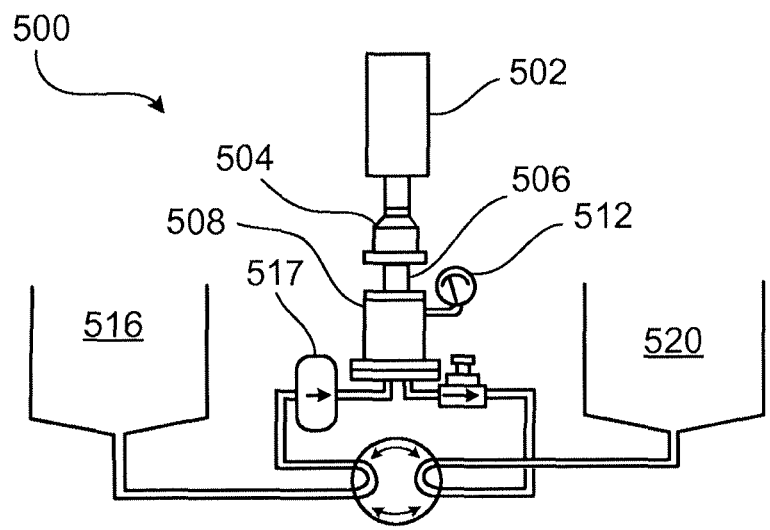
Figure 31:
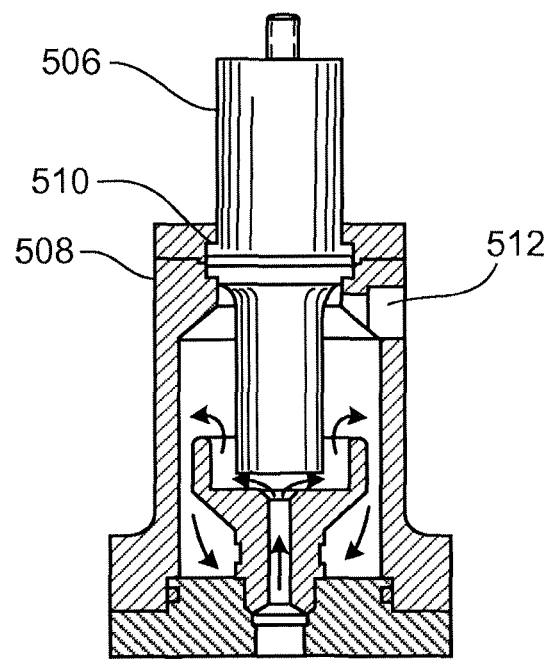
FIG. 31 is a cross-sectional view through the processing cell of FIG. 30.

FIGS. 30 and 31 show the apparatus used for sonication. Apparatus 500 includes a converter 502 connected to booster 504 communicating with a horn 506 fabricated from titanium or an alloy of titanium. The horn, which has a seal 510 made from VITON® about its perimeter on its processing side, forms a liquid tight seal with a processing cell 508. The processing side of the horn is immersed in a liquid, such as water, that has dispersed therein the sample to be sonicated. Pressure in the cell is monitored with a pressure gauge 512. In operation, each sample is moved by pump 517 from tank 516 through the processing cell and is sonicated. After, sonication, the sample is captured in tank 520. The process can be reversed in that the contents of tank 520 can be sent through the processing cell and captured in tank 516. This process can be repeated a number of times until a desired level of processing is delivered to the sample.

Example 16

Scanning Electron Micrographs of Un-Irradiated Switchgrass in Comparison to Irradiated and Irradiated and Sonicated Switchgrass Switchgrass samples for the scanning electron micrographs were applied to carbon tape and gold sputter coated (70 seconds). Images were taken with a JEOL 6500 field emission scanning electron microscope.

Figure 32:
FIG. 32 is a scanning electron micrograph at 1000× magnification of a fibrous material produced from shearing switchgrass on a rotary knife cutter, and then passing the sheared material through a 1/32 inch screen.

FIG. 32 is a scanning electron micrograph at 1000× magnification of a fibrous material produced from shearing switchgrass on a rotary knife cutter, and then passing the sheared material through a 1/32 inch screen.

Figure 33:
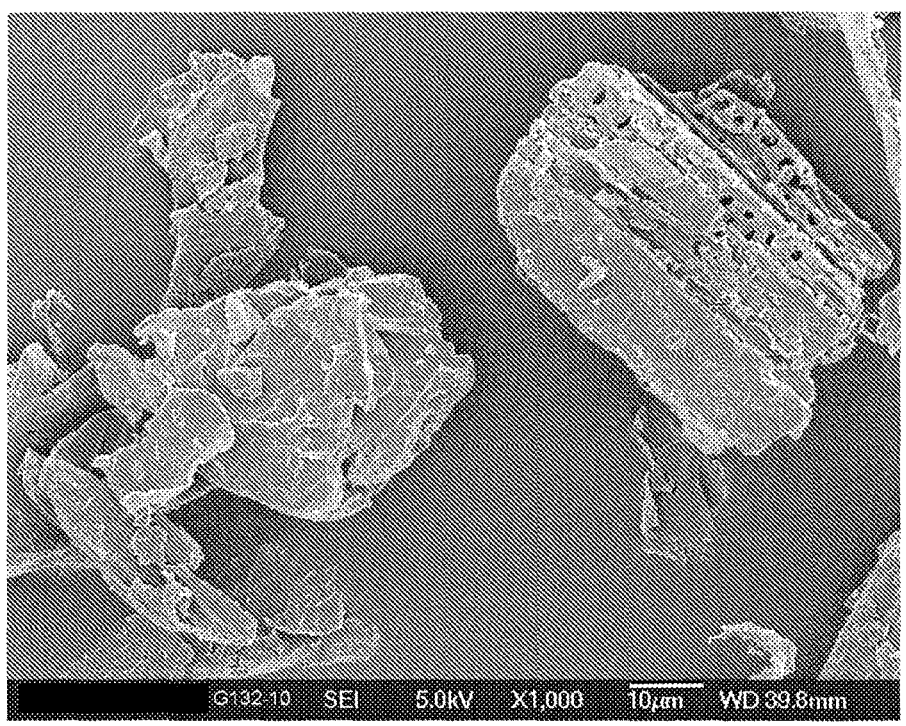
FIGS. 33 and 34 are scanning electron micrographs of the fibrous material of FIG. 32 after irradiation with 10 Mrad and 100 Mrad gamma rays, respectively, at 1000× magnification.
Figure 34:
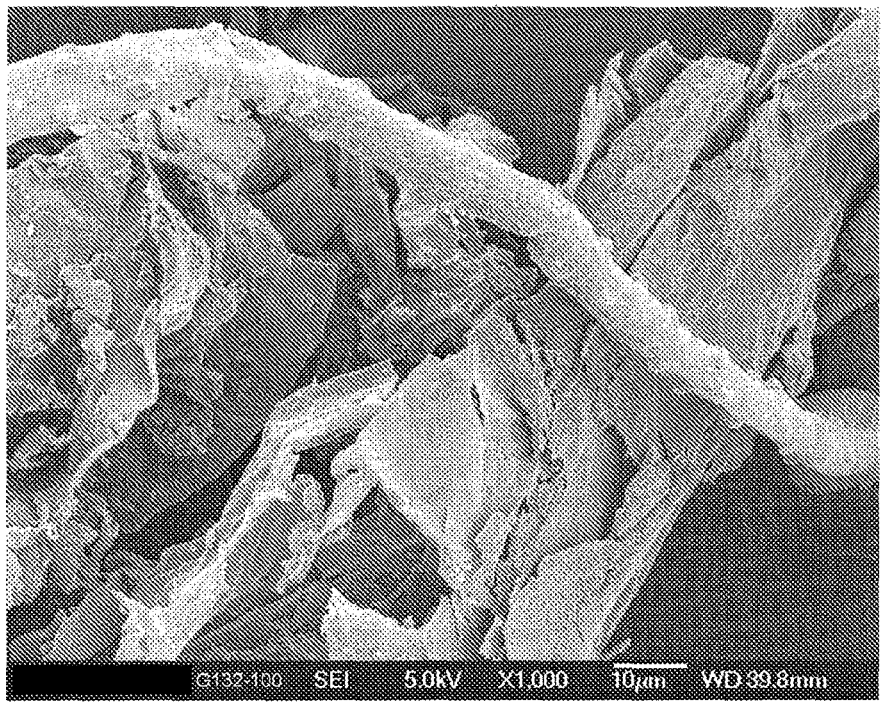

FIGS. 33 and 34 are scanning electron micrographs of the fibrous material of FIG. 32 after irradiation with 10 Mrad and 100 Mrad gamma rays, respectively, at 1000× magnification.

Figure 35:
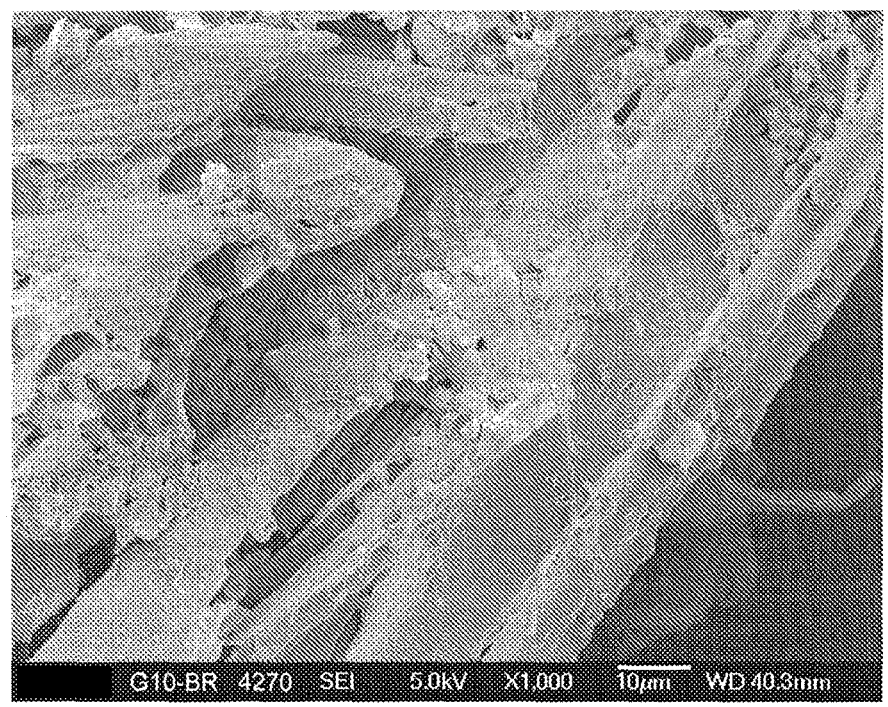
FIG. 35 is a scanning electron micrographs of the fibrous material of FIG. 32 after irradiation with 10 Mrad and sonication at 1000× magnification.

FIG. 35 is a scanning electron micrograph of the fibrous material of FIG. 32 after irradiation with 10 Mrad and sonication at 1000× magnification.

Figure 36:
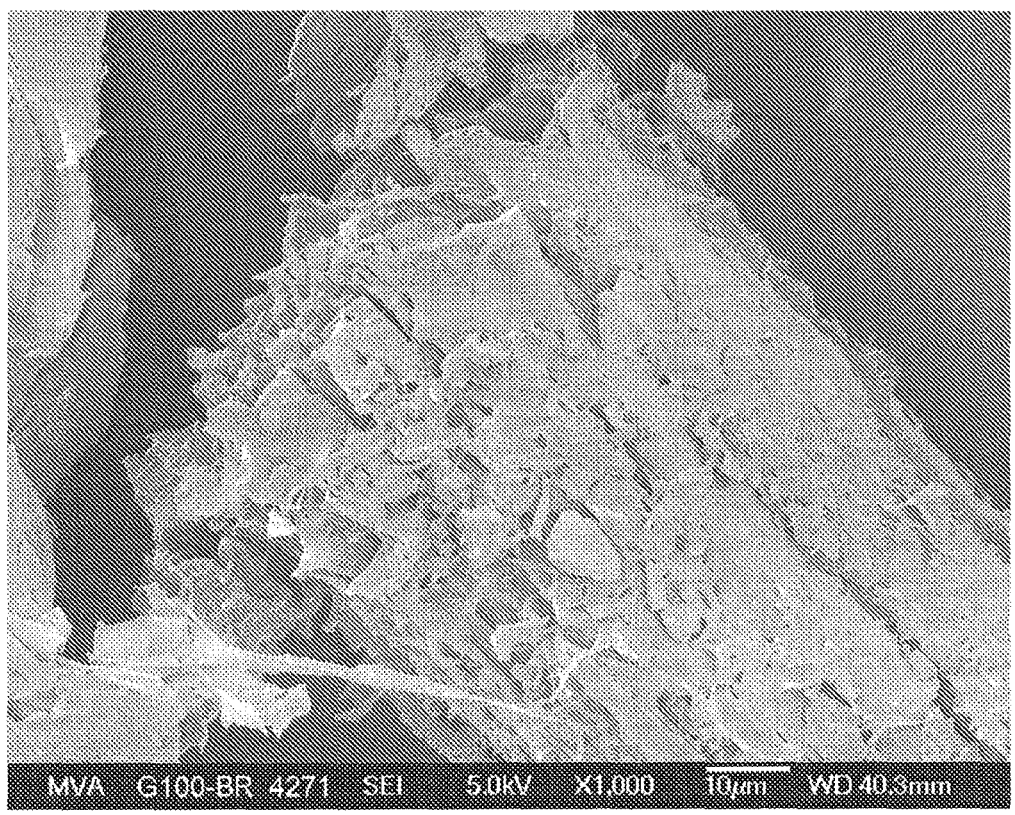
FIG. 36 is a scanning electron micrographs of the fibrous material of FIG. 32 after irradiation with 100 Mrad and sonication at 1000× magnification.

FIG. 36 is a scanning electron micrograph of the fibrous material of FIG. 32 after irradiation with 100 Mrad and sonication at 1000× magnification.

Example 17

Infrared Spectrum of Irradiated Kraft Paper in Comparison to Un-Irradiated Kraft Paper FT-IR analysis was performed using standard methodology on a Nicolet/Impact 400. The results indicate that all samples reported in Table 1 are consistent with a cellulose-based material.

Figure 37:
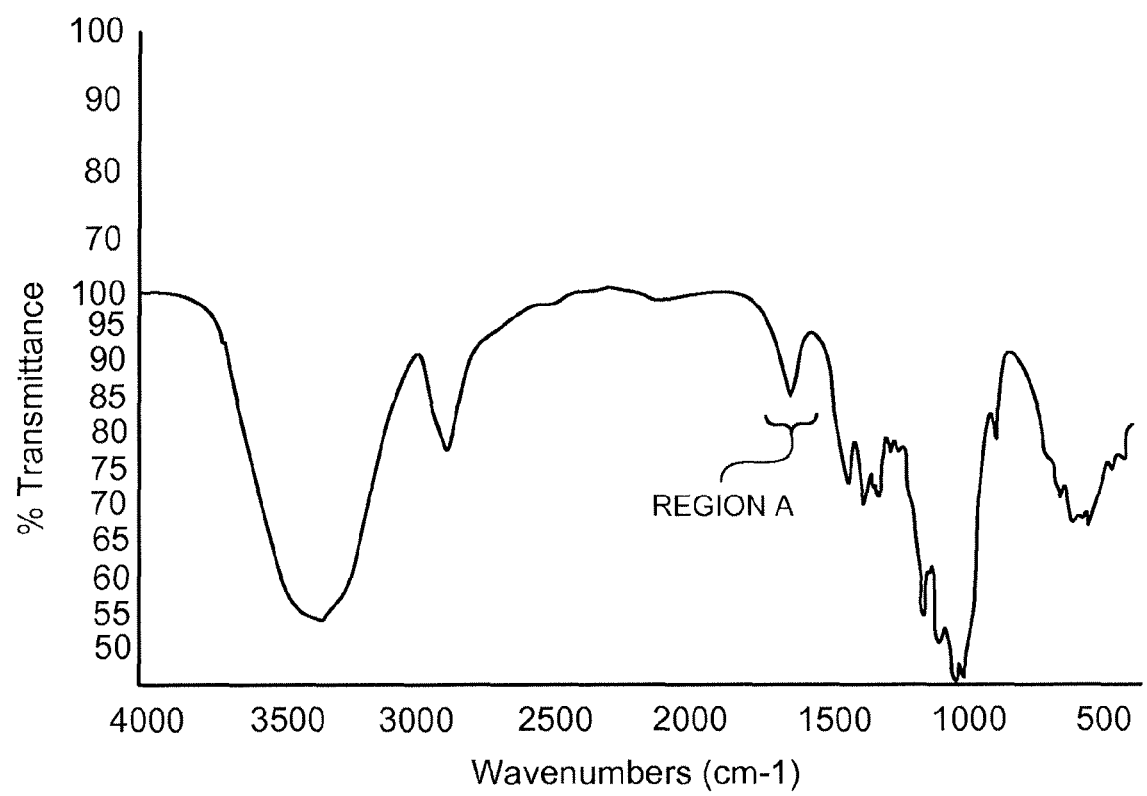
FIG. 37 is an infrared spectrum of Kraft board paper sheared on a rotary knife cutter.
Figure 38:
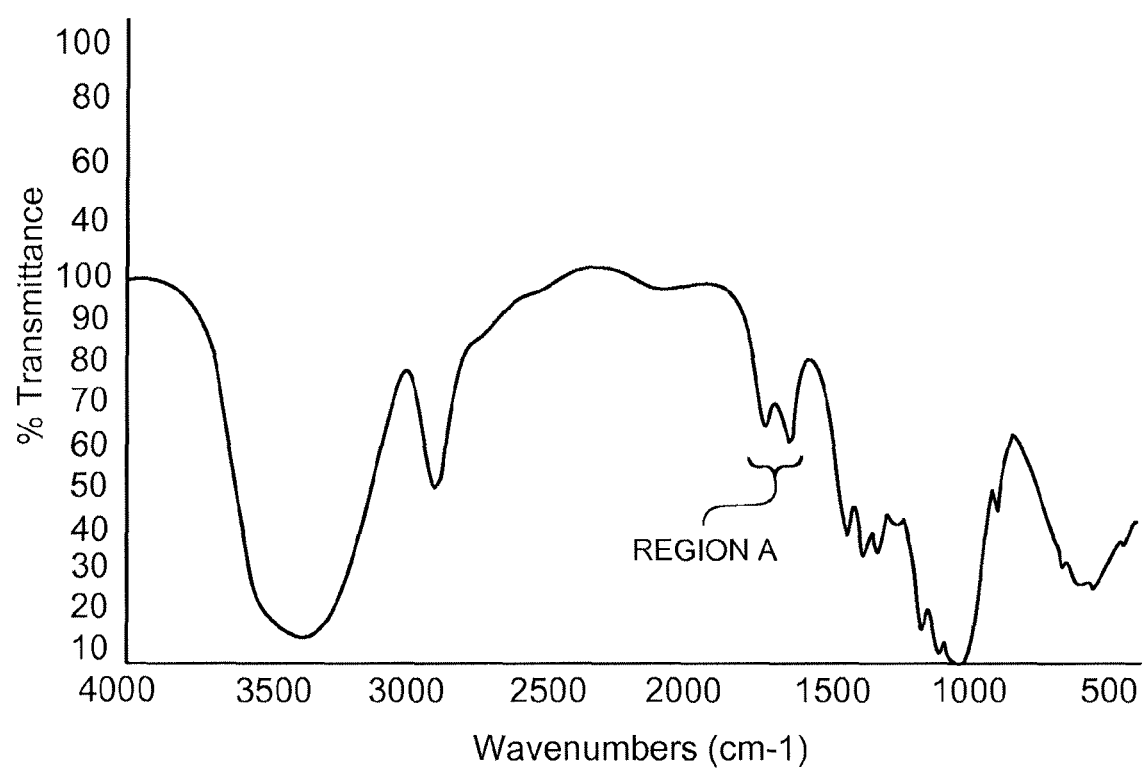
FIG. 38 is an infrared spectrum of the Kraft paper of FIG. 37 after irradiation with 100 Mrad of gamma radiation.

FIG. 37 is an infrared spectrum of Kraft board paper sheared according to Example 4, while FIG. 38 is an infrared spectrum of the Kraft paper of FIG. 38 after irradiation with 100 Mrad of gamma radiation. The irradiated sample shows an additional peak in region A (centered about 1730 cm$^{-1}$) that is not found in the un-irradiated material.

Example 18

Combination of Electron Beam and Sonication Pretreatment

Switchgrass is used as the feedstock and is sheared with a Munson rotary knife cutter into a fibrous material. The fibrous material is then evenly distributed onto an open tray composed of tin with an area of greater than about 500 in$^2$. The fibrous material is distributed so that it has a depth of about 1-2 inches in the open tray. The fibrous material can be distributed in plastic bags at lower doses of irradiation (under 10 MRad), and left uncovered on the metal tray at higher doses of radiation.

Separate samples of the fibrous material are then exposed to successive doses of electron beam radiation to achieve a total dose of 1 Mrad, 2 Mrad, 3, Mrad, 5 Mrad, 10 Mrad, 50 Mrad, and 100 Mrad. Some samples are maintained under the same conditions as the remaining samples, but are not irradiated, to serve as controls. After cooling, the irradiated fibrous material is sent on for further processing through a sonication device.

The sonication device includes a converter connected to booster communicating with a horn fabricated from titanium or an alloy of titanium. The horn, which has a seal made from VITON® about its perimeter on its processing side, forms a liquid tight seal with a processing cell. The processing side of the horn is immersed in a liquid, such as water, into which the irradiated fibrous material to be sonicated is immersed. Pressure in the cell is monitored with a pressure gauge. In operation, each sample is moved by pump through the processing cell and is sonicated.

To prepare the irradiated fibrous material for sonication, the irradiated fibrous material is removed from any container (e.g., plastic bags) and is dispersed in water at a concentration of about 0.10 g/mL. Sonication is performed on each sample for 30 minutes using 20 kHz ultrasound from a 1000 W horn under re-circulating conditions. After sonication, the irradiated fibrous material is captured in a tank. This process can be repeated a number of times until a desired level of processing is achieved based on monitoring the structural changes in the switchgrass. Again, some irradiated samples are kept under the same conditions as the remaining samples, but are not sonicated, to serve as controls. In addition, some samples that were not irradiated are sonicated, again to serve as controls. Thus, some controls are not processed, some are only irradiated, and some are only sonicated.

Example 19

Microbial Testing of Pretreated Biomass

Specific lignocellulosic materials pretreated as described herein are analyzed for toxicity to common strains of yeast and bacteria used in the biofuels industry for the fermentation step in ethanol production. Additionally, sugar content and compatibility with cellulase enzymes are examined to determine the viability of the treatment process. Testing of the pretreated materials is carried out in two phases as follows.

I. Toxicity and Sugar Content

Toxicity of the pretreated grasses and paper feedstocks is measured in yeast *Saccharomyces cerevisiae* (wine yeast) and *Pichia stipitis* (ATCC 66278) as well as the bacteria *Zymomonas mobilis* (ATCC 31821) and *Clostridium thermocellum* (ATCC 31924). A growth study is performed with each of the organisms to determine the optimal time of incubation and sampling.

Each of the feedstocks is then incubated, in duplicate, with *S. cerevisiae*, *P. stipitis*, *Z. mobilis*, and *C. thermocellum* in a standard microbiological medium for each organism. YM broth is used for the two yeast strains, *S. cerevisiae* and *P. stipitis*. RM medium is used for *Z. mobilis* and CM4 medium for *C. thermocellum*. A positive control, with pure sugar added, but no feedstock, is used for comparison. During the incubation, a total of five samples is taken over a 12 hour period at time 0, 3, 6, 9, and 12 hours and analyzed for viability (plate counts for *Z. mobilis* and direct counts for *S. cerevisiae*) and ethanol concentration.

Sugar content of the feedstocks is measured using High Performance Liquid Chromatography (HPLC) equipped with either a Shodex® sugar SP0810 or Biorad Aminex® HPX-87P column. Each of the feedstocks (approx. 5 g) is mixed with reverse osmosis (RO) water for 1 hour. The liquid portion of the mixture is removed and analyzed for glucose, galactose, xylose, mannose, arabinose, and cellobiose content. The analysis is performed according to National Bioenergy Center protocol Determination of Structural Carbohydrates and Lignin in Biomass.

II. Cellulase Compatibility

Feedstocks are tested, in duplicate, with commercially available Accellerase® 1000 enzyme complex, which contains a complex of enzymes that reduces lignocellulosic biomass into fermentable sugars, including two different cellulase preparations, *Trichoderma reesei* and *Aspergillus nidulans*, at the recommended temperature and concentration in an Erlenmeyer flask. The flasks are incubated with moderate shaking at around 200 rpm for 12 hours. During that time, samples are taken every three hours at time 0, 3, 6, 9, and 12 hours to determine the concentration of reducing sugars (Hope and Dean, Biotech 1, 1974, 144:403) in the liquid portion of the flasks.

Example 20

Alcohol Production Using Irradiation-Sonication Pretreatment

The optimum size for biomass conversion plants is affected by factors including economies of scale and the type and availability of biomass used as feedstock. Increasing plant size tends to increase economies of scale associated with plant processes. However, increasing plant size also tends to increase the costs (e.g., transportation costs) per unit of biomass feedstock. Studies analyzing these factors suggest that the appropriate size for biomass conversion plants can range from 2000 to 10,000 dried tons of biomass feedstock per day. The plant described below is sized to process 2000 tons of dry biomass feedstock per day.

Figure 39:
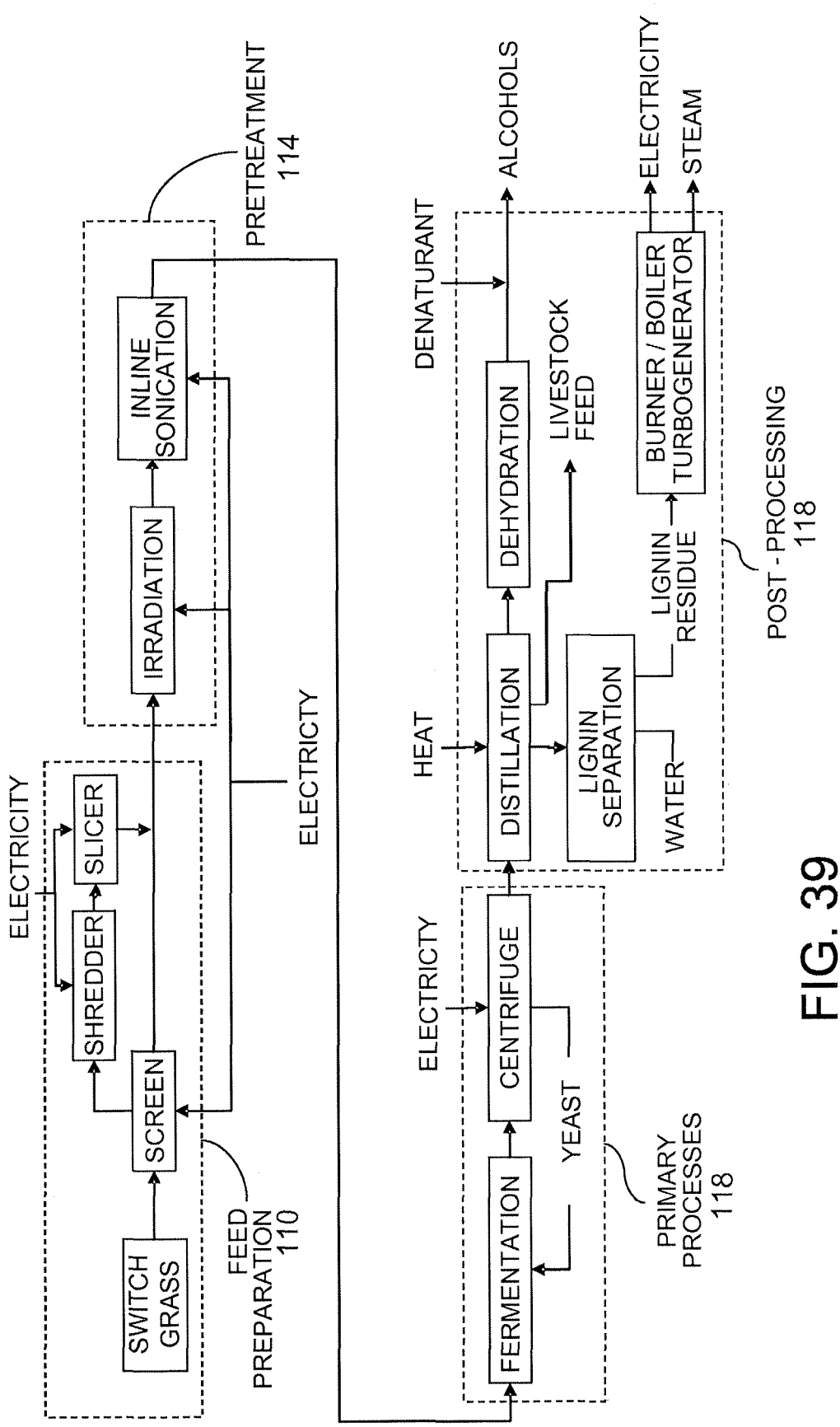
FIG. 39 is a schematic view of a process for biomass conversion.

FIG. 39 shows a process schematic of a biomass conversion system configured to process switchgrass. The feed preparation subsystem processes raw biomass feedstock to remove foreign objects and provide consistently sized particles for further processing. The pretreatment subsystem changes the molecular structure (e.g., reduces the average molecular weight and the crystallinity) of the biomass feedstock by irradiating the biomass feedstock, mixing the irradiated the biomass feedstock with water to form a slurry, and applying ultrasonic energy to the slurry. The irradiation and sonication convert the cellulosic and lignocellulosic components of the biomass feedstock into fermentable materials. The primary process subsystem ferments the glucose and other low weight sugars present after pretreatment to form alcohols.

Feed Preparation

The selected design feed rate for the plant is 2,000 dry tons per day of switchgrass biomass. The design feed is chopped and/or sheared switchgrass.

Biomass feedstock in the form of bales of switchgrass is received by the plant. In some cases, the switchgrass bales are wrapped with plastic net to ensure they don't break apart when handled, and can also be wrapped in plastic film to protect the bale from weather. The bales are either square or round. The bales are received at the plant from off-site storage on large truck trailers. As the trucks are received, they are weighed and unloaded by forklifts. Some bales are sent to on-site storage while others are taken directly to the conveyors.

Since switchgrass is only seasonally available, long-term storage is required to provide feed to the plant year-round. Long-term storage will likely consist of 400-500 acres of uncovered piled rows of bales at a location (or multiple locations) reasonably close to the ethanol plant. On-site short-term storage is provided equivalent to 72 hours of production at an outside storage area. Bales and surrounding access ways as well as the transport conveyors will be on a concrete slab. A concrete slab is used because of the volume of traffic required to deliver the large amount of biomass feedstock required. A concrete slab will minimize the amount of standing water in the storage area, as well as reduce the biomass feedstock's exposure to dirt. The stored material provides a short-term supply for weekends, holidays, and when normal direct delivery of material into the process is interrupted.

The bales are off-loaded by forklifts and are placed directly onto bale transport conveyors or in the short-term storage area. Bales are also reclaimed from short-term storage by forklifts and loaded onto the bale transport conveyors.

Bales travel to one of two bale unwrapping stations. Unwrapped bales are broken up using a spreader bar and then discharged onto a conveyor, which passes a magnetic separator to remove metal prior to shredding. A tramp iron magnet is provided to catch stray magnetic metal and a scalping screen removes gross oversize and foreign material ahead of multiple shredder-shearer trains, which reduce the biomass feedstock to the proper size for pretreatment. The shredder-shearer trains include shredders and rotary knife cutters. The shredders reduce the size of the raw biomass feedstock and feed the resulting material to the rotary knife cutters. The rotary knife cutters concurrently shear the biomass feedstock and screen the resulting material. Finally, the biomass feedstock is conveyed to the pretreatment subsystem.

Three storage silos are provided to limit overall system downtime due to required maintenance on and/or breakdowns of feed preparation subsystem equipment. Each silo can hold approximately 55,000 cubic feet of biomass feedstock (~3 hours of plant operation).

Pretreatment

Figure 40:
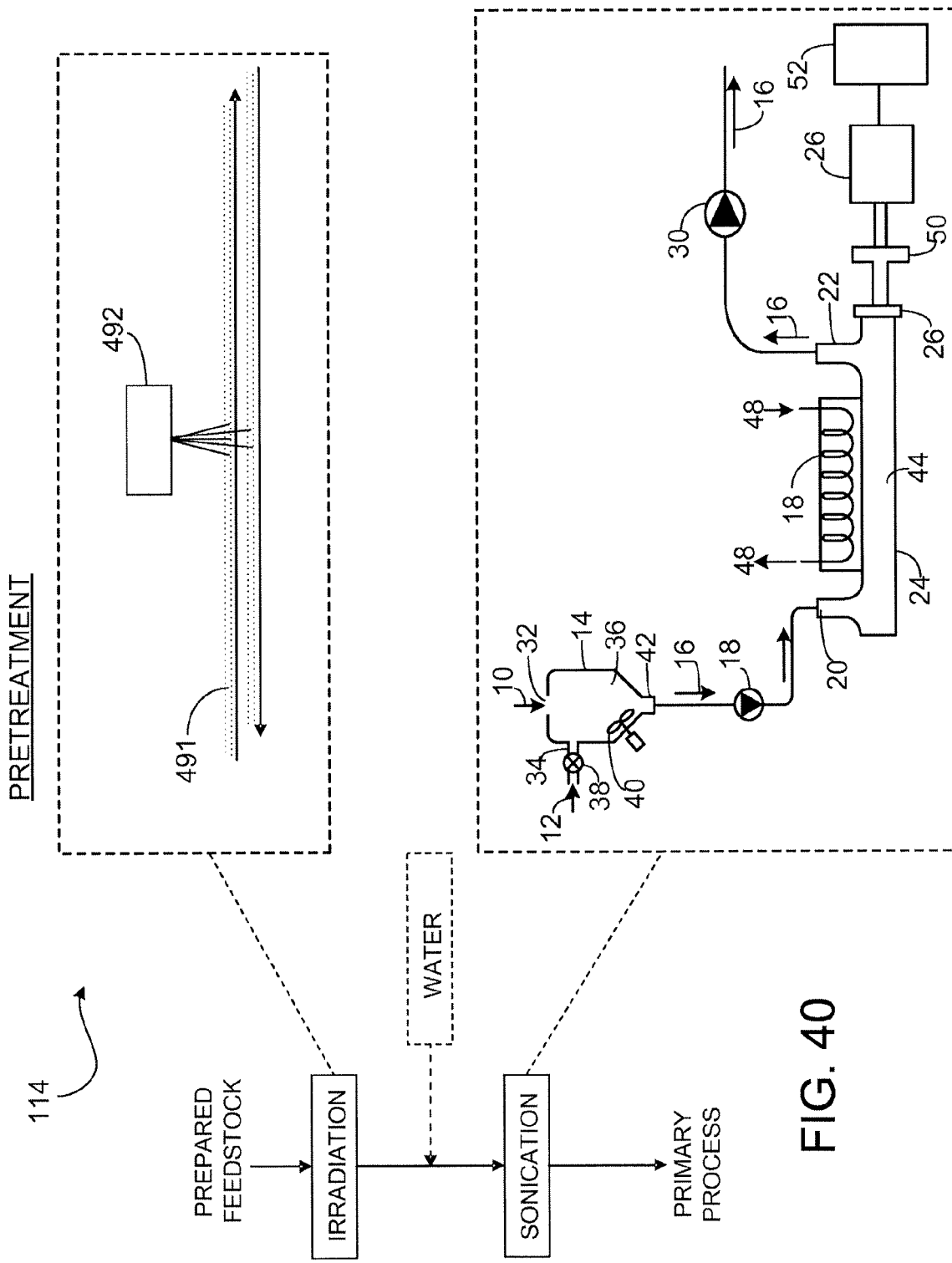
FIG. 40 is schematic view of another process for biomass conversion.
Figure 41:
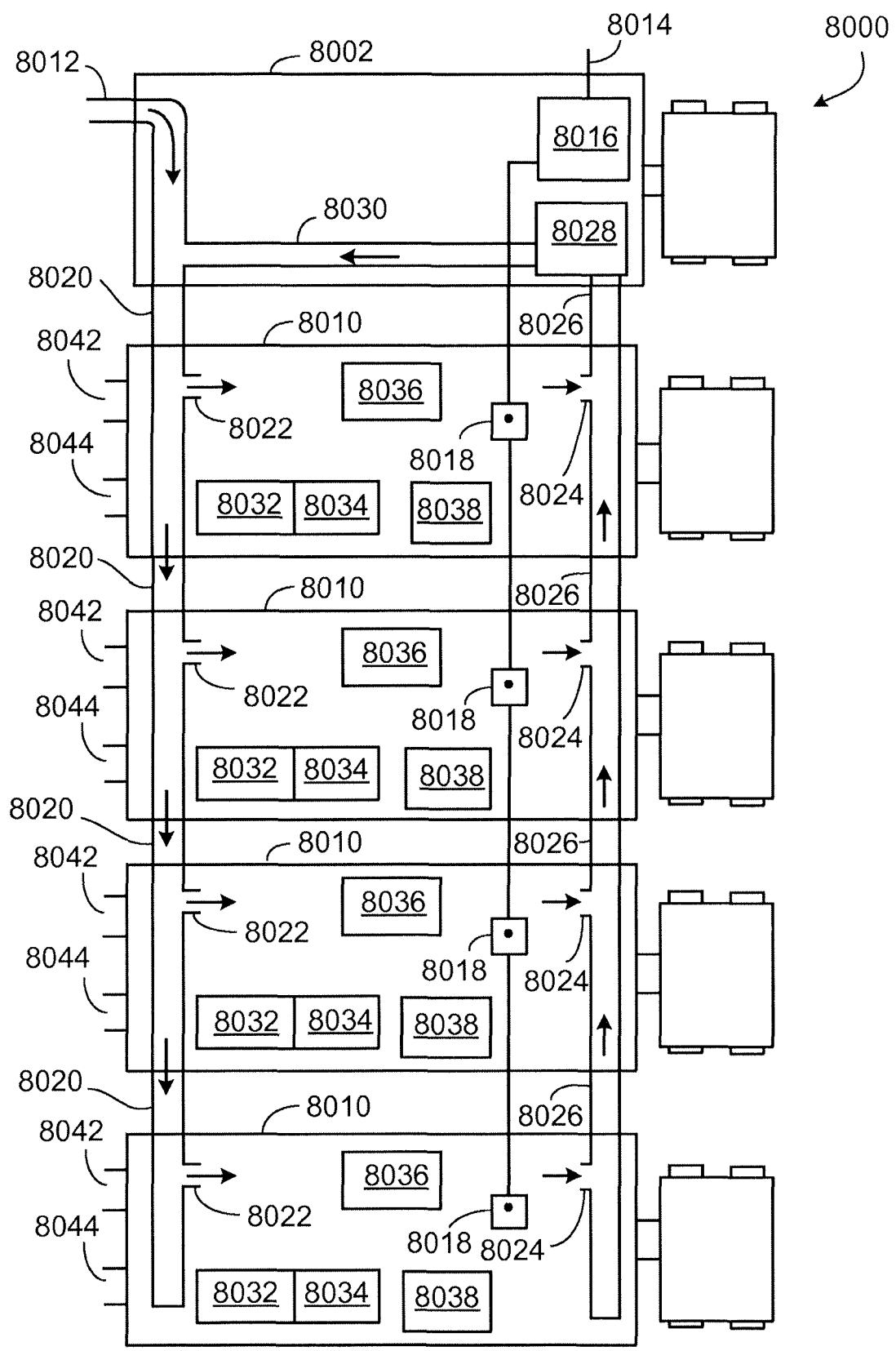
FIG. 41 is a schematic diagram of a truck-based mobile biomass processing facility.
Figure 42:
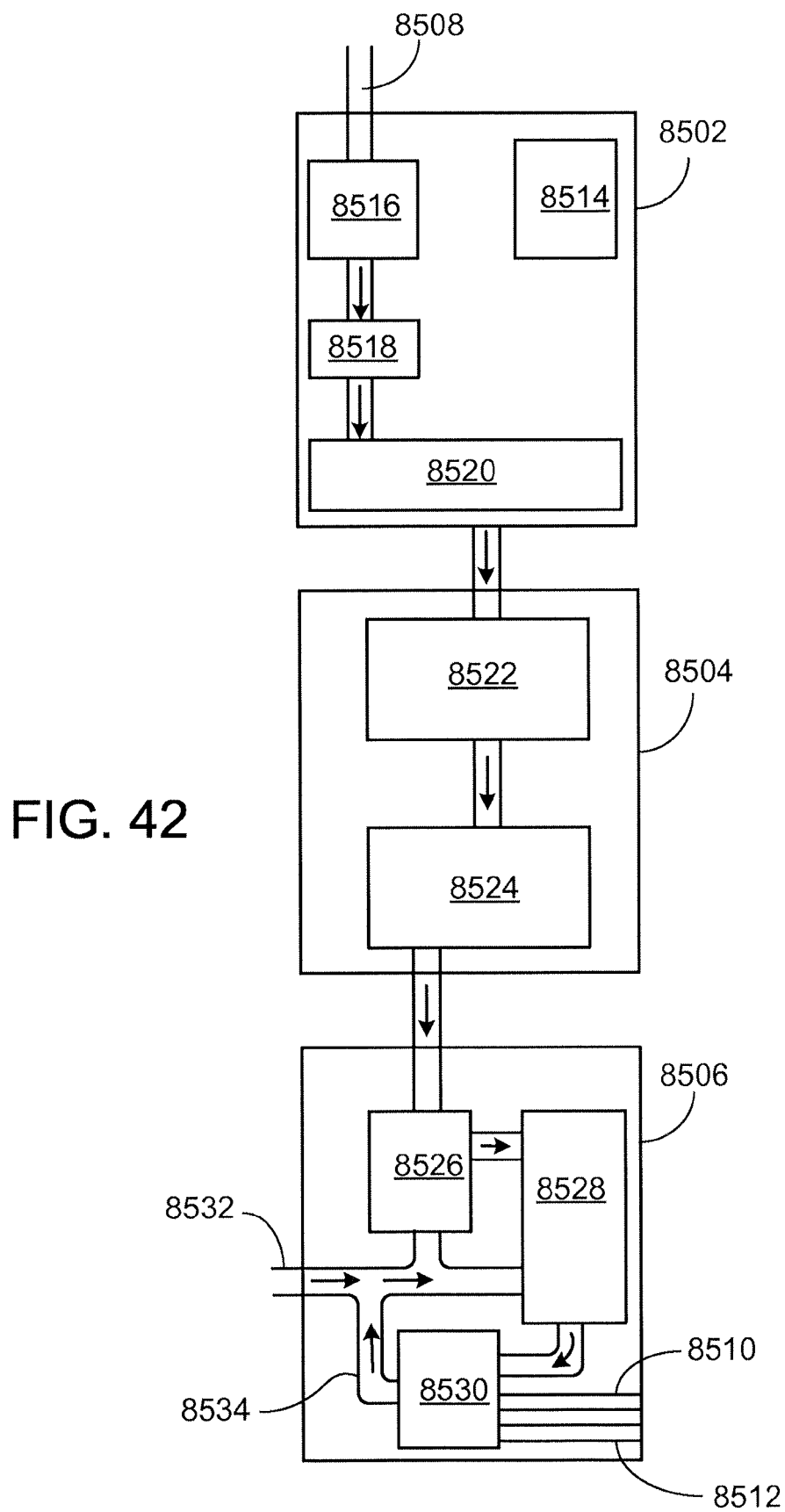
FIG. 42 is a schematic diagram of a train-based mobile biomass processing facility.

A conveyor belt carries the biomass feedstock from the feed preparation subsystem 110 to the pretreatment subsystem 114. As shown in FIG. 40, in the pretreatment subsystem 114, the biomass feedstock is irradiated using electron beam emitters, mixed with water to form a slurry, and subjected to the application of ultrasonic energy. As discussed above, irradiation of the biomass feedstock changes the molecular structure (e.g., reduces the recalcitrance, the average molecular weight, and the crystallinity) of the biomass feedstock. Mixing the irradiated biomass feedstock into a slurry and applying ultrasonic energy to the slurry further changes the molecular structure of the biomass feedstock. Application of the radiation and sonication in sequence can have synergistic effects in that the combination of techniques appears to achieve greater changes to the molecular structure (e.g., reduces the recalcitrance, the average molecular weight, and the crystallinity) than either technique can efficiently achieve on its own. Without wishing to be bound by theory, in addition to reducing the polymerization of the biomass feedstock by breaking intramolecular bonds between segments of cellulosic and lignocellulosic components of the biomass feedstock, the irradiation can make the overall physical structure of the biomass feedstock more brittle. After the brittle biomass feedstock is mixed into a slurry, the application of ultrasonic energy further changes the molecular structure (e.g., reduces the average molecular weight and the crystallinity) and also can reduce the size of biomass feedstock particles.

Electron Beam Irradiation

The conveyor belt 491 carrying the biomass feedstock into the pretreatment subsystem distributes the biomass feedstock into multiple feed streams (e.g., 50 feed streams) each leading to separate electron beam emitters 492. In this embodiment, the biomass feedstock is irradiated while it is dry. Each feed stream is carried on a separate conveyor belt to an associated electron beam emitter. Each irradiation feed conveyor belt can be approximately one meter wide. Before reaching the electron beam emitter, a localized vibration is induced in each conveyor belt to evenly distribute the dry biomass feedstock over the cross-sectional width of the conveyor belt.

Electron beam emitter 492 (e.g., electron beam irradiation devices commercially available from Titan Corporation, San Diego, Calif.) are configured to apply a 100 kilo-Gray dose of electrons applied at a power of 300 kW. The electron beam emitters are scanning beam devices with a sweep width of 1 meter to correspond to the width of the conveyor belt. In some embodiments, electron beam emitters with large, fixed beam widths are used. Factors including belt/beam width, desired dose, biomass feedstock density, and power applied govern the number of electron beam emitters required for the plant to process 2,000 tons per day of dry feed.

Sonication

The irradiated biomass feedstock is mixed with water to form a slurry before ultrasonic energy is applied. There can be a separate sonication system associated with each electron beam feed stream or several electron beam streams can be aggregated as feed for a single sonication system.

In each sonication system, the irradiated biomass feedstock is fed into a reservoir 1214 through a first intake 1232 and water is fed into the reservoir 1214 through second intake 1234. Appropriate valves (manual or automated) control the flow of biomass feedstock and the flow of water to produce a desired ratio of biomass feedstock to water (e.g., 10% cellulosic material, weight by volume). Each reservoir 1214 includes a mixer 1240 to agitate the contents of volume 1236 and disperse biomass feedstock throughout the water.

In each sonication system, the slurry is pumped (e.g., using a recessed impeller vortex pump 1218) from reservoir 1214 to and through a flow cell 1224 including an ultrasonic transducer 1226. In some embodiments, pump 1218 is configured to agitate the slurry 1216 such that the mixture of biomass feedstock and water is substantially uniform at inlet 1220 of the flow cell 1224. For example, the pump 1218 can agitate the slurry 1216 to create a turbulent flow that persists throughout the piping between the first pump and inlet 1220 of flow cell 1224.

Within the flow cell 1224, ultrasonic transducer 1226 transmits ultrasonic energy into slurry 1216 as the slurry flows through flow cell 1224. Ultrasonic transducer 1226 converts electrical energy into high frequency mechanical energy (e.g., ultrasonic energy), which is then delivered to the slurry through booster 48. Ultrasonic transducers are commercially available (e.g., from Hielscher USA, Inc. of Ringwood, N.J.) that are capable of delivering a continuous power of 16 kilowatts.

The ultrasonic energy traveling through booster 1248 in reactor volume 1244 creates a series of compressions and rarefactions in process stream 1216 with an intensity sufficient to create cavitation in process stream 1216. Cavitation disaggregates components of the biomass feedstock including, for example, cellulosic and lignocellulosic material dispersed in process stream 1216 (e.g., slurry). Cavitation also produces free radicals in the water of process stream 1216 (e.g., slurry). These free radicals act to further break down the cellulosic material in process stream 1216. In general, about 250 MJ/m$^3$ of ultrasonic energy is applied to process stream 1216 containing fragments of poplar chips. Other levels of ultrasonic energy (between about 5 and about 4000 MJ/m$^3$, e.g., 10, 25, 50, 100, 250, 500, 750, 1000, 2000, or 3000) can be applied to other biomass feedstocks After exposure to ultrasonic energy in reactor volume 1244, process stream 1216 exits flow cell 24 through outlet 1222.

Flow cell 1224 also includes a heat exchanger 1246 in thermal communication with at least a portion of reactor volume 1244. Cooling fluid 1248 (e.g., water) flows into heat exchanger 1246 and absorbs heat generated when process stream 1216 (e.g., slurry) is sonicated in reactor volume 1244. In some embodiments, the flow of cooling fluid 1248 into heat exchanger 1246 is controlled to maintain an approximately constant temperature in reactor volume 1244. In addition or in the alternative, the temperature of cooling fluid 1248 flowing into heat exchanger 1246 is controlled to maintain an approximately constant temperature in reactor volume 1244.

The outlet 1242 of flow cell 1224 is arranged near the bottom of reservoir 1214 to induce a gravity feed of process stream 1216 (e.g., slurry) out of reservoir 1214 towards the inlet of a second pump 1230 which pumps process stream 1216 (e.g., slurry) towards the primary process subsystem.

Sonication systems can include a single flow path (as described above) or multiple parallel flow paths each with an associated individual sonication units. Multiple sonication units can also be arranged to series to increase the amount of sonic energy applied to the slurry.

Primary Processes

A vacuum rotary drum type filter removes solids from the slurry before fermentation. Liquid from the filter is pumped cooled prior to entering the fermentors. Filtered solids are passed to passed to the post-processing subsystem for further processing.

The fermentation tanks are large, low pressure, stainless steel vessels with conical bottoms and slow speed agitators. Multiple first stage fermentation tanks can be arranged in series. The temperature in the first stage fermentation tanks is controlled to 30 degrees centigrade using external heat exchangers. Yeast is added to the first stage fermentation tank at the head of each series of tanks and carries through to the other tanks in the series.

Second stage fermentation consists of two continuous fermentors in series. Both fermentors are continuously agitated with slow speed mechanical mixers. Temperature is controlled with chilled water in external exchangers with continuous recirculation. Recirculation pumps are of the progressive cavity type because of the high solids concentration.

Off gas from the fermentation tanks and fermentors is combined and washed in a counter-current water column before being vented to the atmosphere. The off gas is washed to recover ethanol rather than for air emissions control.

Post-Processing

Distillation

Distillation and molecular sieve adsorption are used to recover ethanol from the raw fermentation beer and produce 99.5% ethanol. Distillation is accomplished in two columns—the first, called the beer column, removes the dissolved $CO_2$ and most of the water, and the second concentrates the ethanol to a near azeotropic composition.

All the water from the nearly azeotropic mixture is removed by vapor phase molecular sieve adsorption. Regeneration of the adsorption columns requires that an ethanol water mixture be recycled to distillation for recovery.

Fermentation vents (containing mostly $CO_2$, but also some ethanol) as well as the beer column vent are scrubbed in a water scrubber, recovering nearly all of the ethanol. The scrubber effluent is fed to the first distillation column along with the fermentation beer.

The bottoms from the first distillation contain all the unconverted insoluble and dissolved solids. The insoluble solids are dewatered by a pressure filter and sent to a combustor. The liquid from the pressure filter that is not recycled is concentrated in a multiple effect evaporator using waste heat from the distillation. The concentrated syrup from the evaporator is mixed with the solids being sent to the combustor, and the evaporated condensate is used as relatively clean recycle water to the process.

Because the amount of stillage water that can be recycled is limited, an evaporator is included in the process. The total amount of the water from the pressure filter that is directly recycled is set at 25%. Organic salts like ammonium acetate or lactate, steep liquor components not utilized by the organism, or inorganic compounds in the biomass end up in this stream. Recycling too much of this material can result in levels of ionic strength and osmotic pressures that can be detrimental to the fermenting organism's efficiency. For the water that is not recycled, the evaporator concentrates the dissolved solids into a syrup that can be sent to the combustor, minimizing the load to wastewater treatment.

Wastewater Treatment

The wastewater treatment section treats process water for reuse to reduce plant makeup water requirements. Wastewater is initially screened to remove large particles, which are collected in a hopper and sent to a landfill. Screening is followed by anaerobic digestion and aerobic digestion to digest organic matter in the stream. Anaerobic digestion produces a biogas stream that is rich in methane that is fed to the combustor. Aerobic digestion produces a relatively clean water stream for reuse in the process as well as a sludge that is primarily composed of cell mass. The sludge is also burned in the combustor. This screening/anaerobic digestion/aerobic digestion scheme is standard within the current ethanol industry and facilities in the 1-5 million gallons per day range can be obtained as "off-the-shelf" units from vendors.

Combustor, Boiler, and Turbo-Generator

The purpose of the combustor, boiler, and turbo-generator subsystem is to burn various by-product streams for steam and electricity generation. For example, some lignin, cellulose, and hemicellulose remains unconverted through the pretreatment and primary processes. The majority of wastewater from the process is concentrated to a syrup high in soluble solids. Anaerobic digestion of the remaining wastewater produces a biogas high in methane. Aerobic digestion produces a small amount of waste biomass (sludge). Burning these by-product streams to generate steam and electricity allows the plant to be self sufficient in energy, reduces solid waste disposal costs, and generates additional revenue through sales of excess electricity.

Three primary fuel streams (post-distillate solids, biogas, and evaporator syrup) are fed to a circulating fluidized bed combustor. The small amount of waste biomass (sludge) from wastewater treatment is also sent to the combustor. A fan moves air into the combustion chamber. Treated water enters the heat exchanger circuit in the combustor and is evaporated and superheated to 510° C. (950° F.) and 86 atm (1265 psia) steam. Flue gas from the combustor preheats the entering combustion air then enters a baghouse to remove particulates, which are landfilled. The gas is exhausted through a stack.

A multistage turbine and generator are used to generate electricity. Steam is extracted from the turbine at three different conditions for injection into the pretreatment reactor and heat exchange in distillation and evaporation. The remaining steam is condensed with cooling water and returned to the boiler feedwater system along with condensate from the various heat exchangers in the process. Treated well water is used as makeup to replace steam used in direct injection.

Example 21

Preparation of Animal Feed from Switchgrass

A 1500 pound skid of switchgrass is purchased from a farm and transported to the processing site. The material is fed into a 3 hp Flinch Baugh shredder at a rate of approximately 15 to 20 pounds per hour. The shredder is equipped with two 12 inch rotary blades, two fixed blades and a 0.30 inch discharge screen. The gap between the rotary and fixed blades is adjusted to 0.10 inch. The output from the shredder resembles confetti having a width of between 0.1 inch and 0.5 inch, a length of between 0.25 inch and 1 inch, and a thickness equivalent to that of the starting material. The confetti-like material is fed to a Munson rotary knife cutter, Model SC30. The discharge screen has ⅛ inch openings. The gap between the rotary and fixed blades is set to approximately 0.020 inch. The rotary knife cutter shears the confetti-like pieces, releasing a fibrous material at a rate of about one pound per hour. An average length of the fibers is 1.063 mm and an average width of the fibers is 0.0245 mm, giving an average L/D of 43:1.

These processed samples are densified to form pellets suitable for consumption by cows and other livestock. Pellets are distributed to farms and are stored in a storage silo. Required amounts of pellets are fed per cow per day.

Example 22

Preparation of Animal Feed from Switchgrass

A 1500 pound skid of switchgrass is purchased from a farm and transported to the processing site. The material is fed into a 3 hp Flinch Baugh shredder at a rate of approximately 15 to 20 pounds per hour. The shredder is equipped with two 12 inch rotary blades, two fixed blades and a 0.30 inch discharge screen. The gap between the rotary and fixed blades is adjusted to 0.10 inch. The output from the shredder resembles confetti having a width of between 0.1 inch and 0.5 inch, a length of between 0.25 inch and 1 inch, and a thickness equivalent to that of the starting material. The confetti-like material is fed to a Munson rotary knife cutter, Model SC30. The discharge screen has ⅛ inch openings. The gap between the rotary and fixed blades is set to approximately 0.020 inch. The rotary knife cutter shears the confetti-like pieces, releasing a fibrous material at a rate of about one pound per hour. An average length of the fibers is 1.063 mm and an average width of the fibers is 0.0245 mm, giving an average L/D of 43:1.

Samples are treated with an electron beam using a vaulted Rhodotron® TT200 continuous wave accelerator delivering 5 MeV electrons at 80 kW of output power. Table 10 describes the parameters used. Table 11 reports the nominal dose used.

TABLE 10

Rhodotron ® TT 200 Parameters

| Beam | |
|---|---|
| Beam Produced: | Accelerated electrons |
| Beam energy: | Nominal (fixed): 10 MeV (+0 keV-250 keV) |
| Energy dispersion at 10 Mev: | Full width half maximum (FWHM) 300 keV |
| Beam power at 10 MeV: | Guaranteed Operating Range 1 to 80 kW |
| Power Consumption | |
| Stand-by condition (vacuum and cooling ON): | <15 kW |
| At 50 kW beam power: | <210 kW |
| At 80 kW beam power: | <260 kW |
| RF System | |
| Frequency: | 107.5 ± 1 MHz |
| Tetrode type: | Thomson TH781 |
| Scanning Horn | |
| Nominal Scanning Length (measured at 25-35 cm from window): | 120 cm |
| Scanning Range: | From 30% to 100% of Nominal Scanning Length |
| Nominal Scanning Frequency (at max. scanning length): | 100 Hz ± 5% |
| Scanning Uniformity (across 90% of Nominal Scanning Length) | ±5% |

TABLE 11

Dosages Delivered to Samples
Total Dosage (MRad)

1
3

TABLE 11-continued

Dosages Delivered to Samples
Total Dosage (MRad)

5
7
10
15
20
30
50
70
100

These processed samples are densified to form pellets suitable for consumption by cows and other livestock. Pellets are distributed to farms and are stored in a storage silo. Pellets are fed to cows and other livestock.

Example 23

Preparation of Animal Feed from Alfalfa

A 1500 pound skid of alfalfa is fed into a 3 hp Flinch Baugh shredder at a rate of approximately 15 to 20 pounds per hour. The shredder is equipped with two 12 inch rotary blades, two fixed blades and a 0.30 inch discharge screen. The gap between the rotary and fixed blades is adjusted to 0.10 inch. The output from the shredder resembles confetti having a width of between 0.1 inch and 0.5 inch, a length of between 0.25 inch and 1 inch, and a thickness equivalent to that of the starting material. The confetti-like material is fed to a Munson rotary knife cutter, Model SC30. The discharge screen has ⅛ inch openings. The gap between the rotary and fixed blades is set to approximately 0.020 inch. The rotary knife cutter shears the confetti-like pieces, releasing a fibrous material at a rate of about one pound per hour. An average length of the fibers is 1.063 mm and an average width of the fibers is 0.0245 mm, giving an average L/D of 43:1.

These processed samples are densified to form pellets suitable for consumption by cows and other livestock. Pellets are distributed to farms and are stored in a storage silo. These pellets are fed to cows and other livestock.

Example 24

Preparation of Animal Feed from Alfalfa

A 1500 pound skid of alfalfa is fed into a 3 hp Flinch Baugh shredder at a rate of approximately 15 to 20 pounds per hour. The shredder is equipped with two 12 inch rotary blades, two fixed blades and a 0.30 inch discharge screen. The gap between the rotary and fixed blades is adjusted to 0.10 inch. The output from the shredder resembles confetti having a width of between 0.1 inch and 0.5 inch, a length of between 0.25 inch and 1 inch, and a thickness equivalent to that of the starting material. The confetti-like material is fed to a Munson rotary knife cutter, Model SC30. The discharge screen has ⅛ inch openings. The gap between the rotary and fixed blades is set to approximately 0.020 inch. The rotary knife cutter shears the confetti-like pieces, releasing a fibrous material at a rate of about one pound per hour. An average length of the fibers is 1.063 mm and an average width of the fibers is 0.0245 mm, giving an average L/D of 43:1.

Samples are treated with an electron beam using a Rhodotron® TT200 continuous wave accelerator delivering 5 MeV electrons at 80 kW of output power. Table 10 describes the parameters used. Table 11 reports the nominal dose used.

These processed samples are densified to form pellets suitable for consumption by cows and other livestock. Pellets are distributed to farms and are stored in a storage silo. Pellets are fed to cows and other livestock.

Example 25

Preparation of Animal Feed from Paper

A 1500 pound skid of paper is folded flat, and fed into a 3 hp Flinch Baugh shredder at a rate of approximately 15 to 20 pounds per hour. The shredder is equipped with two 12 inch rotary blades, two fixed blades and a 0.30 inch discharge screen. The gap between the rotary and fixed blades is adjusted to 0.10 inch. The output from the shredder resembles confetti having a width of between 0.1 inch and 0.5 inch, a length of between 0.25 inch and 1 inch, and a thickness equivalent to that of the starting material. The confetti-like material is fed to a Munson rotary knife cutter, Model SC30. The discharge screen has ⅛ inch openings. The gap between the rotary and fixed blades is set to approximately 0.020 inch. The rotary knife cutter shears the confetti-like pieces, releasing a fibrous material at a rate of about one pound per hour. An average length of the fibers is 1.063 mm and an average width of the fibers is 0.0245 mm, giving an average L/D of 43:1.

These processed samples are densified to form pellets suitable for consumption by cows and other livestock. Pellets are distributed to farms and are stored in a storage silo. These pellets are fed to cows and other livestock.

Example 26

Preparation of Animal Feed from Paper

A 1500 pound skid of paper is fed into a 3 hp Flinch Baugh shredder at a rate of approximately 15 to 20 pounds per hour. The shredder is equipped with two 12 inch rotary blades, two fixed blades and a 0.30 inch discharge screen. The gap between the rotary and fixed blades is adjusted to 0.10 inch. The output from the shredder resembles confetti having a width of between 0.1 inch and 0.5 inch, a length of between 0.25 inch and 1 inch, and a thickness equivalent to that of the starting material. The confetti-like material is fed to a Munson rotary knife cutter, Model SC30. The discharge screen has ⅛ inch openings. The gap between the rotary and fixed blades is set to approximately 0.020 inch. The rotary knife cutter shears the confetti-like pieces, releasing a fibrous material at a rate of about one pound per hour. An average length of the fibers is 1.063 mm and an average width of the fibers is 0.0245 mm, giving an average L/D of 43:1.

Samples are treated with an electron beam using a Rhodotron® TT200 continuous wave accelerator delivering 5 MeV electrons at 80 kW of output power. Table 10 describes the parameters used. Table 11 reports the nominal dose used.

These processed samples are densified to form pellets suitable for consumption by cows and other livestock. Pellets are distributed to farms and are stored in a storage silo. Pellets are fed to cows and other livestock.

Example 27

Preparation of Animal Feed from Grass

A 1500 pound gaylord of grass is fed into a 3 hp Flinch Baugh shredder at a rate of approximately 15 to 20 pounds per hour. The shredder is equipped with two 12 inch rotary blades, two fixed blades and a 0.30 inch discharge screen. The gap between the rotary and fixed blades is adjusted to 0.10 inch. The output from the shredder resembles confetti having a width of between 0.1 inch and 0.5 inch, a length of between 0.25 inch and 1 inch, and a thickness equivalent to that of the starting material. The confetti-like material is fed to a Munson rotary knife cutter, Model SC30. The discharge screen has 1/8 inch openings. The gap between the rotary and fixed blades is set to approximately 0.020 inch. The rotary knife cutter shears the confetti-like pieces, releasing a fibrous material at a rate of about one pound per hour. An average length of the fibers is 1.063 mm and an average width of the fibers is 0.0245 mm, giving an average L/D of 43:1.

Processed samples are densified to form pellets suitable for consumption by cows and other livestock. Pellets are distributed to farms and are stored in a storage silo. These pellets are fed to cows and other livestock.

Example 28

Preparation of Animal Feed from Grass

A 1500 pound skid of grass is fed into a 3 hp Flinch Baugh shredder at a rate of approximately 15 to 20 pounds per hour. The shredder is equipped with two 12 inch rotary blades, two fixed blades and a 0.30 inch discharge screen. The gap between the rotary and fixed blades is adjusted to 0.10 inch. The output from the shredder resembles confetti having a width of between 0.1 inch and 0.5 inch, a length of between 0.25 inch and 1 inch, and a thickness equivalent to that of the starting material. The confetti-like material is fed to a Munson rotary knife cutter, Model SC30. The discharge screen has 1/8 inch openings. The gap between the rotary and fixed blades is set to approximately 0.020 inch. The rotary knife cutter shears the confetti-like pieces, releasing a fibrous material at a rate of about one pound per hour. An average length of the fibers is 1.063 mm and an average width of the fibers is 0.0245 mm, giving an average L/D of 43:1.

Samples are treated with an electron beam using a Rhodotron® TT200 continuous wave accelerator delivering 5 MeV electrons at 80 kW of output power. Table 10 describes the parameters used. Table 11 reports the nominal dose used.

These processed samples are densified to form pellets suitable for consumption by cows and other livestock. Pellets are distributed to farms and are stored in a storage silo. Pellets are fed to cows and other livestock.

Example 29

Preparation of Animal Feed from Wheatstraw

A 1500 pound skid of wheatstraw is fed into a 3 hp Flinch Baugh shredder at a rate of approximately 15 to 20 pounds per hour. The shredder is equipped with two 12 inch rotary blades, two fixed blades and a 0.30 inch discharge screen. The gap between the rotary and fixed blades is adjusted to 0.10 inch. The output from the shredder resembles confetti having a width of between 0.1 inch and 0.5 inch, a length of between 025 inch and 1 inch, and a thickness equivalent to that of the starting material. The confetti-like material is fed to a Munson rotary knife cutter, Model SC30. The discharge screen has 1/8 inch openings. The gap between the rotary and fixed blades is set to approximately 0.020 inch. The rotary knife cutter shears the confetti-like pieces, releasing a fibrous material at a rate of about one pound per hour. An average length of the fibers is 1.063 mm and an average width of the fibers is 0.0245 mm, giving an average L/D of 43:1.

Processed samples are densified to form pellets suitable for consumption by cows and other livestock. Pellets are distributed to farms and are stored in a storage silo. These pellets are fed to cows and other livestock.

Example 30

Preparation of Animal Feed from Wheatstraw

A 1500 pound skid of wheatstraw is fed into a 3 hp Flinch Baugh shredder at a rate of approximately 15 to 20 pounds per hour. The shredder is equipped with two 12 inch rotary blades, two fixed blades and a 0.30 inch discharge screen. The gap between the rotary and fixed blades is adjusted to 0.10 inch. The output from the shredder resembles confetti having a width of between 0.1 inch and 0.5 inch, a length of between 0.25 inch and 1 inch, and a thickness equivalent to that of the starting material. The confetti-like material is fed to a Munson rotary knife cutter, Model SC30. The discharge screen has 1/8 inch openings. The gap between the rotary and fixed blades is set to approximately 0.020 inch. The rotary knife cutter shears the confetti-like pieces, releasing a fibrous material at a rate of about one pound per hour. An average length of the fibers is 1.063 mm and an average width of the fibers is 0.0245 mm, giving an average L/D of 43:1.

Samples are treated with an electron beam using a Rhodotron® TT200 continuous wave accelerator delivering 5 MeV electrons at 80 kW of output power. Table 10 describes the parameters used. Table 11 reports the nominal dose used.

These processed samples are densified to form pellets suitable for consumption by cows and other livestock. Pellets are distributed to farms and are stored in a storage silo. Pellets are fed to cows and other livestock.

Example 31

Preparation of Animal Feed from Biomass 1500 pound skids of switchgrass, alfalfa, paper, grass, and wheatstraw are fed separately into a 3 hp Flinch Baugh shredder at a rate of approximately 15 to 20 pounds per hour. The shredder is equipped with two 12 inch rotary blades, two fixed blades and a 0.30 inch discharge screen. The gap between the rotary and fixed blades is adjusted to 0.10 inch. The output from the shredder resembles confetti having a width of between 0.1 inch and 0.5 inch, a length of between 0.25 inch and 1 inch, and a thickness equivalent to that of the starting material. The confetti-like material is fed to a Munson rotary knife cutter, Model SC30. The discharge screen has 1/8 inch openings. The gap between the rotary and fixed blades is set to approximately 0.020 inch. The rotary knife cutter shears the confetti-like pieces, releasing a fibrous material at a rate of about one pound per hour. An average length of the fibers is 1.063 mm and an average width of the fibers is 0.0245 mm, giving an average L/D of 43:1.

Processed samples are combined and densified to form pellets suitable for consumption by cows and other livestock. Pellets are distributed to farms and are stored in a storage silo. These pellets are fed to cows and other livestock.

Example 32

Preparation of Animal Feed from Biomass 1500 pound skids of switchgrass, alfalfa, paper, grass, and wheatstraw are fed separately into a 3 hp Flinch Baugh shredder at a rate of approximately 15 to 20 pounds per hour. The shredder is equipped with two 12 inch rotary blades, two fixed blades and a 0.30 inch discharge screen. The gap between the rotary and fixed blades is adjusted to 0.10 inch. The output from the shredder resembles confetti having a width of between 0.1 inch and 0.5 inch, a length of between 0.25 inch and 1 inch, and a thickness equivalent to that of the starting material. The confetti-like material is fed to a Munson rotary knife cutter, Model SC30. The discharge screen has 1/8 inch openings. The gap between the rotary and fixed blades is set to approximately 0.020 inch. The rotary knife cutter shears the confetti-like pieces, releasing a fibrous material at a rate of about one pound per hour. An average length of the fibers is 1.063 mm and an average width of the fibers is 0.0245 mm, giving an average L/D of 43:1.

Samples are treated with an electron beam using a Rhodotron® TT200 continuous wave accelerator delivering 5 MeV electrons at 80 kW of output power. Table 10 describes the parameters used. Table 11 reports the nominal dose used.

Processed samples are combined and densified to form pellets suitable for consumption by cows and other livestock. Pellets are distributed to farms and are stored in a storage silo. These pellets are fed to cows and other livestock.

Example 33

Preparation of Animal Feed from Biomass 1500 pound skids of switchgrass, alfalfa, paper, grass, and wheatstraw are mixed and fed into a 3 hp Flinch Baugh shredder at a rate of approximately 15 to 20 pounds per hour. The shredder is equipped with two 12 inch rotary blades, two fixed blades and a 0.30 inch discharge screen. The gap between the rotary and fixed blades is adjusted to 0.10 inch. The output from the shredder resembles confetti having a width of between 0.1 inch and 0.5 inch, a length of between 0.25 inch and 1 inch, and a thickness equivalent to that of the starting material. The confetti-like material is fed to a Munson rotary knife cutter, Model SC30. The discharge screen has 1/8 inch openings. The gap between the rotary and fixed blades is set to approximately 0.020 inch. The rotary knife cutter shears the confetti-like pieces, releasing a fibrous material at a rate of about one pound per hour. An average length of the fibers is 1.063 mm and an average width of the fibers is 0.0245 mm, giving an average L/D of 43:1.

Processed samples are densified to form pellets suitable for consumption by cows and other livestock. Pellets are distributed to farms and are stored in a storage silo. These pellets are fed to cows and other livestock.

Example 34

Preparation of Animal Feed from Biomass 1500 pound skids of switchgrass, alfalfa, paper, grass, and wheatstraw are mixed and fed into a 3 hp Flinch Baugh shredder at a rate of approximately 15 to 20 pounds per hour. The shredder is equipped with two 12 inch rotary blades, two fixed blades and a 0.30 inch discharge screen. The gap between the rotary and fixed blades is adjusted to 0.10 inch. The output from the shredder resembles confetti having a width of between 0.1 inch and 0.5 inch, a length of between 0.25 inch and 1 inch, and a thickness equivalent to that of the starting material. The confetti-like material is fed to a Munson rotary knife cutter, Model SC30. The discharge screen has 1/8 inch openings. The gap between the rotary and fixed blades is set to approximately 0.020 inch. The rotary knife cutter shears the confetti-like pieces, releasing a fibrous material at a rate of about one pound per hour. An average length of the fibers is 1.063 mm and an average width of the fibers is 0.0245 mm, giving an average L/D of 43:1.

Samples are treated with an electron beam using a Rhodotron® TT200 continuous wave accelerator delivering 5 MeV electrons at 80 kW of output power. Table 10 describes the parameters used. Table 11 reports the nominal dose used.

Processed samples are densified to form pellets suitable for consumption by cows and other livestock. Pellets are distributed to farms and are stored in a storage silo. These pellets are fed to cows and other livestock.

Example 35

Preparation of Animal Feed from Biomass 1500 pound skids of switchgrass, alfalfa, paper, grass, and wheatstraw are mixed and fed into a 3 hp Flinch Baugh shredder at a rate of approximately 15 to 20 pounds per hour. The shredder is equipped with two 12 inch rotary blades, two fixed blades and a 0.30 inch discharge screen. The gap between the rotary and fixed blades is adjusted to 0.10 inch. The output from the shredder resembles confetti having a width of between 0.1 inch and 0.5 inch, a length of between 0.25 inch and 1 inch, and a thickness equivalent to that of the starting material. The confetti-like material is fed to a Munson rotary knife cutter, Model SC30. The discharge screen has 1/8 inch openings. The gap between the rotary and fixed blades is set to approximately 0.020 inch. The rotary knife cutter shears the confetti-like pieces, releasing a fibrous material at a rate of about one pound per hour. An average length of the fibers is 1.063 mm and an average width of the fibers is 0.0245 mm, giving an average L/D of 43:1.

Processed samples are combined with dried distillers grains (DDG) to produce a mixture suitable for consumption by cows and other livestock. These mixtures are distributed to farms and are stored in a storage silo. These pellets are fed to cows and other livestock.

Example 36

Preparation of Animal Feed from Biomass 1500 pound skids of switchgrass, alfalfa, paper, grass, and wheatstraw are mixed and fed into a 3 hp Flinch Baugh shredder at a rate of approximately 15 to 20 pounds per hour. The shredder is equipped with two 12 inch rotary blades, two fixed blades and a 0.30 inch discharge screen. The gap between the rotary and fixed blades is adjusted to 0.10 inch. The output from the shredder resembles confetti having a width of between 0.1 inch and 0.5 inch, a length of between 0.25 inch and 1 inch, and a thickness equivalent to that of the starting material. The confetti-like material is fed to a Munson rotary knife cutter, Model SC30. The discharge screen has 1/8 inch openings. The gap between the rotary and fixed blades is set to approximately 0.020 inch. The rotary knife cutter shears the confetti-like, pieces, releasing a fibrous material at a rate of about one pound per hour. An average length of the fibers is 1.063 mm and an average width of the fibers is 0.0245 mm, giving an average L/D of 43:1.

Samples are treated with an electron beam using a Rhodotron® TT200 continuous wave accelerator delivering 5 MeV electrons at 80 kW of output power. Table 10 describes the parameters used. Table 11 reports the nominal dose used.

Processed samples are combined with dried distillers grains (DDG) to produce a mixture suitable for consumption by cows and other livestock. These mixtures are distributed to farms and are stored in a storage silo. These pellets are fed to cows and other livestock.

Example 37

Self Sufficient Farming

A farmer collects a crop of switchgrass and sends it for processing to a processing plant. The switchgrass is processed as described in Example 21. The processed material is supplied to the farmer in the form of a pellet that is fed to the farmer's cows and other livestock.

Example 38

Self Sufficient Farming

A farmer collects a crop of switchgrass and sends it for processing to a processing plant. The switchgrass is processed as described in Example 22. The processed material is supplied to the farmer in the form of a pellet that is fed to the farmer's cows and other livestock.

Example 39

Self Sufficient Farming

A farmer collects a crop of switchgrass and processes the material using equipment located on site at the farm. The switchgrass is processed as described in Example 21. The processed material is fed to the farmer's cows and other livestock.

Example 40

Self Sufficient Farming

A farmer collects a crop of switchgrass and processes the material using equipment located on site at the farm. The switchgrass is processed as described in Example 22. The processed material is fed to the farmer's cows and other livestock.

Example 41

Shake Flask Fermentation Studies Using *P. stipitis*

Summary

Shake flask fermentation studies using various enzymes, physical treatments, and *Pichia stipitis* were performed.

Protocol

Experiments were performed under the parameters outlined in Table 13.

TABLE 13

Chemicals and Materials Used for the Shake Flask Experiment

| Media Component | Manufacturer | Reference # |
| --- | --- | --- |
| Urea | ScholAR Chemistry | 9472706 |
| Yeast Nitrogen Base | Becton Dickinson | 291940 |
| Peptone | Becton Dickinson | 211677 |
| Xylose | Alfa Aesar | A10643 |
| Glucose | Sigma | G-5400 |
| Yeast Extract | Becton Dickinson | 288620 |
| YM Broth | Becton Dickinson | 271120 |
| Novozyme ® 188 | Novozymes | Sigma #C6105 |
| Celluclast 1,5 FG | Novozymes | Sigma #C2730 |
| Solka Floc | International Fibre Corporation | 200 NF |
| Pluronic F-68 | Sigma | P1300 |
| Accellerase ® 1000 | Genencor | N/A |

Seed Development

A working cell bank of *P. stipitis* NRRL Y-7124 was prepared from a rehydrated lyophilized culture obtained from ARS Culture Collection. Cryovials containing *P. stipitis* culture in 15% v/v glycerol were stored at −75° C. A portion of the thawed working cell bank material were streaked onto a Yeast Mold (YM) Broth+20 g/L agar (pH 5.0) and incubated at 30° C. for 2 days. The plates were held for up to seven days at 4° C. before use.

A 250 mL Erlenmeyer flask containing 100 mL of medium (40 g/L glucose, 1.7 g/L yeast nitrogen base, 2.27 g/L urea, 6.56 g/L peptone, 40 g/L xylose, pH 5.0) were inoculated with one colony and incubated for 24 hours at 25° C. and 150 rpm. After 23 hours of growth, a sample was taken and analyzed for optical density (OD 600 nm in a UV spectrophotometer) and purity (Gram stain). Based on these results, two seed flasks, each having an optical density (OD) of between 4 and 8 and with a clean Gram stain, were combined to inoculate the growth flasks.

Exemplary Experiments

Experiments were performed to 1) determine the correct sonifier output and temperature regulation (below 60° C.) and 2) confirm the concentration of Celluclast 1,5 FG and Novozyme 188 with and without Pluronic F-68.

Five hundred milliliters of water were added to a 1 L glass beaker. The horn of a Branson Model 450 Sonifier was placed ½ inch into the surface of the beaker and set at a maximum constant output for 60 minutes. The temperature of the water was measured every 10 minutes for 60 minutes of sonication.

An experiment was performed to determine if 1) the concentration of Celluclast 1,5 FG and Novozyme 188 (0.5 mL and 0.1 mL per gram of biomass, respectively) was sufficient for the shake flask experiments and 2) if the addition of Pluronic F68 augmented the hydrolysis of cellulose. Four 250 mL flasks were prepared with 100 mL of sterile broth (1.7 g/L yeast nitrogen base, 2.27 g/L urea, 6.56 g/L peptone, pH 5.0). Duplicate flasks contained 1% w/v Pluronic F-68. Solka Floc Crystalline Cellulose (6 g) was added to the flasks and allowed to soak at room temperature for 14 hours. Celluclast 1,5 FG and Novozyme 188 (0.5 mL and 0.1 mL per gram of Solka Floc, respectively) were added and each flask incubated at 50° C. for 24 hours at 100 rpm. Samples were taken prior to the addition of enzyme and 24 hours post enzyme addition from all four flasks and analyzed for glucose concentration using the YSI Biochem Analyzer (YSI, Interscience). One milliliter of *Pichia stipitis* seed flask contents was added to the four flasks and incubated at 25° C. and 125 rpm for 24 hours. Samples were taken from each flask prior to inoculation and after 24 hours incubation and analyzed for ethanol concentration using the YSI Biochem Analyzer (YSI, Interscience).

Test Flasks

The test flasks were 2.8 L Fernbach flasks holding 900 mL of broth (1.7 g/L yeast nitrogen base, 2.27 g/L urea, 6.56 g/L peptone, pH 5.0). Control flasks were 250 mL flasks containing 100 mL of broth (40 g/L glucose, 1.7 g/L yeast nitrogen base, 2.27 g/L urea, 6.56 g/L peptone, 40 g/L xylose, pH 5.0). The exact nature of each flask was decided by Xyleco and is described in Table 80 below.

Samples were not sterilized prior to the start of the experiment. All samples were added to the flasks and allowed to soak for 15 hours at room temperature. Some of the samples were sonicated for one hour using a Branson Model 450 Sonifier equipped with a ½ inch disruptor horn. The original plan was to split the flask contents into two, and sonicate each half continuously at the maximum output for the equipment up to 450 watts (the allowable output depends on the viscosity of the sample) for 1 hour. An output setting of 3 and a Duty cycle of Pulse 90% were sufficient for the mixing of the beaker contents. At an output setting of 3, the meter read between 30 and 40. The output was calculated to be 40-60 watts.

Originally, the plan was to mix some samples (see Table 80) for various times using a POLYTRON PT 10/35 laboratory homogenizer (or rotor/stator) at 25,000 rpm for various times. Samples #22 and #23 were split into two beakers and treated for 30 minutes using the large Kinematica Polytron PT 10/35. The generator (tip) was a PTA 20 with a stator diameter of 20 mm. The instrument was operated at a speed of 11,000 rpm. Operation above 11,000 rpm caused splattering of beaker contents, movement of the beaker, and over-heating of the equipment. After samples #23 and #24, the Polytron PT 10/35 stopped working, presumably from over-use with quite viscous samples. Therefore, the hand-held Polytron PT1200C was used. The generator (tip) was a PT-DA 1212 with a stator diameter of 12 mm. The instrument could be operated at 25,000 rpm. It was noted by the operator that a similar degree of mixing was observed with the hand-held at 25,000 rpm as compared to the larger model at 11,000 rpm. The sample was periodically mixed by the operator to ensure even mixing. Samples 19 through 22 were mixed with the hand-held Polytron PT1200C.

Enzyme pretreatments included: 1) E1=Accellerase® 1000 enzyme complex at a loading density of 0.25 mL per gram of substrate and 2) E2=Celluclast 1,5 FG and Novozyme 188 at a loading concentration of 0.5 and 0.1 mL per gram of substrate, respectively. After physical pretreatment (see Table 80 below), the appropriate enzyme(s) were added and the flasks held at 50° C. and 125 rpm for 20 hours. After 20 hours, the flasks were cooled to room temperature for 1 hour prior to the addition of *P. stipitis*.

TABLE 14

Summary of Test Treatments

| Test Number | Sample Number | Sample Concentration (g/900 mL) | Physical Treatment | Enzyme Treatment (50° C., 21 hours) |
|---|---|---|---|---|
| Control (250 mL flask) performed in duplicate each week | None | — | — | — |
| Week 1 | | | | |
| 1 | SP | 35 | 15 h r.t. soak | None |
| 2 | XP | 35 | 15 h r.t. soak | None |
| 3 | SP | 35 | 15 h r.t. soak | E1 |
| 4 | SP | 35 | 15 h r.t. soak | E2 |
| 5 | XP | 35 | 15 h r.t. soak | E1 |
| 6 | XP | 35 | 15 h r.t. soak | E2 |
| 7 | XP-10e | 35 | 15 h r.t. soak | E2 |
| 8 | XP-30e | 35 | 15 h r.t. soak | E2 |
| 9 | XP-50e | 35 | 15 h r.t. soak | E2 |
| 10 | XP-10e | 35 | 15 h r.t. soak, 1 hour sonication | E2 |
| 11 | XP-30e | 35 | 15 h r.t. soak, 1 hour sonication | E2 |
| 12 | XP-50e | 35 | 15 h r.t. soak, 1 hour sonication | E2 |
| Week 2 | | | | |
| 13 | XP-10e | 35 | 15 h r.t. soak, 10 min sonication | E2 |
| 14 | XP-30e | 35 | 15 h r.t. soak, 10 min sonication | E2 |
| 15 | XP-50e | 35 | 15 h r.t. soak, 10 min sonication | E2 |
| 16 | XP-10e | 35 | 15 h r.t. soak, 30 min sonication | E2 |
| 17 | XP-30e | 35 | 15 h r.t. soak, 30 min sonication | E2 |
| 18 | XP-50e | 35 | 15 h r.t. soak, 30 min sonication | E2 |
| 19 | XP-10e | 35 | 15 h r.t. soak, 10 min rotor/stator | E2 |
| 20 | XP-30e | 35 | 15 h r.t. soak, 10 min rotor/stator | E2 |
| 21 | XP-50e | 35 | 15 h r.t. soak, 10 min rotor/stator | E2 |
| 22 | XP-10e | 35 | 15 h r.t. soak, 30 min rotor/stator | E2 |
| 23 | XP-30e | 35 | 15 h r.t. soak, 30 min rotor/stator | E2 |
| 24 | XP-50e | 35 | 15 h r.t. soak, 30 min rotor/stator | E2 |

Analysis

A sample was taken from each flask after physical and/or enzyme pretreatment (just prior to the addition of *P. stipitis*) and analyzed for glucose concentration using the YSI Biochem Analyzer (YSI, Interscience). Samples were centrifuged at 14,000 rpm for 20 minutes and the supernatant stored at −20° C. The samples were diluted to between 0-25.0 g/L glucose prior to analysis. A glucose standard was analyzed approximately every 30 samples to ensure the integrity of the membrane was maintained.

A total of five samples were taken from each flask at 0, 12, 24, 48, and 72 hours and analyzed for ethanol concentration using the YSI Biochem Analyzer based on the alcohol dehydrogenase assay (YSI, Interscience). Samples were centrifuged at 14,000 rpm for 20 minutes and the supernatant stored at −20° C. and diluted to between 0-3.0 g/L ethanol prior to analysis. A standard of 2.0 g/L ethanol was analyzed approximately every 30 samples to ensure the integrity of the membrane was maintained.

A sample of the seed flask was analyzed in order to determine the initial cell concentration in the test flasks. In addition one sample at 72 hours of incubation was taken from each flask and analyzed for cell concentration. Appropriately diluted samples were mixed with 0.05% Trypan blue and loaded into a Neubauer haemocytometer. The cells were counted under 40× magnification.

Results

Experiments

The results of a sonifier experiment are presented in Table 81. There were no problems with over-heating of the water.

TABLE 15

Sonifier Experiment

| Time | Temperature (° C.) |
|---|---|
| 0 | 18 |
| 10 | 18 |
| 20 | 19 |
| 30 | 19 |
| 40 | 19 |
| 50 | 19 |
| 60 | 19 |

The results of the experiment to confirm the concentration of Celluclast 1,5 FG and Novozyme 188 with and without Pluronic F-68 are presented in Table 82 and 83. A concentration of 60 g/L cellulose (Solka Floc) was added to each flask. After 24 hours of incubation, 33.7 to 35.7 g/L glucose was generated (30.3 to 32.1 g/L cellulose digested).

After 24 hours of incubation with P. stipitis, 23.2-25.7 g/L of glucose remained in the flasks. This indicates that not all of the glucose was used within 24 hours of incubation.

There was no evidence of Pluronic F-68 toxicity toward P. stipitis. However, there was no increase in the amount of glucose generated after a 24 hour enzyme treatment with the addition of Pluronic F-68.

TABLE 16

Glucose Results

| Flask | Glucose Concentration (g/L) | | |
|---|---|---|---|
| | Prior to Enzyme Treatment | After Enzyme Treatment (50° C., 24 hours, 100 rpm) | After P. stipitis for 24 hours |
| Control A | 0.28 | 34.3 | 23.2 |
| Control B | 0.64 | 35.7 | 25.3 |
| Containing Pluronic A | 0.48 | 34.8 | 25.6 |
| Containing Pluronic B | 0.93 | 33.7 | 25.7 |

TABLE 17

Ethanol Results

| Flask | Ethanol Concentration (g/L) at times (hours) | |
|---|---|---|
| | 0 (inoculation, after enzyme treatment) | 24 hours of P. stipitis |
| Control A | 0.01 | 7.23 |
| Control B | 0.01 | 5.75 |
| Containing Pluronic A | 0.01 | 7.57 |
| Containing Pluronic B | 0.00 | 7.36 |

During week one of testing, the seed flask had an optical density (600 nm) of 9.74 and a cell concentration of $4.21 \times 10^8$ cells/mL. Nine mL of seed flask material was added to each of the test flasks and 1 mL to the control flasks (1% v/v). Therefore, the starting cell concentration in each flask was $\times 4.21 \times 10^6$/mL.

During week two of testing, the seed flask had an optical density (600 nm) of 3.02 and a cell concentration of $2.85 \times 10^8$ cells/mL. To account for differences in cell counts and OD, 12 mL of seed flask material was added to each of the test flasks and 1.5 mL to the control flasks (1.5% v/v). Therefore, the starting cell concentration in each flask was $3.80 \times 10^6$/mL.

The ethanol concentration in the flasks is presented in Table 84. The highest concentration of ethanol was observed in Flask #6 (Sample XP, Overnight Soak, treatment with E2 at 50° C. for 21 hours). A concentration of 19.5 g/L (1.7.55 g/per flask) was generated from an original 35 grams of substrate in 48 hours. The yield of ethanol (grams of ethanol/gram of substrate) in flask #6 was 0.50.

TABLE 18

Ethanol Concentration

| Sample Number | Ethanol Concentration (g/L) at Incubation Time (hours) | | | | |
|---|---|---|---|---|---|
| | 0 | 12 | 24 | 48 | 72 |
| Control A | 0.249 | 1.57 | 9.31 | 13.60 | 14.20 |
| Control B | 0.237 | 1.04 | 7.97 | 11.40 | 13.90 |
| 1 | 0.247 | 0.16 | 0.10 | 0.11 | 0.06 |
| 2 | 0.175 | 0.12 | 0.10 | 0.17 | 0.29 |
| 3 | 0.284 | 2.73* | 8.88 | 9.72 | 10.40 |
| 4 | 0.398 | 0.43 | 8.02 | 14.40 | 12.10 |
| 5 | 0.312 | 0.31 | 10.30 | 11.30 | 18.80 |
| 6 | 0.399 | 0.73 | 7.55 | 19.50* | 19.00 |
| 7 | 0.419 | 0.38 | 4.73 | 16.80* | 15.40 |
| 8 | 0.370 | 0.46 | 0.56 | 9.86 | 13.50 |
| 9 | 0.183 | 0.47 | 0.53 | 12.00 | 14.10 |
| 10 | 0.216 | 0.35 | 6.11 | 13.80 | 15.60 |
| 11 | 0.199 | 0.33 | 0.88 | 9.02 | 8.52 |
| 12 | 0.264 | 0.43 | 0.41 | 8.76 | 13.80 |
| Control A | 0.49 | 0.84 | 7.93 | 13.00 | 15.00 |
| Control B | 0.50 | 0.93 | 8.39 | 13.40 | 15.00 |
| 13 | 0.86 | 0.99 | 8.42 | 10.50 | 14.20 |
| 14 | 0.95 | 0.88 | 3.79 | 10.90 | 12.40 |
| 15 | 1.18 | 0.42 | 1.12 | 9.26 | 12.60 |
| 16 | 0.88 | 0.42 | 5.41 | 6.78 | 12.80 |
| 17 | 0.99 | 0.45 | 1.73 | 10.60 | 12.00 |
| 18 | 1.17 | 0.46 | 1.12 | 10.60 | 12.10 |
| 19 | 0.78 | 0.50 | 9.75 | 12.60 | 13.40 |
| 20 | 0.94 | 0.39 | 2.54 | 11.10 | 12.20 |
| 21 | 1.28 | 0.43 | 1.46 | 11.50 | 11.30 |
| 22 | 0.84 | 1.09 | 10.00 | 14.00 | 10.10 |

TABLE 18-continued

Ethanol Concentration

| Sample Number | Ethanol Concentration (g/L) at Incubation Time (hours) | | | | |
|---|---|---|---|---|---|
| | 0 | 12 | 24 | 48 | 72 |
| 23 | 0.96 | 0.57 | 6.77 | 11.10 | 12.10 |
| 24 | 1.20 | 0.42 | 1.91 | 12.10 | 13.10 |

*Samples analyzed twice with the same result.
Flasks with a concentration of greater than 15 g/L ethanol are in BOLD.

The results of the glucose analysis are presented in Table 85. After 21 hours of enzyme treatment, the highest concentration of glucose was 19.6 g/L (17.6 grams per flask) in flask #6 (Sample XP, Overnight Soak, treatment with E2 at 50° C. for 21 hours). This was also the flask with the highest ethanol concentration (see Table 84). After 72 hours, very little glucose remained in the flasks. No glucose was detected in Flasks 1 and 2.

TABLE 19

Glucose Concentration

| Sample Number | Glucose Concentration (g/L) at Incubation Time (hours) | |
|---|---|---|
| | 0 | 72 |
| 1 | 0.0 | 0.00 |
| 2 | 0.0 | 0.00 |
| 3 | 7.2 | 0.02 |
| 4 | 13.3 | 0.03 |
| 5 | 15.9 | 0.05 |
| 6 | 19.6 | 0.05 |
| 7 | 13.9 | 0.04 |
| 8 | 15.4 | 0.06 |
| 9 | 18.3 | 0.09 |
| 10 | 17.1 | 0.05 |
| 11 | 13.0 | 0.04 |
| 12 | 17.0 | 0.08 |
| 13 | 14.4 | 0.03 |
| 14 | 13.7 | 0.04 |
| 15 | 16.3 | 0.08 |
| 16 | 13.2 | 0.03 |
| 17 | 13.4 | 0.04 |
| 18 | 15.8 | 0.06 |
| 19 | 15.3 | 0.04 |
| 20 | 14.3 | 0.04 |
| 21 | 15.5 | 0.06 |
| 22 | 14.7 | 0.04 |
| 23 | 13.5 | 0.04 |
| 24 | 16.6 | 0.07 |

The results of the direct cell counts are presented in Table 86. The concentration of viable cells was higher in the control flasks. The lowest counts were observed in flasks 1 through 4.

TABLE 20

Cell Counts

| Sample Number | Number of Cells (×106/mL) after 72 hours of incubation |
|---|---|
| Control A | 38.30 |
| Control B | 104.00 |
| 1 | 0.02 |
| 2 | 0.08 |
| 3 | 0.07 |
| 4 | 0.06 |
| 5 | 0.15 |
| 6 | 1.05 |
| 7 | 1.50 |
| 8 | 1.95 |
| 9 | 1.05 |
| 10 | 3.60 |
| 11 | 1.28 |
| 12 | 0.90 |
| Control A | 39.80 |
| Control B | 30.80 |
| 13 | 0.98 |
| 14 | 0.40 |
| 15 | 0.63 |
| 16 | 0.71 |
| 17 | 1.15 |
| 18 | 0.83 |
| 19 | 1.25 |
| 20 | 1.02 |
| 21 | 0.53 |
| 22 | 0.56 |
| 23 | 0.59 |
| 24 | 0.59 |

Example 42

Production of Bioconversion Products from Biomass

A 150 pound skid of biomass is fed into a 3 hp Flinch Baugh shredder at a rate of approximately 15 to 20 pounds per hour. The shredder is equipped with two 12 inch rotary blades, two fixed blades and a 0.30 inch discharge screen. The gap between the rotary and fixed blades is adjusted to 0.10 inch. The output from the shredder resembles confetti having a width of between 0.1 inch and 0.5 inch, a length of between 0.25 inch and 1 inch, and a thickness equivalent to that of the starting material. The confetti-like material is fed to a Munson rotary knife cutter, Model SC30. The discharge screen has ⅛ inch openings. The gap between the rotary and fixed blades is set to approximately 0.020 inch. The rotary knife cutter shears the confetti-like pieces, releasing a fibrous material at a rate of about one pound per hour. An average length of the fibers is 1.063 mm and an average width of the fibers is 0.0245 mm, giving an average L/D of 43:1.

Materials are treated with electron beam using a Rhodotron® TT200 continuous wave accelerator delivering 5 MeV electrons at 80 kW of output power. Table 10 describes the parameters used. Table 11 reports the nominal dose used.

The processed materials are dispensed into New Brunswick Scientific sterilizable bench top sterilizable fermenters00 in the form of a liquid medium that is formulated to support the growth, expansion, and/or activity of a microorganism selected for its ability to produce the required bioconversion product. Varying concentrations of the processed materials are added in combination with varying amounts of other supplementary materials that are routinely necessary for the growth, expansion, and/or activity of the selected microorganism. A nitrogen source is also added to the medium. The concentration or amount of the processed materials and each of the supplementary materials (including the nitrogen source) are memorialized in the form of a laboratory notebook or on a computer hard drive.

A starter culture of the selected microorganism is added to each of the various culture solutions in the fermentors. Each of the inoculated culture solutions is incubated at a temperature between about 15° C. and about 40° C. for 4 to 48 hours under aerobic or an anaerobic conditions. Following culture, microorganisms and cell supernatants are collected and optionally separated using centrifugation. Samples are then either frozen for storage or are assessed to determine the level of bioconversion product in the cells or supernatant. Results are memorialized and experiments are repeated until the maximum yield of bioconversion product is obtained. The culture solution and conditions used to obtain this maximum yield are scaled up for use in large scale fermentation.

Example 43

Large Scale Production of Bioconversion Products from Biomass

A 1500 pound skid of biomass is fed into a 3 hp Flinch Baugh shredder at a rate of approximately 15 to 20 pounds per hour. The shredder is equipped with two 12 inch rotary blades, two fixed blades and a 0.30 inch discharge screen. The gap between the rotary and fixed blades is adjusted to 0.10 inch. The output from the shredder resembles confetti having a width of between 0.1 inch and 0.5 inch, a length of between 0.25 inch and 1 inch, and a thickness equivalent to that of the starting material. The confetti-like material is fed to a Munson rotary knife cutter, Model SC30. The discharge screen has ⅛ inch openings. The gap between the rotary and fixed blades is set to approximately 0.020 inch. The rotary knife cutter shears the confetti-like pieces, releasing a fibrous material at a rate of about one pound per hour. An average length of the fibers is 1.063 mm and an average width of the fibers is 0.0245 mm, giving an average L/D of 43:1.

Materials are treated with electron beam using a Rhodotron® TT200 continuous wave accelerator delivering 5 MeV electrons at 80 kW of output power. Table 10 describes the parameters used. Table 11 reports the nominal dose used.

The processed materials are used in the preparation of the culture solution determined in Example 42. The selected microorganism and culture solution are combined in a large volume fixed volume fed-batch fermentor and are maintained using the conditions and for the time period determined in Example 42. Concentrated culture solution containing processed materials is added as required to the fermentor. In addition, bioconversion product and microorganisms are removed from the fermentor and are processed for storage or use.

Example 44

Large Scale Production of Bioconversion Products from Biomass Using Animal Waste as a Nitrogen Source Bioconversion products are produced as described in Example 43 using animal waste as a source of nitrogen. Prior to use, animal waste is sterilized using filtration or steam and high pressure sterilization. Prior to addition to the culture solution, the sterilized animal waste is dried.

Example 45

Large Scale Production of *Fusarium venenatum* (ATCC 20334) from Biomass

*Fusarium venenatum* is cultured using the process described in Example 43. Harvested *F. venenatum* is combined with rehydrated egg white, onions, textured wheat protein (wheat protein, wheat starch), and canola oil, and processed for use as a human food.

OTHER EMBODIMENTS

A number of embodiments of the invention have been described. Nevertheless, it will be understood that various modifications can be made without departing from the spirit and scope of the invention.

In some embodiments, relatively low doses of radiation, optionally, combined with acoustic energy, e.g., ultrasound, are utilized to cross-link, graft, or otherwise increase the molecular weight of a natural or synthetic carbohydrate-containing material, such as any of those materials in any form (e.g., fibrous form) described herein, e.g., sheared or un-sheared cellulosic or lignocellulosic materials, such as cellulose. The cross-linking, grafting, or otherwise increasing the molecular weight of the natural or synthetic carbohydrate-containing material can be performed in a controlled and predetermined manner by selecting the type or types of radiation employed (e.g., e-beam and ultraviolet or e-beam and gamma) and/or dose or number of doses of radiation applied.

For example, a fibrous material that includes a first cellulosic and/or lignocellulosic material having a first molecular weight can be irradiated in a manner to provide a second cellulosic and/or lignocellulosic material having a second molecular weight higher than the first molecular weight. For example, if gamma radiation is utilized as the radiation source, a dose of from about 0.2 Mrad to about 10 Mrad, e.g., from about 0.5 Mrad to about 7.5 Mrad, or from about 2.0 Mrad to about 5.0 Mrad, can be applied. If e-beam radiation is utilized, a smaller dose can be utilized (relative to gamma radiation), such as a dose of from about 0.1 Mrad to about 5 Mrad, e.g., between about 0.2 Mrad to about 3 Mrad, or between about 0.25 Mrad and about 2.5 Mrad.

Any of the following additives can added to the fibrous materials, densified fibrous materials or any other materials described herein. Additives, e.g., in the form of a solid, a liquid or a gas, can be added. Additives include fillers such as calcium carbonate, silica, and talc; inorganic flame retardants such as alumina trihydrate or magnesium hydroxide; and organic flame retardants such as chlorinated or brominated organic compound. Other additives include lignin, fragrances, compatibilizers, processing aids, antioxidants, opacifiers, heat stabilizers, colorants, foaming agents, polymers, e.g., degradable polymers, photostabilizers, biocides, and antistatic agents, e.g., stearates or ethoxylated fatty acid amines. Suitable antistatic compounds include conductive carbon blacks, carbon fibers, metal fillers, cationic compounds, e.g., quaternary ammonium compounds, e.g., N-(3-chloro-2-hydroxypropyl)-trimethylammonium chloride, alkanolamides, and amines. Representative degradable polymers include polyhydroxy acids, e.g., polylactides, polyglycolides and copolymers of lactic acid and glycolic acid, poly(hydroxybutyric acid), poly(hydroxyvaleric acid), poly[lactide-co-(e-caprolactone)], poly[glycolide-co-(e-caprolactone)], polycarbonates, poly(amino acids), poly(hydroxyalkanoate)s, polyanhydrides, polyorthoesters and blends of these polymers.

When described additives are included, they can be present in amounts, calculated on a dry weight basis, of from below 1 percent to as high as 80 percent, based on total weight of the fibrous material. More typically, amounts range from between about 0.5 percent to about 50 percent by weight, e.g., 5 percent, 10 percent, 20 percent, 30, percent or more, e.g., 40 percent.

Any additives described herein can be encapsulated, e.g., spray dried or microencapsulated, e.g., to protect the additives from heat or moisture during handling.

The fibrous materials, densified fibrous materials, resins or additives can be dyed. For example, the fibrous material can be dyed before combining with the resin and compounding to form composites. In some embodiments, this dyeing can be helpful in masking or hiding the fibrous material, especially large agglomerations of the fibrous material, in molded or extruded parts, when this is desired. Such large agglomerations, when present in relatively high concentrations, can show up as speckles in the surfaces of the molded or extruded parts.

For example, the desired fibrous material can be dyed using an acid dye, direct dye or a reactive dye. Such dyes are available from Spectra Dyes, Kearny, N.J. or Keystone Aniline Corporation, Chicago, Ill. Specific examples of dyes include SPECTRA™ LIGHT YELLOW 2G, SPECTRACID™ YELLOW 4GL CONC 200, SPECTRANYL™ RHODAMINE 8, SPECTRANYL™ NEUTRAL RED B, SPECTRAMINE™ BENZOPERPURINE, SPECTRADIAZO™ BLACK OB, SPECTRAMINE™ TURQUOISE G, and SPECTRAMINE™ GREY LVL 200%, each being available from Spectra Dyes.

In some embodiments, resin color concentrates containing pigments are blended with dyes. When such blends are then compounded with the desired fibrous material, the fibrous material can be dyed in-situ during the compounding. Color concentrates are available from Clariant.

It can be advantageous to add a scent or fragrance to the fibrous materials or densified fibrous materials.

Mobile Biomass Processing

Stationary processing facilities for processing biomass have been described. However, depending upon the source of biomass feedstock and the products produced therefrom, it can be advantageous to process biomass in mobile facilities that can be located close to the source of the feedstock and/or close to target markets for products produced from the feedstock. As an example, in some embodiments, various grasses such as switchgrass are used as biomass feedstock. Transporting large volumes of switchgrass from fields where it grows to processing facilities hundreds or even thousands of miles away can be both wasteful energetically and economically costly (for example, transportation of feedstock by train is estimated to cost between $3.00 and $6.00 per ton per 500 miles). Moreover, some of the products of processing switchgrass feedstock can be suitable for markets in regions where biomass feedstock is grown (e.g., ruminant feed for livestock). Once again, transporting ruminant feed hundreds or thousands of miles to market can not be economically viable.

Accordingly, in some embodiments, the processing systems disclosed herein are implemented as mobile, reconfigurable processing facilities. One embodiment of such a mobile facility is shown in FIG. 63. Processing facility 8000 includes five transport trucks 8002, 8004, 8006, 8008, and 8010 (although five trucks are shown in FIG. 63, in general, any number of trucks can be used). Truck 8002 includes water supply and processing systems and electrical supply systems for the other trucks. Trucks 8004, 8006, 8008, and 8010 are each configured to process biomass feedstock in parallel.

Truck 8002 includes a water supply inlet 8012 for receiving water from a continuous supply (such as a water main) or a reservoir (e.g., a tank on another truck, or a tank or other reservoir located at the processing site). Process water is circulated to each of trucks 8004, 8006, 8008, and 8010 through a water supply conduit 8020. Each of trucks 8004, 8006, 8008, and 8010 includes a portion of conduit 8020. When the trucks are positioned next to one another to set up the mobile processing facility, the portions of conduit 8020 are connected to form a continuous water transport conduit. Each of trucks 8004, 8006, 8008, and 8010 includes a water inlet 8022 to supply process water, and a water outlet 8024 to remove used process water. The water outlets 8024 in each of trucks 8004, 8006, 8008, and 8010 lead to a piecewise continuous water disposal conduit 8026, which is similarly joined into a continuous conduit when the trucks are positioned next to one another. Waste process water is circulated to water processor 8028 in truck 8002, which treats the water to remove harmful waste materials and then recycles the treated water via conduit 8030 back into supply conduit 8020. Waste materials removed from the used process water can be disposed of on site, or stored (e.g., in another truck, not shown) and transported to a storage facility.

Truck 8002 also includes an electrical supply station 8016 that provides electrical power to each of trucks 8004, 8006, 8008, and 8010. Electrical supply station 8016 can be connected to an external power source via connection 8014. Alternatively, or in addition, electrical supply station can be configured to generate power (e.g., via combustion of a fuel source). Electrical power is supplied to each of trucks 8004, 8006, 8008, and 8010 via electrical supply conduit 8040. Each of trucks 8004, 8006, 8008, and 8010 includes an electrical power terminal 8018 to which devices on the truck requiring electrical power are connected.

Each of trucks 8004, 8006, 8008, and 8010 includes a feedstock inlet 8042 and a waste outlet 8044. Biomass feedstock enters each of trucks 8004, 8006, 8008, and 8010 through inlet 8042, where it is processed according to the methods disclosed herein. Following processing, waste material is discharged through outlet 8044. Alternatively, in some embodiments, each of trucks 8004, 8006, 8008, and 8010 can be connected to a common feedstock inlet (e.g., positioned in truck 8002), and each truck can discharge waste material through a common outlet (e.g., also positioned in truck 8002).

Each of trucks 8004, 8006, 8008, and 8010 can include various types of processing units; for example, in the configuration shown in FIG. 63, each of trucks 8004, 8006, 8008, and 8010 includes an ion accelerator 8032 (e.g., a horizontal Pelletron-based tandem folded accelerator), a heater/pyrolysis station 8034, a wet chemical processing unit 8036, and a biological processing unit 8038. In general, each of trucks 8004, 8006, 8008, and 8010 can include any of the processing systems disclosed herein. In certain embodiments, each of trucks 8004, 8006, 8008, and 8010 will include the same processing systems. In some embodiments, however, one or more trucks can have different processing systems.

In addition, some or all trucks can have certain processing systems onboard but which are not used, depending upon the nature of the feedstock. In general, the layout of the various onboard processing systems on each of trucks 8004, 8006, 8008, and 8010 is reconfigurable according to the type of material that is processed.

Processing facility 8000 is an exemplary parallel processing facility; each of trucks 8004, 8006, 8008, and 8010 processes biomass feedstock in parallel. In certain embodiments, mobile processing facilities are implemented as serial processing facilities. An embodiment of train-based serial mobile processing facility 8500 is shown in FIG. 64. Processing facility 8500 includes three rail cars 8502, 8504, and 8506 (in general, any number of rail cars can be used), each configured to perform one or more processing steps in an overall biomass processing procedure. Rail car 8502 includes a feedstock inlet for receiving feedstock from a storage repository (e.g., a storage building, or another rail car). Feedstock is conveyed from one processing unit to another among the three rail cars via a continuous conveyor system. Rail car 8502 also includes an electrical supply station 8514 for supplying electrical power to each of rail cars 8502, 8504, and 8506.

Rail car 8502 includes a coarse mechanical processor 8516 and a fine mechanical processor 8518 for converting raw feedstock to a finely divided fibrous material. A third mechanical processor 8520 rolls the fibrous material into a flat, continuous mat. The mat of fibrous material is then transported to an ion accelerator 8522 on rail car 8504 that exposes the fibrous material to an ion beam. Following exposure to the ion beam, the fibrous material is transported to a low energy electron accelerator 8524.

The fibrous material is subsequently transported to a chemical processing unit 8526 on rail car 8506 for one or more chemical treatment steps. Rail car 8506 includes a process water inlet 8532 which receives process water from an external reservoir (e.g., a tank or another rail car).

Following chemical treatment in processing unit 8526, the material is transported to a biological processing unit 8528 to initiate fermentation of liberated sugars from the material. After biological processing is complete, the material is transported to a separator 8530, which diverts useful products into conduit 8510 and waste materials into conduit 8512. Conduit 8510 can be connected to a storage unit (e.g., a tanker car or an external storage tank). Similarly, waste products can be conveyed through conduit 8512 to a storage unit such as a tanker car, and/or to an external storage facility. Separator 8530 also recycles clean process water for subsequent delivery to chemical processing unit 8536 and/or biological processing unit 8528.

As discussed previously, processing facility 8500 is an example of a sequential configuration of a mobile processing facility; each of rail cars 8502, 8504, and 8506 includes a different subset of processing systems; and the feedstock process flow from each car is connected to the next car in series to complete the processing sequence.

In general, a wide variety of different mobile processing configurations can be used to process biomass feedstock. Both truck-based and train-based mobile processing facilities can be configured for either serial operation or parallel operation. Generally, the layout of the various processing units is reconfigurable, and not all processing units can be used for particular feedstocks. When a particular processing unit is not used for a certain feedstock, the processing unit can be withdrawn from the process flow. Alternatively, the processing unit can remain in the overall process flow, but can be deactivated so that feedstock passes through the deactivated unit rapidly without being modified.

Mobile processing facilities can include one or more electronic control devices that automate some or all aspects of the biomass processing procedure and/or the mobile facility setup procedure. For example, an electronic control device can be configured to receive input information about a feedstock material that is to be processed, and can generate a variety of output information including a suggested configuration of the mobile processing facility, and/or values for one or more process parameters involved in the biomass processing procedure that will be implemented.

While transportation by truck has been described above, part or all of the processing facility may be transported by any other means, for example by rail or by a nautical vessel, e.g., a ship, barge, boat, dock, or floating platform. Transporting may also be performed using more than a single mode of transport, e.g., using a container on both a ship and a tractor trailer or train.

In some embodiments, the methods described herein can be performed using, for example, coal (e.g., lignite coal).

Accordingly, other embodiments are within the scope of the following claims.

The invention claimed is:

1. A method comprising:
   (a) irradiating a lignocellulosic or cellulosic biomass material with an ionizing radiation dose of 10 Mrad to 150 Mrad, wherein the irradiation reduces the recalcitrance of the biomass material;
   (b) saccharifying the recalcitrant reduced biomass material, thereby producing a saccharified biomass comprising one or more sugar;
   (c) converting the saccharified biomass material comprising said one or more sugar into a plastic, wherein the plastic is a polyhydroxyalkanoate (PHA) produced by culturing said saccharified biomass or one or more sugar thereof with *Alcaligenes eutropohus* bacteria; and
   (d) obtaining said plastic.

2. The method of claim 1, wherein the one or more sugar comprises a monosaccharide.

3. The method of claim 2, wherein the one or more sugar comprises glucose and/or xylose.

4. The method of claim 1, wherein the one or more sugar comprises a disaccharide.

5. The method of claim 1, wherein the one or more sugar comprises a trisaccharide.

6. The method of claim 1, wherein the method generates at least one of poly-$\beta$-hydroxybutyrate and poly-$\beta$-hydroxyvalerate.

* * * * *